(12) United States Patent
Zischinsky et al.

(10) Patent No.: US 8,309,735 B2
(45) Date of Patent: Nov. 13, 2012

(54) HETEROCYCLIC COMPOUNDS FOR THE INHIBITION OF INTEGRINS AND USE THEREOF

(75) Inventors: Gunther Zischinsky, Berlin (DE); Roland Stragies, Berlin (DE); Frank Osterkamp, Berlin (DE); Dirk Scharn, Berlin (DE); Gerd Hummel, Berlin (DE); Holger Kalkhof, Berlin (DE); Grit Zahn, Berlin (DE); Doerte Vossmeyer, Berlin (DE); Claudia Christner-Albrecht, Berlin (DE); Ulrich Reineke, Berlin (DE)

(73) Assignee: Shire Orphan Therapies GmbH (DE)

( * ) Notice: Subject to any disclaimer, the term of this patent is extended or adjusted under 35 U.S.C. 154(b) by 704 days.

(21) Appl. No.: 12/300,530

(22) PCT Filed: May 14, 2007

(86) PCT No.: PCT/EP2007/004283
§ 371 (c)(1), (2), (4) Date: Dec. 4, 2008

(87) PCT Pub. No.: WO2007/131764
PCT Pub. Date: Nov. 22, 2007

(65) Prior Publication Data
US 2009/0203745 A1    Aug. 13, 2009

(30) Foreign Application Priority Data
May 12, 2006 (EP) ..................... 06009872

(51) Int. Cl.
*C07D 213/72* (2006.01)
*A61K 31/44* (2006.01)
(52) U.S. Cl. .................... 546/304; 514/352
(58) Field of Classification Search ............ None
See application file for complete search history.

(56) References Cited

U.S. PATENT DOCUMENTS

| | | | |
|---|---|---|---|
| 6,388,084 B1 | 5/2002 | Kaplan et al. | |
| 6,521,666 B1 | 2/2003 | Sircar et al. | |
| 2002/0133015 A1 | 9/2002 | Kaplan et al. | |
| 2003/0191118 A1 | 10/2003 | Sircar et al. | |
| 2003/0220268 A1 | 11/2003 | Makino et al. | |
| 2004/0106622 A1 | 6/2004 | Morie et al. | |
| 2005/0192279 A1 | 9/2005 | Barbay et al. | |
| 2006/0223836 A1 | 10/2006 | Makino et al. | |
| 2007/0043113 A1 | 2/2007 | Ward et al. | |
| 2009/0104116 A1 | 4/2009 | Zischinsky et al. | |

FOREIGN PATENT DOCUMENTS

| | | |
|---|---|---|
| EP | 1288205 | 3/2003 |
| EP | 1371646 | 12/2003 |
| WO | WO 03/089410 | 10/2003 |
| WO | 2005061440 | 7/2005 |
| WO | WO 2005/090329 | 9/2005 |
| WO | WO 2007/060408 | 5/2007 |
| WO | WO 2007/060409 | 5/2007 |
| WO | WO 2007/088041 | 11/2007 |
| WO | WO 2007/131764 | 11/2007 |

OTHER PUBLICATIONS

International Search Report for International Application PCT/EP2007/000832, dated Jun. 27, 2007.
International Search Report for International Application PCT/EP2007/004283, dated Oct. 18, 2007.
Non-Final Office Action for U.S. Appl. No. 12/162,798, mailed Nov. 7, 2011.

*Primary Examiner* — Janet Andres
*Assistant Examiner* — Heidi Reese
(74) *Attorney, Agent, or Firm* — Morse, Barnes-Brown & Pendleton, P.C.; Lisa M. Treannie, Esq.

(57) ABSTRACT

The present invention relates to compounds of formula (I) wherein: A is a radical selected from the group comprising aromatic heterocyclic 5-membered ring systems; Ar is a radical selected from the group comprising optionally substituted 5- and 6-membered aromatic ring systems, whereby the ring system contains 0, 1, 2 or 3 heteroatoms selected from the group comprising N, O and S; Z is a linker and Ψ is a radical of formula (II) and their use for the inhibition of integrin.

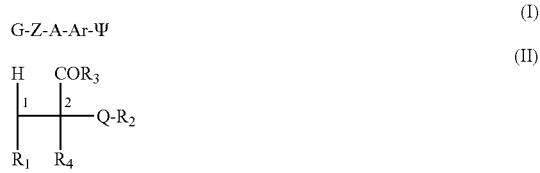

74 Claims, 8 Drawing Sheets

X = OTos, Cl, Br, I, ...

HETEROCYCLIC COMPOUNDS FOR THE INHIBITION OF INTEGRINS AND USE THEREOF

CROSS REFERENCE TO RELATED APPLICATION

This application is a 35 U.S.C. 371 National Phase Entry Application from PCT/EP2007/004283, filed May 14, 2007, which claims the benefit of European Patent Application No. 06009872.0 filed on May 12, 2006, the disclosures of which are incorporated herein in their entirety by reference.

The present invention is related to new compounds and the use of said compounds for the manufacture of medicaments and diagnostics.

Angiogenesis, also called neovascularization, is a fundamental process whereby new blood vessels are formed. Under normal physiological conditions angiogenesis is highly regulated and essential for reproduction, embryonic development and wound healing (Folkman and Shing, 1992, J. Biol. Chem., 267, 10931). However, angiogenesis also occurs under various pathological conditions including ocular neovascularization such as in diabetic retinopathy, age related macular degeneration and various other eye diseases, inflammatory disorders like rheumatoid arthritis, tumor growth and metastasis (Folkman and Shing, 1992, J. Biol. Chem., 267, 10931).

Angiogenesis is a highly regulated process which occurs in response to various proangiogenic stimuli like growth factors, cytokines and other physiological molecules as well as to other factors like hypoxia and low pH (Folkman and Shing, 1992, J. Biol. Chem., 267, 10931). The angiogenic cascade for development of new blood vessels requires the cooperation of a variety of molecules that regulate necessary cellular processes such as extracellular matrix (ECM) remodelling, invasion, migration, proliferation, differentiation and tube formation (Brooks, 1996, Eur. J. Cancer, 32A, 2423). After an initiation phase, proangiogenic molecules like VEGF, bFGF, PDGF and others activate endothelial cells via stimulation of their cell surface receptors such as, e.g., VEGFR2-Flk1/KDR. These activated cells undergo a process of cellular proliferation, elevated expression of cell adhesion molecules, increased secretion of proteolytic enzymes and increased cellular migration and invasion. A number of distinct molecules are involved to promote proliferation and invasion, including members of the integrin, selectin and immunoglobulin gene super family for adhesion as well as proteolytic enzymes such as matrix metalloproteinases and serine proteinases for degrading the ECM (Brooks, 1996, Eur. J. Cancer, 32A, 2423). Finally, a complex cascade of biochemical signals derived from cell surface receptors interacting with ECM components and soluble factors is triggered, leading to lumen formation and differentiation into mature blood vessels.

Inhibition of different molecules involved in the angiogenic cascade has been shown to prevent angiogenesis and results in efficacious treatment of neovascular diseases in animal models and clinical studies (Madhusudan, 2002, Curr. Op. Pharm., 2, 403; Folkman, 2001, Thromb Haemost, 86, 23; Eyetech Study Group, 2003, Opthalmology, 110, 979; Ferrara, 2002, Semin Oncol. 6 Suppl 16, 10) for cancer and age related macular degeneration (AMD). Most of these angiogenic inhibitors are directed towards blocking the initial growth factor mediated activation step induced by VEGF or PDGF. These approaches target only one molecule or a small set out of the multiple set of pro-angiogenic stimuli. However, angiogenesis takes place in response to various growth factors such as VEGF, bFGF, PDGF and others (Folkman and Shing, 1992, J. Biol. Chem., 267, 10931). Therefore, a more general approach for inhibiting angiogenesis based on interference with this whole variety of stimuli would be more beneficial.

Inhibition of cell adhesion to the ECM, the fundamental step for activation, survival, targeting and migration of activated endothelial cells (EC), is a promising target mechanism for anti-angiogenesis. Most of these interactions are mediated by integrins, a family of multifunctional cell adhesion receptors.

Members of the integrin family are non-covalently associated alpha1beta heterodimers that mediate cell-cell, cell-extracellular matrix and cell-pathogene interactions. These type I transmembrane proteins are expressed on a variety of cells and require bivalent cations for their physiological function. Until now, 19 different integrin alpha subunits and 8 different beta subunits are known that combine to form at least 25 different alpha/beta heterodimers with different ligand specificity. The ligands for the extracellular domain of many integrins are the proteins of the extracellular matrix, whereby mostly a consensus motif with the amino acid sequence RGD (arginine-glycine-aspartate) is recognized. The intracellular domains of the integrins are either directly or indirectly connected to intracellular components such as kinases and the cytoskeleton. Integrins serve as bidirectional signalling receptors, whereupon protein activities and gene expression are changed in response to ligand binding to the extracellular integrin domain, which is also referred to as outside-in signalling. On the other hand, the affinity of the integrins is modulated in response to intracellular changes such as binding of proteins to the intracellular domain of the integrin, which is referred to as inside-out signalling (Humphries, 2000, Biochem. Soc. Trans., 28, 311; Hynes, 2002, Cell 110, 673).

A multitude of studies on the integrin pattern on activated endothelial cells, mice gene knockouts and inhibition studies in angiogenic animal models with antibodies, peptides and small molecules provided information about the integrins and ECM proteins involved in critical steps of angiogenesis (Brooks, 1994, Science, 264, 569; Brooks, 1996, Eur. J. Cancer, 32A, 2423; Mousa, 2002, Curr. Opin. Chem. Biol, 6, 534; Hynes, 2002, Cell, 110, 673; Hynes, 2002, Nature Medicine, 8, 918; Kim, 2000, Am. J. Path., 156, 1345). Thereby it becomes clear that above all the vitronectin receptors alphavbeta3, alphavbeta5 and the fibronectin receptor alpha5beta1 play a critical role in angiogenesis. Gene deletion studies of integrins attributed essential roles to almost all integrins. The deletion driven defects suggest widespread contributions of the various integrins to both the maintenance of tissue integrity and the promotion of cellular migration. However, only the deletion of alpha5 and beta1 and its ligand fibronectin, leads to embryogenic lethality with major vascular defects, whereas ablation of alphav, beta3 and beta5 genes fail to block angiogenesis and in some cases even enhance angiogenesis (Hynes, 2002, Nature Medicine, 8, 918). Also, alpha5beta1 is poorly expressed in quiescent endothelium but strongly expressed in proliferating endothelium. Its expression is significantly upregulated on blood vessels in human tumors and after stimulation with growth factors (Kim, 2000, Am. J. Path, 156, 1345; Collo, 1999, J. Cell Sc., 112, 569). The alpha5beta1 fibronectin interaction facilitates the survival of entdothelial cells in vivo and in vitro (Kim, 2002, J. Clin. Invest., 110, 933; Kim, 2000, J. Biol. Chem., 275, 33920). Additionally, experimental studies established a fundamental role of alpha5beta1 in the regulation of alphavbeta3 mediated angiogenesis (Kim, 2000, J. Biol. Chem., 275, 33920).

Only alpha5beta1 genetic and pharmacological data are consistent and confirm the fundamental role of alpha5beta1 for angiogenesis. Therefore, alpha5beta1 is a preferred target for the development of anti-angiogenic drugs. Consequently, antagonists of integrin alpha5beta1 have a great therapeutic potential for the treatment of neovascularization in tumors, in the eye and of inflammatory processes. Angiogenesis induced by multiple growth factors in several models was blocked with alpha5beta1 antagonists (Varner, 1998, 98 (suppl), I-795, 4166; Kim, 2000, Am. J. Path, 156, 1345). Additionally, these antagonists also inhibit tumor angiogenesis, thereby causing regression of human tumors in animal models (Kim, 2000, Am. J. Path, 156, 1345)

In the light of these scientific findings on the importance of integrins in angiogenesis, serious efforts have been undertaken to develop respective inhibitors.

There are at least three major classes of reagents developed as integrin, especially alpha5beta1 integrin antagonists. These include antibodies such as monoclonal antibodies, polyclonal antibodies, and antibody fragments (Kim, 2000, Am. J. Path., 156, 1345, WO2005/092073, WO2004/056308), natural peptides such as venom derived "disintegrin" peptides (Marcinkiewicz, 1999, Biochemistry, 38, 13302), synthetic peptides (Koivunen, 1994, J. Biol. Chem., 124, 373) and non-peptidic small molecules such as spiro compounds (WO97/33887).

Although these compounds are in principle suitable as alpha5beta1 antagonists, they have some drawbacks. For example, antibodies are complex biological molecules with usually high activity and specificity for the targeted molecule. But the non-human source of antibodies could cause an immune response during later treatment of humans or the molecules have to be humanized by special additional procedures. Additionally, the human immune system can develop antibodies against the antigen binding region of the therapeutic antibody (anti-idiotypic antibodies). The development of an immune response against the therapeutic antibody could cause immunological problems in humans and could decrease or inhibit the efficacy of the antibody. Moreover the production of antibodies requires special treatment to avoid any contaminants such as prions or other proteinaceous material, which might have a detrimental effect upon application to a patient. Additionally, the high molecular weight of these molecules constricts the possible administration routes of the medicament in the treatment of patients, usually through the intravenous route. Due to the high molecular weight the tissue penetration may be limited which can cause unsufficient drug delivery. This could be a drawback for the treatment of certain diseases such as solid tumors due to the increased interstitial fluid pressure, or fibrotic disorders due to the dense extracellular matrix within the affected tissue.

There are several peptidic alpha5beta1 inhibitors known that are based on the RGD-sequence derived from the natural ligand, However, these inhibitors show mostly no or only limited specificity against other integrins. Furthermore, peptidic molecules are generally disadvantageous concerning their application as a medicament. One aspect thereof resides in the limited stability against naturally occurring proteases. Another one is the limitation of possible administration routes due to their hydrophilic nature.

One fibronectin derived peptide (U.S. Pat. No. 6,001,965) proposed to act via alpha5beta1, showed anti-metastatic activity in mouse tumor models (Stoeltzing, 2003, Int. J. Cancer 104, 496) and inhibition of cell invasion (Livant, 2000, Cancer Res., 60, 309), but no direct inhibition of alpha5beta1-fibronectin interaction could be shown. The peptide only binds to alpha5beta1 without effecting the fibronectin binding, and to alphavbeta3 integrin (Cianfrocca, conference talk at 6th International Symposium on Anti-Angiogenic Agents, San Diego, 30th Jan.-1[st]Feb. 2004). Therefore, the molecular mechanism of action and the specificity remain unclear and shed some further doubt on the usage of peptides derived from this postulated second, so called synergistic, integrin binding site in fibronectin as inhibitors for alpha5beta1.

The small molecules synthesized in the art are, e.g., described in the international patent application WO 97/33887 which discloses compounds comprising a spiro moiety as a core element which is presenting three moieties obviously needed for integrin binding. However, due to the spiro moiety contained in these compounds they are difficult to synthesize and, owing to the three moieties attached to the core, they provide relatively high molecular weights.

The small molecules disclosed in international patent application WO 2005/090329 comprise a cyclic core structure that is also bearing three moieties necessary for exhaustive interaction with the integrin.

International patent application WO 95/32710 discloses the use of a benzyl residue as a core element. These compounds, however, seem to lack the required specificity for an integrin which is particularly relevant in the pathological mechanism of the aforementioned diseases.

Thus, the objective of the present invention is to provide chemical compounds which are suitable to interact with integrins, more particularly specifically interact with certain integrin species such as integrin alpha5beta1. A further objective of the present invention is to provide antagonists for alpha5beta1, which preferably show enhanced activity, stability, selectivity, and synthetic accessibility. A further objective of the present invention is to provide new modes of treatment for diseases, preferably for diseases involving integrin mediated effects and processes.

In a first aspect the problem underlying the present invention is solved by a compound of formula (I)

$$G\text{-}Z\text{-}A\text{-}Ar\text{-}\Psi \qquad (I)$$

wherein

A is a radical selected from the group comprising aromatic heterocyclic 5-membered ring systems;

Ar is a radical selected from the group comprising optionally substituted 5- and 6-membered aromatic ring systems,
  whereby the ring system contains 0, 1, 2 or 3 heteroatoms selected from the group comprising N, O and S;

Z is a radical individually and independently selected from the group comprising $(CH_2)_n\text{-}E\text{-}(CH_2)_m\text{-}L\text{-}(CH_2)_k$ and $(CH_2)_m\text{-}L\text{-}(CH_2)_k$,
  wherein
  E is a radical which is either absent or present, whereby if E is present, E is selected from the group comprising O, S, NH, $NR^a$, CO, SO, $SO_2$, acetylene and substituted ethylene;
  L is a radical which is either absent or present, whereby if L is present, L is individually and independently selected from the group comprising O, S, NH, $NR^b$, CO, SO, $SO_2$, substituted ethylene and acetylene; and
  k, m and n are individually and independently 0, 1, 2 or 3;

Ψ is a radical of formula (II)

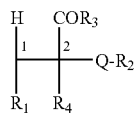

wherein

Q is a radical selected from the group comprising a direct bond, C1-C4alkyl, C=O, C=S, O, S, $CR^aR^b$, $NR^a$—$NR^b$, N=N, $CR^a$=N, N=$CR^a$, (C=O)—O, O—(C=O), $SO_2$, $NR^a$, (C=O)—$NR^a$, $NR^a$—(C=O)—$NR^b$, $NR^c$—(C=O), O—(C=O)—$NR^c$, $NR^c$—(C=O)—O, $NR^c$—(C=S), (C=S)—$NR^c$, $NR^c$—(C=S)—$NR^d$, $NR^c$—$SO_2$ and $SO_2$—$NR^c$.

$R_1$, $R^a$, $R^b$, $R^c$ and $R^d$ are radicals which are individually and independently selected from the group comprising H, alkyl, substituted alkyl, cycloalkyl, substituted cycloalkyl, heterocycloyl, substituted heterocycloyl, aryl, substituted aryl, heteroaryl, substituted heteroaryl, arylalkyl, substituted arylalkyl, heteroarylalkyl, substituted heteroarylalkyl, cycloalkylalkyl, substituted cycloalkylalkyl, heterocyclylalkyl, substituted heterocyclylalkyl, alkyloxy, alkyloxyalkyl, substituted alkyloxyalkyl, alkyloxycycloalkyl, substituted alkyloxycycloalkyl, alkyloxyheterocyclyl, substituted alkyloxyheterocyclyl, alkyloxyaryl, substituted alkyloxyaryl, alkyloxyheteroaryl, substituted alkyloxyheteroaryl, alkylthioalkyl, substituted alkylthioalkyl, alkylthiocycloalkyl and substituted alkylthiocycloalkyl, hydroxy, substituted hydroxy, oxo, thio, substituted thio, aminocarbonyl, substituted aminocarbonyl, formyl, substituted formyl, thioformyl, substituted thioformyl, amino, substituted amino, hydroxyl, substituted hydroxyl, mercapto, substituted mercapto, hydrazino, substituted hydrazino, diazene, substituted diazene, imine, substituted imine, amidino, substituted amidino, iminomethylamino, substituted iminomethylamino, ureido, substituted ureido, formylamino, substituted formylamino, aminocarbonyloxy, substituted aminocarbonyloxy, hydroxycarbonylamino, substituted hydroxycarbonylamino, hydroxycarbonyl, substituted hydroxycarbonyl, formyloxy, substituted formyloxy, thioformylamino, substituted thioformylamino, aminothiocarbonyl, substituted aminothiocarbonyl, thioureido, substituted thioureido, sulfonyl, substituted aminosulfonyl, cyano and halogen;

$R_2$ is a hydrophobic moiety;

$R_3$ is a radical selected from the group comprising OH, C1-C8alkyloxy and aryl C0-C6alkyloxy;

$R_4$ is a radical selected from the group comprising hydrogen, halogen and C1-C4alkyl; and G is a radical containing a basic moiety.

In a first embodiment of the first aspect any of $R_1$, $R^a$, $R^b$, $R^c$ and $R^d$ is a radical individually and independently selected from the group comprising hydrogen, alkyl, substituted alkyl, halogen, cyano, hydroxy, alkyloxy, substituted alkyloxy, oxo, aryl, substituted aryl, arylalkyl, substituted arylalkyl, amino, substituted amino.

In a second embodiment of the first aspect which is also an embodiment of the first embodiment any of $R_1$, $R^a$, $R^b$, $R^c$ and $R^d$ is a radical individually and independently selected from the group comprising hydrogen, fluoro, chloro, bromo, methyl, ethyl, propyl, tert-butyl, phenyl, benzyl, hydroxyl, methoxy, oxo, amino, methylamino, acetylamino, cyano.

In a third embodiment of the first aspect which is also preferably an embodiment of the first and second embodiment one or several of the ring atoms of Ar is/are optionally individually and independently substituted with a substituent, whereby the substituent is $R_5$ and whereby $R_5$ is individually and independently selected from the group comprising H, benzyl, substituted benzyl, phenyl, substituted phenyl, alkyl, substituted alkyl, cycloalkyl, substituted cycloalkyl, heterocyclyl, substituted heterocyclyl, aryl, substituted aryl, heteroaryl, substituted heteroaryl, arylalkyl, substituted arylalkyl, heteroarylalkyl, substituted heteroarylalkyl, cycloalkylalkyl, substituted cycloalkylalkyl, heterocyclylalkyl, substituted heterocyclylalkyl, alkyloxyalkyl, substituted alkyloxyalkyl, alkyloxycycloalkyl, substituted alkyloxycycloalkyl, alkyloxyheterocyclyl, substituted alkyloxyheterocyclyl, alkyloxyaryl, substituted alkyloxyaryl, alkyloxyheteroaryl, substituted alkyloxyheteroaryl, alkylthioalkyl, substituted alkylthioalkyl, alkylthiocycloalkyl and substituted alkylthiocycloalkyl, (C=O)—$NHR^a$, (C=O)$R^a$, (C=S)$R^a$, $NHR^a$, $OR^a$, $SR^a$, $CH_2R^a$, $CR^aR^b$ $R^cNH$—$NHR^a$N=$NR^a$, CH=$NR^a$, N=$CHR^a$, NH—(C=O)—$NHR^a$, NH—(C=O)$R^a$, O—(C=O)—$NHR^a$, NH—(C=O)—$OR^a$, (C=O)—$OR^a$, O—(C=O)$R^a$, NH—(C=S)$R^a$, (C=S)—$NHR^2$, NH—(C=S)—$NHR^2$, $SO_2R^a$, NH—$SO_2R^a$, $SO_2$—$NHR^a$, $NR^cR^a$, (C=O)—$NR^cR^a$, $NR^cR^a$, $NR^c$—(C=O)—$NHR^a$, NH—(C=O)—$NR^cR^a$, $NR^c$—(C=O)—$NR^dR^a$, $NR^c$—(C=O)$R^a$, O—(C=O)—$NR^cR^a$, $NR^c$—(C=O)—$OR^a$, $NR^c$—(C=S)$R^a$, (C=S)—$NR^cR^a$, $NR^c$—(C=S)—$NHR^a$, NH—(C=S)—$NR^cR^a$, $NR^c$—(C=S)_$NR^dR^a$, $NR^c$—$SO_2R^a$, $SO_2$—$NR^cR^a$, $SCHF_2$, $OCHF_2$, CN, halogen, $CF_3$, $CCl_3$ and $OCF_3$, whereby any of $R^a$, $R^b$, $R^c$ and $R^d$ is as defined in any of the previous embodiments of the first aspect.

In a fourth embodiment of the first aspect which is also an embodiment of the third embodiment $R_5$ is selected from the group comprising hydrogen, alkyl, aryl, arylalkyl, halogen, hydroxy, amino, alkoxy, alkylamino, dialkylamino, alkylcarbonyl, alkylaminocarbonyl, dialkylaminocarbonyl, alkyloxycarbonyl, cylcoalkyl, alkylcarbonylamino, aminocarbonyl, cyano and alkylthio.

In a fifth embodiment of the first aspect which is also an embodiment of the fourth embodiment $R_5$ is selected from the group comprising hydrogen, fluoro, chloro, bromo, cyano, amino, methylamino, dimethylamino, methoxycarbonyl, aminocarbonyl, methylaminocarbonyl, dimethylaminocarbonyl, acetylamino, phenyl, benzyl, methyl, ethyl, propyl, tert-butyl, hydroxy, methoxy, trifluoromethyl, trifluoromethyloxy, difluoromethyloxy, acetyl, and methylthio.

In a sixth embodiment of the first aspect which is also an embodiment of the fifth embodiment $R_5$ is hydrogen, fluoro, chloro, cyano, methylamino, dimethylamino, methylaminocarbonyl, acetylamino, phenyl, benzyl, methyl, ethyl, tert-butyl, hydroxy, methoxy, trifluoromethyl.

In a seventh embodiment of the first aspect which is also an embodiment of the first to fifth embodiment, preferably of the sixth embodiment Ar is a radical selected from the group comprising thienyl, pyrrolyl, pyrazolyl, imidazolyl, 1,2,3-triazolyl, 1,2,4-triazolyl, oxazolyl, isoxazolyl, thiazolyl, isothiazolyl, phenyl, pyridyl, pyrimidinyl, pyridazinyl and pyrazinyl, whereby one or several of the ring atoms is/are optionally individually and independently substituted with a substituent, whereby if substituted, the substituent is $R_5$.

In an eighth embodiment of the first aspect which is also an embodiment of the seventh embodiment
Ar is a radical selected from the group comprising phenyl, pyridyl and thienyl,
  whereby one or several of the ring atoms is/are optionally individually and independently substituted with $R_5$,
    whereby $R_5$ is defined as in claims 5 to 7, preferably as in claim 6, more preferably as in claim 7.

In a ninth embodiment of the first aspect which is also an embodiment of the eighth embodiment
Ar is phenyl,
  whereby
    A and Ψ are connected to Ar in the positions para to each other; and
    one or two of the ring atoms of Ar is/are optionally individually and independently substituted with methyl, ethyl, chloro, fluoro or methoxy.

In a tenth embodiment of the first aspect which is also an embodiment of the first to ninth embodiment, preferably of the eighth or ninth embodiment, more preferably of the ninth embodiment
A is a radical selected from the group comprising furyl, thienyl, pyrrolyl, oxazolyl, isooxazolyl, thiazolyl, isothiazolyl, imidazolyl, pyrazolyl, triazolyl oxadiazolyl and thiadiazolyl,
  whereby one or several of the ring atoms of A are individually and independently substituted with 0, 1 or 2 $R_5$,
    whereby $R_5$ is defined as in the fourth to seventh embodiment, preferably as in the fifth embodiment, more preferably as in the sixth embodiment.

In an eleventh embodiment of the first aspect which is also an embodiment of the tenth embodiment
$R_5$ is defined as in the fifth to seventh embodiment, preferably as in the sixth embodiment; and
Z and A are bonded to A in positions meta to each other.

In a twelfth embodiment of the first aspect which is also an embodiment of the first to eleventh embodiment, Ar is preferably as defined in the seventh to ninth embodiment, more preferably as in the ninth embodiment, and A is preferably as defined in the tenth and eleventh embodiment, more preferably as in the eleventh embodiment,
G is $R_9$—NH,
  whereby
    $R_9$ is a radical selected from the group comprising
      (a) 5- or 6-membered aromatic rings and 5- or 7-membered nonaromatic rings comprising ring atoms,
        whereby
          any of the rings contains 0, 1, 2, 3 or 4 heteroatoms,
            whereby the heteroatoms are individually and independently selected from the group comprising N, O and S;
          any or several of the ring atoms is/are optionally and individually and independently substituted with one or several substituents,
            whereby the substituent is $R^a$; and
          if $R_9$ is 2-pyridyl, $R_9$ is substituted with at least one $R^a$ that is not hydrogen.
      (b) 5,5-, 5,6- or 6,6-membered aromatic, nonaromatic or combined aromatic/nonaromatic bicyclic ring systems comprising ring atoms,
        whereby any of the rings contains 0, 1, 2, 3 or 4 heteroatoms,
          whereby the heteroatoms are individually and independently selected from the group comprising N, O and S; and
          any or several of the ring atoms is/are optionally and individually and independently substituted with one or several substituents,
            whereby the substituent is $R^a$.
  whereby
    $R_5$ is defined as in the fourth to sixth embodiment, preferably the fifth embodiment and more preferably the sixth embodiment; and
    any of $R^a$, $R^b$ and $R^c$ is each and independently a radical as defined in first and second embodiment, preferably the first embodiment and more preferably the second embodiment.

In a thirteenth embodiment of the first aspect which is also an embodiment of the twelfth embodiment
$R_9$ is a 5-membered aromatic or nonaromatic heterocyclic ring containing 1, 2 or 3 N-atoms,
  whereby
    said ring is substituted or unsubstituted with one or more substituents $R^a$ each and independently as defined in the first and second embodiment, preferably in the first embodiment and more preferably in the second embodiment; and
    $R_9$ is connected to the NH group of G ortho to one of said ring N-atoms of $R_9$.

In a fourteenth embodiment of the first aspect which is also an embodiment of the twelfth embodiment
$R_9$ is a 6-membered aromatic or nonaromatic heterocyclic ring containing 1, 2 or 3 N-atoms
  whereby
    said ring is substituted or unsubstituted with one or more substituents $R^a$ each and independently as defined in the first and second embodiment, preferably in the first embodiment and more preferably in the second embodiment;
    if $R_9$ is 2-pyridyl, $R_9$ is substituted in addition to the amino group of $R_9$—NH with at least one $R^a$ that is not hydrogen; and
    $R_9$ is connected to the NH group of G ortho to one of said ring N-atoms of $R_9$.

In a fifteenth embodiment of the first aspect which is also an embodiment of the twelfth to fourteenth embodiment, preferably of the thirteenth and fourteenth embodiment
G is a radical selected from the group comprising thiazol-2-ylamino, 4,5,6,7-tetrahydro-1H-benzoimidazol-2-ylamino, 3a,4,5,6,7,7a-hexahydro-1H-benzoimidazol-2-ylamino, 3H-indol-2-ylamino, 3,4-dihydro-quinolin-2-ylamino, 3H-pyrrolo[2,3-b]pyridin-2-ylamino, 3,4-dihydro-[1,8]naphthyridin-2-ylamino, 3H-imidazol-4-ylamino, pyridin-2-ylamino, pyrimidin-2-ylamino, 1H-imidazol-2-ylamino, 4,5-dihydro-1H-imidazol-2-ylamino, 1,4,5,6-tetrahydro-pyrimidin-2-ylamino, 4,5,6,7-tetrahydro-1H-[1,3]diazepin-2-ylamino, 4,5-dihydro-3H-pyrrol-2-ylamino, 3,4,5,6-tetrahydro-pyridin-2-ylamino, 4,5,6,7-tetrahydro-3H-azepin-2-ylamino, 1H-benzoimidazol-2-ylamino, 1H-indol-2-ylamino, pyrazin-2-ylamino, 5,6-dihydro-3H-pyrimidin-4-one-2-ylamino, 3,5-dihydroimidazol-4-one-2-ylamino, oxazol-2-ylamino, 1H-[1,8]naphthyridin-4-one-2-amino, 4,5-dihydro-thiazol-2-ylamino, 4,5-dihydro-oxazol-2-ylamino and pyrimidin-4-ylamino,
  whereby
    Z is attached to these radicals at their amino group;
    each radical represented by G is unsubstituted or substituted with one or more $R^a$ each and independently as defined in the first and second embodiment, preferably in the first embodiment and more preferably in the second embodiment; and
  if G is pyridine-2-ylamino, the pyridine ring is substituted in addition to the amino group with at least one $R^a$ that is not hydrogen.

In a sixteenth embodiment of the first aspect which is also an embodiment of the first to eleventh embodiment, Ar is preferably as defined in the seventh to ninth embodiment, more preferably as in the ninth embodiment and A is preferably as defined in the tenth and eleventh embodiment, more preferably as in the eleventh embodiment,
G is a radical selected from the group comprising
  (a) 5- or 6-membered aromatic rings and 5- or 7-membered nonaromatic rings comprising ring atoms,
    whereby
      any of the rings contains 1, 2, 3 or 4 heteroatoms,
        whereby the heteroatoms are individually and independently selected from the group comprising N, O and S;
      any or several of the ring atoms is/are optionally and individually and independently substituted with one or several substituents,
        whereby the substituent is $R^a$; and
      if G is pyridyl, the pyridyl ring is substituted with at least one $R^a$ that is not hydrogen;
  (b) 5,5-, 5,6- or 6,6-membered aromatic, nonaromatic or combined aromatic/nonaromatic bicyclic ring systems comprising ring atoms,
    whereby
      any of the ring systems contains 1, 2, 3 or 4 heteroatoms,
        whereby the heteroatoms are individually and independently selected from the group comprising N, O and S;
      one or several of the ring atoms is/are optionally and individually and independently substituted with one or several substituents,
        whereby the substituent is $R^a$; and
  (c) (C=$NR^c$)—$NR^b$—$R^a$, $NR^d$—(C=$NR^c$)$NR^b$—$R^a$, $NR^c$(C=$NR^a$)$R^b$ and $NR^aR^b$;
    whereby
      any of $R^a$, $R^b$, $R^c$ and $R^d$ is each and independently a radical as defined in the first and second embodiment, preferably the first embodiment and more preferably the second embodiment.

In a seventeenth embodiment of the first aspect which is also an embodiment of the sixteenth embodiment
G is a heterocyclic 1, 2, 3 or 4 N-atoms containing ring or ring system selected from the group comprising aromatic and nonaromatic 5- or 6-membered rings and bicyclic aromatic and nonaromatic as well as combined aromatic/nonaromatic 5,5-, 5,6- or 6,6-membered ring systems;
  whereby
    said rings or ring systems are unsubstituted or substituted with one or more $R^a$ each and independently as defined in the first and second embodiment, preferably in the first embodiment and even more preferably in the second embodiment;
    if G is pyridyl, the pyridyl ring is substituted with at least one $R^a$ that is not hydrogen; and
    Z is connected to a ring atom of G that is adjacent to one of said ring N-atoms of G.

In an eighteenth embodiment of the first aspect which is also an embodiment of the seventeenth embodiment
G is a radical selected from the group comprising 1,2,3,4-tetrahydro-[1,8]naphthyridin-2-yl, 1,2,3,4-tetrahydro-[1,8]naphthyridine-7-yl, 1H-pyrrolo[2,3-b]pyridin-2-yl, 1H-pyrrolo[2,3-b]pyridin-6-yl, 1,3,4,6,7,8-hexahydro-2H-pyrimido[1,2-a]pyrimidin-2-yl, 2,3,5,6,7,8-hexahydro-imidazo[1,2-a]pyrimidin-7-yl, 5,6,7,8-tetrahydro-imidazo[1,2-a]pyrimidin-7-yl, 5,6,7,8-tetrahydro-imidazo[1,2-a]pyrimidin-2-yl, 4,5,6,7-tetrahydro-3H-imidazo[4,5-b]pyridin-2-yl, 5,6,7,8-tetrahydro-imidazo[1,2-a]pyrimidin-2-yl, 3H-imidazo[4,5-b]pyridin-5-yl, 1H-pyrazolo[3,4-b]pyridin-6-yl, 2,3-dihydro-1H-imidazo[1,2-a]imidazol-6-yl, 2,3-dihydro-1H-pyrrolo[2,3-b]pyridine-6-yl, 2-methylaminopyridin-6-yl, 4-methylaminothiazol-2-yl, 2-methylamino-1H-pyrrol-5-yl, 2-methylamino-1H-imidazol-5-yl and 4-methylamino-1H-imidazol-2-yl;
  wherein
    each radical is unsubstituted or substituted with one or more substituents $R^a$ each and individually as defined in the first and second embodiment, preferably in the first embodiment and even more preferably in the second embodiment;

In a nineteenth embodiment of the first aspect which is also an embodiment of the eighteenth or fifteenth embodiment
G is a radical selected from the group comprising 1H-imidazol-2-ylamino, 4,5-dihydro-1H-imidazol-2-ylamino, 1,4,5,6-tetrahydro-pyrimidin-2-ylamino, 4,5-dihydro-3H-pyrrol-2-ylamino, 3,4,5,6-tetrahydro-pyridin-2-ylamino, 1H-benzoimidazol-2-ylamino, 1,2,3,4-tetrahydro-[1,8]naphthyridine-7-yl, 5,6-dihydro-3H-pyrimidin-4-one-2-ylamino, 3,5-dihydroimidazol-4-one-2-ylamino, 2,3-dihydro-1H-pyrrolo[2,3-b]pyridine-6-yl, 2-methylaminopyridin-6-yl, 4-methylpyridin-2-ylamino, 5-methylpyridin-2-ylamino, 4-methoxypyridin-2-ylamino, 4-fluoropyridin-2-ylamino and 2-methylamino-1H-imidazol-5-yl.

In a twentieth embodiment of the first aspect which is also an embodiment of the sixteenth embodiment
  G is a radical selected from the group comprising amino, amidino, aminomethyleneamino, guanidino; aminobenzylideneamino, aminoethylideneamino.

In a twenty-first embodiment of the first aspect which is also an embodiment of the first to twentieth embodiment, Ar is preferably as defined in the seventh to ninth embodiment, more preferably as in the ninth embodiment, and A is preferably as defined in the tenth to eleventh embodiment, more preferably as in the eleventh embodiment; G is preferably as defined in the twelfth to twentieth embodiment, more preferably as in claims fifteenth, eighteenth and twentieth embodiment, even more preferably as in the nineteenth and twentieth embodiment,
Z is a direct bond, $CH_2$ or CO.

In a twenty-second embodiment of the first aspect which is also an embodiment of the first to twenty-first embodiment Ar is preferably as defined in the seventh to ninth embodiment, more preferably as the ninth embodiment, and A is preferably as defined in the tenth to eleventh embodiment, more preferably as in the eleventh embodiment; G is preferably as defined in the twelfth to twentieth embodiment, more preferably as in the fifteenth, eighteenth, nineteenth or twentieth embodiment, even more preferably as in the nineteenth embodiment,
$R_2$ is a radical selected from the group comprising phenyl, substituted phenyl, heterocyclyl, substituted heterocyclyl, aryl, substituted aryl, heteroaryl, substituted heteroaryl, cycloalkyl and substituted cycloalkyl,
  whereby Q is attached to $R_2$ at one of the ring atoms of $R_2$.

In a twenty-third embodiment of the first aspect which is also an embodiment of the twenty-second embodiment $R_2$ is a radical of formula (III)

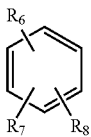

(III)

wherein
0 or 1 ring carbon atom in formula (III) is substituted by a nitrogen atom;
$R_6$, $R_7$ and $R_8$ are each radicals and individually and independently selected from the group comprising hydrogen, halogen, cyano, alkyl, substituted alkyl, alkoxy, substituted alkoxy, substituted aminocarbonyl, aryl, substituted aryl, heteroaryl, and substituted heteroaryl; and
$R_2$ is attached to Q via a ring atom of the radical of formula (III).

In a twenty-fourth embodiment of the first aspect which is also an embodiment of the twenty-third embodiment $R_2$ is a radical of formula (IV)

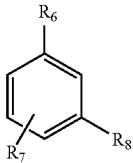

(IV)

wherein
0 or 1 ring carbon atom in formula (IV) is substituted by a nitrogen atom;
$R_6$, $R_7$ and $R_8$ are each radicals and individually and independently selected from the group comprising hydrogen, fluoro, chloro, bromo, methyl, ethyl, propyl, tert-butyl, phenyl, benzyl, hydroxyl, methoxy, amino, acetylamino, cyano, nitro, benzyloxy, trifluoromethyl, 1-oxoethyl, dimethylaminocarbonyl, methylaminocarbonyl, aminocarbonyl, trifluoromethoxy, trichloromethyl, methoxycarbonyl, methylsulfonyl, trifluoromethylsulfonyl, methylthio, aminosulfonyl, methylaminosulfonyl, dimethylaminosulfonyl, 2-oxazolyl, 2-imidazolyl, 1-imidazolyl and 4,5-dihydro-oxazol-2-yl; and
Q is attached to the ring of formula (IV) in the position ortho to $R_6$ and $R_8$.

In a twenty-fifth embodiment of the first aspect which is also an embodiment of the twenty-fourth embodiment $R_2$ is a radical selected from the group comprising phenyl, 2,4,6-trimethylphenyl, 2,6-dimethylphenyl, 4-cyanophenyl, 2,4,6-tribromophenyl, 2-bromo-6-methylphenyl, 4-benzyloxyphenyl, 2-methylphenyl, 2-ethyl-6-methylphenyl, 2-methyl-6-trifluoromethylphenyl, 4-fluoro-2-ethyl-6-methylphenyl, 4-chloro-2-ethyl-6-methylphenyl, 4-cyano-2-ethyl-6-methylphenyl, 4-trifluoromethyl-2-ethyl-6-methylphenyl, 4-(1-oxoethyl)-2-ethyl-6-methylphenyl, 4-dimethylcarbamoyl-2-ethyl-6-methyl-phenyl, 4-methylcarbamoyl-2-ethyl-6-methyl-phenyl, 4-carbamoyl-2-ethyl-6-methyl-phenyl, 4-trifluoromethoxy-2-ethyl-6-methyl-phenyl, 4-(1H-imidazo-1-yl)-2-ethyl-6-methyl-phenyl, 4-chloro-2,6-dimethylphenyl, 4-fluoro-2,6-dimethylphenyl, 4-cyano-2,6-dimethylphenyl, 4-trifluoromethyl-2,6-dimethylphenyl, 4-(1-oxoethyl)-2,6-dimethylphenyl, 4-trifluoromethoxy-2,6-dimethylphenyl, 4-(1H-imidazo-1-yl)-2,6-dimethylphenyl, pyridine-3-yl, 2-methyl-pyridine-3-yl, 2-methyl-4-trifluoromethyl-pyridine-3-yl, 2,4-dimethyl-pyridine-3-yl, 4-chloro-2-methyl-6-methylthio-phenyl, 4-fluoro-2-methyl-6-methylthio-phenyl, 2-methyl-6-methylthio-phenyl, 4-fluoro-2-(2-propyl)-6-methylphenyl, 4-cyano-2-methyl-6-methylthio-phenyl, 4-trifluoromethyl-2-methyl-6-methylthio-phenyl, 2-isopropyl-6-methylphenyl, 4-fluoro-2-(2-propyl)-6-methylphenyl, 2-ethyl-4-methyl-pyridine-3-yl, 4-trichloromethyl-2-ethyl-6-methylphenyl, 4-nitro-2-ethyl-6-methylphenyl, 4-methyloxycarbonyl-2-ethyl-6-methylphenyl, 4-methylsulfonyl-2-ethyl-6-methylphenyl, 4-trifluoromethylsulfonyl-2-ethyl-6-methylphenyl, 4-amino sulfonyl-2-ethyl-6-methylphenyl, 4-methylaminosulfonyl-2-ethyl-6-methylphenyl, 4-dimethylaminosulfonyl-2-ethyl-6-methylphenyl, 4-methylaminocarbonyl-2-ethyl-6-methylphenyl, 4-dimethylaminocarbonyl-2-ethyl-6-methylphenyl, 4-aminocarbonyl-2-ethyl-6-methylphenyl, 2-ethyl-6-methyl-4-(2-oxazolyl)phenyl, 2-ethyl-6-methyl-4-(2-imidazolyl)phenyl, 4-trifluormethylcarbonyl-2-ethyl-6-methylphenyl, 4-trichloromethyl-2,6-dimethylphenyl, 4-nitro-2,6-dimethylphenyl, 4-methyloxycarbonyl-2,6-dimethylphenyl, 4-methylsulfonyl-2,6-dimethylphenyl, 4-trifluoromethylsulfonyl-2,6-dimethylphenyl, 4-aminosulfonyl-2,6-dimethylphenyl, 4-methylaminosulfonyl-2,6-dimethylphenyl, 4-dimethylaminosulfonyl-2,6-dimethylphenyl, 4-methylaminocarbonyl-2,6-dimethylphenyl, 4-dimethylaminocarbonyl-2,6-dimethylphenyl, 4-aminocarbonyl-2,6-dimethylphenyl, 2,6-dimethyl-4-(2-oxazolyl)phenyl, 2,6-dimethyl-4-(2-imidazolyl)phenyl and 4-trifluormethylcarbonyl-2,6-dimethylphenyl.

In a twenty-sixth embodiment of the first aspect which is also an embodiment of the twenty-second embodiment $R_2$ is a radical of formula (V)

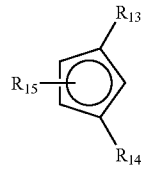

(V)

wherein
1, 2 or 3 ring atoms in formula (V) are hetero atoms selected from the group comprising N, O and S;
$R_{13}$, $R_{14}$ and $R_{15}$ are each radicals and individually and independently selected from the group comprising hydrogen, halogen, cyano, alkyl, substituted alkyl, alkoxy, substituted alkoxy, aryl, substituted aryl, heteroaryl, and substituted heteroaryl; and
Q is attached to the ring in formula (V) in the position ortho to both, $R_{13}$ and $R_{14}$.

In a twenty-seventh embodiment of the first aspect which is also an embodiment of the twenty-sixth embodiment $R_2$ is a radical selected from the group comprising 3,5-dimethylisoxazol-4-yl, 5-methyl-3-trifluoromethylisoxazol-4-yl, 3-isopropyl-5-methylisoxazol-4-yl, 5-methyl-3-phenylisoxazol-4-yl, 3,5-diethylisoxazol-4-yl, 2-methyl-4,5,6,7-tetrahydrobenzofuran-3-yl, 2,4-dimethylfuran-3-yl, 1,3,5-trimethyl-1H-pyrazol-4-yl, 1-tert-butyl-3,5-dimethyl-1H-pyrazol-4-yl, 1-benzyl-3,5-dimethyl-1H-pyrazol-4-yl, 2,4-dimethylthiophen-3-yl and 3-ethyl-5-methylisoxazol-4-yl.

In a twenty-eighth embodiment of the first aspect which is also an embodiment of the twenty-second embodiment
R₂ is a cycloalkyl radical selected from the group comprising cyclohexyl, cyclopentyl, 1-phenylcyclopentyl, 1-methylcyclohexyl, 1-phenylcyclohexyl, bicyclo[3.2.1]octane-6-yl, adamantan-1-yl, 2,2,6,6-tetramethylcyclohexyl, 2,4,6-trimethylcyclohexyl, and 2-methylcyclohexyl.

In a twenty-ninth embodiment of the first aspect which is also an embodiment of the first to twenty-first embodiment, Ar is preferably as defined in the seventh to ninth embodiment, more preferably as in the ninth embodiment, and A is preferably as defined in tenth to eleventh embodiment, more preferably as in the eleventh embodiment; G is preferably as defined in the twelfth to twentieth embodiment, more preferably as in the fifteenth, eighteenth, nineteenth or twentieth embodiment, even more preferably as in the nineteenth embodiment,
R₂ is a radical selected from the group comprising H, alkyl, branched alkyl, substituted branched alkyl, substituted alkyl, benzyl, substituted benzyl, arylalkyl, substituted arylalkyl, heteroarylalkyl, substituted heteroarylalkyl, cycloalkylalkyl, substituted cycloalkylalkyl, heterocyclylalkyl and substituted heterocyclylalkyl,
whereby
R₂ is preferably selected from the group comprising arylalkyl, substituted arylalkyl, branched alkyl, substituted branched alkyl; and
R₂ is attached via its alkyl moiety to Q.

In a thirtieth embodiment of the first aspect which is also an embodiment of the twenty-ninth embodiment
R₂ is a substituted alkyl radical selected from the group comprising 1,I-dimethylethyl, 1,1-dimethylpropyl, 1-methyl-1-phenylethyl, 1-phenylpropyl, 2-methyl-1-phenylpropyl, 1-methylbutyl, 1-ethyl-1-methylpropyl, 1-ethylpropyl, and 1-isopropyl-2-methylpropyl.

In a thirty-first embodiment of the first aspect which is also an embodiment of the first to the thirtieth embodiment, Ar is preferably as defined in seventh to ninth embodiment, more preferably as in the ninth embodiment, and A is preferably as defined in the tenth to eleventh embodiment, more preferably as in the eleventh embodiment; G is preferably as defined in the twelfth to twentieth embodiment, more preferably as in the fifteenth, eighteenth, nineteenth or twentieth embodiment, even more preferably as in the nineteenth embodiment; R₂ is preferably as defined in the twenty-second to thirtieth embodiment, more preferably as in the twenty-fifth, twenty-sixth, twenty-eighth or thirtieth embodiment,
Q is selected from the group comprising C0-C3alkyl, NHCO, CONH and NHSO₂.

In a thirty-second embodiment of the first aspect which is also an embodiment of the first to twenty-first embodiment, Ar is preferably as defined in seventh to ninth embodiment, more preferably as in the ninth embodiment, and A is preferably as defined in the tenth to eleventh embodiment, more preferably as in the eleventh embodiment; G is preferably as defined in the twelfth to twentieth embodiment, more preferably as in the fifteenth, eighteenth or twentieth embodiment, even more preferably as in the nineteenth or twentieth embodiment,
Q is a direct bond;
R₂ is a lactame radical selected from the group comprising azetidine-2-ones, pyrrolidine-2-ones, and piperidine-2-ones,
whereby any of the radicals is either
geminal substituted with R$^a$ and R$^b$
whereby R$^a$ and R$^b$ are individually and independently selected; or
ortho-fused with an aromatic or nonaromatic 5- or 6-membered ring; or
spiro-fused with a nonaromatic 5- or 6-membered ring, whereby
ring atoms of the rings that are ortho- or spiro-fused to said lactame rings are individually and independently substituted with 0, 1, 2, 3 or 4 R$^c$;
R$^a$, R$^b$ and R$^c$ are defined as in the first and second embodiment, preferably the first embodiment and more preferably in the second embodiment; and
said lactames are directly bound at their ring N-atom to C-atom number 2 in formula (II).

In a thirty-third embodiment of the first aspect which is also an embodiment of the thirty-second embodiment
R₂ is a radical selected from the group comprising formulas (VI) to (XI)

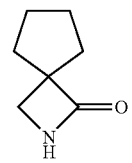
(VI)

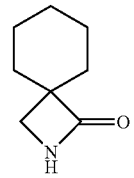
(VII)

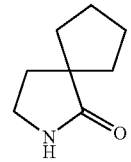
(VIII)

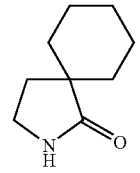
(IX)

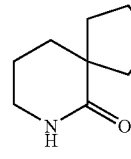
(X)

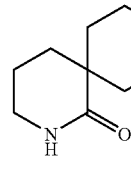
(XI)

whereby
any of the formulas (VI) to (XI) is directly bound to C-atom number 2 in formula (II) at the ring N-atoms of the respective formulas (VI) to (XI);

the cycloalkyl rings spiro-fused to the heterocycles in any of the formulas (VI) to (XI) are optionally ortho-fused with an aromatic 5- or 6-membered ring; and any of the formulas (VI) to (XI) is individually and independently substituted with 0, 1 or 2 $R^a$, whereby $R^a$ is defined as in the first aspect, preferably the first embodiment thereof and even more preferably in the second embodiment thereof.

In a thirty-fourth embodiment of the first aspect which is also an embodiment of the thirty-third embodiment $R_2$ is a radical selected from the group comprising formulas (XII) to (XVI)

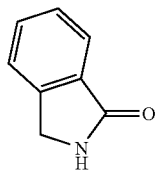
(XII)

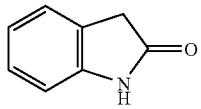
(XIII)

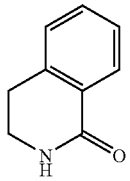
(XIV)

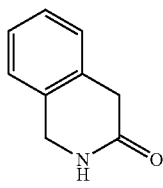
(XV)

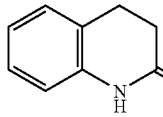
(XVI)

whereby any of the formulas (XII) to (XVI) is directly bound to C-atom number 2 in formula (II) at the ring N-atom of the respective formulas (XII) to (XVI); and any of the formulas (XII) to (XVI) is independently and individually substituted with 0, 1 or 2 $R^a$ as defined in the first and second embodiment, preferably as defined in the first embodiment, more preferably as defined in the second embodiment.

In a thirty-fifth embodiment of the first aspect which is also an embodiment of the thirty-second embodiment $R_2$ is a radical selected from the group comprising formulas (XVII) to (XXI)

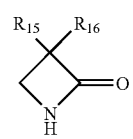
(XVII)

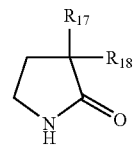
(XVIII)

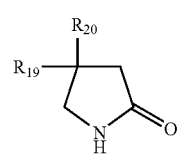
(XIX)

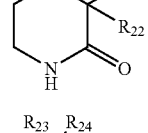
(XX)

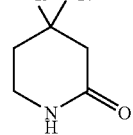
(XXI)

whereby any of the formulas (XVII) to (XXI) is directly bound to C-atom number 2 in formula (II) at the ring N-atom;

$R_{15}$, $R_{16}$, $R_{17}$, $R_{18}$, $R_{19}$, $R_{20}$, $R_{21}$, $R_{22}$, $R_{23}$ and $R_{24}$ are each radicals and are individually and independently selected from the group comprising hydrogen, halogen, C1-C6alkyl, C3-C6cycloalkyl, substituted C3-C6cycloalkyl, phenyl, substituted phenyl, benzyl, and substituted benzyl; and any of the formulas (XVII) to (XXI) is independently and individually substituted with 0, 1 or 2 $R^a$ as defined in the first and second embodiment, preferably as defined in the first embodiment, more preferably as defined in the second embodiment.

In a second aspect the problem underlying the present invention is solved by a compound, preferably a compound according to the embodiments of the first aspect, having formula (XXII)

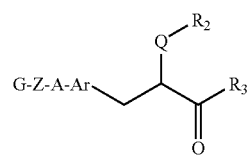
(XXII)

wherein

Ar is a radical selected from the group comprising phenyl, pyridyl and thienyl;

A is a radical selected from the group comprising furyl, thienyl, pyrrolyl, oxazolyl, isooxazolyl, thiazolyl, isothiazolyl, imidazolyl, pyrazolyl, triazolyl oxadiazolyl and thiadiazolyl, whereby
ring atoms are individually and independently substituted with 0, 1 or 2 substituents $R^a$ each and independently as defined in the first aspect, preferably in the first embodiment of the first aspect and more preferably in the second embodiment of the first aspect; and Z and the Ar ring in structure (XXII) are connected to A in meta position to each other;

Q is selected from the group comprising a direct bond, C1-C4alkyl, CO—NH, NH—CO, CO—NH, NH—SO$_2$ and SO$_2$—NH;

$R_2$ is a radical as defined in any of the twenty-second to the thirty-fifth embodiment of the first aspect;

$R_3$ is a radical selected from the group comprising OH, OMe and OEt;

Z is selected from the group comprising a direct bond, CH$_2$, CH$_2$—CH$_2$ and CO; and G is a radical as defined in any of the twelfth to twentieth embodiment of the first aspect.

In a first embodiment of the second aspect the compound is having formula (XXIII)

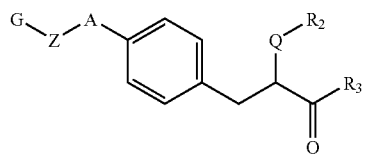

(XXIII)

In a second embodiment of the second aspect which is also an embodiment of the first embodiment of the second aspect Q is selected from the group comprising a direct bond, NH—CO and NHSO$_2$; and Z is selected from the group comprising a direct bond, CH$_2$ and CO.

In a third embodiment of the second aspect which is also an embodiment of the second embodiment of the second aspect A is furyl and the compound is represented by formulas (XXIV) to (XXVI),

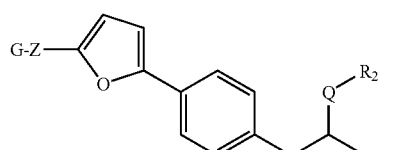

(XXIV)

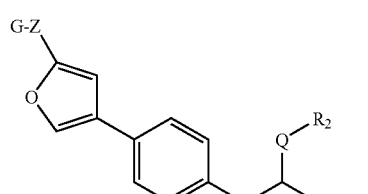

(XXV)

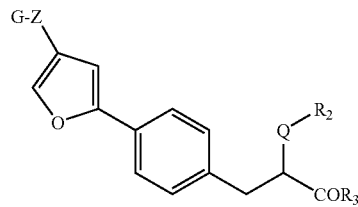

(XXVI)

whereby the furyl and the phenyl ring atoms in formulas (XXIV) to (XXVI) are each and independently substituted with 0, 1 or 2 $R_5$, whereby $R_5$ is defined as in the sixth embodiment of the first aspect.

In a fourth embodiment of the second aspect which is also an embodiment of the third embodiment of the second aspect the compound has one of formulas (XXVII) to (XXIX),

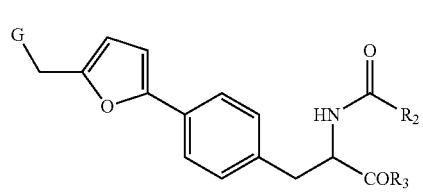

(XXIV)

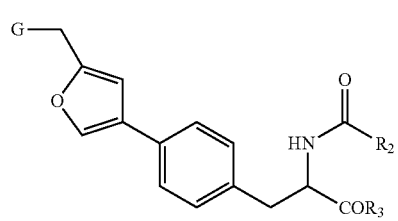

(XXV)

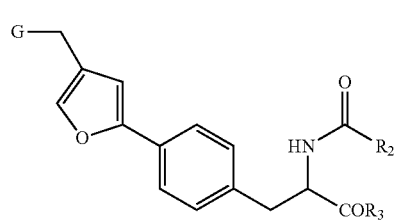

(XXVI)

wherein $R_2$ is a radical selected from the groups defined in any of the twenty-fifth, twenty-seventh, twenty-eighth and thirtieth embodiments of the first aspect, preferable the twenty-fifth embodiment of the first aspect; and G is a radical selected from the group comprising 1H-imidazol-2-ylamino, 4,5-dihydro-1H-imidazol-2-ylamino, 1,4,5,6-tetrahydro-pyrimidin-2-ylamino, 4,5-dihydro-3H-pyrrol-2-ylamino, 3,4,5,6-tetrahydro-pyridin-2-ylamino, 1H-benzoimidazol-2-ylamino, 5,6-dihydro-3H-pyrimidin-4-one-2-ylamino, 3,5-dihydroimidazol-4-one-2-ylamino, 4-methylpyridin-2-ylamino, 5-methylpyridin-2-ylamino, 4-methoxypyridin-2-ylamino, and 4-fluoropyridin-2-ylamino.

In a fifth embodiment of the second aspect which is also an embodiment of the second embodiment of the second aspect A is pyrrolyl and the compound is represented by formulas (XXX) to (XXXIII)

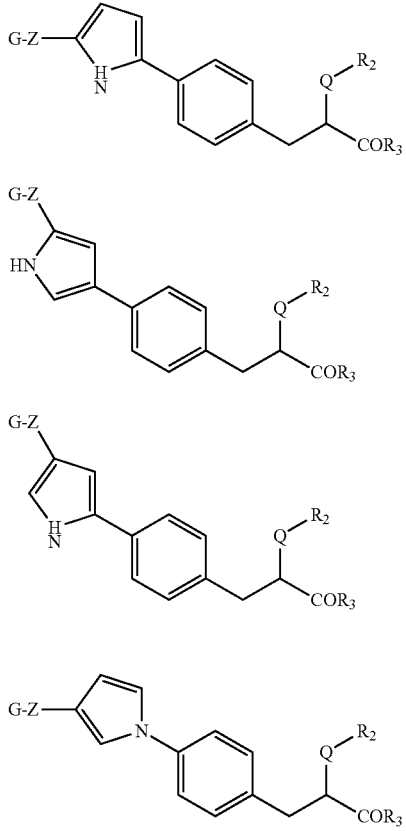

(XXX)

(XXXI)

(XXXII)

(XXXIII)

whereby the pyrrolyl and the phenyl ring atoms in formulas (XXX) to (XXXIII) are each and independently substituted with 0, 1 or 2 $R_5$, whereby $R_5$ is defined as in the sixth embodiment of the first aspect.

In a sixth embodiment of the second aspect which is also an embodiment of the fifth embodiment of the second aspect the compound is having one of formulas (XXXIV) to (XXXVII)

(XXXIV)

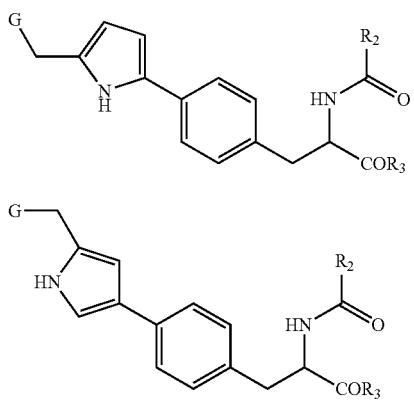

(XXXV)

(XXXVI)

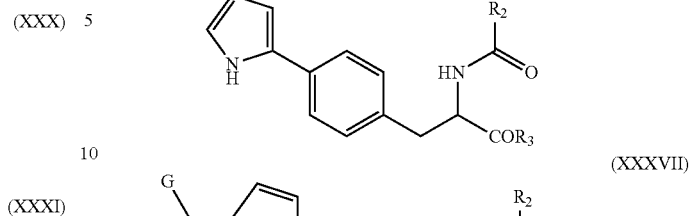

(XXXVII)

wherein any NH-moiety of the pyrrolyl rings in formulas (XXXIV), (XXXV) and (XXXVI) is optionally substituted with methyl;

$R_2$ is a radical selected from the groups defined in the twenty-fifth, twenty-seventh, twenty-eighth or thirtieth embodiment of the first aspect, preferable the twenty-fifth embodiment of the first aspect; and G is a radical selected from the group comprising 1H-imidazol-2-ylamino, 4,5-dihydro-1H-imidazol-2-ylamino, 1,4,5,6-tetrahydro-pyrimidin-2-ylamino, 4,5-dihydro-3H-pyrrol-2-ylamino, 3,4,5,6-tetrahydro-pyridin-2-ylamino, 1H-benzoimidazol-2-ylamino, 5,6-dihydro-3H-pyrimidin-4-one-2-ylamino, 3,5-dihydroimidazol-4-one-2-ylamino, 4-methylpyridin-2-ylamino, 5-methylpyridin-2-ylamino, 4-methoxypyridin-2-ylamino, and 4-fluoropyridin-2-ylamino.

In a seventh embodiment of the second aspect which is also an embodiment of the second embodiment of the second aspect A is pyrazolyl and the compound is represented by formulas (XXXVIII) to (XXXIX)

(XXXVIII)

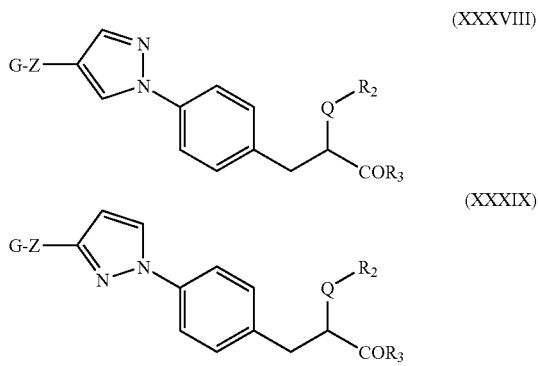

(XXXIX)

whereby the pyrazolyl and the phenyl ring atoms in formulas (XXXVIII) to (XXXIX) are each and independently substituted with 0, 1 or 2 $R_5$, whereby $R_5$ is defined as in the sixth embodiment of the first aspect.

In an eighth embodiment of the second aspect which is also an embodiment of the seventh embodiment of the second aspect having one of formulas (XL) to (XLI)

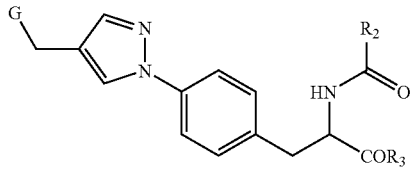
(XL)

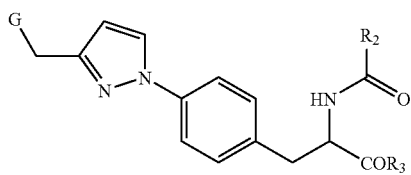
(XLI)

wherein
- R₂ is a radical selected from the groups defined in the twenty-fifth, twenty-seventh, twenty-eighth or thirtieth embodiment of the first aspect, preferable the twenty-fifth embodiment of the first aspect; and
- G is a radical selected from the group comprising 1H-imidazol-2-ylamino, 4,5-dihydro-1H-imidazol-2-ylamino, 1,4,5,6-tetrahydro-pyrimidin-2-ylamino, 4,5-dihydro-3H-pyrrol-2-ylamino, 3,4,5,6-tetrahydro-pyridin-2-ylamino, 1H-benzoimidazol-2-ylamino, 5,6-dihydro-3H-pyrimidin-4-one-2-ylamino, 3,5-dihydroimidazol-4-one-2-ylamino, 4-methylpyridin-2-ylamino, 5-methylpyridin-2-ylamino, 4-methoxypyridin-2-ylamino, and 4-fluoropyridin-2-ylamino.

In a ninth embodiment of the second aspect which is also an embodiment of the second embodiment of the second aspect
A is imidazolyl and the compound is represented by formulas (XLII) to (XLV)

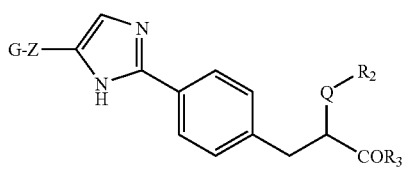
(XLII)

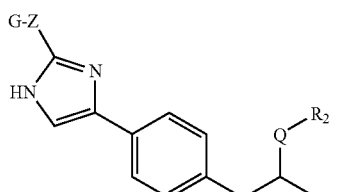
(XLIII)

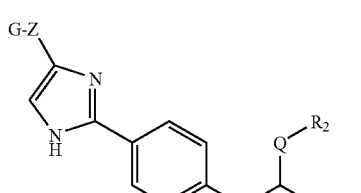
(XLIV)

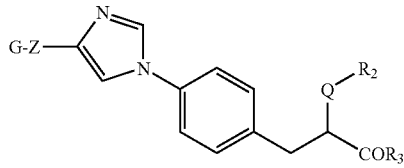
(XLV)

whereby the imidazolyl and the phenyl ring atoms in formulas (XLII) to (XLV) are each and independently substituted with 0, 1 or 2 R₅,
whereby R₅ is preferably defined as in the sixth embodiment of the first aspect.

In a tenth embodiment of the second aspect which is also an embodiment of the ninth embodiment of the second aspect the compound is
having one of formulas (XLVI) to (XLIX)

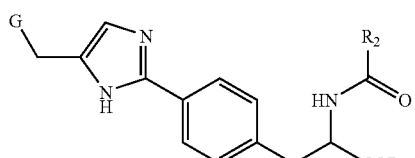
(XLVI)

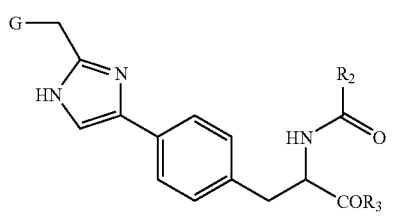
(XLVII)

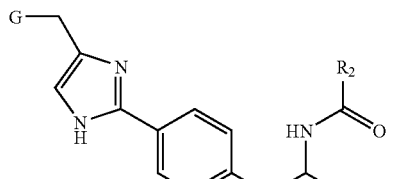
(XLVIII)

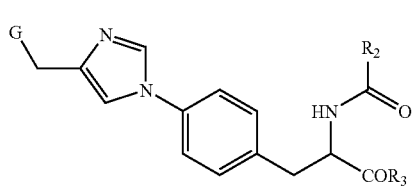
(XLIX)

wherein
- any NH-moiety of the imidazolyl rings in formulas (XLI) to (XLVIII) is optionally substituted with methyl;
- R₂ is a radical selected from the groups defined in the twenty-fifth, twenty-seventh, twenty-eighth or thirtieth embodiment of the first aspect, preferable the twenty-fifth embodiment of the first aspect; and
- G is a radical selected from the group comprising 1H-imidazol-2-ylamino, 4,5-dihydro-1H-imidazol-2-ylamino, 1,4,5,6-tetrahydro-pyrimidin-2-ylamino, 4,5-dihydro-3H-pyrrol-2-ylamino, 3,4,5,6-tetrahydro-pyridin-2-ylamino, 1H-benzoimidazol-2-ylamino, 5,6-dihydro-3H-pyrimidin-4-one-2-ylamino, 3,5-dihydroimidazol-4-one-2-ylamino, 4-methylpyridin-2-ylamino, 5-methylpyridin-2-ylamino, 4-methoxypyridin-2-ylamino, and 4-fluoropyridin-2-ylamino.

In an eleventh embodiment of the second aspect which is also an embodiment of the second embodiment of the second aspect the compound is A is thienyl and the compound is represented by formulas (L) to (LII)

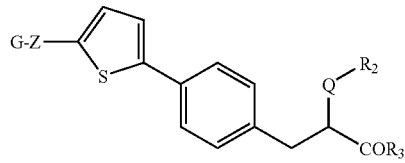
(L)

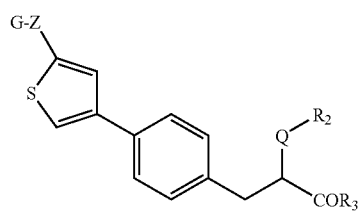
(LI)

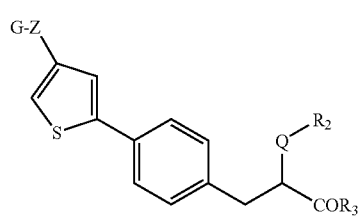
(LII)

whereby the thienyl and the phenyl ring atoms in formulas (L) to (LII) are each and independently substituted with 0, 1 or 2 $R_5$, whereby $R_5$ is defined as in the sixth embodiment of the first aspect.

In a twelfth embodiment of the second aspect which is also an embodiment of the eleventh embodiment of the second aspect the compound is having one of formulas (LIII) to (LV)

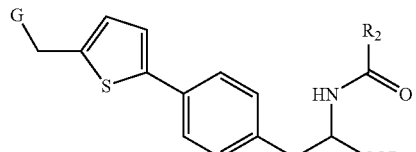
(LIII)

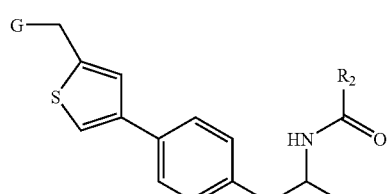
(LIV)

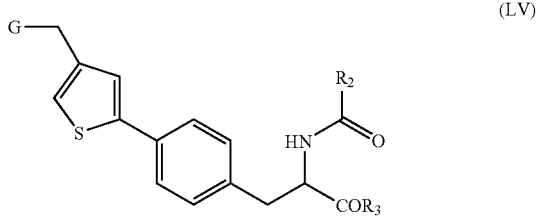
(LV)

wherein $R_2$ is a radical selected from the groups defined in the twenty-fifth, twenty-seventh, twenty-eighth or thirtieth embodiment of the first aspect, preferable the twenty-fifth embodiment of the first aspect; and G is a radical selected from the group comprising 1H-imidazol-2-ylamino, 4,5-dihydro-1H-imidazol-2-ylamino, 1,4,5,6-tetrahydro-pyrimidin-2-ylamino, 4,5-dihydro-3H-pyrrol-2-ylamino, 3,4,5,6-tetrahydro-pyridin-2-ylamino, 1H-benzoimidazol-2-ylamino, 5,6-dihydro-3H-pyrimidin-4-one-2-ylamino, 3,5-dihydroimidazol-4-one-2-ylamino, 4-methylpyridin-2-ylamino, 5-methylpyridin-2-ylamino, 4-methoxypyridin-2-ylamino, and 4-fluoropyridin-2-ylamino.

In a thirteenth embodiment of the second aspect which is also an embodiment of the second embodiment of the second aspect A is isoxazolyl and the compound is represented by formulas (LVI) to (LVII)

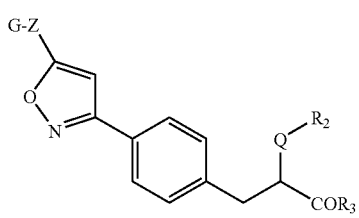
(LVI)

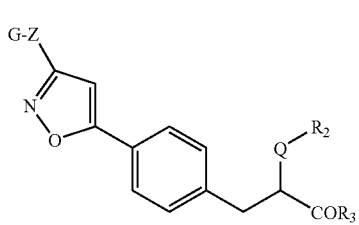
(LVII)

whereby the isoxazolyl and the phenyl rings in formulas (LVI) to (LVII) are each and independently substituted with 0, 1 or 2 $R_5$, whereby $R_5$ is defined as in the sixth embodiment of the first aspect.

In a fourteenth embodiment of the second aspect which is also an embodiment of the thirteenth embodiment of the second aspect the compound is having one of formulas (LVIII) to (LIX)

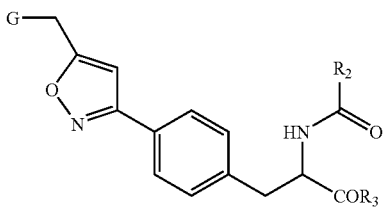
(LVIII)

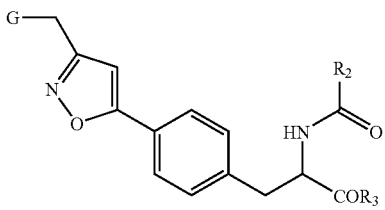
(LIX)

wherein
R$_2$ is a radical selected from the groups defined in the twenty-fifth, twenty-seventh, twenty-eighth or thirtieth embodiment of the first aspect, preferable the twenty-fifth embodiment of the first aspect; and
G is a radical selected from the group comprising 1H-imidazol-2-ylamino, 4,5-dihydro-1H-imidazol-2-ylamino, 1,4,5,6-tetrahydro-pyrimidin-2-ylamino, 4,5-dihydro-3H-pyrrol-2-ylamino, 3,4,5,6-tetrahydro-pyridin-2-ylamino, 1H-benzoimidazol-2-ylamino, 5,6-dihydro-3H-pyrimidin-4-one-2-ylamino, 3,5-dihydroimidazol-4-one-2-ylamino, 4-methylpyridin-2-ylamino, 5-methylpyridin-2-ylamino, 4-methoxypyridin-2-ylamino, and 4-fluoropyridin-2-ylamino.

In a fifteenth embodiment of the second aspect which is also an embodiment of the second embodiment of the second aspect
A is oxazolyl and the compound is represented by formulas (LX) to (LXIII)

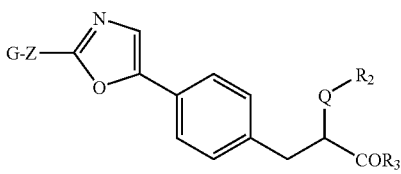
(LX)

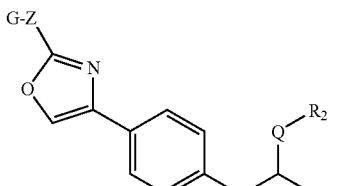
(LXI)

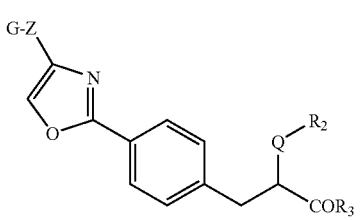
(LXII)

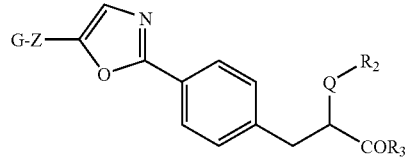
(LXIII)

whereby the oxazolyl and the phenyl ring atoms in formulas (LX) to (LXIII) are each and independently substituted with 0, 1 or 2 R$_5$,
whereby R$_5$ is defined as in the sixth embodiment of the first aspect.

In a sixteenth embodiment of the second aspect which is also an embodiment of the fifteenth embodiment of the second aspect the compound is
having one of formulas (LXIV) to (LXVII)

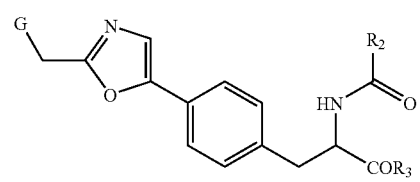
(LXIV)

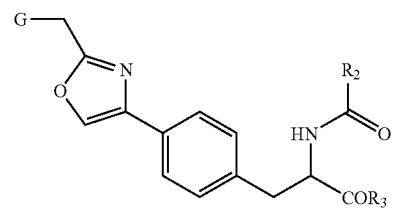
(LXV)

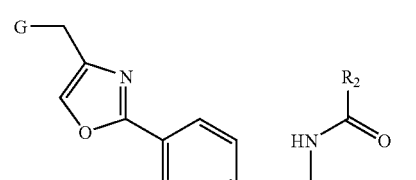
(LXVI)

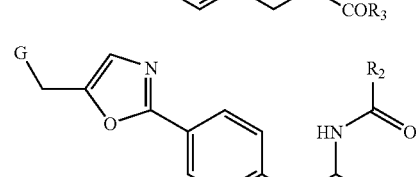
(LXVII)

wherein
R$_2$ is a radical selected from the groups defined in the twenty-fifth, twenty-seventh, twenty-eighth or thirtieth embodiment of the first aspect, preferable the twenty-fifth embodiment of the first aspect; and
G is a radical selected from the group comprising 1H-imidazol-2-ylamino, 4,5-dihydro-1H-imidazol-2-ylamino, 1,4,5,6-tetrahydro-pyrimidin-2-ylamino, 4,5-dihydro-3H-pyrrol-2-ylamino, 3,4,5,6-tetrahydro-pyridin-2-ylamino, 1H-benzoimidazol-2-ylamino, 5,6-dihydro-3H-pyrimidin-4-one-2-ylamino, 3,5-dihydroimidazol-4-one-2-ylamino, 4-methylpyridin-2-ylamino, 5-methylpyridin-2-ylamino, 4-methoxypyridin-2-ylamino, and 4-fluoropyridin-2-ylamino.

In a seventeenth embodiment of the second aspect which is also an embodiment of the second embodiment of the second aspect A is thiazolyl and the compound is represented by formulas (LXVIII) to (LXXI)

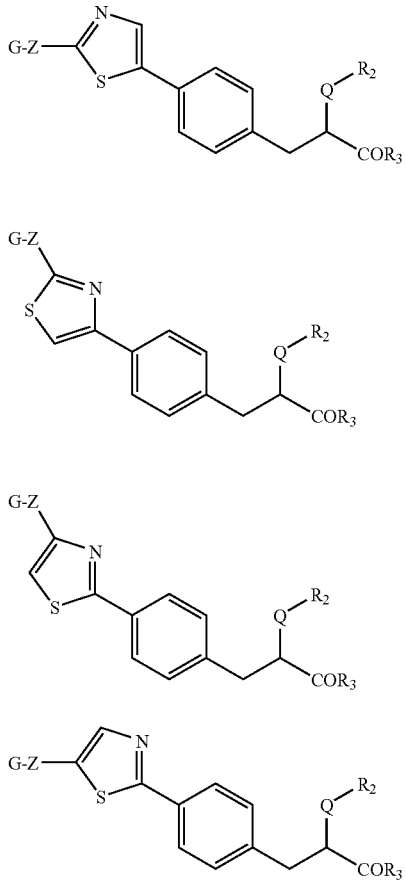

whereby the thiazolyl and the phenyl ring atoms in formulas (LXVIII) to (LXXI) are each and independently substituted with 0, 1 or 2 $R_5$, whereby $R_5$ is defined as in the sixth embodiment of the first aspect; and G is a radical as defined in the twelfth to fifteenth embodiment of the first aspect.

In an eighteenth embodiment of the second aspect which is also an embodiment of the seventeenth embodiment of the second aspect the compound has one of formulas (LXXII) to (LXXV)

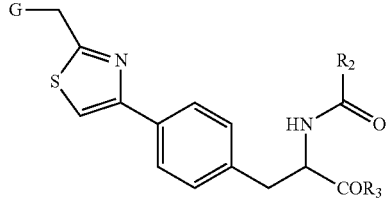

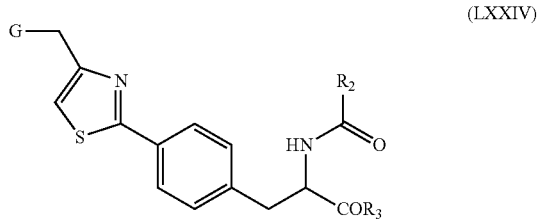

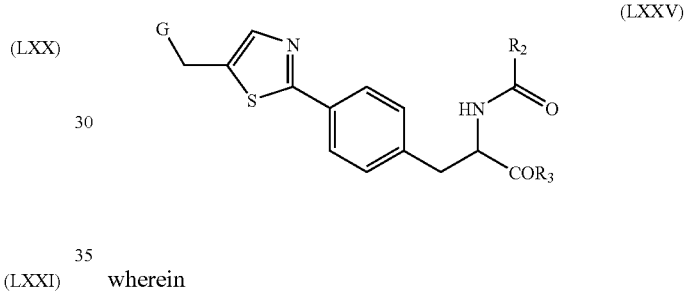

wherein $R_2$ is a radical selected from the groups defined in the twenty-fifth, twenty-seventh, twenty-eighth or thirtieth embodiment of the first aspect, preferable the twenty-fifth embodiment of the first aspect; and G is a radical selected from the group comprising 1H-imidazol-2-ylamino, 4,5-dihydro-1H-imidazol-2-ylamino, 1,4,5,6-tetrahydro-pyrimidin-2-ylamino, 4,5-dihydro-3H-pyrrol-2-ylamino, 3,4,5,6-tetrahydro-pyridin-2-ylamino, 1H-benzoimidazol-2-ylamino, 5,6-dihydro-3H-pyrimidin-4-one-2-ylamino, 3,5-dihydroimidazol-4-one-2-ylamino, 4-methylpyridin-2-ylamino, 5-methylpyridin-2-ylamino, 4-methoxypyridin-2-ylamino, and 4-fluoropyridin-2-ylamino.

In a nineteenth embodiment of the second aspect which is also an embodiment of the second embodiment of the second aspect A is thiadiazoyl and the compound is represented by formulas (LXXVI) to (LXXVIII),

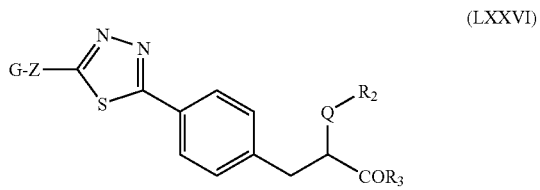

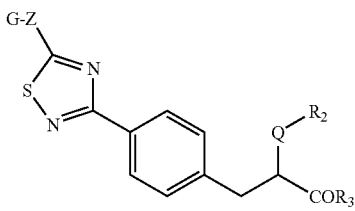
(LXXVII)

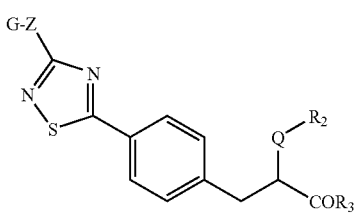
(LXXVIII)

whereby the thiadiazolyl and the phenyl ring atoms in formulas (LXXVI) to (LXXVIII) are each and independently substituted with 0, 1 or 2 $R_5$,
whereby $R_5$ is defined as in the sixth embodiment of the first aspect.

In a twentieth embodiment of the second aspect which is also an embodiment of the nineteenth embodiment of the second aspect the compound has one of formulas (LXXIX) to (LXXXI)

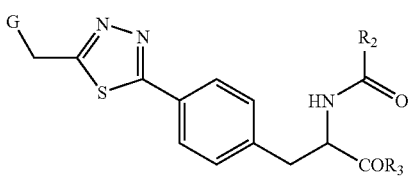
(LXXIX)

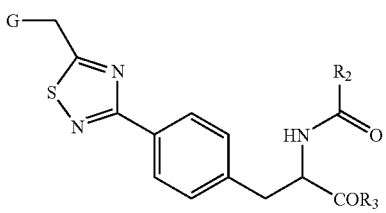
(LXXX)

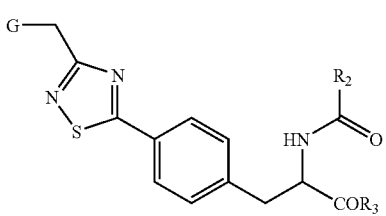
(LXXXI)

wherein
$R_2$ is a radical selected from the groups defined in the twenty-fifth, twenty-seventh, twenty-eighth or thirtieth embodiment of the first aspect, preferable the twenty-fifth embodiment of the first aspect; and
G is a radical selected from the group comprising 1H-imidazol-2-ylamino, 4,5-dihydro-1H-imidazol-2-ylamino, 1,4,5,6-tetrahydro-pyrimidin-2-ylamino, 4,5-dihydro-3H-pyrrol-2-ylamino, 3,4,5,6-tetrahydro-pyridin-2-ylamino, 1H-benzoimidazol-2-ylamino, 5,6-dihydro-3H-pyrimidin-4-one-2-ylamino, 3,5-dihydroimidazol-4-one-2-ylamino, 4-methylpyridin-2-ylamino, 5-methylpyridin-2-ylamino, 4-methoxypyridin-2-ylamino, and 4-fluoropyridin-2-ylamino.

In a twenty-first embodiment of the second aspect which is also an embodiment of the second embodiment of the second aspect
A is oxadiazolyl and the compound is represented by formula (LXXXII)

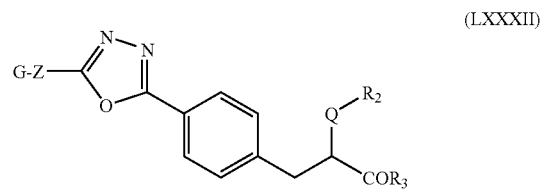
(LXXXII)

whereby the oxadiazolyl and the phenyl ring atoms in formula (LXXXII) are each and independently substituted with 0, 1 or 2 $R_5$,
whereby $R_5$ is defined as in the sixth embodiment of the first aspect.

In a twenty-second embodiment of the second aspect which is also an embodiment of the twenty-first embodiment of the second aspect the compound
has formula (LXXXIII)

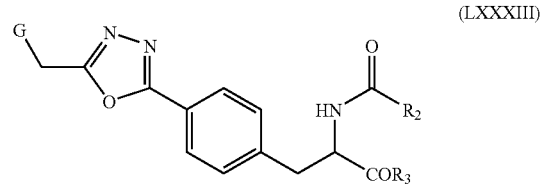
(LXXXIII)

wherein
$R_2$ is a radical selected from the groups defined in the twenty-fifth, twenty-seventh, twenty-eighth or thirtieth embodiment of the first aspect, preferable the twenty-fifth embodiment of the first aspect; and
G is a radical selected from the group comprising 1H-imidazol-2-ylamino, 4,5-dihydro-1H-imidazol-2-ylamino, 1,4,5,6-tetrahydro-pyrimidin-2-ylamino, 4,5-dihydro-3H-pyrrol-2-ylamino, 3,4,5,6-tetrahydro-pyridin-2-ylamino, 1H-benzoimidazol-2-ylamino, 5,6-dihydro-3H-pyrimidin-4-one-2-ylamino, 3,5-dihydroimidazol-4-one-2-ylamino, 4-methylpyridin-2-ylamino, 5-methylpyridin-2-ylamino, 4-methoxypyridin-2-ylamino, and 4-fluoropyridin-2-ylamino.

In a twenty-third embodiment of the second aspect which is also an embodiment of the second embodiment of the second aspect A is isothiazolyl and the compound is represented by formulas (LXXXIV) to (LXXXV)

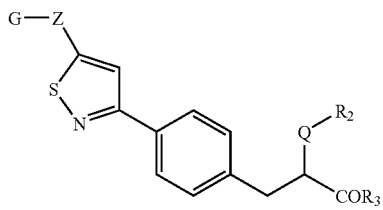
(LXXXIV)

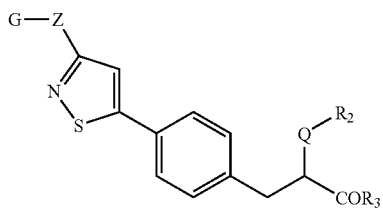
(LXXXV)

whereby
the isothiazolyl and the phenyl ring atoms in formulas (LXXXIV) to (LXXXV) are each and independently substituted with 0, 1 or 2 $R_5$,
whereby $R_5$ is defined as in the sixth embodiment of the first aspect.

In a twenty-fourth embodiment of the second aspect which is also an embodiment of the twenty-third embodiment of the second aspect the compound
has one of formulas (LXXXVI) to (LXXXVII)

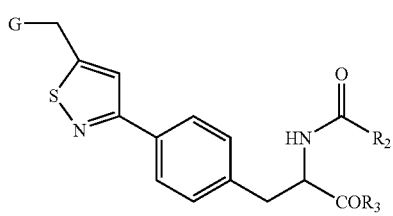
(LXXXVI)

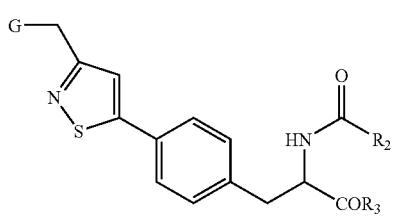
(LXXXVII)

wherein
$R_2$ is a radical selected from the groups defined in the twenty-fifth, twenty-seventh, twenty-eighth or thirtieth embodiment of the first aspect, preferable the twenty-fifth embodiment of the first aspect; and
G is a radical selected from the group comprising 1H-imidazol-2-ylamino, 4,5-dihydro-1H-imidazol-2-ylamino, 1,4,5,6-tetrahydro-pyrimidin-2-ylamino, 4,5-dihydro-3H-pyrrol-2-ylamino, 3,4,5,6-tetrahydro-pyridin-2-ylamino, 1H-benzoimidazol-2-ylamino, 5,6-dihydro-3H-pyrimidin-4-one-2-ylamino, 3,5-dihydroimidazol-4-one-2-ylamino, 4-methylpyridin-2-ylamino, 5-methylpyridin-2-ylamino, 4-methoxypyridin-2-ylamino, and 4-fluoropyridin-2-ylamino.

In a twenty-fifth embodiment of the second aspect which is also an embodiment of the second embodiment of the second aspect
A is trialzolyl and the compound is represented by formulas (LXXXVIII) to (XC)

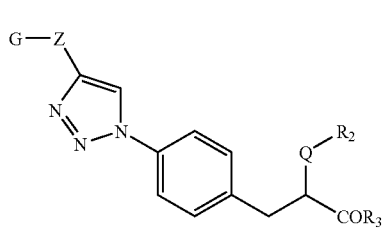
(LXXXVIII)

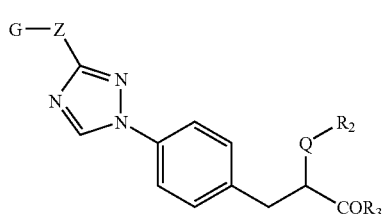
(LXXXIX)

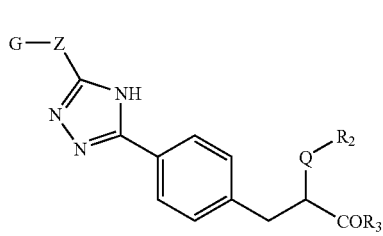
(XC)

whereby the triazolyl and the phenyl ring atoms in formulas (LXXXVIII) to (XC) are each and independently substituted with 0, 1 or 2 $R_5$,
whereby $R_5$ is defined as in the sixth embodiment of the first aspect.

In a twenty-sixth embodiment of the second aspect which is also an embodiment of the twenty-fifth embodiment of the second aspect the compound
has one of formulas (XCI) to (XCIII)

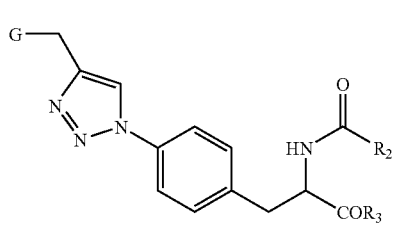
(XCI)

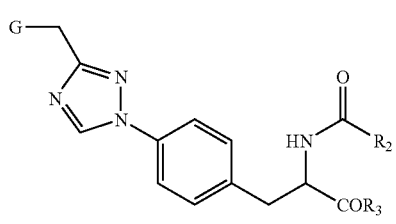
(XCII)

-continued

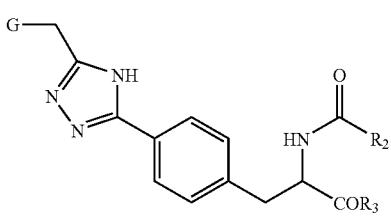

(XCIII)

wherein
R₂ is a radical selected from the groups defined in the twenty-fifth, twenty-seventh, twenty-eighth or thirtieth embodiment of the first aspect, preferable the twenty-fifth embodiment of the first aspect; and
G is a radical selected from the group comprising 1H-imidazol-2-ylamino, 4,5-dihydro-1H-imidazol-2-ylamino, 1,4,5,6-tetrahydro-pyrimidin-2-ylamino, 4,5-dihydro-3H-pyrrol-2-ylamino, 3,4,5,6-tetrahydro-pyridin-2-ylamino, 1H-benzoimidazol-2-ylamino, 5,6-dihydro-3H-pyrimidin-4-one-2-ylamino, 3,5-dihydroimidazol-4-one-2-ylamino, 4-methylpyridin-2-ylamino, 5-methylpyridin-2-ylamino, 4-methoxypyridin-2-ylamino, and 4-fluoropyridin-2-ylamino.

In a twenty-seventh embodiment of the second aspect which is also an embodiment of the third, fifth, seventh, ninth, eleventh, thirteenth, fifteenth, seventeenth, nineteenth, twenty-first, twenty-third or twenty-fifth embodiment of the second aspect
R₂ is a radical selected from the groups defined in the thirty-second to thirty-fifth embodiment of the first aspect, preferable the thirty-third or thirty-fifth embodiment of the first aspect;
Q is a direct bond;
G is a radical selected from the group comprising 1H-imidazol-2-ylamino, 4,5-dihydro-1H-imidazol-2-ylamino, 1,4,5,6-tetrahydro-pyrimidin-2-ylamino, 4,5-dihydro-3H-pyrrol-2-ylamino, 3,4,5,6-tetrahydro-pyridin-2-ylamino, 1H-benzoimidazol-2-ylamino, 5,6-dihydro-3H-pyrimidin-4-one-2-ylamino, 3,5-dihydroimidazol-4-one-2-ylamino, 4-methylpyridin-2-ylamino, 5-methylpyridin-2-ylamino, 4-methoxypyridin-2-ylamino, 4-fluoropyridin-2-ylamino, guanidino, amidino, aminobenzylideneamino, aminoethylideneamino;
R₅ is H; and
Z is a radical selected from the group comprising CH₂ and CO.

In a twenty-eighth embodiment of the second aspect which is also an embodiment of all preceeding embodiments of the first and the second aspect
selected form the group consisting of
compound (6) 3-(4-{3-[(4-Methyl-pyridin-2-ylamino)-methyl]-isoxazol-5-yl}-phenyl)-2-(2,4,6-trimethyl-benzoylamino)-propionic acid
compound (9) 3-(4-{5-[(4-Methyl-pyridin-2-ylamino)-methyl]-thiazol-2-yl}-phenyl)-2-(2,4,6-trimethyl-benzoylamino)-propionic acid
compound (12) 3-(4-{4-[(4-Methyl-pyridin-2-ylamino)-methyl]-furan-2-yl}-phenyl)-2-(2,4,6-trimethyl-benzoylamino)-propionic acid
compound (15) 3-(4-{4-[(4-Methyl-pyridin-2-ylamino)-methyl]-[1,2,3]triazol-1-yl}-phenyl)-2-(2,4,6-trimethyl-benzoylamino)-propionic acid
compound (19) 3-(4-{4-[(4-Methyl-pyridin-2-ylamino)-methyl]-thiophen-2-yl}-phenyl)-2-(2,4,6-trimethyl-benzoylamino)-propionic acid
compound (22) 2-[(1-Methyl-cyclohexanecarbonyl)-amino]-3-(4-{3-[(4-methyl-pyridin-2-ylamino)-methyl]-pyrrol-1-yl}-phenyl)-propionic acid
compound (23) 2-[(1-Methyl-cyclohexanecarbonyl)-amino]-3-(4-{5-[(4-methyl-pyridin-2-ylamino)-methyl]-thiazol-2-yl}-phenyl)-propionic acid
compound (24) 3-(4-{4-[(4-Methoxy-pyridin-2-ylamino)-methyl]-[1,2,3]triazol-1-yl}-phenyl)-2-(2,4,6-trimethyl-benzoylamino)-propionic acid
compound (25) 3-{4-[4-(Thiazol-2-ylaminomethyl)-[1,2,3]triazol-1-yl]-phenyl}-2-(2,4,6-trimethyl-benzoylamino)-propionic acid
compound (26) 3-{4-[4-(Isoxazol-3-ylaminomethyl)-[1,2,3]triazol-1-yl]-phenyl}-2-(2,4,6-trimethyl-benzoylamino)-propionic acid
compound (27) 3-(4-{4-[(5-Methyl-thiazol-2-ylamino)-methyl]-[1,2,3]triazol-1-yl}-phenyl)-2-(2,4,6-trimethyl-benzoylamino)-propionic
compound (28) 3-{4-[4-(Benzothiazol-2-ylaminomethyl)-[1,2,3]triazol-1-yl]-phenyl}-2-(2,4,6-trimethyl-benzoylamino)-propionic
compound (29) 3-(4-{4-[(1H-Benzoimidazol-2-ylamino)-methyl]-[1,2,3]triazol-1-yl}-phenyl)-2-(2,4,6-trimethyl-benzoylamino)-propionic
compound (30) 2-(2,6-Dimethyl-benzoylamino)-3-(4-{4-[(4-methyl-pyridin-2-ylamino)-methyl]-[1,2,3]triazol-1-yl}-phenyl)-propionic acid
compound (31) 2-(2-Ethyl-6-methyl-benzoylamino)-3-(4-{4-[(4-methyl-pyridin-2-ylamino)-methyl]-[1,2,3]triazol-1-yl}-phenyl)-propionic acid
compound (32) 2-(4-Fluoro-2,6-dimethyl-benzoylamino)-3-(4-{4-[(4-methyl-pyridin-2-ylamino)-methyl]-[1,2,3]triazol-1-yl}-phenyl)-propionic acid
compound (33) 3-(4-{4-[(4-Methyl-pyridin-2-ylamino)-methyl]-thiophen-2-yl}-phenyl)-2-(2,4,6-trimethyl-benzoylamino)-propionic acid
compound (34) 3-(4-{4-[(4-Fluoro-pyridin-2-ylamino)-methyl]-furan-2-yl}-phenyl)-2-(2,4,6-trimethyl-benzoylamino)-propionic acid
compound (35) 2-(2,6-Dimethyl-benzoylamino)-3-(4-{4-[(4-methyl-pyridin-2-ylamino)-methyl]-furan-2-yl}-phenyl)-propionic acid
compound (36) 2-(2-Ethyl-6-methyl-benzoylamino)-3-(4-{4-[(4-methyl-pyridin-2-ylamino)-methyl]-furan-2-yl}-phenyl)-propionic acid
compound (37) 2-(4-Fluoro-2,6-dimethyl-benzoylamino)-3-(4-{4-[(4-methyl-pyridin-2-ylamino)-methyl]-furan-2-yl}-phenyl)-propionic acid
compound (38) 2-(2-Ethyl-4-fluoro-6-methyl-benzoylamino)-3-(4-{4-[(4-methyl-pyridin-2-ylamino)-methyl]-furan-2-yl}-phenyl)-propionic acid
compound (39) 3-(4-{4-[(5-Methyl-pyridin-2-ylamino)-methyl]-furan-2-yl}-phenyl)-2-(2,4,6-trimethyl-benzoylamino)-propionic acid
compound (40) 3-(4-{4-[(5-Trifluoromethyl-pyridin-2-ylamino)-methyl]-furan-2-yl}-phenyl)-2-(2,4,6-trimethyl-benzoylamino)-propionic acid
compound (41) 3-(4-{4-[(5-Chloro-pyridin-2-ylamino)-methyl]-furan-2-yl}-phenyl)-2-(2,4,6-trimethyl-benzoylamino)-propionic acid
compound (42) 3-(4-{4-[(3-Methyl-pyridin-2-ylamino)-methyl]-furan-2-yl}-phenyl)-2-(2,4,6-trimethyl-benzoylamino)-propionic acid
compound (43) 2-(2-Ethyl-4-fluoro-6-methyl-benzoylamino)-3-(4-{5-[(4-methyl-pyridin-2-ylamino)-methyl]-furan-2-yl}-phenyl)-propionic acid compound (44) 2-(2-Ethyl-4-fluoro-6-methyl-benzoylamino)-3-(4-{5-[(5-oxo-4,5-dihydro-1H-pyrazol-3-ylamino)-methyl]-furan-2-yl}-phenyl)-propionic acid compound (45) 3-(4-{5-[(1H-Benzoimidazol-2-ylamino)-methyl]-furan-2-yl}-phenyl)-2-(2-ethyl-4-fluoro-6-methyl-benzoylamino)-propionic acid compound (46) [2-(4-{4-[(4-Methyl-pyridin-2-ylamino)-methyl]-furan-2-yl}-benzyl)-4-(2,4,6-trimethyl-phenyl)-butyric acid compound (47) 3-(4-(5-((1H-imidazol-2-ylamino)methyl)furan-2-yl)phenyl)-2-(2,4,6-trimethylbenzamido)propanoic acid compound (48) 3-(4-(5-((1H-benzo[d]imidazol-2-ylamino)methyl)furan-2-yl)phenyl)-2-(2,4,6-trimethylbenzamido)propanoic acid compound (49) 3-(4-(5-((4-methylpyridin-2-ylamino)methyl)furan-2-yl)phenyl)-2-(2,4,6-trimethylbenzamido)propanoic acid compound (50) 3-(4-(5-((4-methoxypyridin-2-ylamino)methyl)furan-2-yl)phenyl)-2-(2,4,6-trimethylbenzamido)propanoic acid compound (51) 3-(4-(5-((1H-imidazol-2-ylamino)methyl)furan-2-yl)phenyl)-2-(2-ethyl-4-fluoro-6-methylbenzamido)propanoic acid compound (52) 3-(4-(5-((1H-benzo[d]imidazol-2-ylamino)methyl)furan-2-yl)phenyl)-2-(2-ethyl-4-fluoro-6-methylbenzamido)propanoic acid compound (53) 2-(2-ethyl-4-fluoro-6-methylbenzamido)-3-(4-(5-((4-methoxypyridin-2-ylamino)methyl)furan-2-yl)phenyl)propanoic acid compound (54) 3-(4-(5-((1H-imidazol-2-ylamino)methyl)furan-3-yl)phenyl)-2-(2,4,6-trimethylbenzamido)propanoic acid compound (55) 3-(4-(5-((1H-benzo[d]imidazol-2-ylamino)methyl)furan-3-yl)phenyl)-2-(2,4,6-trimethylbenzamido)propanoic acid compound (56) 3-(4-(5-((4-methylpyridin-2-ylamino)methyl)furan-3-yl)phenyl)-2-(2,4,6-trimethylbenzamido)propanoic acid compound (57) 3-(4-(5-((4-methoxypyridin-2-ylamino)methyl)furan-3-yl)phenyl)-2-(2,4,6-trimethylbenzamido)propanoic acid compound (58) 3-(4-(5-((1H-imidazol-2-ylamino)methyl)furan-3-yl)phenyl)-2-(2-ethyl-4-fluoro-6-methylbenzamido)propanoic acid compound (59) 3-(4-(5-((1H-benzo[d]imidazol-2-ylamino)methyl)furan-3-yl)phenyl)-2-(2-ethyl-4-fluoro-6-methylbenzamido)propanoic acid compound (60) 2-(2-ethyl-4-fluoro-6-methylbenzamido)-3-(4-(5-((4-methylpyridin-2-ylamino)methyl)furan-3-yl)phenyl)propanoic acid compound (61) 2-(2-ethyl-4-fluoro-6-methylbenzamido)-3-(4-(5-((4-methoxypyridin-2-ylamino)methyl)furan-3-yl)phenyl)propanoic acid compound (62) 3-(4-(4-((1H-imidazol-2-ylamino)methyl)furan-2-yl)phenyl)-2-(2,4,6-trimethylbenzamido)propanoic acid compound (63) 3-(4-(4-((1H-benzo[d]imidazol-2-ylamino)methyl)furan-2-yl)phenyl)-2-(2,4,6-trimethylbenzamido)propanoic acid compound (64) 3-(4-(4-((4-methoxypyridin-2-ylamino)methyl)furan-2-yl)phenyl)-2-(2,4,6-trimethylbenzamido)propanoic acid compound (65) 3-(4-(4-((1H-imidazol-2-ylamino)methyl)furan-2-yl)phenyl)-2-(2-ethyl-4-fluoro-6-methylbenzamido)propanoic acid compound (66) 2-(2-ethyl-4-fluoro-6-methylbenzamido)-3-(4-(4-((4-methoxypyridin-2-ylamino)methyl)furan-2-yl)phenyl)propanoic acid compound (67) 3-(4-(5-((1H-imidazol-2-ylamino)methyl)-1H-pyrrol-2-yl)phenyl)-2-(2,4,6-trimethylbenzamido)propanoic acid compound (68) 3-(4-(5-((1H-benzo[d]imidazol-2-ylamino)methyl)-1H-pyrrol-2-yl)phenyl)-2-(2,4,6-trimethylbenzamido)propanoic acid compound (69) 3-(4-(5-((4-methylpyridin-2-ylamino)methyl)-1H-pyrrol-2-yl)phenyl)-2-(2,4,6-trimethylbenzamido)propanoic acid compound (70) 3-(4-(5-((4-methoxypyridin-2-ylamino)methyl)-1H-pyrrol-2-yl)phenyl)-2-(2,4,6-trimethylbenzamido)propanoic acid compound (71) 3-(4-(5-((1H-imidazol-2-ylamino)methyl)-1H-pyrrol-2-yl)phenyl)-2-(2-ethyl-4-fluoro-6-methylbenzamido)propanoic acid compound (72) 3-(4-(5-((1H-benzo[d]imidazol-2-ylamino)methyl)-1H-pyrrol-2-yl)phenyl)-2-(2-ethyl-4-fluoro-6-methylbenzamido)propanoic acid compound (73) 2-(2-ethyl-4-fluoro-6-methylbenzamido)-3-(4-(5-((4-methylpyridin-2-ylamino)methyl)-1H-pyrrol-2-yl)phenyl)propanoic acid compound (74) 2-(2-ethyl-4-fluoro-6-methylbenzamido)-3-(4-(5-((4-methoxypyridin-2-ylamino)methyl)-1H-pyrrol-2-yl)phenyl)propanoic acid compound (75) 3-(4-(5-((1H-imidazol-2-ylamino)methyl)-1H-pyrrol-3-yl)phenyl)-2-(2,4,6-trimethylbenzamido)propanoic acid compound (76) 3-(4-(5-((1H-benzo[d]imidazol-2-ylamino)methyl)-1H-pyrrol-3-yl)phenyl)-2-(2,4,6-trimethylbenzamido)propanoic acid compound (77) 3-(4-(5-((4-methylpyridin-2-ylamino)methyl)-1H-pyrrol-3-yl)phenyl)-2-(2,4,6-trimethylbenzamido)propanoic acid compound (78) 3-(4-(5-((4-methoxypyridin-2-ylamino)methyl)-1H-pyrrol-3-yl)phenyl)-2-(2,4,6-trimethylbenzamido)propanoic acid compound (79) 3-(4-(5-((1H-imidazol-2-ylamino)methyl)-1H-pyrrol-3-yl)phenyl)-2-(2-ethyl-4-fluoro-6-methylbenzamido)propanoic acid compound (80) 3-(4-(5-((1H-benzo[d]imidazol-2-ylamino)methyl)-1H-pyrrol-3-yl)phenyl)-2-(2-ethyl-4-fluoro-6-methylbenzamido)propanoic acid compound (81) 2-(2-ethyl-4-fluoro-6-methylbenzamido)-3-(4-(5-((4-methylpyridin-2-ylamino)methyl)-1H-pyrrol-3-yl)phenyl)propanoic acid compound (82) 2-(2-ethyl-4-fluoro-6-methylbenzamido)-3-(4-(5-((4-methoxypyridin-2-ylamino)methyl)-1H-pyrrol-3-yl)phenyl)propanoic acid compound (83) 3-(4-(4-((1H-imidazol-2-ylamino)methyl)-1H-pyrrol-2-yl)phenyl)-2-(2,4,6-trimethylbenzamido)propanoic acid compound (84) 3-(4-(4-((1H-benzo[d]imidazol-2-ylamino)methyl)-1H-pyrrol-2-yl)phenyl)-2-(2,4,6-trimethylbenzamido)propanoic acid compound (85) 3-(4-(4-((4-methylpyridin-2-ylamino)methyl)-1H-pyrrol-2-yl)phenyl)-2-(2,4,6-trimethylbenzamido)propanoic acid compound (86) 3-(4-(4-((4-methoxypyridin-2-ylamino)methyl)-1H-pyrrol-2-yl)phenyl)-2-(2,4,6-trimethylbenzamido)propanoic acid compound (87) 3-(4-(4-((1H-imidazol-2-ylamino)methyl)-1H-pyrrol-2-yl)phenyl)-2-(2-ethyl-4-fluoro-6-methylbenzamido)propanoic acid compound (88) 3-(4-(4-((1H-benzo[d]imidazol-2-ylamino)methyl)-1H-pyrrol-2-yl)phenyl)-2-(2-ethyl-4-fluoro-6-methylbenzamido)propanoic acid compound (89) 2-(2-ethyl-4-fluoro-6-methylbenzamido)-3-(4-(4-((4-methylpyridin-2-ylamino)methyl)-1H-pyrrol-2-yl)phenyl)propanoic acid compound (90) 2-(2-ethyl-4-fluoro-6-methylbenzamido)-3-(4-(4-((4-methoxypyridin-2-ylamino)methyl)-1H-pyrrol-2-yl)phenyl)propanoic acid compound (91) 3-(4-(3-((1H-imidazol-2-ylamino)methyl)-1H-pyrrol-1-yl)phenyl)-2-(2,4,6-trimethylbenzamido)propanoic acid compound (92) 3-(4-(3-((1H-benzo[d]imidazol-2-ylamino)methyl)-1H-pyrrol-1-yl)phenyl)-2-(2,4,6-trimethylbenzamido)propanoic acid compound (93) 3-(4-(3-((4-methylpyridin-2-ylamino)methyl)-1H-pyrrol-1-yl)phenyl)-2-(2,4,6-trimethylbenzamido)propanoic acid compound (94) 3-(4-(3-((4-methoxypyridin-2-ylamino)methyl)-1H-pyrrol-1-yl)phenyl)-2-(2,4,6-trimethylbenzamido)propanoic acid compound (95) 3-(4-(3-((1H-imidazol-2-ylamino)methyl)-1H-pyrrol-1-yl)phenyl)-2-(2-ethyl-4-fluoro-6-methylbenzamido)propanoic acid compound (96) 3-(4-(3-((1H-benzo[d]imidazol-2-ylamino)methyl)-1H-pyrrol-1-yl)phenyl)-2-(2-ethyl-4-fluoro-6-methylbenzamido)propanoic acid compound (97) 2-(2-ethyl-4-fluoro-6-methylbenzamido)-3-(4-(3-((4-methylpyridin-2-ylamino)methyl)-1H-pyrrol-1-yl)phenyl)propanoic acid compound (98) 2-(2-ethyl-4-fluoro-6-methylbenzamido)-3-(4-(3-((4-methoxypyridin-2-ylamino)methyl)-1H-pyrrol-1-yl)phenyl)propanoic acid compound (99) 3-(4-(4-((1H-imidazol-2-ylamino)methyl)-1H-pyrazol-1-yl)phenyl)-2-(2,4,6-trimethylbenzamido)propanoic acid compound (100) 3-(4-(4-((1H-benzo[d]imidazol-2-ylamino)methyl)-1H-pyrazol-1-yl)phenyl)-2-(2,4,6-trimethylbenzamido)propanoic acid compound (101) 3-(4-(4-((4-methylpyridin-2-ylamino)methyl)-1H-pyrazol-1-yl)phenyl)-2-(2,4,6-trimethylbenzamido)propanoic acid compound (102) 3-(4-(4-((4-methoxypyridin-2-ylamino)methyl)-1H-pyrazol-1-yl)phenyl)-2-(2,4,6-trimethylbenzamido)propanoic acid compound (103) 3-(4-(4-((1H-imidazol-2-ylamino)methyl)-1H-pyrazol-1-yl)phenyl)-2-(2-ethyl-4-fluoro-6-methylbenzamido)propanoic acid compound (104) 3-(4-(4-((1H-benzo[d]imidazol-2-ylamino)methyl)-1H-pyrazol-1-yl)phenyl)-2-(2-ethyl-4-fluoro-6-methylbenzamido)propanoic acid compound (105) 2-(2-ethyl-4-fluoro-6-methylbenzamido)-3-(4-(4-((4-methylpyridin-2-ylamino)methyl)-1H-pyrazol-1-yl)phenyl)propanoic acid compound (106) 2-(2-ethyl-4-fluoro-6-methylbenzamido)-3-(4-(4-((4-methoxypyridin-2-ylamino)methyl)-1H-pyrazol-1-yl)phenyl)propanoic acid compound (107) 3-(4-(3-((1H-imidazol-2-ylamino)methyl)-1H-pyrazol-1-yl)phenyl)-2-(2,4,6-trimethylbenzamido)propanoic acid compound (108) 3-(4-(3-((1H-benzo[d]imidazol-2-ylamino)methyl)-1H-pyrazol-1-yl)phenyl)-2-(2,4,6-trimethylbenzamido)propanoic acid compound (109) 3-(4-(3-((4-methylpyridin-2-ylamino)methyl)-1H-pyrazol-1-yl)phenyl)-2-(2,4,6-trimethylbenzamido)propanoic acid compound (110) 3-(4-(3-((4-methoxypyridin-2-ylamino)methyl)-1H-pyrazol-1-yl)phenyl)-2-(2,4,6-trimethylbenzamido)propanoic acid compound (111) 3-(4-(3-((1H-imidazol-2-ylamino)methyl)-1H-pyrazol-1-yl)phenyl)-2-(2-ethyl-4-fluoro-6-methylbenzamido)propanoic acid compound (112) 3-(4-(3-((1H-benzo[d]imidazol-2-ylamino)methyl)-1H-pyrazol-1-yl)phenyl)-2-(2-ethyl-4-fluoro-6-methylbenzamido)propanoic acid compound (113) 2-(2-ethyl-4-fluoro-6-methylbenzamido)-3-(4-(3-((4-methylpyridin-2-ylamino)methyl)-1H-pyrazol-1-yl)phenyl)propanoic acid compound (114) 2-(2-ethyl-4-fluoro-6-methylbenzamido)-3-(4-(3-((4-methoxypyridin-2-ylamino)methyl)-1H-pyrazol-1-yl)phenyl)propanoic acid compound (115) 3-(4-(5-((1H-imidazol-2-ylamino)methyl)-1H-imidazol-2-yl)phenyl)-2-(2,4,6-trimethylbenzamido)propanoic acid compound (116) 3-(4-(5-((1H-benzo[d]imidazol-2-ylamino)methyl)-1H-imidazol-2-yl)phenyl)-2-(2,4,6-trimethylbenzamido)propanoic acid compound (117) 3-(4-(5-((4-methylpyridin-2-ylamino)methyl)-1H-imidazol-2-yl)phenyl)-2-(2,4,6-trimethylbenzamido)propanoic acid compound (118) 3-(4-(5-((4-methoxypyridin-2-ylamino)methyl)-1H-imidazol-2-yl)phenyl)-2-(2,4,6-trimethylbenzamido)propanoic acid compound (119) 3-(4-(5-((1H-imidazol-2-ylamino)methyl)-1H-imidazol-2-yl)phenyl)-2-(2-ethyl-4-fluoro-6-methylbenzamido)propanoic acid compound (120) 3-(4-(5-((1H-benzo[d]imidazol-2-ylamino)methyl)-1H-imidazol-2-yl)phenyl)-2-(2-ethyl-4-fluoro-6-methylbenzamido)propanoic acid compound (121) 2-(2-ethyl-4-fluoro-6-methylbenzamido)-3-(4-(5-((4-methylpyridin-2-ylamino)methyl)-1H-imidazol-2-yl)phenyl)propanoic acid compound (122) 2-(2-ethyl-4-fluoro-6-methylbenzamido)-3-(4-(5-((4-methoxypyridin-2-ylamino)methyl)-1H-imidazol-2-yl)phenyl)propanoic acid compound (123) 3-(4-(2-((1H-imidazol-2-ylamino)methyl)-1H-imidazol-4-yl)phenyl)-2-(2,4,6-trimethylbenzamido)propanoic acid compound (124) 3-(4-(2-((1H-benzo[d]imidazol-2-ylamino)methyl)-1H-imidazol-4-yl)phenyl)-2-(2,4,6-trimethylbenzamido)propanoic acid compound (125) 3-(4-(2-((4-methylpyridin-2-ylamino)methyl)-1H-imidazol-4-yl)phenyl)-2-(2,4,6-trimethylbenzamido)propanoic acid compound (126) 3-(4-(2-((4-methoxypyridin-2-ylamino)methyl)-1H-imidazol-4-yl)phenyl)-2-(2,4,6-trimethylbenzamido)propanoic acid compound (127) 3-(4-(2-((1H-imidazol-2-ylamino)methyl)-1H-imidazol-4-yl)phenyl)-2-(2-ethyl-4-fluoro-6-methylbenzamido)propanoic acid compound (128) 3-(4-(2-((1H-benzo[d]imidazol-2-ylamino)methyl)-1H-imidazol-4-yl)phenyl)-2-(2-ethyl-4-fluoro-6-methylbenzamido)propanoic acid compound (129) 2-(2-ethyl-4-fluoro-6-methylbenzamido)-3-(4-(2-((4-methylpyridin-2-ylamino)methyl)-1H-imidazol-4-yl)phenyl)propanoic acid compound (130) 2-(2-ethyl-4-fluoro-6-methylbenzamido)-3-(4-(2-((4-methoxypyridin-2-ylamino)methyl)-1H-imidazol-4-yl)phenyl)propanoic acid compound (131) 3-(4-(4-((1H-imidazol-2-ylamino)methyl)-1H-imidazol-1-yl)phenyl)-2-(2,4,6-trimethylbenzamido)propanoic acid compound (132) 3-(4-(4-((1H-benzo[d]imidazol-2-ylamino)methyl)-1H-imidazol-1-yl)phenyl)-2-(2,4,6-trimethylbenzamido)propanoic acid compound (133) 3-(4-(4-((4-methylpyridin-2-ylamino)methyl)-1H-imidazol-1-yl)phenyl)-2-(2,4,6-trimethylbenzamido)propanoic acid compound (134) 3-(4-(4-((4-methoxypyridin-2-ylamino)methyl)-1H-imidazol-1-yl)phenyl)-2-(2,4,6-trimethylbenzamido)propanoic acid compound (135) 3-(4-(4-((1H-imidazol-2-ylamino)methyl)-1H-imidazol-1-yl)phenyl)-2-(2-ethyl-4-fluoro-6-methylbenzamido)propanoic acid compound (136) 3-(4-(4-((1H-benzo[d]imidazol-2-ylamino)methyl)-1H-imidazol-1-yl)phenyl)-2-(2-ethyl-4-fluoro-6-methylbenzamido)propanoic acid compound (137) 2-(2-ethyl-4-fluoro-6-methylbenzamido)-3-(4-(4-((4-methylpyridin-2-ylamino)methyl)-1H,-imidazol-1-yl)phenyl)propanoic acid compound (138) 2-(2-ethyl-4-fluoro-6-methylbenzamido)-3-(4-(4-((4-methoxypyridin-2-ylamino)methyl)-1H-imidazol-1-yl)phenyl)propanoic acid compound (139) 3-(4-(5-((1H-imidazol-2-ylamino)methyl)thiophen-2-yl)phenyl)-2-(2,4,6-trimethylbenzamido)propanoic acid compound (140) 3-(4-(5-((1H-benzo[d]imidazol-2-ylamino)methyl)thiophen-2-yl)phenyl)-2-(2,4,6-trimethylbenzamido)propanoic acid compound (141) 3-(4-(5-((4-methylpyridin-2-ylamino)methyl)thiophen-2-yl)phenyl)-2-(2,4,6-trimethylbenzamido)propanoic acid compound (142) 3-(4-(5-((4-methoxypyridin-2-ylamino)methyl)thiophen-2-yl)phenyl)-2-(2,4,6-trimethylbenzamido)propanoic acid compound (143) 3-(4-(5-((1H-imidazol-2-ylamino)methyl)thiophen-2-yl)phenyl)-2-(2-ethyl-4-fluoro-6-methylbenzamido)propanoic acid compound (144) 3-(4-(5-((1H-benzo[d]imidazol-2-ylamino)methyl)thiophen-2-yl)phenyl)-2-(2-ethyl-4-fluoro-6-methylbenzamido)propanoic acid compound (145) 2-(2-ethyl-4-fluoro-6-methylbenzamido)-3-(4-(5-((4-methylpyridin-2-ylamino)methyl)thiophen-2-yl)phenyl)propanoic acid compound (146) 2-(2-ethyl-4-fluoro-6-methylbenzamido)-3-(4-(5-((4-methoxypyridin-2-ylamino)methyl)thiophen-2-yl)phenyl)propanoic acid compound (147) 3-(4-(5-((1H-imidazol-2-ylamino)methyl)thiophen-3-yl)phenyl)-2-(2,4,6-trimethylbenzamido)propanoic acid compound (148) 3-(4-(5-((1H-benzo[d]imidazol-2-ylamino)methyl)thiophen-3-yl)phenyl)-2-(2,4,6-trimethylbenzamido)propanoic acid compound (149) 3-(4-(5-((4-methylpyridin-2-ylamino)methyl)thiophen-3-yl)phenyl)-2-(2,4,6-trimethylbenzamido)propanoic acid compound (150) 3-(4-(5-((4-methoxypyridin-2-ylamino)methyl)thiophen-3-yl)phenyl)-2-(2,4,6-trimethylbenzamido)propanoic acid compound (151) 3-(4-(5-((1H-imidazol-2-ylamino)methyl)thiophen-3-yl)phenyl)-2-(2-ethyl-4-fluoro-6-methylbenzamido)propanoic acid compound (152) 3-(4-(5-((1H-benzo[d]imidazol-2-ylamino)methyl)thiophen-3-yl)phenyl)-2-(2-ethyl-4-fluoro-6-methylbenzamido)propanoic acid compound (153) 2-(2-ethyl-4-fluoro-6-methylbenzamido)-3-(4-(5-((4-methylpyridin-2-ylamino)methyl)thiophen-3-yl)phenyl)propanoic acid compound (154) 2-(2-ethyl-4-fluoro-6-methylbenzamido)-3-(4-(5-((4-methoxypyridin-2-ylamino)methyl)thiophen-3-yl)phenyl)propanoic acid compound (155) 3-(4-(4-((1H-imidazol-2-ylamino)methyl)thiophen-2-yl)phenyl)-2-(2,4,6-trimethylbenzamido)propanoic acid compound (156) 3-(4-(4-((1H-benzo[d]imidazol-2-ylamino)methyl)thiophen-2-yl)phenyl)-2-(2,4,6-trimethylbenzamido)propanoic acid compound (157) 3-(4-(4-((4-methoxypyridin-2-ylamino)methyl)thiophen-2-yl)phenyl)-2-(2,4,6-trimethylbenzamido)propanoic acid compound (158) 3-(4-(4-((1H-imidazol-2-ylamino)methyl)thiophen-2-yl)phenyl)-2-(2-ethyl-4-fluoro-6-methylbenzamido)propanoic acid compound (159) 3-(4-(4-((1H-benzo[d]imidazol-2-ylamino)methyl)thiophen-2-yl)phenyl)-2-(2-ethyl-4-fluoro-6-methylbenzamido)propanoic acid compound (160) 2-(2-ethyl-4-fluoro-6-methylbenzamido)-3-(4-(4-((4-methylpyridin-2-ylamino)methyl)thiophen-2-yl)phenyl)propanoic acid compound (161) 2-(2-ethyl-4-fluoro-6-methylbenzamido)-3-(4-(4-((4-methoxypyridin-2-ylamino)methyl)thiophen-2-yl)phenyl)propanoic acid compound (162) 3-(4-(5-((1H-imidazol-2-ylamino)methyl)isoxazol-3-yl)phenyl)-2-(2,4,6-trimethylbenzamido)propanoic acid compound (163) 3-(4-(5-((1H-benzo[d]imidazol-2-ylamino)methyl)isoxazol-3-yl)phenyl)-2-(2,4,6-trimethylbenzamido)propanoic acid compound (164) 3-(4-(5-((4-methylpyridin-2-ylamino)methyl)isoxazol-3-yl)phenyl)-2-(2,4,6-trimethylbenzamido)propanoic acid compound (165) 3-(4-(5-((4-methoxypyridin-2-ylamino)methyl)isoxazol-3-yl)phenyl)-2-(2,4,6-trimethylbenzamido)propanoic acid compound (166) 3-(4-(5-((1H-imidazol-2-ylamino)methyl)isoxazol-3-yl)phenyl)-2-(2-ethyl-4-fluoro-6-methylbenzamido)propanoic acid compound (167) 3-(4-(5-((1H-benzo[d]imidazol-2-ylamino)methyl)isoxazol-3-yl)phenyl)-2-(2-ethyl-4-fluoro-6-methylbenzamido)propanoic acid compound (168) 2-(2-ethyl-4-fluoro-6-methylbenzamido)-3-(4-(5-((4-methylpyridin-2-ylamino)methyl)isoxazol-3-yl)phenyl)propanoic acid compound (169) 2-(2-ethyl-4-fluoro-6-methylbenzamido)-3-(4-(5-((4-methoxypyridin-2-ylamino)methyl)isoxazol-3-yl)phenyl)propanoic acid compound (170) 3-(4-(3-((1H-imidazol-2-ylamino)methyl)isoxazol-5-yl)phenyl)-2-(2,4,6-trimethylbenzamido)propanoic acid compound (171) 3-(4-(3-((1H-benzo[d]imidazol-2-ylamino)methyl)isoxazol-5-yl)phenyl)-2-(2,4,6-trimethylbenzamido)propanoic acid compound (172) 3-(4-(3-((4-methoxypyridin-2-ylamino)methyl)isoxazol-5-yl)phenyl)-2-(2,4,6-trimethylbenzamido)propanoic acid compound (173) 3-(4-(3-((1H-imidazol-2-ylamino)methyl)isoxazol-5-yl)phenyl)-2-(2-ethyl-4-fluoro-6-methylbenzamido)propanoic acid compound (174) 3-(4-(3-((1H-benzo[d]imidazol-2-ylamino)methyl)isoxazol-5-yl)phenyl)-2-(2-ethyl-4-fluoro-6-methylbenzamido)propanoic acid compound (175) 2-(2-ethyl-4-fluoro-6-methylbenzamido)-3-(4-(3-((4-methylpyridin-2-ylamino)methyl)isoxazol-5-yl)phenyl)propanoic acid compound (176) 2-(2-ethyl-4-fluoro-6-methylbenzamido)-3-(4-(3-((4-methoxypyridin-2-ylamino)methyl)isoxazol-5-yl)phenyl)propanoic acid compound (177) 3-(4-(2-((1H-imidazol-2-ylamino)methyl)oxazol-5-yl)phenyl)-2-(2,4,6-trimethylbenzamido)propanoic acid compound (178) 3-(4-(2-((1H-benzo[d]imidazol-2-ylamino)methyl)oxazol-5-yl)phenyl)-2-(2,4,6-trimethylbenzamido)propanoic acid compound (179) 3-(4-(2-((4-methylpyridin-2-ylamino)methyl)oxazol-5-yl)phenyl)-2-(2,4,6-trimethylbenzamido)propanoic acid compound (180) 3-(4-(2-((4-methoxypyridin-2-ylamino)methyl)oxazol-5-yl)phenyl)-2-(2,4,6-trimethylbenzamido)propanoic acid compound (181) 3-(4-(2-((1H-imidazol-2-ylamino)methyl)oxazol-5-yl)phenyl)-2-(2-ethyl-4-fluoro-6-methylbenzamido)propanoic acid compound (182) 3-(4-(2-((1H-benzo[d]imidazol-2-ylamino)methyl)oxazol-5-yl)phenyl)-2-(2-ethyl-4-fluoro-6-methylbenzamido)propanoic acid compound (183) 2-(2-ethyl-4-fluoro-6-methylbenzamido)-3-(4-(2-((4-methylpyridin-2-ylamino)methyl)oxazol-5-yl)phenyl)propanoic acid compound (184) 2-(2-ethyl-4-fluoro-6-methylbenzamido)-3-(4-(2-((4-methoxypyridin-2-ylamino)methyl)oxazol-5-yl)phenyl)propanoic acid compound (185) 3-(4-(2-((1H-imidazol-2-ylamino)methyl)oxazol-4-yl)phenyl)-2-(2,4,6-trimethylbenzamido)propanoic acid compound (186) 3-(4-(2-((1H-benzo[d]imidazol-2-ylamino)methyl)oxazol-4-yl)phenyl)-2-(2,4,6-trimethylbenzamido)propanoic acid compound (187) 3-(4-(2-((4-methylpyridin-2-ylamino)methyl)oxazol-4-yl)phenyl)-2-(2,4,6-trimethylbenzamido)propanoic acid compound (188) 3-(4-(2-((4-methoxypyridin-2-ylamino)methyl)oxazol-4-yl)phenyl)-2-(2,4,6-trimethylbenzamido)propanoic acid compound (189) 3-(4-(2-((1H-imidazol-2-ylamino)methyl)oxazol-4-yl)phenyl)-2-(2-ethyl-4-fluoro-6-methylbenzamido)propanoic acid compound (190) 3-(4-(2-((1H-benzo[d]imidazol-2-ylamino)methyl)oxazol-4-yl)phenyl)-2-(2-ethyl-4-fluoro-6-methylbenzamido)propanoic acid compound (191) 2-(2-ethyl-4-fluoro-6-methylbenzamido)-3-(4-(2-((4-methylpyridin-2-ylamino)methyl)oxazol-4-yl)phenyl)propanoic acid compound (192) 2-(2-ethyl-4-fluoro-6-methylbenzamido)-3-(4-(2-((4-methoxypyridin-2-ylamino)methyl)oxazol-4-yl)phenyl)propanoic acid compound (193) 3-(4-(4-((1H-imidazol-2-ylamino)methyl)oxazol-2-yl)phenyl)-2-(2,4,6-trimethylbenzamido)propanoic acid compound (194) 3-(4-(4-((1H-benzo[d]imidazol-2-ylamino)methyl)oxazol-2-yl)phenyl)-2-(2,4,6-trimethylbenzamido)propanoic acid compound (195) 3-(4-(4-((4-methylpyridin-2-ylamino)methyl)oxazol-2-yl)phenyl)-2-(2,4,6-trimethylbenzamido)propanoic acid compound (196) 3-(4-(4-((4-methoxypyridin-2-ylamino)methyl)oxazol-2-yl)phenyl)-2-(2,4,6-trimethylbenzamido)propanoic acid compound (197) 3-(4-(4-((1H-imidazol-2-ylamino)methyl)oxazol-2-yl)phenyl)-2-(2-ethyl-4-fluoro-6-methylbenzamido)propanoic acid compound (198) 3-(4-(4-((1H-benzo[d]imidazol-2-ylamino)methyl)oxazol-2-yl)phenyl)-2-(2-ethyl-4-fluoro-6-methylbenzamido)propanoic acid compound (199) 2-(2-ethyl-4-fluoro-6-methylbenzamido)-3-(4-(4-((4-methylpyridin-2-ylamino)methyl)oxazol-2-yl)phenyl)propanoic acid compound (200) 2-(2-ethyl-4-fluoro-6-methylbenzamido)-3-(4-(4-((4-methoxypyridin-2-ylamino)methyl)oxazol-2-yl)phenyl)propanoic acid compound (201) 3-(4-(5-((1H-imidazol-2-ylamino)methyl)oxazol-2-yl)phenyl)-2-(2,4,6-trimethylbenzamido)propanoic acid compound (202) 3-(4-(5-((1H-benzo[d]imidazol-2-ylamino)methyl)oxazol-2-yl)phenyl)-2-(2,4,6-trimethylbenzamido)propanoic acid compound (203) 3-(4-(5-((4-methylpyridin-2-ylamino)methyl)oxazol-2-yl)phenyl)-2-(2,4,6-trimethylbenzamido)propanoic acid compound (204) 3-(4-(5-((4-methoxypyridin-2-ylamino)methyl)oxazol-2-yl)phenyl)-2-(2,4,6-trimethylbenzamido)propanoic acid compound (205) 3-(4-(5-((1H-imidazol-2-ylamino)methyl)oxazol-2-yl)phenyl)-2-(2-ethyl-4-fluoro-6-methylbenzamido)propanoic acid compound (206) 3-(4-(5-((1H-benzo[d]imidazol-2-ylamino)methyl)oxazol-2-yl)phenyl)-2-(2-ethyl-4-fluoro-6-methylbenzamido)propanoic acid compound (207) 2-(2-ethyl-4-fluoro-6-methylbenzamido)-3-(4-(5-((4-methylpyridin-2-ylamino)methyl)oxazol-2-yl)phenyl)propanoic acid compound (208) 2-(2-ethyl-4-fluoro-6-methylbenzamido)-3-(4-(5-((4-methoxypyridin-2-ylamino)methyl)oxazol-2-yl)phenyl)propanoic acid compound (209) 3-(4-(2-((1H-imidazol-2-ylamino)methyl)thiazol-5-yl)phenyl)-2-(2,4,6-trimethylbenzamido)propanoic acid compound (210) 3-(4-(2-((1H-benzo[d]imidazol-2-ylamino)methyl)thiazol-5-.  yl)phenyl)-2-(2,4,6-trimethylbenzamido)propanoic acid compound (211) 3-(4-(2-((4-methylpyridin-2-ylamino)methyl)thiazol-5-yl)phenyl)-2-(2,4,6-trimethylbenzamido)propanoic acid compound (212) 3-(4-(2-((4-methoxypyridin-2-ylamino)methyl)thiazol-5-yl)phenyl)-2-(2,4,6-trimethylbenzamido)propanoic acid compound (213) 3-(4-(2-((1H-imidazol-2-ylamino)methyl)thiazol-5-yl)phenyl)-2-(2-ethyl-4-fluoro-6-methylbenzamido)propanoic acid compound (214) 3-(4-(2-((1H-benzo[d]imidazol-2-ylamino)methyl)thiazol-5-yl)phenyl)-2-(2-ethyl-4-fluoro-6-methylbenzamido)propanoic acid compound (215) 2-(2-ethyl-4-fluoro-6-methylbenzamido)-3-(4-(2-((4-methylpyridin-2-ylamino)methyl)thiazol-5-yl)phenyl)propanoic acid compound (216) 2-(2-ethyl-4-fluoro-6-methylbenzamido)-3-(4-(2-((4-methoxypyridin-2-ylamino)methyl)thiazol-5-yl)phenyl)propanoic acid compound (217) 3-(4-(2-((1H-imidazol-2-ylamino)methyl)thiazol-4-yl)phenyl)-2-(2,4,6-trimethylbenzamido)propanoic acid compound (218) 2-(4-chloro-2-ethyl-6-methylbenzamido)-3-(4-(5-((4-methylpyridin-2-ylamino)methyl)furan-2-yl)phenyl)propanoic acid compound (219) 2-(4-chloro-2-ethyl-6-methylbenzamido)-3-(4-(5-((4-methylpyridin-2-ylamino)methyl)furan-3-yl)phenyl)propanoic acid compound (220) 3-(4-(2-((1H-benzo[d]imidazol-2-ylamino)methyl)thiazol-4-yl)phenyl)-2-(2,4,6-trimethylbenzamido)propanoic acid compound (221) 3-(4-(2-((4-methylpyridin-2-ylamino)methyl)thiazol-4-yl)phenyl)-2-(2,4,6-trimethylbenzamido)propanoic acid compound (222) 3-(4-(2-((4-methoxypyridin-2-ylamino)methyl)thiazol-4-yl)phenyl)-2-(2,4,6-trimethylbenzamido)propanoic acid compound (223) 3-(4-(2-((1H-imidazol-2-ylamino)methyl)thiazol-4-yl)phenyl)-2-(2-ethyl-4-fluoro-6-methylbenzamido)propanoic acid compound (224) 3-(4-(2-((1H-benzo[d]imidazol-2-ylamino)methyl)thiazol-4-yl)phenyl)-2-(2-ethyl-4-fluoro-6-methylbenzamido)propanoic acid compound (225) 2-(2-ethyl-4-fluoro-6-methylbenzamido)-3-(4-(2-((4-methylpyridin-2-ylamino)methyl)thiazol-4-yl)phenyl)propanoic acid compound (226) 2-(2-ethyl-4-fluoro-6-methylbenzamido)-3-(4-(2-((4-methoxypyridin-2-ylamino)methyl)thiazol-4-yl)phenyl)propanoic acid compound (227) 3-(4-(4-((1H-imidazol-2-ylamino)methyl)thiazol-2-yl)phenyl)-2-(2,4,6-trimethylbenzamido)propanoic acid compound (228) 3-(4-(4-((1H-benzo[d]imidazol-2-ylamino)methyl)thiazol-2-yl)phenyl)-2-(2,4,6-trimethylbenzamido)propanoic acid compound (229) 3-(4-(4-((4-methylpyridin-2-ylamino)methyl)thiazol-2-yl)phenyl)-2-(2,4,6-trimethylbenzamido)propanoic acid compound (230) 3-(4-(4-((4-methoxypyridin-2-ylamino)methyl)thiazol-2-yl)phenyl)-2-(2,4,6-trimethylbenzamido)propanoic acid compound (231) 3-(4-(4-((1H-imidazol-2-ylamino)methyl)thiazol-2-yl)phenyl)-2-(2-ethyl-4-fluoro-6-methylbenzamido)propanoic acid compound (232) 3-(4-(4-((1H-benzo[d]imidazol-2-ylamino)methyl)thiazol-2-yl)phenyl)-2-(2-ethyl-4-fluoro-6-methylbenzamido)propanoic acid compound (233) 2-(2-ethyl-4-fluoro-6-methylbenzamido)-3-(4-(4-((4-methylpyridin-2-ylamino)methyl)thiazol-2-yl)phenyl)propanoic acid compound (234) 2-(2-ethyl-4-fluoro-6-methylbenzamido)-3-(4-(4-((4-methoxypyridin-2-ylamino)methyl)thiazol-2-yl)phenyl)propanoic acid compound (235) 3-(4-(5-((1H-imidazol-2-ylamino)methyl)thiazol-2-yl)phenyl)-2-(2,4,6-trimethylbenzamido)propanoic acid compound (236) 3-(4-(5-((1H-benzo[d]imidazol-2-ylamino)methyl)thiazol-2-yl)phenyl)-2-(2,4,6-trimethylbenzamido)propanoic acid compound (237) 3-(4-(5-((4-methoxypyridin-2-ylamino)methyl)thiazol-2-yl)phenyl)-2-(2,4,6-trimethylbenzamido)propanoic acid compound (238) 3-(4-(5-((1H-imidazol-2-ylamino)methyl)thiazol-2-yl)phenyl)-2-(2-ethyl-4-fluoro-6-methylbenzamido)propanoic acid compound (239) 3-(4-(5-((1H-benzo[d]imidazol-2-ylamino)methyl)thiazol-2-yl)phenyl)-2-(2-ethyl-4-fluoro-6-methylbenzamido)propanoic acid compound (240) 2-(2-ethyl-4-fluoro-6-methylbenzamido)-3-(4-(5-((4-methylpyridin-2-ylamino)methyl)thiazol-2-yl)phenyl)propanoic acid compound (241) 2-(2-ethyl-4-fluoro-6-methylbenzamido)-3-(4-(5-((4-methoxypyridin-2-ylamino)methyl)thiazol-2-yl)phenyl)propanoic acid compound (242) 3-(4-(5-((1H-imidazol-2-ylamino)methyl)-1,3,4-thiadiazol-2-yl)phenyl)-2-(2,4,6-trimethylbenzamido)propanoic acid compound (243) 3-(4-(5-((1H-benzo[d]imidazol-2-ylamino)methyl)-1,3,4-thiadiazol-2-yl)phenyl)-2-(2,4,6-trimethylbenzamido)propanoic acid compound (244) 3-(4-(5-((4-methylpyridin-2-ylamino)methyl)-1,3,4-thiadiazol-2-yl)phenyl)-2-(2,4,6-trimethylbenzamido)propanoic acid compound (245) 3-(4-(5-((4-methoxypyridin-2-ylamino)methyl)-1,3,4-thiadiazol-2-yl)phenyl)-2-(2,4,6-trimethylbenzamido)propanoic acid compound (246) 3-(4-(5-((1H-imidazol-2-ylamino)methyl)-1,3,4-thiadiazol-2-yl)phenyl)-2-(2-ethyl-4-fluoro-6-methylbenzamido)propanoic acid compound (247) 3-(4-(5-((1H-benzo[d]imidazol-2-ylamino)methyl)-1,3,4-thiadiazol-2-yl)phenyl)-2-(2-ethyl-4-fluoro-6-methylbenzamido)propanoic acid compound (248) 2-(2-ethyl-4-fluoro-6-methylbenzamido)-3-(4-(5-((4-methylpyridin-2-ylamino)methyl)-1,3,4-thiadiazol-2-yl)phenyl)propanoic acid compound (249) 2-(2-ethyl-4-fluoro-6-methylbenzamido)-3-(4-(5-((4-methoxypyridin-2-ylamino)methyl)-1,3,4-thiadiazol-2-yl)phenyl)propanoic acid compound (250) 3-(4-(5-((1H-imidazol-2-ylamino)methyl)-1,2,4-thiadiazol-3-yl)phenyl)-2-(2,4,6-trimethylbenzamido)propanoic acid compound (251) 3-(4-(5-((1H-benzo[d]imidazol-2-ylamino)methyl)-1,2,4-thiadiazol-3-yl)phenyl)-2-(2,4,6-trimethylbenzamido)propanoic acid compound (252) 3-(4-(5-((4-methylpyridin-2-ylamino)methyl)-1,2,4-thiadiazol-3-yl)phenyl)-2-(2,4,6-trimethylbenzamido)propanoic acid compound (253) 3-(4-(5-((4-methoxypyridin-2-ylamino)methyl)-1,2,4-thiadiazol-3-yl)phenyl)-2-(2,4,6-trimethylbenzamido)propanoic acid compound (254) 3-(4-(5-((1H-imidazol-2-ylamino)methyl)-1,2,4-thiadiazol-3-yl)phenyl)-2-(2-ethyl-4-fluoro-6-methylbenzamido)propanoic acid compound (255) 3-(4-(5-((1H-benzo[d]imidazol-2-ylamino)methyl)-1,2,4-thiadiazol-3-yl)phenyl)-2-(2-ethyl-4-fluoro-6-methylbenzamido)propanoic acid compound (256) 2-(2-ethyl-4-fluoro-6-methylbenzamido)-3-(4-(5-((4-methylpyridin-2-ylamino)methyl)-1,2,4-thiadiazol-3-yl)phenyl)propanoic acid compound (257) 2-(2-ethyl-4-fluoro-6-methylbenzamido)-3-(4-(5-((4-methoxypyridin-2-ylamino)methyl)-1,2,4-thiadiazol-3-yl)phenyl)propanoic acid compound (258) 3-(4-(3-((1H-imidazol-2-ylamino)methyl)-1,2,4-thiadiazol-5-yl)phenyl)-2-(2,4,6-trimethylbenzamido)propanoic acid compound (259) 3-(4-(3-((1H-benzo[d]imidazol-2-ylamino)methyl)-1,2,4-thiadiazol-5-yl)phenyl)-2-(2,4,6-trimethylbenzamido)propanoic acid compound (260) 3-(4-(3-((4-methylpyridin-2-ylamino)methyl)-1,2,4-thiadiazol-5-yl)phenyl)-2-(2,4,6-trimethylbenzamido)propanoic acid compound (261) 3-(4-(3-((4-methoxypyridin-2-ylamino)methyl)-1,2,4-thiadiazol-5-yl)phenyl)-2-(2,4,6-trimethylbenzamido)propanoic acid compound (262) 3-(4-(3-((1H-imidazol-2-ylamino)methyl)-1,2,4-thiadiazol-5-yl)phenyl)-2-(2-ethyl-4-fluoro-6-methylbenzamido)propanoic acid compound (263) 3-(4-(3-((1H-benzo[d]imidazol-2-ylamino)methyl)-1,2,4-thiadiazol-5-yl)phenyl)-2-(2-ethyl-4-fluoro-6-methylbenzamido)propanoic acid compound (264) 2-(2-ethyl-4-fluoro-6-methylbenzamido)-3-(4-(3-((4-methylpyridin-2-ylamino)methyl)-1,2,4-thiadiazol-5-yl)phenyl)propanoic acid compound (265) 2-(2-ethyl-4-fluoro-6-methylbenzamido)-3-(4-(3-((4-methoxypyridin-2-ylamino)methyl)-1,2,4-thiadiazol-5-yl)phenyl)propanoic acid compound (266) 3-(4-(5-((1H-imidazol-2-ylamino)methyl)-1,3,4-oxadiazol-2-yl)phenyl)-2-(2,4,6-trimethylbenzamido)propanoic acid compound (267) 3-(4-(5-((1H-benzo[d]imidazol-2-ylamino)methyl)-1,3,4-oxadiazol-2-yl)phenyl)-2-(2,4,6-trimethylbenzamido)propanoic acid compound (268) 3-(4-(5-((4-methylpyridin-2-ylamino)methyl)-1,3,4-oxadiazol-2-yl)phenyl)-2-(2,4,6-trimethylbenzamido)propanoic acid compound (269) 3-(4-(5-((4-methoxypyridin-2-ylamino)methyl)-1,3,4-oxadiazol-2-yl)phenyl)-2-(2,4,6-trimethylbenzamido)propanoic acid compound (270) 3-(4-(5-((1H-imidazol-2-ylamino)methyl)-1,3,4-oxadiazol-2-yl)phenyl)-2-(2-ethyl-4-fluoro-6-methylbenzamido)propanoic acid compound (271) 3-(4-(5-((1H-benzo[d]imidazol-2-ylamino)methyl)-1,3,4-thiadiazol-2-yl)phenyl)-2-(2-ethyl-4-fluoro-6-methylbenzamido)propanoic acid compound (272) 2-(2-ethyl-4-fluoro-6-methylbenzamido)-3-(4-(5-((4-methylpyridin-2-ylamino)methyl)-1,3,4-thiadiazol-2-yl)phenyl)propanoic acid compound (273) 2-(2-ethyl-4-fluoro-6-methylbenzamido)-3-(4-(5-((4-methoxypyridin-2-ylamino)methyl)-1,3,4-thiadiazol-2-yl)phenyl)propanoic acid compound (274) 3-(4-(5-((1H-imidazol-2-ylamino)methyl)-1,2,4-thiadiazol-3-yl)phenyl)-2-(2,4,6-trimethylbenzamido)propanoic acid compound (275) 3-(4-(5-((1H-benzo[d]imidazol-2-ylamino)methyl)-1,2,4-thiadiazol-3-yl)phenyl)-2-(2,4,6-trimethylbenzamido)propanoic acid compound (276) 3-(4-(5-((4-methylpyridin-2-ylamino)methyl)-1,2,4-thiadiazol-3-yl)phenyl)-2-(2,4,6-trimethylbenzamido)propanoic acid compound (277) 3-(4-(5-((4-methoxypyridin-2-ylamino)methyl)-1,2,4-thiadiazol-3-yl)phenyl)-2-(2,4,6-trimethylbenzamido)propanoic acid compound (278) 3-(4-(5-((1H-imidazol-2-ylamino)methyl)-1,2,4-thiadiazol-3-yl)phenyl)-2-(2-ethyl-4-fluoro-6-methylbenzamido)propanoic acid compound (279) 3-(4-(5-((1H-benzo[d]imidazol-2-ylamino)methyl)-1,2,4-thiadiazol-3-yl)phenyl)-2-(2-ethyl-4-fluoro-6-methylbenzamido)propanoic acid compound (280) 2-(2-ethyl-4-fluoro-6-methylbenzamido)-3-(4-(5-((4-methylpyridin-2-ylamino)methyl)-1,2,4-thiadiazol-3-yl)phenyl)propanoic acid compound (281) 2-(2-ethyl-4-fluoro-6-methylbenzamido)-3-(4-(5-((4-methoxypyridin-2-ylamino)methyl)-1,2,4-thiadiazol-3-yl)phenyl)propanoic acid compound (282) 3-(4-(3-((1H-imidazol-2-ylamino)methyl)-1,2,4-thiadiazol-5-yl)phenyl)-2-(2,4,6-trimethylbenzamido)propanoic acid compound (283) 3-(4-(3-((1H-benzo[d]imidazol-2-ylamino)methyl)-1,2,4-thiadiazol-5-yl)phenyl)-2-(2,4,6-trimethylbenzamido)propanoic acid compound (284) 3-(4-(3-((4-methylpyridin-2-ylamino)methyl)-1,2,4-thiadiazol-5-yl)phenyl)-2-(2,4,6-trimethylbenzamido)propanoic acid compound (285) 3-(4-(3-((4-methoxypyridin-2-ylamino)methyl)-1,2,4-thiadiazol-5-yl)phenyl)-2-(2,4,6-trimethylbenzamido)propanoic acid compound (286) 3-(4-(3-((1H-imidazol-2-ylamino)methyl)-1,2,4-thiadiazol-5-yl)phenyl)-2-(2-ethyl-4-fluoro-6-methylbenzamido)propanoic acid compound (287) 3-(4-(3-((1H-benzo[d]imidazol-2-ylamino)methyl)-1,2,4-thiadiazol-5-yl)phenyl)-2-(2-ethyl-4-fluoro-6-methylbenzamido)propanoic acid compound (288) 2-(2-ethyl-4-fluoro-6-methylbenzamido)-3-(4-(3-((4-methylpyridin-2-ylamino)methyl)-1,2,4-thiadiazol-5-yl)phenyl)propanoic acid compound (289) 2-(2-ethyl-4-fluoro-6-methylbenzamido)-3-(4-(3-((4-methoxypyridin-2-ylamino)methyl)-1,2,4-thiadiazol-5-yl)phenyl)propanoic acid compound (290) 3-(4-(5-((1H-imidazol-2-ylamino)methyl)-1,3,4-oxadiazol-2-yl)phenyl)-2-(2,4,6-trimethylbenzamido)propanoic acid compound (291) 3-(4-(5-((1H-benzo[d]imidazol-2-ylamino)methyl)-1,3,4-oxadiazol-2-yl)phenyl)-2-(2,4,6-trimethylbenzamido)propanoic acid compound (292) 3-(4-(5-((4-methylpyridin-2-ylamino)methyl)-1,3,4-oxadiazol-2-yl)phenyl)-2-(2,4,6-trimethylbenzamido)propanoic acid compound (293) 3-(4-(5-((4-methoxypyridin-2-ylamino)methyl)-1,3,4-oxadiazol-2-yl)phenyl)-2-(2,4,6-trimethylbenzamido)propanoic acid compound (294) 3-(4-(5-((1H-imidazol-2-ylamino)methyl)-1,3,4-oxadiazol-2-yl)phenyl)-2-(2-ethyl-4-fluoro-6-methylbenzamido)propanoic acid compound (295) 3-(4-(5-((1H-benzo[d]imidazol-2-ylamino)methyl)-1,3,4-oxadiazol-2-yl)phenyl)-2-(2-ethyl-4-fluoro-6-methylbenzamido)propanoic acid compound (296) 2-(2-ethyl-4-fluoro-6-methylbenzamido)-3-(4-(5-((4-methylpyridin-2-ylamino)methyl)-1,3,4-oxadiazol-2-yl)phenyl)propanoic acid compound (297) 2-(2-ethyl-4-fluoro-6-methylbenzamido)-3-(4-(5-((4-methoxypyridin-2-ylamino)methyl)-1,3,4-oxadiazol-2-yl)phenyl)propanoic acid compound (298) 3-(4-(5-((1H-imidazol-2-ylamino)methyl)isothiazol-3-yl)phenyl)-2-(2,4,6-trimethylbenzamido)propanoic acid compound (299) 3-(4-(5-((1H-benzo[d]imidazol-2-ylamino)methyl)isothiazol-3-yl)phenyl)-2-(2,4,6-trimethylbenzamido)propanoic acid compound (300) 3-(4-(5-((4-methylpyridin-2-ylamino)methyl)isothiazol-3-yl)phenyl)-2-(2,4,6-trimethylbenzamido)propanoic acid compound (301) 3-(4-(5-((4-methoxypyridin-2-ylamino)methyl)isothiazol-3-yl)phenyl)-2-(2,4,6-trimethylbenzamido)propanoic acid compound (302) 3-(4-(5-((1H-imidazol-2-ylamino)methyl)isothiazol-3-yl)phenyl)-2-(2-ethyl-4-fluoro-6-methylbenzamido)propanoic acid compound (303) 3-(4-(5-((1H-benzo[d]imidazol-2-ylamino)methyl)isothiazol-3-yl)phenyl)-2-(2-ethyl-4-fluoro-6-methylbenzamido)propanoic acid compound (304) 2-(2-ethyl-4-fluoro-6-methylbenzamido)-3-(4-(5-((4-methylpyridin-2-ylamino)methyl)isothiazol-3-yl)phenyl)propanoic acid compound (305) 2-(2-ethyl-4-fluoro-6-methylbenzamido)-3-(4-(5-((4-methoxypyridin-2-ylamino)methyl)isothiazol-3-yl)phenyl)propanoic acid.

compound (306) 3-(4-(3-((1H-imidazol-2-ylamino)methyl)isothiazol-5-yl)phenyl)-2-(2,4,6-trimethylbenzamido)propanoic acid compound (307) 3-(4-(3-((1H-benzo[d]imidazol-2-ylamino)methyl)isothiazol-5-yl)phenyl)-2-(2,4,6-trimethylbenzamido)propanoic acid compound (308) 3-(4-(3-((4-methylpyridin-2-ylamino)methyl)isothiazol-5-yl)phenyl)-2-(2,4,6-trimethylbenzamido)propanoic acid compound (309) 3-(4-(3-((4-methoxypyridin-2-ylamino)methyl)isothiazol-5-yl)phenyl)-2-(2,4,6-trimethylbenzamido)propanoic acid compound (310) 3-(4-(3-((1H-imidazol-2-ylamino)methyl)isothiazol-5-yl)phenyl)-2-(2-ethyl-4-fluoro-6-methylbenzamido)propanoic acid compound (311) 3-(4-(3-((1H-benzo[d]imidazol-2-ylamino)methyl)isothiazol-5-yl)phenyl)-2-(2-ethyl-4-fluoro-6-methylbenzamido)propanoic acid compound (312) 2-(2-ethyl-4-fluoro-6-methylbenzamido)-3-(4-(3-((4-methylpyridin-2-ylamino)methyl)isothiazol-5-yl)phenyl)propanoic acid compound (313) 2-(2-ethyl-4-fluoro-6-methylbenzamido)-3-(4-(3-((4-methoxypyridin-2-ylamino)methyl)isothiazol-5-yl)phenyl)propanoic acid compound (314) 3-(4-(4-((1H-imidazol-2-ylamino)methyl)-1H-1,2,3-triazol-1-yl)phenyl)-2-(2,4,6-trimethylbenzamido)propanoic acid compound (315) 3-(4-(4-((1H-imidazol-2-ylamino)methyl)-1H-1,2,3-triazol-1-yl)phenyl)-2-(2-ethyl-4-fluoro-6-methylbenzamido)propanoic acid compound (316) 3-(4-(4-((1H-benzo[d]imidazol-2-ylamino)methyl)-1H-1,2,3-triazol-1-yl)phenyl)-2-(2-ethyl-4-fluoro-6-methylbenzamido)propanoic acid compound (317) 2-(2-ethyl-4-fluoro-6-methylbenzamido)-3-(4-(4-((4-methylpyridin-2-ylamino)methyl)-1H-1,2,3-triazol-1-yl)phenyl)propanoic acid compound (318) 2-(2-ethyl-4-fluoro-6-methylbenzamido)-3-(4-(4-((4-methoxypyridin-2-ylamino)methyl)-1H-1,2,3-triazol-1-yl)phenyl)propanoic acid compound (319) 3-(4-(3-((1H-imidazol-2-ylamino)methyl)-1H-1,2,4-triazol-1-yl)phenyl)-2-(2,4,6-trimethylbenzamido)propanoic acid compound (320) 3-(4-(3-((1H-benzo[d]imidazol-2-ylamino)methyl)-1H-1,2,4-triazol-1-yl)phenyl)-2-(2,4,6-trimethylbenzamido)propanoic acid compound (321) 3-(4-(3-((4-methylpyridin-2-ylamino)methyl)-1H-1,2,4-triazol-1-yl)phenyl)-2-(2,4,6-trimethylbenzamido)propanoic acid compound (322) 3-(4-(3-((4-methoxypyridin-2-ylamino)methyl)-1H-1,2,4-triazol-1-yl)phenyl)-2-(2,4,6-trimethylbenzamido)propanoic acid compound (323) 3-(4-(3-((1H-imidazol-2-ylamino)methyl)-1H-1,2,4-triazol-1-yl)phenyl)-2-(2-ethyl-4-fluoro-6-methylbenzamido)propanoic acid compound (324) 3-(4-(3-((1H-benzo[d]imidazol-2-ylamino)methyl)-1H-1,2,4-triazol-1-yl)phenyl)-2-(2-ethyl-4-fluoro-6-methylbenzamido)propanoic acid compound (325) 2-(2-ethyl-4-fluoro-6-methylbenzamido)-3-(4-(3-((4-methylpyridin-2-ylamino)methyl)-1H-1,2,4-triazol-1-yl)phenyl)propanoic acid compound (326) 2-(2-ethyl-4-fluoro-6-methylbenzamido)-3-(4-(3-((4-methoxypyridin-2-ylamino)methyl)-1H-1,2,4-triazol-1-yl)phenyl)propanoic acid compound (327) 3-(4-(5-((1H-imidazol-2-ylamino)methyl)-4H-1,2,4-triazol-3-yl)phenyl)-2-(2,4,6-trimethylbenzamido)propanoic acid compound (328) 3-(4-(5-((1H-benzo[d]imidazol-2-ylamino)methyl)-4H-1,2,4-triazol-3-yl)phenyl)-2-(2,4,6-trimethylbenzamido)propanoic acid compound (329) 3-(4-(5-((4-methylpyridin-2-ylamino)methyl)-4H-1,2,4-triazol-3-yl)phenyl)-2-(2,4,6-trimethylbenzamido)propanoic acid compound (330) 3-(4-(5-((4-methoxypyridin-2-ylamino)methyl)-4H-1,2,4-triazol-3-yl)phenyl)-2-(2,4,6-trimethylbenzamido)propanoic acid compound (331) 3-(4-(5-((1H-imidazol-2-ylamino)methyl)-4H-1,2,4-triazol-3-yl)phenyl)-2-(2-ethyl-4-fluoro-6-methylbenzamido)propanoic acid compound (332) 3-(4-(5-((1H-benzo[d]imidazol-2-ylamino)methyl)-4H-1,2,4-triazol-3-yl)phenyl)-2-(2-ethyl-4-fluoro-6-methylbenzamido)propanoic acid compound (333) 2-(2-ethyl-4-fluoro-6-methylbenzamido)-3-(4-(5-((4-methylpyridin-2-ylamino)methyl)-4H-1,2,4-triazol-3-yl)phenyl)propanoic acid compound (334) 2-(2-ethyl-4-fluoro-6-methylbenzamido)-3-(4-(5-((4-methoxypyridin-2-ylamino)methyl)-4H-1,2,4-triazol-3-yl)phenyl)propanoic acid compound (335) 2-(4-chloro-2-ethyl-6-methylbenzamido)-3-(4-(4-((4-methylpyridin-2-ylamino)methyl)furan-2-yl)phenyl)propanoic acid compound (336) 2-(4-chloro-2-ethyl-6-methylbenzamido)-3-(4-(5-((4-methylpyridin-2-ylamino)methyl)-1H-pyrrol-2-yl)phenyl)propanoic acid compound (337) 2-(4-chloro-2-ethyl-6-methylbenzamido)-3-(4-(5-((4-methylpyridin-2-ylamino)methyl)-1H-pyrrol-3-yl)phenyl)propanoic acid compound (338) 2-(4-chloro-2-ethyl-6-methylbenzamido)-3-(4-(4-((4-methylpyridin-2-ylamino)methyl)-1H-pyrrol-2-yl)phenyl)propanoic acid compound (339) 2-(4-chloro-2-ethyl-6-methylbenzamido)-3-(4-(3-((4-methylpyridin-2-ylamino)methyl)-1H-pyrrol-1-yl)phenyl)propanoic acid compound (340) 2-(4-chloro-2-ethyl-6-methylbenzamido)-3-(4-(4-((4-methylpyridin-2-ylamino)methyl)-1H-pyrazol-1-yl)phenyl)propanoic acid compound (341) 2-(4-chloro-2-ethyl-6-methylbenzamido)-3-(4-(3-((4-methylpyridin-2-ylamino)methyl)-1H-pyrazol-1-yl)phenyl)propanoic acid compound (342) 2-(4-chloro-2-ethyl-6-methylbenzamido)-3-(4-(5-((4-methylpyridin-2-ylamino)methyl)-1H-imidazol-2-yl)phenyl)propanoic acid compound (343) 2-(4-chloro-2-ethyl-6-methylbenzamido)-3-(4-(2-((4-methylpyridin-2-ylamino)methyl)-1H-imidazol-4-yl)phenyl)propanoic acid compound (344) 2-(4-chloro-2-ethyl-6-methylbenzamido)-3-(4-(4-((4-methylpyridin-2-ylamino)methyl)-1H-imidazol-1-yl)phenyl)propanoic acid compound (345) 2-(4-chloro-2-ethyl-6-methylbenzamido)-3-(4-(5-((4-methylpyridin-2-ylamino)methyl)thiophen-2-yl)phenyl)propanoic acid compound (346) 2-(4-chloro-2-ethyl-6-methylbenzamido)-3-(4-(5-((4-methylpyridin-2-ylamino)methyl)thiophen-3-yl)phenyl)propanoic acid compound (347) 2-(4-chloro-2-ethyl-6-methylbenzamido)-3-(4-(4-((4-methylpyridin-2-ylamino)methyl)thiophen-2-yl)phenyl)propanoic acid compound (348) 2-(4-chloro-2-ethyl-6-methylbenzamido)-3-(4-(5-((4-methylpyridin-2-ylamino)methyl)isoxazol-3-yl)phenyl)propanoic acid compound (349) 2-(4-chloro-2-ethyl-6-methylbenzamido)-3-(4-(3-((4-methylpyridin-2-ylamino)methyl)isoxazol-5-yl)phenyl)propanoic acid compound (350) 2-(4-chloro-2-ethyl-6-methylbenzamido)-3-(4-(2-((4-methylpyridin-2-ylamino)methyl)oxazol-5-yl)phenyl)propanoic acid compound (351) 2-(4-chloro-2-ethyl-6-methylbenzamido)-3-(4-(2-((4-methylpyridin-2-ylamino)methyl)oxazol-4-yl)phenyl)propanoic acid compound (352) 2-(4-chloro-2-ethyl-6-methylbenzamido)-3-(4-(4-((4-methylpyridin-2-ylamino)methyl)oxazol-2-yl)phenyl)propanoic acid
compound (353) 2-(4-chloro-2-ethyl-6-methylbenzamido)-3-(4-(5-((4-methylpyridin-2-ylamino)methyl)oxazol-2-yl)phenyl)propanoic acid
compound (354) 2-(4-chloro-2-ethyl-6-methylbenzamido)-3-(4-(2-((4-methylpyridin-2-ylamino)methyl)thiazol-5-yl)phenyl)propanoic acid
compound (355) 2-(4-chloro-2-ethyl-6-methylbenzamido)-3-(4-(2-((4-methylpyridin-2-ylamino)methyl)thiazol-4-yl)phenyl)propanoic acid
compound (356) 2-(4-chloro-2-ethyl-6-methylbenzamido)-3-(4-(4-((4-methylpyridin-2-ylamino)methyl)thiazol-2-yl)phenyl)propanoic acid
compound (357) 2-(4-chloro-2-ethyl-6-methylbenzamido)-3-(4-(5-((4-methylpyridin-2-ylamino)methyl)thiazol-2-yl)phenyl)propanoic acid
compound (358) 2-(4-chloro-2-ethyl-6-methylbenzamido)-3-(4-(5-((4-methylpyridin-2-ylamino)methyl)-1,3,4-thiadiazol-2-yl)phenyl)propanoic acid
compound (359) 2-(4-chloro-2-ethyl-6-methylbenzamido)-3-(4-(5-((4-methylpyridin-2-ylamino)methyl)-1,2,4-thiadiazol-3-yl)phenyl)propanoic acid
compound (360) 2-(4-chloro-2-ethyl-6-methylbenzamido)-3-(4-(3-((4-methylpyridin-2-ylamino)methyl)-1,2,4-thiadiazol-5-yl)phenyl)propanoic acid
compound (361) 2-(4-chloro-2-ethyl-6-methylbenzamido)-3-(4-(5-((4-methylpyridin-2-ylamino)methyl)-1,3,4-oxadiazol-2-yl)phenyl)propanoic acid
compound (362) 2-(4-chloro-2-ethyl-6-methylbenzamido)-3-(4-(5-((4-methylpyridin-2-ylamino)methyl)isothiazol-3-yl)phenyl)propanoic acid
compound (363) 2-(4-chloro-2-ethyl-6-methylbenzamido)-3-(4-(3-((4-methylpyridin-2-ylamino)methyl)isothiazol-5-yl)phenyl)propanoic acid
compound (364) 2-(4-chloro-2-ethyl-6-methylbenzamido)-3-(4-(4-((4-methylpyridin-2-ylamino)methyl)-1H-1,2,3-triazol-1-yl)phenyl)propanoic acid
compound (365) 2-(4-chloro-2-ethyl-6-methylbenzamido)-3-(4-(3-((4-methylpyridin-2-ylamino)methyl)-1H-1,2,4-triazol-1-yl)phenyl)propanoic acid
compound (366) 2-(4-chloro-2-ethyl-6-methylbenzamido)-3-(4-(5-((4-methylpyridin-2-ylamino)methyl)-4H-1,2,4-triazol-3-yl)phenyl)propanoic acid
compound (367) 2-(4-cyano-2-ethyl-6-methylbenzamido)-3-(4-(5-((4-methylpyridin-2-ylamino)methyl)furan-2-yl)phenyl)propanoic acid
compound (368) 2-(4-cyano-2-ethyl-6-methylbenzamido)-3-(4-(5-((4-methylpyridin-2-ylamino)methyl)furan-3-yl)phenyl)propanoic acid
compound (369) 2-(4-cyano-2-ethyl-6-methylbenzamido)-3-(4-(4-((4-methylpyridin-2-ylamino)methyl)furan-2-yl)phenyl)propanoic acid
compound (370) 2-(4-cyano-2-ethyl-6-methylbenzamido)-3-(4-(5-((4-methylpyridin-2-ylamino)methyl)-1H-pyrrol-2-yl)phenyl)propanoic acid
compound (371) 2-(4-cyano-2-ethyl-6-methylbenzamido)-3-(4-(5-((4-methylpyridin-2-ylamino)methyl)-1H-pyrrol-3-yl)phenyl)propanoic acid
compound (372) 2-(4-cyano-2-ethyl-6-methylbenzamido)-3-(4-(4-((4-methylpyridin-2-ylamino)methyl)-1H-pyrrol-2-yl)phenyl)propanoic acid
compound (373) 2-(4-cyano-2-ethyl-6-methylbenzamido)-3-(4-(3-((4-methylpyridin-2-ylamino)methyl)-1H-pyrrol-1-yl)phenyl)propanoic acid
compound (374) 2-(4-cyano-2-ethyl-6-methylbenzamido)-3-(4-(4-((4-methylpyridin-2-ylamino)methyl)-1H-pyrazol-1-yl)phenyl)propanoic acid
compound (375) 2-(4-cyano-2-ethyl-6-methylbenzamido)-3-(4-(3-((4-methylpyridin-2-ylamino)methyl)-1H-pyrazol-1-yl)phenyl)propanoic acid
compound (376) 2-(4-cyano-2-ethyl-6-methylbenzamido)-3-(4-(5-((4-methylpyridin-2-ylamino)methyl)-1H-imidazol-2-yl)phenyl)propanoic acid
compound (377) 2-(4-cyano-2-ethyl-6-methylbenzamido)-3-(4-(2-((4-methylpyridin-2-ylamino)methyl)-1H-imidazol-4-yl)phenyl)propanoic acid
compound (378) 2-(4-cyano-2-ethyl-6-methylbenzamido)-3-(4-(4-((4-methylpyridin-2-ylamino)methyl)-1H-imidazol-1-yl)phenyl)propanoic acid
compound (379) 2-(4-cyano-2-ethyl-6-methylbenzamido)-3-(4-(5-((4-methylpyridin-2-ylamino)methyl)thiophen-2-yl)phenyl)propanoic acid
compound (380) 2-(4-cyano-2-ethyl-6-methylbenzamido)-3-(4-(5-((4-methylpyridin-2-ylamino)methyl)thiophen-3-yl)phenyl)propanoic acid
compound (381) 2-(4-cyano-2-ethyl-6-methylbenzamido)-3-(4-(4-((4-methylpyridin-2-ylamino)methyl)thiophen-2-yl)phenyl)propanoic acid
compound (382) 2-(4-cyano-2-ethyl-6-methylbenzamido)-3-(4-(5-((4-methylpyridin-2-ylamino)methyl)isoxazol-3-yl)phenyl)propanoic acid
compound (383) 2-(4-cyano-2-ethyl-6-methylbenzamido)-3-(4-(3-((4-methylpyridin-2-ylamino)methyl)isoxazol-5-yl)phenyl)propanoic acid
compound (384) 2-(4-cyano-2-ethyl-6-methylbenzamido)-3-(4-(2-((4-methylpyridin-2-ylamino)methyl)oxazol-5-yl)phenyl)propanoic acid
compound (385) 2-(4-cyano-2-ethyl-6-methylbenzamido)-3-(4-(2-((4-methylpyridin-2-ylamino)methyl)oxazol-4-yl)phenyl)propanoic acid
compound (386) 2-(4-cyano-2-ethyl-6-methylbenzamido)-3-(4-(4-((4-methylpyridin-2-ylamino)methyl)oxazol-2-yl)phenyl)propanoic acid
compound (387) 2-(4-cyano-2-ethyl-6-methylbenzamido)-3-(4-(5-((4-methylpyridin-2-ylamino)methyl)oxazol-2-yl)phenyl)propanoic acid
compound (388) 2-(4-cyano-2-ethyl-6-methylbenzamido)-3-(4-(2-((4-methylpyridin-2-ylamino)methyl)thiazol-5-yl)phenyl)propanoic acid
compound (389) 2-(4-cyano-2-ethyl-6-methylbenzamido)-3-(4-(2-((4-methylpyridin-2-ylamino)methyl)thiazol-4-yl)phenyl)propanoic acid
compound (390) 2-(4-cyano-2-ethyl-6-methylbenzamido)-3-(4-(4-((4-methylpyridin-2-ylamino)methyl)thiazol-2-yl)phenyl)propanoic acid
compound (391) 2-(4-cyano-2-ethyl-6-methylbenzamido)-3-(4-(5-((4-methylpyridin-2-ylamino)methyl)thiazol-2-yl)phenyl)propanoic acid
compound (392) 2-(4-cyano-2-ethyl-6-methylbenzamido)-3-(4-(5-((4-methylpyridin-2-ylamino)methyl)-1,3,4-thiadiazol-2-yl)phenyl)propanoic acid
compound (393) 2-(4-cyano-2-ethyl-6-methylbenzamido)-3-(4-(5-((4-methylpyridin-2-ylamino)methyl)-1,2,4-thiadiazol-3-yl)phenyl)propanoic acid
compound (394) 2-(4-cyano-2-ethyl-6-methylbenzamido)-3-(4-(3-((4-methylpyridin-2-ylamino)methyl)-1,2,4-thiadiazol-5-yl)phenyl)propanoic acid
compound (395) 2-(4-cyano-2-ethyl-6-methylbenzamido)-3-(4-(5-((4-methylpyridin-2-ylamino)methyl)-1,3,4-oxadiazol-2-yl)phenyl)propanoic acid compound (396) 2-(4-cyano-2-ethyl-6-methylbenzamido)-3-(4-(5-((4-methylpyridin-2-ylamino)methyl)isothiazol-3-yl)phenyl)propanoic acid compound (397) 2-(4-cyano-2-ethyl-6-methylbenzamido)-3-(4-(3-((4-methylpyridin-2-ylamino)methyl)isothiazol-5-yl)phenyl)propanoic acid compound (398) 2-(4-cyano-2-ethyl-6-methylbenzamido)-3-(4-(4-((4-methylpyridin-2-ylamino)methyl)-1H-1,2,3-triazol-1-yl)phenyl)propanoic acid compound (399) 2-(4-cyano-2-ethyl-6-methylbenzamido)-3-(4-(3-((4-methylpyridin-2-ylamino)methyl)-1H-1,2,4-triazol-1-yl)phenyl)propanoic acid compound (400) 2-(4-cyano-2-ethyl-6-methylbenzamido)-3-(4-(5-((4-methylpyridin-2-ylamino)methyl)-4H-1,2,4-triazol-3-yl)phenyl)propanoic acid In a twenty-ninth embodiment of the second aspect which is also an embodiment of all preceding embodiments of the first and second aspect the compound comprises a further moiety, preferably a moiety which is selected from the group comprising a targeted moiety, a delivery moiety, and a detection moiety.

In a thirtieth embodiment of the second aspect which is also an embodiment of the twenty-ninth embodiment of the second aspect further moiety is attached or incorporated, preferably conjugated to the compound according to any of the preceding embodiments of the first and second aspect.

In a thirty-first embodiment of the second aspect which is also an embodiment of the twenty-ninth and thirtieth embodiment of the second aspect the detection moiety is a label, whereby preferably the label is selected from the group comprising radionuclide labels, paramagnetic material, X-ray attenuating material, immune labels, colored labels, infrared labels, chemiluminescent labels, luminescent labels, fluorescent labels, enzyme substrates, enzymes, and labels complexing detectable ions.

In a thirty-second embodiment of the second aspect which is also an embodiment of the twenty-ninth to thirty-first embodiment of the second aspect the moiety is a targeted moiety, whereby the targeted moiety is preferably a pharmaceutically active moiety, whereby the pharmaceutically active moiety is selected from the group comprising cytotoxins, chemotherapeutics, antibodies, radionuclides and cytotoxic proteins.

In a thirty-third embodiment of the second aspect which is also an embodiment of the twenty-ninth to thirty-second embodiment of the second aspect the targeted moiety is selected from the group comprising antibodies, linker molecules and liposomes.

In a third aspect the problem underlying the present invention is solved by the use of a compound according to any of the preceding embodiments of the first and the second aspect, as an inhibitor.

In a first embodiment of the third aspect the compound is an inhibitor to an integrin.

In a second embodiment of the third aspect which is also an embodiment of the first embodiment of the third aspect the integrin is alpha5beta1 integrin.

In a fourth aspect the problem underlying the present invention is solved by the use of a compound according to any of the preceding embodiments of the first and the second aspect for the manufacture of a medicament, preferably a medicament for the treatment and/or prevention of a disease.

In a first embodiment of the fourth aspect the medicament is for a disease mediated by or involving alpha5beta1 integrin.

In a second embodiment of the fourth aspect which is also an embodiment of the first embodiment of the fourth aspect the disease is selected from the group comprising diseases based on pathological angiogenesis and/or diseases based on interaction of an integrin with a ligand, whereby preferably the ligand is present on the extracellular matrix and/or in body fluids and/or on any cell surface.

In a third embodiment of the fourth aspect which is also an embodiment of the first and second embodiment of the fourth aspect the disease is related to an ocular tissue, the skin, joints, synovial tissue, liver, kidney, lung, heart, bladder, neoplasm, intestinal tissue, blood, connective tissue and/or the bone tissue.

In a fourth embodiment of the fourth aspect which is also an embodiment of the first to third embodiment of the fourth aspect the disease is a disease of an ocular tissue, preferably diabetic retinopathy, retinopathy of prematurity or macular degeneration, more preferably age related macular degeneration.

In a fifth embodiment of the fourth aspect which is also an embodiment of the first to third embodiment of the fourth aspect the disease is a disease of the skin, more preferably hemangioma and psoriasis.

In a sixth embodiment of the fourth aspect which is also an embodiment of the first to third embodiment of the fourth aspect the disease is a disease of or affecting the joints, more preferably primary arthritis including rheumatoid arthritis, psoriatic arthritis, osteoarthritis, and secondary arthritis.

In a seventh embodiment of the fourth aspect which is also an embodiment of the first to third embodiment of the fourth aspect the disease is a neoplasm, more preferably a malignant neoplasm.

In an eighth embodiment of the fourth aspect which is also an embodiment of the seventh embodiment of the fourth aspect the malignant neoplasm is selected from the group comprising sarcoma, carcinoma, osteosarcoma, adenocarcinoma, blastoma, myeloma, leukaemia, lymphoma, including but not limited to breast cancer, gynaecological cancers, pancreatic cancer, bladder cancer, mesothelioma, teratocarcinoma, astrocytoma, melanoma, angioma and glioblastoma, renal cancer, prostate cancer, brain cancer, lung cancer, head and neck cancer, parotid cancer, thyroid cancer, fibrosarcoma, gastrointestinal cancer, endocrine cancer, AIDS-related cancers, adrenal cancer, eye cancer, hepatocellular cancer, skin cancer, thymus cancer, and testicular cancer.

In a ninth embodiment of the fourth aspect which is also an embodiment of the first and second embodiment of the fourth aspect the disease is based on an interaction of an integrin with a ligand in the extracellular matrix or on the cell surface, preferably the disease is an inflammatory disease.

In a tenth embodiment of the fourth aspect which is also an embodiment of the first and second embodiment of the fourth aspect the disease is based on an interaction of an integrin with a ligand in the extracellular matrix or on the cell surface, preferably the disease is an infectious disease.

In an eleventh embodiment of the fourth aspect which is also an embodiment of the first to third embodiment of the fourth aspect or the ninth embodiment of the fourth aspect the inflammatory disease is a disease selected from the group comprising rheumatoid arthritis, juvenile arthritis, psoriatic arthritis, osteoarthritis, glomerulonephritis, gingivitis, inflammatory bowel disease, ulcerative colitis, systemic lupus erythematosus associated glomerulonephritis, irritable bowel syndrome, bronchial asthma, multiple sclerosis, pemphigus, pemphigoid, scleroderma, myasthenia gravis, Wegener's granulomatosis, Churg-Strauss-allergic granulomatosis, Sjogren's syndrome, Sicca syndrome, Goopasture's disease, autoimmune haemolytic and thrombocytopenic states, pulmonary hemorrhage, vasculitis, Crohn's disease, and dermatomyositis, ankylosing spondylitis, burns, lung injury, myocardial infarction, coronary thrombosis, vascular occlusion, post-surgical vascular reocclusion, IgA nephropathy, sarcoidosis, eosinophilic granulomata, midline granuloma, arteritis temporalis, Takayasu's arteritis, pterygia, Kawasaki's disease, atherosclerosis, traumatic central nervous system injury, ischemic heart disease and ischemia-reperfusion injury, acute respiratory distress syndrome, systemic inflammatory response syndrome, multiple organ dysfunction syndrome, tissue graft rejection and hyperacute rejection of transplanted organs, uveitis, psoriasis, rosacea, transplantation and asthma.

In a twelfth embodiment of the fourth aspect which is also an embodiment of the first to third embodiment of the fourth aspect and the ninth to tenth embodiment of the fourth aspect the disease is an infectious disease, more preferably the disease is an infection caused by or involving fungi, bacteria and/or viruses.

In a thirteenth embodiment of the fourth aspect which is also an embodiment of the first to third embodiment of the fourth aspect and the ninth to tenth embodiment of the fourth aspect the disease is connected with a non-neoplastic cell proliferation and/or tissue remodelling.

In a fourteenth embodiment of the fourth aspect which is also an embodiment of the first to third embodiment of the fourth aspect, the ninth, tenth or thirteenth embodiment of the fourth aspect the disease is a non-neoplastic cell proliferative and/or tissue remodelling disorder, preferably this disorder is selected from the group comprising fibrotic disorders, more preferably the fibrotic disorder is fibrosis.

In a fifteenth embodiment of the fourth aspect which is also an embodiment of the first to third embodiment of the fourth aspect, the ninth, tenth, thirteenth or fourteenth embodiment of the fourth aspect the disease is a hepatic disorder, preferably, liver fibrosis, liver cirrhosis, reperfusion injury after hepatic transplantation or necrotizing hepatitis.

In a sixteenth embodiment of the fourth aspect which is also an embodiment of the first to third embodiment of the fourth aspect, the ninth, tenth, thirteenth or fourteenth embodiment of the fourth aspect the disease is a renal disorder, preferably renal fibrosis, glomrulonephritis, IgA nephropathy, reperfusion injury after kidney transplantation, chronic renal allograft dysfunction, amyloidosis, diabetic nephropathy, mesangio proliferative glomrulonephritis, nephrosclerosis.

In a seventeenth embodiment of the fourth aspect which is also an embodiment of the first to third embodiment of the fourth aspect, the ninth, tenth, thirteenth or fourteenth embodiment of the fourth aspect the disease is a fibrotic disorder, preferably lung fibrosis comprising interstitial pulmonary fibrosis, idiophatic fibrosis, drug-induced fibrosis, sarcoidosis, diffuse alveolar damage disease, pulmonary hypertension, chronic obstructive pulmonary disease, respiratory distress syndrome; skin fibrosis such as scleroderma, keloid, hypertrophic scar, dermatofibroma, chronic wounds, psoriasis, dupuytren's contracture, pemphegoid, burn; stomach and intestinal fibrosis comprising abnormal intestinal motility, hypertrophic pyloric stenosis, Hirschsprung's disease, megacolon of piebaldism, idiopathic obstruction, collagenous colitis, villious atrophy and crypt hyperplasia, polyp formation, fibrosis of Crohn's disease, gastric ulcer; eye fibrosis comprising acute and fibrotic sympathetic ophthalmia, Grave's disease, fibrosis after glaucoma surgery, fibrosis after cataract surgery, anterior capsular cataract, corneal scarring, pemphigoid, diabetic microaneurism, capsule opacification; or any other fibrosis comprising systemic sclerosis, artherosclerosis, restenosis, chronic myeloproliferative disorders, fibrodysplasia ossificans progressive, myelodysplasia, osteoporosis, myelofibrosis, osteosclerosis, rheumatoid pannus formation in rheumatoid arthritis, peritoneal fibrosis, myocardial fibrosis, pancreatic fibrosis, chronic pancreatitis, glial scar tissue formation in HIV associated cognitive motor disease and spongiform encephalopathy, gingival hypertrophy secondary to drugs and fibrocystic disease.

In an eighteenth embodiment of the fourth aspect which is also an embodiment of the first to third embodiment of the fourth aspect, the ninth, tenth, thirteenth or fourteenth embodiment of the fourth aspect, the disease is an ocular disorder, preferably connected with pathological proliferation and/or transdifferentiation of RPE cells, more preferably proliferative diabetic retinopathy, retinal detachment, age related macular degeneration or proliferative vitreoretinopathy.

In a fifth aspect the problem underlying the present invention is solved by the use of a compound according to any of the preceding embodiments of the first and the second aspect as a diagnostic tool or for the manufacture of a diagnostic tool, whereby preferably such diagnostic tool is useful for in vivo and/or for ex vivo application.

In a first embodiment of the fifth aspect the compound comprises a detection moiety, whereby the detection moiety is a label, whereby preferably the label is selected from the group comprising radionuclide labels, paramagnetic material, X-ray attenuating material, immune labels, colored labels, chemiluminescent labels, luminescent labels, fluorescent labels, infrared labels, enzyme substrates, enzymes, and labels complexing detectable ions.

In a second embodiment of the fifth aspect which is also an embodiment of the first embodiment of the fifth aspect the diagnostic tool is used in an in vivo imaging method and/or an ex vivo imaging method, more particularly radionuclide imaging, positron emission tomography, computerized axial tomography, magnetic resonance imaging, X-ray, infrared spectroscopy, luminescence, fluorescence, and chemiluminescence.

In a sixth aspect the problem underlying the present invention is solved by a pharmaceutical composition comprising a compound according to any of the preceding embodiments of the first and the second aspect and a pharmaceutically acceptable carrier, diluent or excipient.

In a first embodiment of the sixth aspect the pharmaceutical composition comprises an additional pharmaceutically active compound.

In a second embodiment of the sixth aspect which is also an embodiment of the first embodiment of the sixth aspect the compound is present as a pharmaceutically acceptable salt or a pharmaceutically active solvate.

In a third embodiment of the sixth aspect which is also an embodiment of the first and second embodiment of the sixth aspect the compound is either alone or in combination with any of the ingredients of the composition present in a multitude of individualised dosages and/or administration forms.

In a fourth embodiment of the sixth aspect the pharmaceutical composition is for the treatment of a disease, whereby the disease is selected from diseases mediated by or involving alpha5beta1 integrin.

In a fifth embodiment of the sixth aspect the disease is any of the diseases defined in the first embodiment to the eighteenth embodiment of the fourth aspect.

In a sixth embodiment of the sixth aspect the pharmaceutical composition is for use together with a method of treatment for a disease, preferably a disease defined in the fourth aspect and more preferably in the second embodiment to the eighteenth embodiment of the fourth aspect.

In a seventh embodiment of the sixth aspect the method of treatment is a sequential or combination therapy with the treatment selected from the group comprising chemotherapy, anti-proliferative, anti-hormone therapy, radiation therapy, photodynamic therapy, surgery, anti-fibrotic therapy, anti-inflammatory therapy, immunosuppressive therapy and anti-angiogenic therapy.

In a seventh aspect the problem underlying the present invention is solved by a method for treating an integrin associated state in a subject comprising administering to said subject an effective amount of a compound according to any of the embodiments of the first and second aspect such that said integrin associated state is treated.

In a first embodiment of the seventh aspect the integrin is alpha5beta1 integrin.

In an eighth aspect the problem underlying the present invention is solved by a method for treating a disease in a subject comprising administering to said subject an effective amount of a compound according to any of the embodiments of the first and second aspect such that the disease is treated.

In a first embodiment of the eighth aspect the disease is any of the diseases defined in the first embodiment to the eighteenth embodiment of the fourth aspect.

It is to be acknowledged that whenever it is referred herein to any aspect of the present invention such referenced aspect factually also constitutes an embodiment. Such embodiment shall always be comprised by any reference to the first embodiment made herein.

The inventors have surprisingly found that the compounds according to the present invention are particularly suitable to interact with integrins, more particularly with integrin alpha5beta1 which is also referred to herein as alpha5beta1.

Without wishing to be bound by any theory the inventors assume that the structure underlying the compounds according to the present invention, more particularly comprising a central core structure represented by A-Ar in formula (I) and a total of two radii emerging therefrom, namely the radius Z-G, and the radius A, provides for this effect.

It seems that this design surprisingly confers to the compounds according to the present invention the ability to specifically interact with the integrin, typically reflected in a low $IC_{50}$ value. Additionally, this simple core structure provides preferable physicochemical properties, enhanced stability, selectivity and synthetic accessibility.

The compounds according to the present invention seem to be particularly binding to and specific, respectively, for integrin alpha5beta1. However, it is also within the present invention that the compounds of the present invention show cross-reactivity with other compounds, preferably with other integrins.

According to the current understanding of the inventors and without wishing to be bound by any theory, the various radii contributing in a synergistic manner to the binding of the compounds according to the present invention to the integrins and preferably to integrin alpha5beta1, can be assigned the following functions.

According to the present invention the interaction of any of the molecules described herein with integrins requires one basic and one acidic moiety to be present in said molecule. These moieties are represented in the compounds according to the present invention by radius Z-G and radius $\Psi$, respectively. Insofar, the inventors clearly depart from the design of small molecules of the prior art which interact with integrins and which comprise a tri-radial core such as disclosed in WO 97/33887 and WO 2005/090329.

The basic radius G-Z, more specifically the radius G can interact with carboxylic group(s) of the integrin protein. Basic functional groups like guanidine, amidine or aromatic nitrogen containing heterocycles are widely used as interaction partners. The term "basic" refers in so far to a functional group which is positively charged under physiologic conditions. However, also non-charged functional groups like amide or urea serve this requirement. The further design of this radius may be taken from the respective more detailed disclosure of the present application.

The acidic radius $\Psi$ bears usually a carboxylic acid and interacts with metal ions which are incorporated into the protein structure. Such interaction is also referred to herein as acidic interaction. Esters such as alkyl or aryl esters and amides such as mono- and dialkyl or aryl amides being derivatives of this carboxylic acid group may advantageously be used as prodrugs of the corresponding active compound. Such prodrugs are compounds which undergo biotransformation prior to exhibiting their pharmacological effects and the invention particularly extends to prodrugs of the acid, whereby the prodrug character is conferred by or resides in the acid moiety of the molecule and its derivatization. Such prodrugs are well known in the art and, for example, described in International Patent Application No. WO00/26419, Bodor, N. (Alfred Benzon Symposium, 1982, 17, 156), Singh, G. et al. (J. Sci. Ind. Res., 1996, 55, 497) and Bundgaard, H., (Design of Prodrugs, 1985, Elsevier, Amsterdam). It is thus within the present invention that the compounds according to the present invention also comprise the prodrug form of the compounds disclosed herein.

For this acidic interaction realized by the compounds according to the present invention a carboxylic acid group is preferably used as interaction partner for the interacting group of the integrin. Preferably, the interacting group of the integrin is a counter ion on the integrin and more preferably a metal ion. However, this interaction does not necessarily require a carboxylic acid functional group provided by the compounds according to the present invention. Other functional groups like tetrazole, phosphates and acylsulfonamides can also serve as a binding partner for the interacting group of the integrin interacting with said compound according to the present invention. These other groups which may interact with the interacting group of the integrin, are bioisosteres for the carboxylic group. Respective bioisosters for the carboxylic group in addition to tetrazole, phosphates and acylsulfonamides are known to the ones skilled in the art. Thus the compounds according to the present invention also comprise those compounds where the carboxylic group is replaced by a bioisoster of such carboxylic group.

Starting from such a scaffold described for the first time in European patent application EP 06002005.4 where moiety A of the central core was either a non-aromatic heterocyclic or homocyclic ring, the inventors have further surprisingly found that also an aromatic heterocyclic 5-membered ring system can actually be used as moiety A.

This latter finding is insofar surprising as it was assumed that in order to provide for a specific interaction with integrin alpha5beta1 moiety A had to be rather flexible. Such flexibility was, in accordance with said earlier application, conferred by said non-aromatic heterocyclic or homocyclic ring. According to the current understanding of the inventors, however, it seems that such flexibility is actually not needed to confer this and other characteristics to integrin and more specifically integrin alpha5beta1 specific interaction partners. Rather an aromatic heterocyclic 5-membered ring system used as moiety A in accordance with the present invention provides for an insofar effective interaction partner.

Without wishing to be bound by any theory, this surprising finding seems to reside in the specific molecular fit of said integrin and the compounds of the present invention and more specifically moiety A thereof. The combination of the rigidity provided by the aromatic character and the additional valences provided by the heterocyclic ring system of moiety A in accordance with the present invention are surprisingly a suitable alternative to the flexibility one would expect to be necessary for providing an interaction with said integrins.

Each of the following terms, used alone or in conjunction with other terms, is preferably used in the following meaning (except where noted to the contrary). Insofar the definitions given herein are in each and any case only preferred embodiments.

In organic nomenclature radicals are considered formally as derived from parent compounds by the removal of one or more hydrogen atoms from one or more atoms of a parent compound. It should be understood that the term "radical" in this application includes also di- or triradicals. The resulting radicals feature one or more unpaired electrons. An atom of a radical on which an unpaired electron is largely localized, is called radical center. Radical centers represent the positions where the radical moiety is connected to other molecular moieties of compounds disclosed in this application and of compounds according to the present invention. Names of radicals usually contain the suffix "-yl". For reason of simplicity within this application also names or structures/formulas of parent compounds are used synonymously for radicals. For example if "piperidine" is listed in a group of radicals it should be understood, that it can be a mono-, di- or triradical with the radical centers at any reasonable ring position.

The same is true for drawn structures indicated in this application and referred to as radicals. If for example the term "a radical selected from the group comprising structures" is used and the related structures or formulas are drawn without any radical center, it should be understood that this structure represents the parent compound and related radicals as generated by the removal of 1, 2 or 3 hydrogen atoms at any position unless otherwise radical center positions are indicated in the accompanying text.

It should also be clear, that if a moiety is not explicitly referred to as a radical in this application but is nonetheless a molecular part or moiety of a compound disclosed in this application that this moiety is preferably a radical. This is also true for names or structures/formulas of parent compounds used to describe structural properties within this application.

The term "basic moiety" preferably refers to a functional group, chemical species, moiety or molecular entity having an available pair of electrons capable of forming a covalent bond with a proton. The resulting protonated moiety is positively charged. A "basic moiety" can also be called "base". In this application those basic moieties are of special interest that are protonated under physiologic conditions.

The term "acidic moiety" or "acid" preferably refers to a functional group, chemical species, moiety or molecular entity having a tendency to act as a proton donor, i.e., breaking the covalent bond to a proton thereby liberating the proton or donating it to a base. In this application those acidic moieties are of special interest that are completely or to some degree deprotonated in water under physiologic conditions.

If a radical is defined by the term "direct bond" or is said to be a "direct bond", this means, that the radical is replaced or represented by a single bond. For example if in a compound with the hypothetical formula "A-B—C" B is defined as "direct bond", A is directly and covalently connected to C by a single bond and the resulting compound is "A-C".

The term "alkyl" refers, in a preferred embodiment of the present invention, to a saturated aliphatic radical containing from one to ten carbon atoms or a mono- or polyunsaturated aliphatic hydrocarbon radical containing from two to twelve carbon atoms, containing at least one double and triple bound, respectively. Thus in a preferred embodiment, the term alkyl also comprises alkenyl and alkynyl. "Alkyl" refers to both branched and unbranched, i.e., non-linear alkyl groups. Preferred alkyl groups are straight chain alkyl groups containing from one to eight carbon atoms. More preferred alkyl groups are straight chain alkyl groups containing from one to six carbon atoms and branched alkyl groups containing from three to six carbon atoms. It should be understood that any combination term using an "alk" or "alkyl" prefix refers to analogs according to the above definition of "alkyl". For example, terms such as "alkoxy", "alkylthio" refer to alkyl groups linked to a second group via an oxygen or sulfur atom. "Alkanoyl" refers to an alkyl group linked to a carbonyl group (C=O). "Substituted alkyl" refers to alkyl groups straight or branched further bearing one or more substituents. One substituent also means mono-substituted and more substitutents mean poly-substituted. It should be understood that any combination term using a "substituted alkyl" prefix refers to analogs according to the above definition of "substituted alkyl". For example, a term such as "substituted alkylaryl" refers to substituted alkyl group linked to an aryl group. Additionally, it is within the present invention that the term alky, particularly in the branched embodiment, also comprises embodiments where the branch of the branched alky residue or moiety is either linear or branched in itself.

The term Cv-C$\xi$alkyl refers to an alkyl radical consisting of a number of v to $\xi$ carbon atoms according to the above definition of "alkyl". For example C0-C2alkyl refers to an alkyl radical which is either not present or methyl, methylene, methylidyne, ethyl, ethylene, ethylidene, ethylidyne or the related higher radicals.

The term "cycloalkyl" refers, in a preferred embodiment of the present invention, to the cyclic analogue of an alkyl group, as defined above, optionally unsaturated and/or substituted. Preferred cycloalkyl groups are saturated cycloalkyl groups, more particularly those containing from three to eight carbon atoms, and even more preferably three to six carbon atoms. "Substituted cycloalkyl" refers to cycloalkyl groups further bearing one or more substituents. "Mono-unsaturated cycloalkyl" refers to cycloalkyl containing one double bond or one triple bond. "Poly-unsaturated cycloalkyl" refers to cycloalkyl containing at least two double bonds or two triple bonds or a combination of at least one double bond and one triple bond.

The term "alkenyl" refers, in a preferred embodiment of the present invention, to an unsaturated hydrocarbon group containing at least one carbon-carbon double bond, including straight-chain, branched-chain, and cyclic groups. Preferred alkenyl groups have two to twelve carbons. More preferred alkenyl groups have two to six carbons. "Substituted alkenyl" refers to alkenyl groups further bearing one or more substitutents.

The term "cycloalkenyl" refers, in a preferred embodiment of the present invention, to the cyclic analog of an alkenyl group, as defined above, optionally substituted. Preferred cycloalkenyl groups are containing from four to eight carbon atoms. "Substituted cycloalkenyl" refers to cycloalkenyl groups further bearing one or more substituents. "Mono-unsaturated cycloalkenyl" refers to cycloalkenyl containing one double bond. "Poly-unsaturated cycloalkenyl" refers to cycloalkenyl containing at least two double bonds. In a more preferred embodiment the term "cycloalkenyl" comprises also "aryl". In an alternative more preferred embodiment the term "cycloalkenyl" does not comprise "aryl".

The term "alkynyl" refers, in a preferred embodiment of the present invention, to an unsaturated hydrocarbon group containing at least one carbon-carbon triple bond, including straight-chain, branched-chain, and cyclic groups. Preferred alkynyl groups have two to twelve carbons. More preferred alkynyl groups have two to six carbons. "Substituted alkynyl" refers to alkynyl groups further bearing one or more substitutents.

The term "aryl" refers, in a preferred embodiment of the present invention, to aromatic groups having in the range of 6 to 14 carbon atoms and "substituted aryl" refers to aryl groups further bearing one or more substituents. It should be understood that any combination term using an "ar" or "aryl" prefix refers to analogs according to the above definition of "aryl". For example, a term such as "aryloxy" refers to aryl group linked to a second group via an oxygen atom.

Each of the above defined "alkyl", "cycloalkyl", and "aryl" shall be understood to include their halogenated analogs, whereby the halogenated analogs may comprise one or several halogen atoms. The halogenated analogs thus comprise any halogen radical as defined in the following.

The term "halo" refers, in a preferred embodiment of the present invention, to a halogen radical selected from fluoro, chloro, bromo, iodo. Preferred halo groups are fluoro, chloro and bromo.

The term "heteroaryl" refers, in a preferred embodiment of the present invention, to a stable 5 to 8 membered, preferably 5 or 6 membered monocyclic or 8 to 11 membered bicyclic aromatic heterocycle radical. Each heterocycle consists of carbon atoms and from 1 to 4 heteroatoms selected from the group consisting of nitrogen, oxygen, sulfur. The heterocycle may be attached by any atom of the cycle, which preferably results in the creation of a stable structure. Preferred heteroaryl radicals as used herein include, for example, furanyl, thienyl, pyrrolyl, oxazolyl, thiazolyl, imidazolyl, pyrazolyl, isoxazolyl, isothiazolyl, oxadiazolyl, triazolyl, tetrazolyl, thiadiazolyl, pyridinyl, pyridazinyl, pyrimidinyl, pyrazinyl, indolizinyl, indolyl, isoindolyl, benzofuranyl, benzothienyl, indazolyl, benzimidazolyl, benzthiazolyl, benzoxazolyl, purinyl, quinolizinyl, quinolinyl, isoquinolinyl, cinnolinyl, phthalazinyl, quinazolinyl, quinoxalinyl, naphthridinyl, pteridinyl, carbazolyl, acridinyl, phenazinyl, phenothiazinyl and phenoxazinyl. "Substituted heteroaryl" refers to heteroaryl groups further bearing one or more substituents.

The term "heterocyclyl" refers to a stable 5 to 8 membered, preferably 5 or 6 membered monocyclic or 8 to 11 membered bicyclic heterocycle radical which may be either saturated or unsaturated, and is non-aromatic. Each heterocycle consists of carbon atom(s) and from 1 to 4 heteroatoms selected from the group consisting of nitrogen, oxygen and sulfur. The heterocycle may be attached by any atom of the cycle, which preferably results in the creation of a stable structure. Preferred heterocycle radicals as used herein include, for example, pyrrolinyl, pyrrolidinyl, pyrazolinyl, pyrazolidinyl, piperidinyl, morpholinyl, thiomorpholinyl, pyranyl, thiopyranyl, piperazinyl, indolinyl, azetidinyl, tetrahydropyranyl, tetrahydrothiopyranyl, tetrahydrofuranyl, hexahydropyrimidinyl, hexahydropyridazinyl, 1,4,5,6-tetrahydropyrimidin-2-ylamine, dihydro-oxazolyl, 1,2-thiazinanyl-1,1-dioxide, 1,2,6-thiadiazinanyl-1,1-dioxide, isothiazolidinyl-1,1-dioxide and imidazolidinyl-2,4-dione. "Mono-unsaturated heterocyclyl" refers to heterocyclyl containing one double bond or one triple bond. "Poly-unsaturated heterocyclyl" refers to heterocyclyl containing at least two double bonds or two triple bonds or a combination of at least one double bond and one triple bond.

The term "substituted heterocyclyl" refers, in a preferred embodiment of the present invention, to heterocyclyl groups further bearing one or more substituents.

The terms "heterocyclyl", "heteroaryl" and "aryl", when associated with another moiety, unless otherwise specified, shall have the same meaning as given above. For example, "aroyl" refers to phenyl or naphthyl linked to a carbonyl group (C=O).

Each aryl or heteroaryl unless otherwise specified includes its partially or fully hydrogenated derivative. For example, quinolinyl may include decahydroquinolinyl and tetrahydroquinolinyl, naphthyl may include its hydrogenated derivatives such as tetrahydronaphthyl.

As used herein above and throughout this application, the terms "nitrogen" or "N" and "sulfur", "thio" or "S" include any oxidized form of nitrogen and sulfur, e.g., sulfoxide, sulfone, nitrone, nitro or N-oxide. The terms "nitrogen" or "N" also include quaternized forms of any basic nitrogen.

As used herein the term "aromatic heterocyclic 5-membered ring system" preferably means an 5-membered aromatic ring containing 1 to 4 heteroatoms whereby such heteroatoms are selected from the group comprising N, O and S. Preferred aromatic heterocyclic 5-membered ring system as used herein include the following radicals: furyl, thienyl, pyrrolyl, oxazolyl, isooxazolyl, thiazolyl, isothiazolyl, imidazolyl, pyrazolyl, triazolyl oxadiazolyl and thiadiazolyl.

As used herein, the wording "and any derivative of each thereof" as contained in a recitation of a group of compounds, means that any of the compound can be present as a derivative. Such derivative can be any derivative disclosed herein and is more preferably any derivative specified in connection with said compounds and group of compounds, respectively. It is also within the present invention that any substitution of any compound can be attached to said compound at any position, preferably any position which allows the formation of a chemically stable compound.

As used herein a wording defining the limits of a range of length such as, e.g., "from 1 to 5" means any integer from 1 to 5, i.e., 1, 2, 3, 4 and 5. In other words, any range defined by two integers explicitly mentioned is meant to comprise any integer defining said limits and any integer comprised in said range.

As used herein the term substituted shall mean that one or more H atom of the group or compound which is substituted, is replaced by a different atom, a group of atoms, a molecule or a molecule moiety. Such atom, group of atoms, molecule or molecule moiety is also referred to herein as substituent.

It is also within the present invention that any substitutent may in turn be substituted by a substituent. A group, structure, moiety or the like which is substituted may comprise several substituents which may either be different or the same.

The substituent can be selected from any of the groups, moieties and substituents disclosed herein However, the substituent is preferably selected from but is not limited to the group comprising H, alkyl, substituted alkyl, cycloalkyl, substituted cycloalkyl, heterocyclyl, substituted heterocyclyl, aryl, substituted aryl, heteroaryl, substituted heteroaryl, hydroxy, substituted hydroxy, thiol, substituted thiol, formyl, substituted formyl, aminocarbonyl, substituted aminocarbonyl, formylamino, substituted formylamino, aminocarbonylamino, substituted aminocarbonylamino, aminosulfonyl, substituted aminosulfonyl, substituted sulfonylamino, aminosulfonylamino, substituted aminosulfonylamino, aminocarbonyloxy, substituted aminocarbonyloxy, amino, substituted amino, substituted thiocarbonylamino, aminothiocarbonyl, substituted aminothiocarbonyl, aminothiocarbonylamino, substituted aminothiocarbonylamino, aminothiocarbonyloxy, substituted aminothiocarbonyloxy, substituted oxythiocarbonylamino, substituted sulfinyl, sulfonyl, substituted sulfonyl, substituted carbonyloxy, substituted oxycarbonyl, alkyloxy-heterocyclyl, substituted alkyloxy-heterocyclyl, halogen, trifluoromethyl, difluoromethyl, cyano, nitrone, ox, acyl, oxyacyl, carboxyl, carbamate, sulfonamide, sulfuryl, nitro, and substituted or unsubstituted cycloalkyalkyl, heterocyclylalkyl, arylalkyl, heteroarylalkyl, hydroxyalkyl, carbonylalkyl, aminocarbonylalkyl, carbonylaminoalkyl, aminocarbonylaminoalkyl, sulfonylaminoalkyl, aminosulfonylalkyl, aminosulfonylaminoalkyl, aminocarbonyloxyalkyl, oxycarbonylaminoalkyl, thioalkyl, sulfinylalkyl, sulfonylalkyl, carbonyloxyalkyl, oxycarbonyl alkyl, aminoalkyl, thiocarbonylaminoalkyl, aminothiocarbonylalkyl, aminothiocarbonyloxyalkyl, aminothiocarbonylaminoalkyl, oxythicarbonylaminoalkyl, alkylcycloalkyl, alkylheterocyclyl, alkylaryl, alkylheteroaryl, alkyloxy, alkylcarbonyl, alkylaminocarbonyl, alkylcarbonylamino, alkylaminocarbonylamino, alkylsulfonylamino, alkylaminosulfonyl, alkylaminosulfonylamino, alkylaminocarbonyloxy, alkyloxycarbonylamino, alkylthio, alkylsulfinyl, alkylsulfonyl, alkylcarbonyloxy, alkyloxycarbonyl, alkylamino, dialkylamino, alkylthiocarbonylamino, alkylaminothiocarbonyl, alkylaminothiocarbonyloxy, alkylaminothiocarbonylamino, alkyloxythicarbonylamino, arylalkylcycloalkyl, arylalkylheterocyclyl, arylalkylaryl, arylalkylheteroaryl, arylalkyloxy, arylalkylcarbonyl, arylalkylaminocarbonyl, arylalkylcarbonylamino, arylalkylaminocarbonylamino, arylalkylsulfonylamino, arylalkylaminosulfonyl, arylalkylaminosulfonylamino, arylalkylaminocarbonyloxy, arylalkyloxycarbonylamino, arylalkylthio, arylalkylsulfinyl, arylalkylsulfonyl, arylalkylcarbonyloxy, arylalkyloxycarbonyl, arylalkylamino, arylalkylthiocarbonylamino, arylalkylaminothiocarbonyl, arylalkylaminothiocarbonyloxy, arylalkylaminothiocarbonylamino, arylalkyloxythicarbonylamino, arylcycloalkyl, arylheterocyclyl, arylaryl, arylheteroaryl, aryloxy, arylcarbonyl, arylaminocarbonyl, arylcarbonylamino, arylaminocarbonylamino, arylsulfonylamino, arylaminosulfonyl, arylaminosulfonylamino, arylaminocarbonyloxy, aryloxycarbonylamino, arylthio, arylsulfinyl, arylsulfonyl, arylcarbonyloxy, aryloxycarbonyl, arylamino, arylthiocarbonylamino, arylaminothiocarbonyl, arylaminothiocarbonyloxy, arylaminothiocarbonylamino, aryloxythicarbonylamino, cycloalkylalkylcycloalkyl, cycloalkylalkylheterocyclyl, cycloalkylalkylaryl, cycloalkylalkylheteroaryl, cycloalkylalkyloxy, cycloalkylalkylcarbonyl, cycloalkylalkylaminocarbonyl, cycloalkylalkylcarbonylamino, cycloalkylalkyl aminocarbonylamino, cycloalkylalkylsulfonyl amino, cycloalkylalkylaminosulfonyl, cycloalkylalkylaminosulfonylamino, cycloalkylalkylaminocarbonyloxy, cycloalkylalkyloxycarbonylamino, cycloalkylalkylthio, cycloalkylalkylsulfinyl, cycloalkylalkylsulfonyl, cycloalkylalkylcarbonyloxy, cycloalkylalkyloxycarbonyl, cycloalkylalkylamino, cycloalkylalkylthiocarbonylamino, cycloalkylalkylaminothiocarbonyl, cycloalkylalkylaminothiocarbonyloxy, cycloalkylalkylaminothiocarbonylamino, cycloalkylalkyloxythicarbonylamino, cycloalkylcycloalkyl, cycloalkylheterocyclyl, cycloalkylaryl, cycloalkylheteroaryl, cycloalkyloxy, cycloalkylcarbonyl, cycloalkylaminocarbonyl, cycloalkylcarbonylamino, cycloalkylaminocarbonylamino, cycloalkylsulfonylamino, cycloalkylaminosulfonyl, cycloalkylaminosulfonylamino, cycloalkylaminocarbonyloxy, cycloalkyloxycarbonylamino, cycloalkylthio, cycloalkylsulfinyl, cycloalkylsulfonyl, cycloalkylcarbonyloxy, cycloalkyloxycarbonyl, cycloalkylamino, cycloalkylthiocarbonylamino, cycloalkylaminothiocarbonyl, cycloalkylaminothiocarbonyloxy, cycloalkylaminothiocarbonylamino, cycloalkyloxythicarbonylamino, heterocyclylcycloalkyl, heterocyclylheterocyclyl, heterocyclylaryl, heterocyclylheteroaryl, heterocyclyloxy, heterocyclylcarbonyl, heterocyclylaminocarbonyl, heterocyclylcarbonylamino, heterocyclylaminocarbonylamino, heterocyclylsulfonylamino, heterocyclylaminosulfonyl, heterocyclylaminosulfonylamino, heterocyclylaminocarbonyloxy, heterocyclyloxycarbonylamino, heterocyclylthio, heterocyclylsulfinyl, heterocyclylsulfonyl, heterocyclylcarbonyloxy, heterocyclyloxycarbonyl, heterocyclylamino, heterocyclylthiocarbonylamino, heterocyclylaminothiocarbonyl, heterocyclylaminothiocarbonyloxy, heterocyclylaminothiocarbonylamino, heterocyclyloxythicarbonylamino, heterocyclylalkylcycloalkyl, heterocyclylalkylheterocyclyl, heterocyclylalkylaryl, heterocyclylalkylheteroaryl, heterocyclylalkyloxy, heterocyclylalkylcarbonyl, heterocyclylalkylaminocarbonyl, heterocyclylalkylcarbonylamino, heterocyclylalkylaminocarbonylamino, heterocyclylalkylsulfonylamino, heterocyclylalkylaminosulfonyl, heterocyclylalkylaminosulfonylamino, heterocyclylalkylaminocarbonyloxy, heterocyclylalkyloxycarbonylamino, heterocyclylalkylthio, heterocyclylalkylsulfinyl, heterocyclylalkylsulfonyl, heterocyclylalkylcarbonyloxy, heterocyclylalkyloxycarbonyl, heterocyclylalkylamino, heterocyclylalkylthiocarbonylamino, heterocyclylalkylaminothiocarbonyl, heterocyclylalkylaminothiocarbonyloxy, heterocyclylalkylaminothiocarbonylamino, heterocyclylalkyloxythicarbonylamino, heteroarylcycloalkyl, heteroarylheterocyclyl, heteroarylaryl, heteroarylheteroaryl, heteroaryloxy, heteroarylcarbonyl, heteroarylaminocarbonyl, heteroarylcarbonylamino, heteroarylaminocarbonylamino, heteroarylsulfonylamino, heteroarylaminosulfonyl, heteroarylaminosulfonylamino, heteroarylaminocarbonyloxy, heteroaryloxycarbonylamino, heteroarylthio, heteroarylsulfinyl, heteroarylsulfonyl, heteroarylcarbonyloxy, heteroaryloxycarbonyl, heteroarylamino, heteroarylthiocarbonylamino, heteroarylaminothiocarbonyl, heteroarylaminothiocarbonyloxy, heteroarylaminothiocarbonylamino, heteroaryloxythicarbonylamino, heteroarylalkylcycloalkyl, heteroarylalkylheterocyclyl, heteroarylalkylaryl, heteroarylalkylheteroaryl, heteroarylalkyloxy, heteroarylalkylcarbonyl, heteroarylalkylaminocarbonyl, heteroarylalkylcarbonylamino, heteroarylalkylaminocarbonylamino, heteroarylalkylsulfonylamino, heteroarylalkylaminosulfonyl, heteroarylalkylaminosulfonylamino, heteroarylalkylaminocarbonyloxy, heteroarylalkyloxycarbonylamino, heteroarylalkylthio, heteroarylalkylsulfinyl, heteroarylalkylsulfonyl, heteroarylalkylcarbonyloxy, heteroarylalkyloxycarbonyl, heteroarylalkylamino, heteroarylalkylthiocarbonylamino, heteroarylalkylaminothiocarbonyl, heteroarylalkylaminothiocarbonyloxy, heteroarylalkylaminothiocarbonylamino, heteroarylalkyloxythicarbonylamino, alkylcycloalkylalkyl, alkylheterocyclylalkylalkyl, alkylarylalkylalkyl, alkylheteroarylalkylalkyl, alkyloxyalkylalkyl, alkylcarbonylalkylalkyl, alkylaminocarbonylalkylalkyl, alkylcarbonylaminoalkylalkyl, alkylaminocarbonylaminoalkylalkyl, alkylsulfonylaminoalkylalkyl, alkylaminosulfonylalkylalkyl, alkylaminosulfonylaminoalkylalkyl, alkylaminocarbonyloxyalkylalkyl, alkyloxycarbonylaminoalkylalkyl, alkylthioalkylalkyl, alkylsulfinylalkylalkyl, alkylsulfonylalkylalkyl, alkylcarbonyloxyalkylalkyl, alkyloxycarbonylalkylalkyl, alkylaminoalkylalkyl, alkylthiocarbonylaminoalkylalkyl, alkylaminothiocarbonylalkylalkyl, alkylaminothiocarbonyloxyalkylalkyl, alkylaminothiocarbonylaminoalkylalkyl, alkyloxythicarbonylaminoalkylalkyl, arylalkylcycloalkyalkylalkyl, arylalkylheterocyclylalkylalkyl, arylalkylarylalkylalkyl, arylalkylheteroarylalkylalkyl, arylalkyloxyalkylalkyl, arylalkylcarbonylalkylalkyl, arylalkylaminocarbonylalkyl, arylalkylcarbonylaminoalkyl, arylalkylaminocarbonylaminoalkyl, arylalkylsulfonylaminoalkyl, arylalkylaminosulfonylalkyl, arylalkylaminosulfonylaminoalkyl, arylalkylaminocarbonyloxyalkyl, arylalkyloxycarbonylaminoalkyl, arylalkylthioalkyl, arylalkylsulfinylalkyl, arylalkylsulfonylalkyl, arylalkylcarbonyloxyalkyl, arylalkyloxycarbonylalkyl, arylalkylaminoalkyl, arylalkylthiocarbonylaminoalkyl, arylalkylaminothiocarbonylalkyl, arylalkylaminothiocarbonyloxyalkyl, arylalkylaminothiocarbonylaminoalkyl, arylalkyloxythicarbonylaminoalkyl, arylcycloalkylalkyl, arylheterocyclylalkyl, arylarylalkyl, arylheteroarylalkyl, aryloxyalkyl, arylcarbonylalkyl, arylaminocarbonylalkyl, arylcarbonylaminoalkyl, arylaminocarbonylaminoalkyl, arylsulfonylaminoalkyl, arylaminosulfonylalkyl, arylaminosulfonylaminoalkyl, arylaminocarbonyloxyalkyl, aryloxycarbonylaminoalkyl, arylthioalkyl, arylsulfinylalkyl, arylsulfonylalkyl, arylcarbonyloxyalkyl, aryloxycarbonylalkyl, arylaminoalkyl, arylthiocarbonylaminoalkyl, arylaminothiocarbonylalkyl, arylaminothiocarbonyloxyalkyl, arylaminothiocarbonylaminoalkyl, aryloxythicarbonylaminoalkyl, cycloalkylalkylcycloalkylalkyl, cycloalkylalkylheterocyclylalkyl, cycloalkylalkylarylalkyl, cycloalkylalkylheteroarylalkyl, cycloalkylalkyloxyalkyl, cycloalkylalkylcarbonylalkyl, cycloalkylalkylaminocarbonylalkyl, cycloalkylalkylcarbonylaminoalkyl, cycloalkylalkylaminocarbonylaminoalkyl, cycloalkylalkylsulfonylaminoalkyl, cycloalkylalkylaminosulfonylalkyl, cycloalkylalkylaminosulfonylaminoalkyl, cycloalkylalkylaminocarbonyloxyalkyl, cycloalkylalkyloxycarbonylaminoalkyl, cycloalkylalkylthioalkyl, cycloalkylalkylsulfinylalkyl, cycloalkylalkylsulfonylalkyl, cycloalkylalkylcarbonyloxyalkyl, cycloalkylalkyloxycarbonylalkyl, cycloalkylalkylaminoalkyl, cycloalkylalkylthiocarbonylaminoalkyl, cycloalkylalkylaminothiocarbonylalkyl, cycloalkylalkylaminothiocarbonyloxyalkyl, cycloalkylalkylaminothiocarbonylaminoalkyl, cycloalkylalkyloxythicarbonylaminoalkyl, cycloalkylcycloalkylalkyl, cycloalkylheterocyclylalkyl, cycloalkylarylalkyl, cycloalkylheteroarylalkyl, cycloalkyloxyalkyl, cycloalkylcarbonylalkyl, cycloalkylaminocarbonylalkyl, cycloalkylcarbonylaminoalkyl, cycloalkylaminocarbonylaminoalkyl, cycloalkylsulfonylaminoalkyl, cycloalkylaminosulfonylalkyl, cycloalkylaminosulfonylaminoalkyl, cycloalkylaminocarbonyloxyalkyl, cycloalkyloxycarbonylaminoalkyl, cycloalkylthioalkyl, cycloalkylsulfinylalkyl, cycloalkylsulfonylalkyl, cycloalkylcarbonyloxyalkyl, cycloalkyloxycarbonylalkyl, cycloalkylaminoalkyl, cycloalkylthiocarbonylaminoalkyl, cycloalkylaminothiocarbonylalkyl, cycloalkylaminothiocarbonyloxyalkyl, cycloalkylaminothiocarbonylaminoalkyl, cycloalkyloxythicarbonylaminoalkyl, heterocyclylcycloalkylalkyl, heterocyclylheterocyclylalkyl, heterocyclylarylalkyl, heterocyclylheteroarylalkyl, heterocyclyloxyalkyl, heterocyclylcarbonylalkyl, heterocyclylaminocarbonylalkyl, heterocyclylcarbonylaminoalkyl, heterocyclylaminocarbonylaminoalkyl, heterocyclylsulfonylaminoalkyl, heterocyclylaminosulfonylalkyl, heterocyclylaminosulfonylaminoalkyl, heterocyclylaminocarbonyloxyalkyl, heterocyclyloxycarbonylaminoalkyl, heterocyclylthioalkyl, heterocyclylsulfinylalkyl, heterocyclylsulfonylalkyl, heterocyclylcarbonyloxyalkyl, heterocyclyloxycarbonylalkyl, heterocyclylaminoalkyl, heterocyclylthiocarbonylaminoalkyl, heterocyclylaminothiocarbonylalkyl, heterocyclylaminothiocarbonyloxyalkyl, heterocyclylaminothiocarbonylaminoalkyl, heterocyclyloxythicarbonylaminoalkyl, heterocyclylalkylcycloalkylalkyl, heterocyclylalkylheterocyclylalkyl, heterocyclylalkylarylalkyl, heterocyclylalkylheteroarylalkyl, heterocyclylalkyloxyalkyl, heterocyclylalkylcarbonylalkyl, heterocyclylalkylaminocarbonylalkyl, heterocyclylalkylcarbonylaminoalkyl, heterocyclylalkylaminocarbonylaminoalkyl, heterocyclylalkylsulfonylaminoalkyl, heterocyclylalkylaminosulfonylalkyl, heterocyclylalkylaminosulfonylaminoalkyl, heterocyclylalkylaminocarbonyloxyalkyl, heterocyclylalkyloxycarbonylaminoalkyl, heterocyclylalkylthioalkyl, heterocyclylalkylsulfinylalkyl, heterocyclylalkylsulfonylalkyl, heterocyclylalkylcarbonyloxyalkyl, heterocyclylalkyloxycarbonylalkyl, heterocyclylalkylaminoalkyl, heterocyclylalkylthiocarbonylaminoalkyl, heterocyclylalkylaminothiocarbonylalkyl, heterocyclylalkylaminothiocarbonyloxyalkyl, heterocyclylalkylaminothiocarbonylaminoalkyl, heterocyclylalkyloxythicarbonylaminoalkyl, heteroarylcycloalkylalkyl, heteroarylheterocyclylalkyl, heteroarylarylalkyl, heteroarylheteroarylalkyl, heteroaryloxyalkyl, heteroarylcarbonylalkyl, heteroarylaminocarbonylalkyl, heteroarylcarbonylaminoalkyl, heteroarylaminocarbonylaminoalkyl, heteroarylsulfonylaminoalkyl, heteroarylaminosulfonylalkyl, heteroarylaminosulfonylaminoalkyl, heteroarylaminocarbonyloxyalkyl, heteroaryloxycarbonylaminoalkyl, heteroarylthioalkyl, heteroarylsulfinylalkyl, heteroarylsulfonylalkyl, heteroarylcarbonyloxyalkyl, heteroaryloxycarbonylalkyl, heteroarylaminoalkyl, heteroarylthiocarbonylaminoalkyl, heteroarylaminothiocarbonylalkyl, heteroarylaminothiocarbonyloxyalkyl, heteroarylaminothiocarbonylaminoalkyl, heteroaryloxythicarbonylaminoalkyl, heteroarylalkylcycloalkylalkyl, heteroarylalkylheterocyclylalkyl, heteroarylalkylarylalkyl, heteroarylalkylheteroarylalkyl, heteroarylalkyloxyalkyl, heteroarylalkylcarbonylalkyl, heteroarylalkylaminocarbonylalkyl, heteroarylalkylcarbonylaminoalkyl, heteroarylalkylaminocarbonylaminoalkyl, heteroarylalkylsulfonylaminoalkyl, heteroarylalkylaminosulfonylalkyl, heteroarylalkylaminosulfonylaminoalkyl,
heteroarylalkylaminocarbonyloxyalkyl, heteroarylalkyloxycarbonylaminoalkyl, heteroarylalkylthioalkyl, heteroarylalkylsulfinylalkyl, heteroarylalkylsulfonylalkyl, heteroarylalkylcarbonyloxyalkyl, heteroarylalkyloxycarbonylalkyl, heteroarylalkylaminoalkyl, heteroarylalkylthiocarbonylaminoalkyl, heteroarylalkylaminothiocarbonylalkyl,
heteroarylalkylaminothiocarbonyloxyalkyl, heteroarylalkylaminothiocarbonylaminoalkyl, heteroarylalkyloxythicarbonylaminoalkyl,
alkyloxyaryl, substituted alkyloxyaryl,
alkyloxyheteroaryl, substituted alkyloxyheteroaryl,
alkylthiocycloalkyl and substituted alkylthiocycloalkyl.

Any of the substituents may be substituted itself by any of the aforementioned substituents. This applies preferably to cycloalkyl, heterocyclic, aryl, heteroaryl and aryloxy. It is also preferred that alkoxy and mercapto are those of a lower alkyl group. It is to be acknowledged that any of the definition provided herein also applies to any substituent.

As used herein in connection with an embodiment of the various aspects of the present invention the term "each and independently selected from a group" or "are individually and independently from each other selected from the group" refers to two or more atoms, groups, substituents, moieties or whatsoever and describes that the single atom, group, substituent or moiety mentioned can be selected from the group. The wording used is a truncation which avoids unnecessary repetition as otherwise for each of the atoms, groups etc. the same group definition would have to be repeated.

As used herein in connection with an embodiment of the various aspects of the present invention the term "each and individually absent" refers to two or more atoms, groups, substituents, moieties or whatsoever and describes that the single atom, group, substituent or moiety mentioned can be absent regardless whether any of the other atoms, groups etc. mentioned is absent. The wording used is a truncation which avoids unnecessary repetition as otherwise for each of the atoms, groups etc. the fact that it may be absent in an embodiment of the invention would have to be repeated.

It is within the present invention that at least some of the substituents are non-symmetrical in their design and, therefore, provide different orientations and optionally reaction sites or positions which can be used to attach the substituent to another moiety of the compound. Based on this the linkage between the substituent and the respective moiety of the compound varies depending on the particular orientation and thus site(s) of the substituent used for such linkage in various embodiments of the compounds disclosed herein. It is within the present invention that any such orientation of the substituent and thus linkage is covered by the present disclosure and representations. The same applies also to other groups or moieties. It should therefore be understood that for example if X in a hypothetical molecule A-X—Y is NHCO, both orientations of X are included and the resulting molecules are A-NHCO—Y and A-CONH—Y.

It is within the present invention that the features of the various embodiments of the present invention can be realized either alone or in combination with the features of any other embodiment(s) of the present invention. Thus any combination of an/the individual feature or the combination of features of an embodiment of the present invention with an/the individual feature(s) or the combination of features of any other embodiment(s), either alone or in combination with (an) other embodiment(s), shall be disclosed by the present specification. This applies particularly to the various embodiments and features, respectively, of the compounds disclosed herein.

In a further aspect the present invention is related to a pharmaceutical composition comprising a compound according to any of the aspects of the present invention and a pharmaceutically acceptable carrier, diluent or excipient.

In compounds disclosed in the present invention stereogenic carbons may be in the R or S configuration and therefore compounds with one or more stereogenic carbons may occur as any possible stereoisomere or combination thereof. In consequence any of the compounds according to the present invention containing one symmetric carbon atom may occur as racemate, racemic mixture or as one of the two single enantiomers. In analogy, any of the compounds according to the present invention containing more than one asymmetric carbon atom may occur as racemate, racemic mixture, any enantiomer, diastereomeric mixture or as one of the possible individual diastereomers. All such isomeric forms of these compounds are expressly included in the present invention.

It shall be understood by the one of ordinary skill in the art that all compounds of the invention are preferably those which are chemically stable. This applies to any of the various uses of the compounds according to the present invention disclosed herein.

In a further aspect the compounds according to the present invention comprise a further moiety. Such further moiety preferably confers functional features to the compounds. It is to be acknowledged that such further moiety is preferably attached or incorporated to any other part of the compounds according to the present invention, although it is also within the present invention that the moiety and moieties, more preferably the individual chemical or functional group or arrangement of such group, present in the compounds according to the present invention provides for the functional feature(s). More preferably such further moiety is an additional moiety, most preferably a compound on its own, which is attached, preferably conjugated to any of the compounds according to the present invention. Such further moiety is preferably selected from the group comprising a detection moiety, a targeted moiety and a delivery moiety. It is to be understood that the same moiety can have several functions. Accordingly, any specification in so far is not limiting the purpose for which such further moiety is incorporated into any of the compounds according to the present invention.

A detection moiety is preferably a moiety which allows the detection of the compound in vitro, ex vivo, in vivo and/or in situ. A preferred detection moiety is a label.

In a preferred embodiment the compound according to the present invention comprises a label and is also referred to herein as a labeled compound according to the present invention. By a "labeled compound according to the present invention" herein is meant a compound according to the present invention that has at least one element, isotope or chemical compound attached or incorporated to enable the detection of the compound or the compound bound to a target such as an integrin. It is within the present invention that the label is preferably either part of the compounds according to the present invention or part of any of the further moieties described herein which confer functional features to the compounds, whereby in an even more preferred embodiment such functional feature is the provision of a label and in particular a radioactive label to the compound(s). In general, labels as used herein, may be taken from any of the following classes: a) isotopic labels, which are preferably radioactive or heavy isotopes, including paramagnetic material; b) X-ray attenuating material; c) immune labels which comprise but are not limited to antibodies, antigens, or labels recognized by antibodies or other proteins such as biotin or antibody epitopes; d) colored, chemiluminescent, luminescent or fluorescent labels; e) enzyme substrates or enzymes; and f) other labels complexing detectable ions such as hexahistidine sequence. The labels may be incorporated into the compound at any position using well known methods, which are selected, in part, based on the chemical nature of the compound and the label. More preferred labels include $^{14}C$, $^{13}C$, $^{15}N$, $^{3}H$, $^{99}Tc$, biotin, and fluorescent labels as are well known in the art.

A specifically bound labeled compound could be detected by using in vivo imaging methods like radionucleotide imaging, positron emission tomography, computerized axial tomography, X-ray, infrared imaging, or magnetic imaging resonance methods. The specifically bound labeled compound could be also detected using ex vivo imaging methods, wherein, following the administration of such compound isolated cells or tissue probes are obtained from the individual and the integrin bound compound will be detected in these probes. Alternatively, the labeled compound could be applied to the isolated cells or tissue probes after obtaining the probes from the individuals. The specific binding of the labeled compound to the integrin could be detected directly or via the label moiety by radioactivity, fluorescence, luminescence, infrared imaging, X-ray, and immunological or enzymatic reactions. For example, the compound is directly coupled to an enzyme substrate, i.e., labeled with an enzyme substrate, which could be detected after incubation with the enzyme via a chromogenic, fluorescent or luminescent reaction, or the label could be recognized by an other molecule such as an antibody which is conjugated to an enzyme such as horseradish peroxidase, alkaline phosphatase, beta-galactosidase and others that are well known in the art.

In a further embodiment the further moiety is a targeted moiety. Preferably, the targeted moiety is a pharmaceutically active compound, which could be targeted by the compound according to the present invention to the site of action via specific interaction of the compound according to the present invention with the integrin, more preferably alpha5beta1.

As mentioned above, the targeted moiety can also be active as detection moiety. The targeted moiety is preferably selected from the group comprising cytotoxins, radionuclides, chemotherapeutics, pharmaceutically active proteins like antibodies or cytotoxic proteins, linker molecules for delivery of gentherapeutic vectors, or liposomes.

More preferably and generally applicable to any further moiety described herein, the attachment of the chemical compound according to the present invention to the further moiety is achieved through a binding mechanism which is selected from the group comprising covalent binding, non-covalent binding. For example, where the pharmaceutical active agent is a cytotoxin coupled to the compounds according to the present invention. This complex should bind specifically to the integrin alpha5beta1, which is poorly expressed on quiescent vasculature, but significantly upregulated on endothelial cells in tumors and after stimulation with growth factors. Therefore this complex should bind only to activated endothelial cells, which are symptomatic for disorders connected with angiogenesis, kill these cells exclusively and stop consequently the pathological angiogenesis.

In a preferred embodiment the further moiety is a delivery moiety. Such delivery moiety is any agent which is suitable to improve the stability, solubility and pharmacokinetic properties of the compound to optimize the bioavailability after administration. Therefore, the compound shows improved properties through the moiety itself or in combination with a particular formulation. For example, the addition of a fluorine group to the molecule increases the solubility in polyfluorated vehicles and improves the bioavailability of the compound in combination with this special vehicle.

In an embodiment the composition comprises a further pharmaceutically active compound, preferably such further pharmaceutically active compound is selected from the group comprising chemotherapeutic agents, anti-hormones, agents influencing the vascular permeability, agents for photodynamic therapy, anti-inflammatory, anti-fibrotic, and anti-angiogenic drugs. The combination of integrin inhibiting drugs with different mechanisms of action may lead to additive or synergistic therapeutic effects.

Any of these agents are known to the ones skilled in the art. Preferred chemotherapeutic agents are 5-fluorouracil, gemcitabine, carboplatin, paclitaxel, taxol, oxaliplatin, irinotecan, and cisplatin. Preferred agents used as anti-hormones are cyproterone acetate and tamoxifen. Preferred agents influencing vascular permeability and/or angiogenesis are COX-2 inhibitors, NO-synthase inhibitors, bradykinin receptor antagonists, such as Icatibant, and others. Also preferred anti-angiogenic drugs are compounds effecting VEGF activity, such as, VEGF or VEGF-receptor antibodies or fragments, e.g., Avastin, Lucentis, soluble VEGF-receptor fragments, VEGF binding aptamers (Macugen, Eye001), VEGF-receptor-kinase inhibitors, e.g., SU5416, Bay 43-9006 or PTK787/ZK222584, VEGF or VEGF-receptor mRNA interfering drugs e.g. Cand5 or Sirna 027 or agents affecting the action of other angiogenic growth factors such as PDGF and others. Other preferred anti-angiogenic drugs are inhibitors of matrix metalloproteases, endogenous inhibitors, such as endostatin and angiostatin, other integrin inhibitors, thalidomide and derivatives and others. A preferred agent used for photodynamic therapy is Visudyne. Preferred agents used as anti-inflammatory drugs are steroids, nonsteroidal anti-inflammatory drugs including aspirin, folic acid antagonists (e.g. methotrexate), hydroxychloroquine, sulfasalazine, pyrimidine synthesis inhibitors (leflunomide), COX-2 inhibitors as well as biologics such as compounds directed against cytokines (e.g. TNF antagonists like Enbrel, Infliximab, Adalimumab), compounds directed against T cells, antigen presenting cells (e.g. Alefacept, Efalizumab) and anti-inflammatory cytokines. Preferred agents used as anti-fibrotic drugs are interferons, TGFβ inhibitors (e.g. TGFβ antibodies or soluble TGFβ decoy receptor), inhibitors for other integrins (e.g. alphavbeta3 or alphavbeta6), Endothelin A receptor antagonists (e.g. LU135252), anti-oxidants (e.g. silymarin), phosphodiesterase inhibitors (e.g. pentoxifylline), thiazolidinediones, immunsuppressive agents (e.g. rapamycin and mycophenolate mofetil), halofuginone and inhibitors of the renin-angiotensin system.

In a preferred embodiment of the composition the compound is present as a pharmaceutically acceptable salt or a pharmaceutically active solvate.

In an even more preferred embodiment the pharmaceutically active compound is either alone or in combination with any of the ingredients of the composition present in a multitude of individualized dosages and/or administration forms.

It is also within the present invention that the pharmaceutical composition as well as the medicament which is manufactured using the compounds according to the present invention, is used with other therapies used in the prevention and/or treatment of any disease disclosed herein, preferably any disease for the prevention and/or treatment of which the pharmaceutical composition and/or the medicament which is manufactured using the compounds according to the present invention, is used. Such other therapies are selected from the group comprising chemotherapy, anti-hormone therapy, radiation therapy, photodynamic therapy, anti-angiogenic therapy and surgery. These other therapies are known to the ones skilled in the art. Basically chemotherapy means the standard chemotherapy usually applied to cancer patients as well as the metronomic therapy, the frequent application of low dose chemotherapeutics (Hahnfeldt, 2003, J Theor Biol., 220, 545). Anti-hormone therapy preferably means the standard hormone therapy usually applied to cancer patients with hormone dependent cancers such as breast or prostate cancer. Photodynamic therapy is the current standard treatment for defined stages of age related macular degeneration based on the photochemical injury of the blood vessels in the neovascular membranes of AMD patients, through the properties of a photo-active compound and a targeted laser treatment of the affected areas in the eye (Verteporfin in Visudyne, Novartis).

In a further aspect the present invention is related to the use of the compounds according to the present invention as a medicament and for the manufacture of a medicament, respectively. It is to be understood that any of the compounds according to the present invention can be used for the treatment of or for the manufacture of a medicament for the treatment of any of the diseases disclosed herein, irrespective of the mode of action or the causative agent involved as may be specified herein. Of course, it may particularly be used for any form of such disease where the particular causative agent is involved. Causative agent as used herein also means any agent which is observed in connection with the particular disease described and such agent is not necessarily causative in the sense that it causes the observed diseases or diseased condition. It is within the present invention that the medicament is preferably a pharmaceutical composition as described herein. The features disclosed. in connection with the medicament and its manufacture are also applicable to the pharmaceutical composition and the features disclosed in connection with the pharmaceutical composition are also applicable to the medicament. More preferably, the pharmaceutical composition according to the present invention can be used for the treatment and/or prevention of any of the diseases disclosed herein.

The same applies also to each and any other use of the compounds according to the present invention, more particularly to the use of the compounds according to the present invention as diagnostic tools including in vivo and ex vivo diagnostics, the use of said compounds in the method for the treatment of any of the diseases disclosed herein and the use of said compounds as inhibitors, preferably as inhibitors to an integrin and more preferable the alpha5beta1 integrin.

As used herein, the term "disease" describes any disease, diseased condition or pathological condition including injuries, disabilities, syndromes, symptoms, deviant behaviors, and atypical variations of structure and function as well as conditions of unknown etiology. In connection with the present invention the terms disease and disorder shall be used and understood in an interchangeable way, if not explicitly indicated to the contrary. Such disease may also be defined as abnormal condition, preferably connected with pathological angiogenesis or pathological proliferation, migration and differentiation of cells. Also, in case of a pathogen, disease means a condition where a pathogen or an unwanted organism is present or present in a concentration or compartment where it is undesired and thus subject to reduction in numbers, removal, elimination, prevention of invasion and/or destruction by using the compounds according to the present invention.

The term "treatment" as used herein comprises both treatment and prevention of a disease. It also comprises follow-up treatment and a combination treatment of a disease. Follow-up treatment is realized upon a treatment of a disease using compounds preferably different from the one according to the present invention, for example, after a failed or insufficient pre-treatment of the targeted disease, such as chemotherapy, anti-hormone therapy, radiation therapy, photodynamic therapy, other anti-angiogenic therapy, anti-inflammatory therapy, anti-fibrotic therapy or surgical treatment. Follow-up treatment also means continuation of the same treatment preferably at lower dosage. Combination treatment means the treatment of a disease with a compound according to the present invention in combination with another therapeutically active compound or method. Such compounds could be for example chemotherapeutic agents, anti-hormones, an agent for photodynamic therapy, agents influencing the vascular permeability, anti-inflammatory agents, anti-fibrotic agents or anti-angiogenic compounds, like compounds affecting the VEGF activity, or agents affecting the action of other angiogenic growth factors, such as PDGF. Such methods could be radiation therapy, or photodynamic therapy.

The term "angiogenesis" includes hemangiogenesis which is the process of formation of new blood vessels from sprouts of existing vessels, lymphangiogenesis which is the process of formation of lymphatic vessels, and vasculogenesis which means that vessels arise from endothelial cell precursors (Gasparini et al., 2005, J Clin Oncol, 23, 1295; Alitalo et al., 2005, Nature 438, 946).

The term "inhibition of angiogenesis" preferably means the inhibition of angiogenesis in a tissue in an individual, by administering a compound according to the present invention, whereby the compound interacts with an integrin, preferably alpha5beta1, thereby reducing or inhibiting angiogenesis in the tissue in the individual. Such inhibition provides the reduction of severity of a pathological condition associated with angiogenesis. Inhibition of angiogenesis means also the reduction of the amount of newly formed blood vessels in a tissue in the presence of the compound according to the present invention compared to the tissue in the absence of this compound. Methods for determining the amount of blood vessel formation in a tissue are described in the example and are well known in the art.

The term "inhibition of inflammation" preferably means the inhibition of processes connected with a chronic or acute pathological immune response such as vascular and cellular reactions mediated by chemical factors that are derived from plasma proteins or cells and are produced in response to or activated by the inflammatory stimulus, by administering a compound according to the present invention, whereby the compound interacts with an integrin, preferably alpha5beta1, thereby reducing or inhibiting inflammation in the tissue in the individual. Such inhibition provides the reduction of severity of a pathological condition associated with inflammation. Inhibition of inflammation additionally or alternatively means the reduction of the amount of immigrated and activated immune cells or the level of mediators of inflammation in the tissue in the presence of the compound according to the present invention compared to the tissue in the absence of this compound. Methods for determining the severity of inflammation in a tissue are well known in the art.

The term "inhibition of fibrosis" preferably means the inhibition of processes connected with a non-physiological wound healing or similar irritations following a persistent exogenous or endogenous stimulus, by administering a compound according to the present invention, whereby the compound interacts with an integrin, preferably alpha5beta1, thereby reducing or inhibiting fibrosis in the tissue in the individual. Such inhibition provides the reduction of severity of a pathological condition associated with tissue remodelling and hypertrophic scarring. Inhibition of fibrosis additionally or alternatively means the reduction of the amount of extracellular matrix protein deposits, profibrotic mediators and myofibroblasts in the tissue in the presence of the compound according to the present invention compared to the tissue in the absence of this compound. Methods for determining the severity of fibrosis in a tissue are well known in the art.

The compounds according to the present invention can be characterized by the $IC_{50}$ value, which is also referred to herein as $IC_{50}$. The term "$IC_{50}$" means the inhibition constant and describes the inhibition of the interaction between the integrin and the most preferred ligand of this integrin. The integrin is preferably alpha5beta1, but for determining the selectivity of the compound, also another integrin can be used. The term "selectivity" preferably means a more than 10-fold and more preferably a more than 100-fold lower $IC_{50}$ value for integrin alpha5beta1 in comparison to the other integrin(s).

The compounds according to the present invention are understood to bind to an integrin thus interfering with the binding of the integrin to a ligand. Preferably, such ligand is expressed in the extracellular matrix of a tissue, in body fluids or on a cell surface. The specificity of interaction of the compounds according to the present invention with the integrins, more preferably with alpha5beta1, defines the molecular environment where the compounds according to the present invention are active in terms of integrin inhibition and as compounds for the treatment of a disease. Integrins are crucial in mediating a number of biological processes, whereby particularly integrin alpha5beta1 is an integrin strongly associated with angiogenesis, and even more preferably related to pathological angiogenesis. As used herein, pathological angiogenesis is any angiogenesis which is undesired. An undesired angiogenesis is any angiogenesis which results in a disease or condition which is different from a desired condition, at least from a medical point of view. Additionally, alpha5beta1 is also strongly associated with other processes based on pathological migration, proliferation and differentiation of cells. Further diseases which can be addressed using the compounds according to the present invention are those which are connected with or where one of the following processes is involved: proliferation, migration and differentiation of alpha5beta1 expressing cells.

However, the mode of action of the compounds according to the present invention is not limited to competitive inhibition of the binding of an integrin and its ligand, but a compound according to the present invention can also change the binding characteristics of the integrin to the ligand and, optionally, also vice versa, preferably through a different mechanism, such as an allosteric mechanism, which includes uncompetitive and noncompetitive inhibition, upon which either the integrin or the ligand is changed so as to modulate the interaction between the integrin and a ligand thereof. Finally, in principle, the compounds according to the present invention can also induce partial antagonistic and/or agonistic effects on integrins (Humphries, 2000, Trends Pharmacol Science, 21, 29) or act via irreversible inhibition of integrins. Any of these situations, i.e., an inhibitory as well as a stimulatory situation with regard to the binding of an integrin and a ligand thereof regardless of the particular underlying mode of action, represent an integrin associated state, which can be influenced by the compounds according to the present invention and thus be a reduction or inhibition of angiogenesis or induction of agonistic effects on integrins, as used herein. The term integrin associated state is preferably any of the diseases disclosed herein. Also insofar a disease in the meaning of the present invention is angionesis, neovascularization, inflammation and fibrosis.

The wealth of potential applications in terms of medical conditions or diseases which may be treated using the compounds according to the present invention can also be explained by the impact of said compounds on the proliferation and migration of alpha5beta1 expressing cells. Beside the expression of alpha5beta1 on activated endothelial cells this integrin is also up-regulated on other types of proliferating cells such as tumor cells, retinal pigment epithelial cells, fibroblasts, inflammatory cells and others (WO2005/092073; Thannickal 2003, J. Biol. Chem. 278, 12384; Proulx, 2003, Molecular Vision, 9, 473; Kloss 1999, J Comp Neurol 411, 162; Shang 1998, J 1 mm 160, 467; Issekutz Inflam Res. 1998 47, S123; Bums 2001 J Imm 166, 4644; Dastych, 2001, Allergy and Immunology 125, 152; Furgeson 1991 PNAS 88, 8072). Furthermore, alpha5beta1 influences the differentiation of certain cell types during several pathogenetic processes, e.g., myofibroblast development during fibrosis (Thannickal 2003, J. Biol. Chem. 278, 12384), RPE cell transdifferentiation during AMD (US2005/0002930) and tumor cell immortalization during cancer. In several other diseases the alpha5beta1 ligand fibronectin is up-regulated in the affected tissue and therefore inhibition of alpha5beta1-fibronectin interaction could interfere with disease progression.

Therefore, given the bio distribution of the integrins and particularly of alpha5beta1 in tissues, organs and cells, respectively and the appearance of pathological angiogenesis, inflammation and fibrosis, the compounds-according to the present invention can be used in the treatment of diseases of or involving various tissues and organs, respectively. Such tissues comprise but are not limited to ocular tissues, such as cornea, retina and macula and other tissues and organs such as the skin, the joints, liver, kidney, lung, heart, bladder, thyroid, brain, blood and neoplasms. Further tissues are the synovial tissue, intestinal tissues, connective tissue, reproductive tissue, and the bone tissue.

Based on this, the compounds according to the present invention are preferably used for the treatment of diabetic retinopathy and age related macular degeneration, as an example for diseases related to ocular tissues, preferably age related macular degeneration by neovascularization, for the treatment of skin diseases such as hemangioma and inflammatory diseases from the group comprising psoriasis, rosacea, gingivitis, arthritic conditions such as rheumatoid arthritis, psoriatric arthritis, juvenile arthritis and osteoarthritis, inflammatory bowel diseases, ulcerative colitis, Crohn's disease, and others. It will be acknowledged by the ones skilled in the art that some of the diseases can be grouped into different categories. In so far, the categorization presented is not limiting the actual use of the compounds according to the present invention. Rather, the compounds according to the present invention can be used for the treatment of any of the diseases disclosed herein.

Other ocular diseases contemplated to be treated using compounds according to the present invention are diseases which are connected with choroidal neovascularization such as, e.g., ocular histoplasmosis syndrome, high myopia, angoid streaks, choroidal rupture, optic disc drusen, optic pits, acute posterior multifocal placoid pigment epitheliopathy, serpiginous choroiditis, Harada's disease, Stargard's disease, toxoplasmosis, sarcoidosis, central serous retinopathy, congenital ribella, coloboma, morning glory syndrome, choroidal hemangioma, choroidal melanoma, choroidal nevus, choroidal osteoma, toxocariasis, branch retinal vein occlusion, central retinal vein occlusion, parafoveal telangiectasis, retinitis pigmentosa, Best's disease, adult foveal macular dystrophy, problems after photocoagulation or retinal vascular diseases such as, e.g., hypertensive retinopathy, diabetic retinopathy, sickle cell retinopathy, retinopathy of prematurity, background retinopathy, or other eye diseases connected with neovascularization and/or integrin mediated interactions, such as, e.g., proliferative vitreoretinopathy, proliferative diabetic retinopathy, Behçet's disease, cavernous hemangioma of the retina, choroidal rupture, retinal telangiectasia, cystoid maculopathy, Eale's disease, idiopathic central serous choroidopathy, iris neovascularization, malignant choroidal melanoma, preretinal macula fibrosis, ocular histoplasmosis, retinal capillary hemangiomaretinal tumors, tumors of the iris and ciliary body, diseases with pathological corneal neovascularization, pterygiae.

In connection with these ocular diseases the pathological growth of new blood vessels causes the loss of vision. The leading cause of blindness in individuals over the age of 65 is the age related macular degeneration (AMD), characterized by the growth of new blood vessels from the choroid, which remain beneath the retinal pigment epithelium (RPE), or breach the RPE and enter the subretinal space, leading to hemorrhage, detachment of RPE and formation of subretinal scars followed by blindness (Ambati, 2003, Survey of Opthalmology, 48, 257). The leading cause of blindness in individuals under the age of 55 years is proliferative diabetic retinopathy (PDR), whereby retinal blood vessels proliferate along the surface of the retina and into the posterior vitreous due to ischaemic stimuli (Klein, 1994, Arch Opthalmol. 112, Friedlander, 1996, PNAS, 93, 9764).

Particularly in connection with AMD, a variety of different factors influence the pathogenesis thereof. Beside the pathological neovascularization vascular leakage, inflammation and fibrosis are connected with the progression of AMD. Macrophages and transdifferentiated RPE cells play an important role in triggering the inflammation and the following fibrosis as well as vascular leakage and angiogenesis by producing growth factors such as VEGF (Tezel, 2004, Trends Mol Med 10, 417; Lopez, 1996, IOVS 37, 855; Grossniklaus 2002, Mol V is 8, 119,). Proliferating fibroblasts and RPE cells, activated macrophages as well as myofibroblasts in fibrotic tissues have up-regulated the alpha5beta1 expression (Thannickal 2003, J. Biol. Chem. 278, 12384; Proulx, 2003, Molecular Vision, 9, 473; Shang 1998, J 1 mm 160, 467). Furthermore inhibition of integrin signaling in proliferating RPE cells in vitro caused a reduction of VEGF secretion (Jabali 2005 ARVO #462/B436). Therefore alpha5beta1 seems to play an important role for the proliferation of RPE cells outside the normal RPE cell layer, for the transdifferentiation of RPE cells to the pathological phenotype, for the secretion of growth factors from pathological RPE cells, for the infiltration of macrophages into the AMD lesion and the progression of fibrosis following inflammation and angiogenesis. Therefore, these in vitro and in vivo data indicate alpha5beta1 inhibitors may interfere with all processes important for the pathogenesis of AMD such as angiogenesis, inflammation, fibrosis and vascular leakage. Insofar, AMD also comprises aspects of inflammation and fibrosis which shall be dealt with herein separately again. Nevertheless, there are other—ocular—diseases which are connected to or which involve fibrosis and proliferation as well as transdifferentiation of RPE cells such as proliferative vitreoretinopathy which shall be discussed in more detail in the following.

In their normal state, RPE cells are strongly adherent to Bruch's membrane, but in certain pathological conditions such as retinal detachment, the RPE cell layer begins to dissociate from the membrane. This RPE-Bruch's membrane separation may be mediated by several stimuli or partly derived from the RPE themselves (Hiscott 1999, Prog Retin Eye Res 18, 167). Concomitant with the RPE disassociation, the cells begin to lose tertiary differentiation characteristics and gain macrophage-like features. These "free" RPE cells start to proliferate, migrate and create a provisional matrix triggering the formation of PVR membranes. Some of the cells adopt a fibroblast-like phenotype, similar to that of the dermal fibroblasts during cutaneous wound repair. These fibroblastic RPE cells synthesize ECM proteins like fibronectin, components found also in healing skin wounds. The ECM molecules in turn further modulate the activities of the cells via several families of cell surface receptors such as the integrin alpha5beta1. The resulting tissue (PVR membrane) displays many of the features of a contractile scar and is the hallmark of PVR. Thus the development of PVR, and the resulting tractional distortion of the neuroretina, could be dependent on RPE-matrix interactions such as alpha5beta1-fibronectin.

Several experimental data prove this fundamental role of alpha5beta1. Thus, alpha5beta1 is connected with proliferation, migration and fibrotic modifications of RPE cells in vitro whereas quiescent RPE have no alpha5beta1 expression (Proulx, 2003, Molecular Vision, 9, 473; Jin 2000, IOVS 41, 4324). The increase of alpha5beta1 expression in RPE cells is linked to an increase in mobility (Meitinger 2001 Exp Eye Res, 73, 681). In animal models for retinal detachment integrin inhibitors decreased the RPE cell induced tractional retinal detachment (Yang 1996, IOVS, 37, 843).

Other cells are also connected with the pathogenesis of PVR such as macrophages and fibroblasts. Macrophages could be derived from transdifferentiated RPE cells or come from the systemic circulation (Pastor 2002 Prog Ret Eye Res 21, 127). The fibroblasts and/or myofibroblasts as major component of pathological membranes originate probably also from the transformed RPE cells (Pastor 2002 Prog Ret Eye Res 21, 127). The inhibition of alpha5beta1 interaction could interfere with the proliferation, migration as well as transdifferentiation of RPE cells and infiltration of macrophages as well as development of myofibroblasts. Similar processes are obtained in the pathogenesis of proliferative diabetic retinopathy (PDR, Marano 1995, Exp Eye res 60, 5).

The compounds according to the present invention are useful in inhibiting and thus in the treatment of diseases involving or comprising undesired cell proliferation, including but not limited to proliferative disorders in ocular tissues such as proliferative vitreoretinopathy.

The compounds according to the present invention are also useful for the treatment of neoplasms, whereby the neoplasm is the formation of a tumor, which is characterized, in part, by angiogenesis. The neoplasm can be benign such as hemangioma, glioma, teratoma or malignant such as sarcoma, carcinoma, osteosarcoma, adenocarcinoma, blastoma, myeloma, leukemia and lymphoma, whereby the malignant neoplasm may or may not be a metastatic. The malignant neoplasm can be solid tumors, and hematopoeitic cancers such as lymphoma and leukemia. More preferably, the solid tumor is selected from the group comprising carcinoma, sarcoma, osteoma, fibrosarcoma, chondrosarcoma, glioblastoma astrocytoma, neuroblastoma, retinoblastoma, and others.

More preferably, the malignant disorder or malignant neoplasm is selected from the group comprising breast cancer, gynaecological cancers, pancreatic cancer, bladder cancer, brain cancer, mesothelioma, teratocarcinoma, astrocytoma, melanoma, angioma and glioblastoma, renal cancer, prostate cancer, lung cancer, head and neck cancer, parotid cancer, thyroid cancer, fibrosarcoma, gastrointestinal cancer, endocrine cancer, AIDS-related cancers, adrenal cancer, eye cancer, hepatocellular cancer, skin cancer, thymus cancer, and testicular cancer and sarcomas such as osteosarcoma and Kaposi's sarcoma. Preferably, the lung cancer is non-small cell lung cancer.

Without wishing to be bound by any theory, the reasons for the applicability of the compounds according to the present invention in this particular field resides in the following findings. In many types of tumors alpha5beta1 integrin is upregulated on the surface of tumor epithelial cells (in addition to endothelial cells of the tumor vasculature) as well as on tumor cells (WO2005/092073). Alpha5beta1 integrin is overexpressed on tumor cell lines originating from at least the following cancers: bladder cancer, breast cancer, colon cancer, fibrosarcoma, lung cancer, metastatic melanoma, pancreatic cancer, prostate cancer, ovarian cancer, and renal cell carcinoma. In addition, cancer cells and cancer cell lines of other origin and representing other tumor indications may also overexpress alpha5beta1. It has been shown that alpha5beta1 overexpressing tumor cells are susceptible to direct tumor cell killing using anti-alpha5beta1 antibodies. There is a direct anti-proliferative effect by anti-alpha5beta1 antibodies on the tumor cell proliferation (WO2005/092073). Furthermore, loss of the interaction between alpha5 and fibronectin diminished cell survival and induced apoptosis in tumor cells. The integrin alpha5beta1 was shown to be the most relevant receptor of tumor cells for binding to fibronectin (Nista et al 1997, Int. J. Cancer 72, 133). Function-blocking alpha5 antibodies attenuate tumor cell migration (Maschler 2005 Oncogene 24, 2032). Alpha5beta1 integrin has been reported to promote tumor cell invasion and metastasis (Qian et al. 2005, Biochem Biophys Res Commun. 333, 1269; Han et al. 2003 Lung Cancer 41, 65). High expression of alpha5 integrin subunit seems to be associated with the most invasive cancer phenotypes. Anti-alpha5beta1 antibodies inhibit tumor growth in vivo, e.g., in NW231 and LOX mouse tumor xenograft models as well as in a rabbit VX2 tumor model.

Additionally, alpha5beta1 is important for the survival, proliferation and migration of lymphatic endothelial cells (Zhang 2005, J Cell Physiol 202, 205). Therefore, the inhibition of alpha5beta1 on lymphatic endothelial cells is a promising approach for inhibition of lymphangiogenesis in many therapeutic areas. Lymphangiogenesis is a very important process in tumor progression. The extravasation of tumor cells via lymphatic vessels plays an essential role in tumor dissimination and therefore metastasis.

From a physiological point of view, the newly formed blood vessels in this kind of neovascular disorder provide the tumor cells with oxygen and nutrients. They are necessary for further tumor growth above 1-2 mm$^3$ and form a gateway for tumor cells to enter the circulation and to metastasize to distant sites of the body (Folkman and Shing, 1992, J. Biol. Chem., 267, 10931).

Thus, by acting through the above described multiple mechanisms alpha5beta1 antagonists prevent tumor growth, invasiveness and metastasis.

Several other diseases also involve integrin mediated effects and processes, such as atherosclerosis progression and restenosis. Particularly, angiogenesis and migration are the critical steps of plaque development during atherosclerosis (Hoshiga, 1995, Circ. Res. 77, 1129), and undesired vascular repair processes in vessels of atherosclerotic patients cause coronary restenosis (Panda, 1997, PNAS, 94, 9308).

It is to be understood that the aforementioned diseases are particularly diseases which are based on pathological angiogenesis. However, the compounds according to the present invention are not limited to the use in connection with this kind of diseases but can in alternative embodiments also be used for the treatment of diseases which are generally based on the interaction of integrin with ligands such as fibronectin in the extracellular matrix or on a cell surface. Thereby the compounds are useful in the inhibition of cell adhesion and migration. The following diseases are currently understood as to be based on this kind of interaction. Accordingly, the compounds according to the present invention may also be used for the treatment of immune based and/or inflammatory diseases, more preferably rheumatoid arthritis, inflammatory bowel disease, Crohn's disease, psoriasis, osteoarthritis, ulcerative colitis, and infectious diseases which are caused by microbial infection, including fungal infections, bacterial infections and viral infections. Again, it is to be noted, that any of the diseases specifically disclosed herein can be treated by the compound according to the present invention without being limited to the particular mode of action.

In a still further embodiment the immune based and/or inflammatory disease is an autoimmune disease or autoimmune disorder. In a further embodiment, the immune based and/or inflammatory disease is selected from the group comprising rheumatoid arthritis, juvenile arthritis, osteoarthritis, psoriatric arthritis, glomerulonephritis, gingivitis, inflammatory bowel disease, ulcerative colitis, systemic lupus erythematosus associated glomerulonephritis, irritable bowel syndrome, bronchial asthma, multiple sclerosis, pemphigus, pemphigoid, scleroderma, myasthenia gravis, Wegener's Granulomatosis, Churg-Strauss-allergic granulomatosis, Sjogren's syndrome, Sicca syndrome, Goopasture's disease, autoimmune haemolytic and thrombocytopenic states, pulmonary hemorrhage, vasculitis, Crohn's disease, psoriasis, asthma, ankylosing spondylitis and dermatomyositis.

In a still further embodiment the immune based and/or inflammatory disease is selected from the group comprising inflammation associated with ankylosing spondylitis, burns, lung injury, myocardial infarction, coronary thrombosis, vascular occlusion, post-surgical vascular reocclusion, IgA nephropathy, sarcoidosis, eosinophilic granulomata, midline granuloma, arteritis temporalis, Takayasu's arteritis, pterygia, Kawasaki's disease, atherosclerosis, traumatic central nervous system injury, ischemic heart disease and ischemia-reperfusion injury, respiratory distress syndrome, systemic inflammatory response syndrome, multiple organ dysfunction syndrome, tissue graft rejection, burns, lung injury, uveitis, asthma, rosacea and hyperacute rejection of transplanted organs.

The following observations support the use of the compounds according to the present invention in connection with inflammatory diseases. Basically, the influx of inflammatory cells into the inflammatory region stimulates angiogenesis and following this, the increased vasculature enables a greater influx of leukocytes, which promote the inflammatory process, such as destruction of cartilage and bone in the joint during arthritis. Furthermore, the lymphatic system plays also an important role in initiating the immune response via directing leukocytes and antigens from the tissues to the lymphnodes (Pepper 2003, J. Biol. Chem. 163, 209) and is important during many inflammatory processes such as rejection reactions after transplantation (Cursiefen 2004, J Clin Invest 113, 1040). Expression of alpha5beta1 on immune cells such as activated macrophages, neutrophils, mast cells or T-lymphocytes points to an important role for migration of immune cells into the inflamed tissue (Kloss 1999, J Comp Neurol 411, 162; Shang 1998, J 1 mm 160, 467; Issekutz Inflam Res.

1998 47, S123; Burns 2001 J Imm 166, 4644; Dastych, 2001, Allergy and Immunology 125, 152; Furgeson 1991 PNAS 88, 8072).

Whereas the transendothelial migration of inflammatory cells depends mainly on the integrin alpha4beta1 the migration within the inflamed tissue is mediated by alpha5beta1 and its ligand fibronectin. (Loike 1999 J Cell Biol 144, 1047; Shang 1998 I Immunol 160, 467). Animal studies with an alpha5beta1 inhibitor have shown the protection against severe ischemia/reperfusion injury after liver transplantation via inhibition of macrophage invasion into the transplanted organ (Fondevila 2005 Transpl Proc 37, 1679). Therefore inflammatory diseases mediated by infiltrating macrophages and neutrophils could be treated by alpha5beta1 inhibition.

Many inflammatory diseases after granumloma formation develop toward fibrosis. Addressing the invasion of immune cells as well as the development of myofibroblasts provides a powerful approach for treating chronic inflammatory diseases. Many of them are connected with alpha5beta1 up-regulation such as sarcoidosis, psoriasis or other inflammatory diseases (Shigehara 1998 Virchows Ach 433, 55; Bata-Csorgo 1998 J Clin Inv 101, 1509).

The compounds according to the present invention are additionally useful in inhibiting pathogenic organisms and are, therefore, useful for treating infectious diseases. Many pathogens interact directly or mediated by extracellular matrix proteins with host cells, causing cell adhesion and invasion of these pathogens. This interaction is mediated by host cell integrins such as alpha5beta1 (Cue, 2000, PNAS, 97, 2858; Frankel, 1996, J. Biol. Chem., 271, 20359; van Putten, 1998, Mol. Microbiology, 29, 369; Finlay, 1997, Microbiol. Mol. Biol. Rev., 61, 136). Additionally pathogens can also express integrins themselves to enter the host cell.

In a preferred embodiment the infectious disease is selected from the group comprising fungal, viral, bacterial and parasite infection.

Fungal infections contemplated for treatment using the compounds and methods according to the present invention include systemic fungal infections, dermatophytoses and fungal infections of the genito-urinary tract. Fungal infections, preferably systemic fungal infections, include those caused by *Histoplasma, Coccidioides, Cryptococcus, Blastomyces, Paracoccidioides, Aspergillus, Nocardia, Sporothrix, Rhizopus, Absidia, Mucor, Hormodendrum, Phialophora, Rhinosporidium,* and the like. Dermatophyte infections include those caused by *Microsporum, Trichophyton, Epidermophyton, Candida, Pityrosporum,* and the like. Fungal disorders of the genito-urinary tract include infections caused by *Candida, Cryptococcus, Aspergillus, Zygomycodoides,* and the like. Infection by such organisms causes a wide variety of disorders such as ringworm, thrush or candidiasis, San Joaquin fever or Valley fever or coccidiodomycosis, Gilchrist's disease or blastomycosis, aspergillosis, cryptococcosis, histioplasmosis, paracoccidiomycosis, zygomycosis, mycotic keratitis, nail hair and skin disease, Lobo's disease, lobomycosis, chromoblastomycosis, mycetoma, and the like. These infections can be particularly serious, and even fatal, in patients with a depressed immune system such as organ transplant recipients and persons with acquired immunodeficiency syndrome (AIDS). Insofar patient groups which can be treated using the inhibitors according to the present invention are persons with AIDS, particularly those suffering from any of the infectious diseases described herein.

In a further embodiment the bacterial infection is selected from the group comprising infections caused by both Gram-positive and Gram-negative bacteria, including infections caused by *Staphylococcus, Clostridium, Streptococcus, Enterococcus, Diplococcus, Hemophilus, Neisseria,* Erysipelothricosis, *Listeria, Bacillus, Salmonella, Shigella, Escherichia, Klebsiella, Enterobacter, Serratia, Proteus, Morganella, Providencia, Yersinia, Camphylobacter,* Mycobacteria, *Helicobacter, Legionalla, Nocardia* and the like.

In a preferred embodiment the bacterial infection causes a wide variety of diseases. Said disorders are selected, among others, from the group comprising pneumonia, diarrhea, dysentery, anthrax, rheumatic fever, toxic shock syndrome, mastoiditis, meningitis, gonorrhea, typhoid fever, brucellis, Lyme disease, gastroenteritis, tuberculosis, cholera, tetanus and bubonic plague.

In another embodiment the disease is a viral infection, more particularly a viral infection caused by a virus selected from the group comprising retrovirus, HIV, Papilloma virus, Epstein-Barr, Herpes virus, Hepatitis virus, Papova virus, Influenza virus, Rabies, JC, encephalitis causing virus, hemorrhagic fever causing virus such as Ebola Virus and Marburg Virus.

In a further embodiment the parasite infection is selected from the group comprising infections caused by *Trypanosoma, Leishmania, Trichinella, Echinococcus,* Nematodes, Classes Cestoda, Trematoda, Monogenea, *Toxoplasma, Giardia, Balantidium, Paramecium, Plasmodium* or *Entamoeba*.

In case the disease is a non-neoplastic cell proliferative disorder, it is preferably selected from the group comprising fibrotic disorder. Preferably, the fibrotic disorder is fibrosis.

A disease connected with non-neoplastic cell proliferation and/or tissue remodeling preferably means that the disease is associated in a causative or non-causative manner with the proliferation and/or differentiation of non-neoplastic cells.

The disease may also be a non-neoplastic cell proliferative disorder which is selected from the group comprising prostatic hypertrophy, preferably benign prostatic hypertrophy, endometriosis, uterine fibroid, keloid scar formation, scleroderma, psoriasis, tissue repair and wound healing.

Fibrotic disorders which may be treated using the compounds according to the present invention are generally characterized by inappropriate overproliferation or transdifferentiation of non-cancerous mostly fibroblastic cells. Examples thereof include fibromyalgia, fibrosis, more particularly cystic, hepatic, renal, ocular, lung, stomach, intestinal, skin, idopathic pulmonary, and pericardial fibrosis and the like, cardiac fibromas, fibromuscular hyperplasia, restenosis, atherosclerosis, fibromyositis, and the like.

In a preferred embodiment the fibrotic disorder is a hepatic disorder preferably liver fibrosis, liver cirrhosis, reperfusion injury after hepatic transplantation, necrotizing hepatitis or renal disorders preferably renal fibrosis, glomrulonephritis, IgA nephropathy, reperfusion injury after kidney transplantation, chronic renal allograft dysfunction, amyloidosis, diabetic nephropathy, mesangio proliferative glomrulonephritis, nephrosclerosis or other fibrotic disorders preferably lung fibrosis comprising interstitial pulmonary fibrosis, idiophatic fibrosis, drug-induced fibrosis, sarcoidosis, diffuse alveolar damage disease, pulmonary hypertension, chronic obstructive pulmonary disease, respiratory distress syndrome; skin fibrosis such as scleroderma, keloid, hypertrophic scar, dermatofibroma, chronic wounds, psoriasis, dupuytren's contracture, pemphegoid, burn; stomach and intestinal fibrosis comprising abnormal intestinal motility, hypertrophic pyloric stenosis, Hirschsprung's disease, megacolon of piebaldism, idiopathic obstruction, collagenous colitis, villious atrophy and crypt hyperplasia, polyp formation, fibrosis of Crohn's disease, gastric ulcer; eye fibrosis comprising acute and fibrotic sympathetic ophthalmia, Grave's disease, fibrosis after glaucoma surgery, fibrosis after cataract surgery, anterior capsular cataract, corneal scarring, pemphigoid, diabetic microaneurism, capsule opacification; or any other fibrosis comprising systemic sclerosis, artherosclerosis, restenosis, chronic myeloproliferative disorders, fibrodysplsia ossificans progressive, myelodysplasia, osteoporosis, myelofibrosis, osteosclerosis, rheumatoid pannus formation in rheumatoid arthritis and osteoarthritis, peritoneal fibrosis, myocardial fibrosis, pancreatic fibrosis, chronic pancreatitis, glial scar tissue formation in HIV associated cognitive motor disease and spongiform encephalopathy, gingival hypertrophy secondary to drugs and fibrocystic disease.

Fibrosis is a pathological condition with non-physiological wound healing following a persistent exogenous or endogenous stimulus and is mostly mediated by or associated with an inflammatory response. During the fibrotic response tissue remodelling and hypertrophic scarring take place connected with excessive deposition of extracellular matrix proteins and transdifferentiation of certain cell types (tissue dependent) to myofibroblasts. The common endpoint of all fibrotic diseases is the development of myofibroblasts which trigger the fibrosis by secretion of pro-fibrotic factors such as cytokines, inflammatory mediators, growth factors as well as ECM proteins (Powell 1999, Am J Physiol 277, C1-C19). Myofibroblasts are active participants in normal wound repair, but persistence of these cells in injured tissues prevents normal healing and promotes a dysregulated repair process characterized by progressive connective tissue remodelling and fibrosis (Tomasek 2002, Nat Rev Mol Cell Biol 3, 349). Transformation of fibroblasts or other cells to myofibroblasts is primarily mediated by pro-fibrotic cytokines such as transforming growth factor (TGFβ) or PDGF (Border 1994, New Engl J Med 331, 1286; Friedman, 2000, J. Biol. Chem. 275, 2247). Due to the ubiquitous presence in all tissues, myofibroblasts play an important role in various organs such as liver, skin, lung, kidney, eye and others.

There are several hints for the involvement of alpha5beta1 in the pathogenesis of fibrotic disorders in several tissues. In vitro data have shown the up-regulation of alpha5beta1 expression after stimulation of fibroblast or other myofibroblast precursor cells with the profibrotic growth factor TGFβ, PDGF or connective growth factor (CTGF) and the promotion of fibrotic differentiation by fibronectin (Thannickal 2003, J. Biol. Chem. 278, 12384; Nesbit 2001 Lab Invest 81, 1263; Roberts, 1988, J. Biol. Chem., 263, 4586; Weston 2003 J Am Soc Nephrol 14, 601).

Many other data provide evidence for the important role of alpha5beta1 in vivo. Thus, alpha5beta1 is up-regulated in renal fibrotic disorders such as renal fibrosis (Norman 1999 Exp Nephrol 7, 167), glomerulonephritis (Roy-Chaudhury 1997 Kidney Int 52, 103) as well as IgA nephropathy (Wagrowska-Danilewicz 2004, Int Urol Nephr 36, 81), lung fibrosis and sacoidosis (Pilewski, 1997 μm J Physiol 273, L256; Shigehara 1998 Virchows Ach 433, 55). During the pathogenesis of liver fibrosis alpha5beta1 is up-regulated within the fibrotic tissue (Zhou 2000 Chin Med J 113, 272) and on activated hepatic stellate cells, the myofibroblast precursors, during fibrotic differentiation (Iwamoto 1998 J Hepatol 29, 752; Milliano 2003 J Hepatol 39, 32). Alpha5beta1 is also connected with the pathogenesis of skin fibrosis due to the up-regulation on fibroblasts, proliferating and migrating keratinocytes as well in fibrotic skin such as from Psoriasis patients (Frazier 1196 J Invest Dermatol 107, 404; Juhazs 1993 Am J Path 143, 1458; Bata-Csorgo 1998 J Clin Invest 101, 1509). Alpha5beta1 expression in synovial fibroblasts or articular chondrocytes indicates an essential role in rheumatoid arthritis and osteoarthritis (Kitagawa 2005, Ann. Rheum Dis, Fukumoto Osteoarthritis and Cartilage 2002 10, 135).

Other fibrotic disorders with involvement of alpha5beta1 are chronic myeloproliferative disorders (Schmitz 1998 J Cell Physiol 176, 445) or fibrodysplasia ossificans progressiva (Tang 2003, J Bone Min Res 18, 502; Moursi 1997 J Cell Sci 110, 2187; Gannon 2001 Human Path 32, 842) as well as Artherosclerosis (Yee 1999 Thromb Haemost 82, 762) or acute and fibrotic sympathetic ophthalmia (Kuppner 1993 Curr Eye res 12, 923).

In a further embodiment the compounds according to the present invention can be used as agonistic effectors on integrin thus promoting neovascularisation. Accordingly, the compounds according to the present invention are used in a preferred embodiment for the treatment of diseases which require or are treated by neovascularization or induction thereof. This kind of disease is a disease which can be selected from the group comprising wound healing, stroke, infertility, ulcer, scleroderma, transplantation, peripheral arterial disease and coronary heart disease.

It is also within the present invention that the compounds according to the present invention may be used for the treatment of a patient suffering from a disease or diseased condition as defined above. Such treatment comprises the administration of one or several of the compounds according to the present invention or a medicament or pharmaceutical composition described herein.

Toxicity and therapeutic efficacy of a compound can be determined by standard pharmaceutical procedures in vitro such as biochemical assays and in cell culture or experimental animals. Biochemical assays, cell culture assays and animal studies can be used to determine the $LD_{50}$ (the dose lethal to 50% of a population) and the $ED_{50}$ (the dose therapeutically effective in 50% of a population). The dose ratio between toxic and therapeutic effects is the therapeutic index, which can be expressed as the ratio $LD_{50}/ED_{50}$. Compounds which exhibit large therapeutic indices are preferred. The data obtained from these cell culture assays and animal studies can be used in formulating a range of dosages suitable for use in humans. The dosage may vary within this range depending upon a variety of factors, e.g., the dosage form employed, the route of administration utilized, the condition of the subject, and the disease, which has to be treated.

For any compound according to the present invention, the therapeutically effective dose can be estimated initially from protein binding and cell culture assays by determining an $IC_{50}$ (i.e., the concentration of the test substance which achieves a half-maximal inhibition of integrin binding or cell adhesion). A dose can then be formulated in animal models to achieve a circulating concentration range in plasma or other compartments such as, e.g., vitreous humor, synovial liquid or other, that includes the $IC_{50}$ as determined in binding assays. Such information can be used to more accurately determine useful doses in humans. Levels in plasma or other compartments may be measured, for example, by HPLC, LC/MS, or ELISA.

It should be noted that the attending physician would know how and when to terminate, interrupt, or adjust administration due to toxicity, to organ dysfunction, and the like. Conversely, the attending physician would also know to adjust treatment to higher levels if the clinical response were not adequate (precluding toxicity). The magnitude of an administered dose in the management of the disorder of interest will vary with the severity of the condition to be treated, with the route of administration, and the like. The severity of the condition may, for example, be evaluated, in part, by standard prognostic evaluation methods. Further, the dose and perhaps dose frequency will also vary according to the age, body weight, and response of the individual patient. Typically, the dose will be between about 0.0001-100 mg/kg of body weight or 1 ng-1 mg per eye or comparable concentrations for other compartments. About 0.001 mg to about 1000 mg will preferably be administered to a child, and between 0.01 mg and about 7000 mg, more preferably 100 mg to 3000 mg, will preferably be administered to an adult.

A program comparable to that discussed above may be used in veterinary medicine. The exact dose will depend on the disorder to be treated and will be ascertainable by one skilled in the art using known techniques.

Depending on the specific conditions to be treated, such compounds may be formulated and administrated systemically or locally. Techniques for formulation and administration may be found in "Remington's Pharmaceutical Sciences", 1990, $18^{th}$ ed., Mack Publishing Co., Easton, Pa. The administration of a compound according to the present invention can be done in a variety of ways, including, but not limited to, orally, subcutaneously, intravenously, intranasally, transdermally, intraperitoneally, intramuscularly, intrapulmonary, vaginally, rectally, or intraocularly, perioculary, intraorbitally, intracapsulary, intrasynovially, intracisternally, topically, just to name a few. In some instances, for example, in the treatment of wounds and inflammation, the compound according to the present invention may be directly applied as an ointment, powder, solution or spray. Topical administration also comprises passive or facilitated adsorption, preferably through the skin, including skin patches and iontophoresis.

Depending on the route of administration some formulations are particularly advantageous. For the administration of the compound to the eye and other tissues such as neoplastic and non-neoplastic tissues, fibrotic tissues, inflamed tissues the following formulations are preferred. In case of local administration, intraocular or periocular injection, local implants, drops and ointments are preferred. In case of systemic administration, injection and oral administration are preferred. In case of intraocular injection intravitreal, intracameral or sub-retinal injections are preferred. Periocular injections are selected from group comprising subconjunctival, para/retro bulbar, juxtascleral, sub-tenual, and others. In the case of local implants specialized sustained-release devices will be administered intraocular or periocular, to enable a constant, slow release of compound to the eye (Robinson, 2002, Exp. Eye Res, 74, 309; Geroski, 2000, 41, 961), other sustained release systems are microspheres, liposomes, nanoparticles or other polymer matrices (Bourlais, 1998, Prog. Retin Eye Res. 17, 33). In order to improve the stability and pharmacological properties of the compound for ocular administration, the compound could be modified, as described before, and/or administered in combination with a special formulation, addition of penetration enhancers, bioadhesives and/or biodegradable polymers (Clark, 2003, Nature Rev. Drug Discovery, 2, 448; Sasaki, 1999, Crit. Rev Ther Drug Carrier Syst., 16, 85; Kauer, 2002, Drug Dev Ind Pharm., 28, 473; Kimura, 2001, Opthalmologica, 215, 143). An example for a sustained release of compound in the eye is the preparation of a dry compound pellet which will be coated with a silicone layer. After implantation into the eye the pharmaceutically active compound will be released constantly over a long period of time (Robinson, 2002, Exp. Eye Res, 74, 309). Particulate drug carriers that offer unique opportunities to improve tumor, antifibrotic and anti-inflammatory therapy through several different mechanisms are preferred. Liposomes may (1) assist in formulation of poorly-soluble therapeutic agents, (2) provide a slow-release vehicle to achieve pharmacokinetic profiles that maximize the therapeutic index, or (3) behave as long-circulating nano-particulates that can for instance extravasate in the hyperpermeable regions of tumor vasculature. An example for the sustained systemic release of compounds for treatment of neoplasms is doxorubicin which entrapped in a within sterically-stabilized liposomes (SSL-DXR) represents a long-circulating formulation that can extravasate within tumors and enhance drug deposition (Straubinger et al., 2004, Anticancer Res. 24, 397). Examples for sustained systemic release of compounds for treatment of precocious puberty, prostate and breast cancer, endometriosis, uterine leiomyoma, polycystic ovarian disease, and various other disorders are GnRH analogues (Filicori M, Flamigni C, 1988, Drugs 35, 63; Lahlou N., 2005, Ann Urol (Paris). 39 Suppl 3: S78).

In a further aspect the present invention is related to a medicament or a pharmaceutical composition comprising at least one active compound and at least one pharmaceutically acceptable carrier, excipient or diluent. As used herein, the active compound is a compound according to the present invention, a pharmaceutically salt or base thereof or a prodrug thereof, if not indicated to the contrary.

For injection, compounds of the invention may be formulated in aqueous solution, preferably in physiologically compatible buffers such as Hank's solution, Ringer's solution, or physiologically saline buffer. For transmucosal administration, penetrants appropriate to the barrier to be permeated are used in the formulation. Such penetrants are generally known in the art.

The use of pharmaceutical acceptable carriers to formulate the compounds according to the present invention into dosages or pharmaceutical compositions suitable for systemic administration is within the scope of the present invention. With proper choice of carrier and suitable manufacturing practice, the compositions of the present invention, in particular those formulated as solutions, may be administered parenterally, such as by intravenous injection. The compounds can be readily formulated using pharmaceutically acceptable carriers well known in the art into dosages suitable for oral administration. Such carriers enable the compounds according to the present invention to be formulated as tablets, pills, capsules, dragees, liquids, gels, syrups, slurries, suspensions and the like, for oral ingestion by a subject to be treated.

Compounds according to the present invention or medicaments comprising them, intended to be administered intracellularly may be administered using techniques well known to those of ordinary skill in the art. For example, such agents may be encapsulated into liposomes, and then administered as described above. Liposomes are spherical lipid bilayers with aqueous interiors. All molecules present in an aqueous solution at the time of liposome formation are incorporated into the aqueous interior. The liposomal contents are both protected from the external microenvironment and, because liposomes fuse with cell membranes, are efficiently delivered into the cell cytoplasm. Delivery systems involving liposomes are disclosed in international patent application WO 91/19501, as well as U.S. Pat. No. 4,880,635 to Janoff et al. The publications and patents provide useful descriptions of techniques for liposome drug delivery and are incorporated by reference herein in their entirety.

Pharmaceutical compositions comprising a compound according to the present invention for parenteral administration include aqueous solutions of the active compound(s) in water-soluble form. Additionally, suspensions of the active compounds may be prepared as appropriate oily injection suspensions. Suitable lipophilic solvents or vehicles include fatty oils such as sesame oil or castor oil, or synthetic fatty acid esters, such as ethyl oleate or triglycerides, or liposomes. Aqueous injection suspensions may contain compounds which increase the viscosity of the suspension, such as sodium carboxymethyl cellulose, sorbitol, dextran, or the like. Optionally, the suspension may also contain suitable stabilizers or agents which increase the solubility of the compounds to allow for the preparation of highly concentrated solutions.

Pharmaceutical compositions comprising a compound according to the present invention for oral use can be obtained by combining the active compound(s) with solid excipient, optionally grinding the resulting mixture, and processing the mixture of granules, after adding suitable auxiliaries, if desired, to obtain tablets or dragee cores.

Suitable excipients are, in particular, fillers such as sugars, including lactose, sucrose, mannitol, sorbitol, and the like; cellulose preparations, such as, for example, maize starch, wheat starch, rice starch, potato starch, gelatin, gum tragacanth, methyl cellulose, hydroxypropylmethyl cellulose, sodium carboxymethyl cellulose, polyvinylpyrrolidone (PVP) and the like, as well as mixtures of any two or more thereof. If desired, disintegrating agents may be added, such as cross-linked polyvinyl pyrrolidone, agar, alginic acid or a salt thereof such as sodium alginate, and the like.

Dragee cores as a pharmaceutical composition comprising a compound according to the present invention are provided with suitable coatings. For this purpose, concentrated sugar solutions may be used, which may optionally contain gum arabic, talc, polyvinyl pyrrolidone, carbopol gel, polyethylene glycol, titanium dioxide, lacquer solutions, suitable organic solvents or solvent mixtures, and the like. Dyestuffs or pigments may be added to the tablets or dragee coatings for identification or to characterize different combinations of active compound doses.

Pharmaceutical preparations comprising a compound according to the present invention which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added.

A "patient" for the purposes of the present invention, i.e., to whom a compound according to the present invention or a pharmaceutical composition according to the present invention is or is to be administered, includes both humans and other animals and organisms. Thus the compounds, pharmaceutical compositions and methods are applicable to or in connection with both human therapy and veterinary applications including diagnostic(s), diagnostic procedures and methods as well as staging procedures and methods. For example, the veterinary applications include, but are not limited to, canine, bovine, feline, porcine, caprine, equine, and ovine animals, as well as other domesticated animals including reptiles, such as iguanas, turtles and snakes, birds such as finches and members of the parrot family, lagomorphs such as rabbits, rodents such as rats, mice, guinea pigs, monkeys, hamsters, amphibians, fish, and arthropods. Valuable non-domesticated animals, such as zoo animals, may also be treated. In the preferred embodiment the patient is a mammal, and in the most preferred embodiment the patient is human.

The pharmaceutical composition according to the present invention comprises at least one compound according to the present invention in a form suitable for administration to a patient. Preferably, a compound according to the present application is in a water soluble form, such as being present as a pharmaceutically acceptable salt, which is meant to include both acid and base addition salts which are also generally referred to herein as pharmaceutically acceptable salts. "Acid addition salt", and more particularly "pharmaceutically acceptable acid addition salts" refers to those salts that retain the biological effectiveness of the free bases and that are not biologically or otherwise undesirable, formed with inorganic acids such as hydrochloric acid, hydrobromic acid, sulfuric acid, nitric acid, phosphoric acid and the like, and organic acids such as acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid and the like. "Base addition salts" and more particularly "pharmaceutically acceptable base addition salts" include those derived from inorganic bases such as sodium, potassium, lithium, ammonium, calcium, magnesium, iron, zinc, copper, manganese, aluminum salts and the like. Particularly preferred are the ammonium, potassium, sodium, calcium, and magnesium salts. Salts derived from pharmaceutically acceptable organic non-toxic bases include salts of primary, secondary, and tertiary amines, substituted amines including naturally occurring substituted amines, cyclic amines and basic ion exchange resins, such as isopropylamine, trimethylamine, diethylamine, triethylamine, tripropylamine, and ethanolamine. The pharmaceutical compositions according to the present invention may also include one or more of the following: carrier proteins such as serum albumin; buffers; fillers such as microcrystalline cellulose, lactose, corn and other starches; binding agents; sweeteners and other flavoring agents; coloring agents; and polyethylene glycol. Additives are well known in the art, and are used in a variety of formulations.

The compounds according to the present invention are, in a further embodiment, administered to a subject either alone or in a pharmaceutical composition where the compound(s) is mixed with suitable carriers or excipient(s). In treating a subject, a therapeutically effective dose of compound (i.e. active ingredient) is administered. A therapeutically effective dose refers to that amount of the active ingredient that produces amelioration of symptoms or a prolongation of survival of a subject which can be determined by the one skilled in the art doing routine testing.

In an embodiment of the various aspects of the present invention, a compound according to the present invention is administered together with a further pharmaceutically active compound. More preferably, such further pharmaceutically active compound is selected from the group comprising chemotherapeutic agents such as, e.g., 5-fluorouracil, gemcitabine, carboplatin, paclitaxel, cisplatin, taxol, oxaliplatin, irinotecan and others, agents for anti-hormone therapy such as, e.g., acetate, tamoxifen and others, agents for photodynamic therapy, agents influencing the vascular permeability and/or angiogenesis such as, e.g., COX-2 inhibitors, NO-synthase inhibitors, bradykinin receptor antagonists or others, or anti-angiogenic compounds, like compounds affecting VEGF activity (like VEGF or VEGF-receptor antibodies, soluble VEGF-receptor fragments, VEGF-receptor-kinase inhibitors), or other agents affecting the action of angiogenic growth factors. The combination of compounds effecting different steps of angiogenic pathway or targeting different mechanism, which causes the diseases, could be beneficial for an optimal treatment of disease.

In addition the pharmaceutically active compound is preferably selected from the group consisting of anti-inflammatory agents such as, e.g., steroids, nonsteroidal anti-inflammatory drugs including aspirin, folic acid antagonists (e.g.

methotrexate), hydroxychloroquine, sulfasalazine, pyrimidine synthesis inhibitors (leflunomide), COX-2 inhibitors as well as biologics such as compounds directed against cytokines (e.g. TNF antagonists like Enbrel, Infliximab, Adalimumab), compounds directed against T cells, antigen presenting cells (e.g. Alefacept, Efalizumab) and anti-inflammatory cytokines or anti-fibrotic agents such as, e.g., interferons, TGFβ inhibitors (e.g. TGFβ antibodies or soluble TGFβ decoy receptor), inhibitors for other integrins (e.g. alphavbeta3 or alphavbeta6) Endothelin A receptor antagonists (e.g. LU135252), anti-oxidants (e.g. silymarin), phosphodiesterase inhibitors (e.g. pentoxifylline), thiazolidinidiones, immunsuppressive agents (e.g. rapamycin and mycophenolate mofetil), halofuginone and inhibitors of the renin-angiotensin system.

According to the present invention the compounds disclosed herein, also referred to as compounds according to the present invention, may be used as a medicament or for the manufacture of medicament or in a method of treatment of a patient in need thereof. Insofar any of these compounds constitute a pharmaceutical compound. The use of this kind of compound also comprises the use of pharmaceutically acceptable derivatives of such compounds.

In addition, the compounds according to the present invention may be transformed upon application to an organism such as a patient, into the pharmaceutically active compound. Insofar the compounds according to the present invention may be prodrugs which, however, are nevertheless used for the manufacture of the medicaments as disclosed herein given the fact that at least in the organism they are changed in a form which allows the desired effect.

It is to be understood that any of the pharmaceutical compositions according to the present invention may be used for any of the diseases described herein.

The pharmaceutical compositions according to the present invention may be manufactured in a manner that is known as such, e.g., by means of conventional mixing, dissolving, granulating, dragee-mixing, levigating, emulsifying, encapsulating, entrapping, lyophilizing, processes, or the like.

In a further aspect, the present invention is related to the use of the compounds according to the present invention as a diagnostic means. As used herein, a diagnostic means is the same as a diagnostic or a diagnostic tool. More preferably, the compounds according to the present invention can be used for the manufacture of such diagnostic.

This use of the compounds according to the present invention is particularly based on the fact that said compounds interact specifically with integrins, more particularly alpha5beta1. Because of the very restricted expression of alpha5beta1 on activated endothelial cell in tumors, after stimulation with growth factors (Kim, 2000, Am. J. Path, 156, 1345; Collo, 1999, J. Cell Sc., 112, 569), on activated immune cells and myofibroblasts (Shang 1998, J 1 mm 160, 467, Thannickal 2003, J. Biol. Chem. 27), this molecule is a suitable marker for angiogenesis, inflammation and fibrosis in pathological conditions.

In preferred embodiments, the compounds according to the present invention are labeled compounds according to the present invention. The label is preferably a detectable label and allows the use of the respective compounds particularly in the performance of in vivo imaging methods such as radionuclide imaging, positron emission tomography, computerized axial tomography, infrared imaging and magnetic resonance imaging. Most preferably, a radionuclide or a paramagnetic material is used as a label in the aforementioned methods. Additionally the specific interaction of the compound with the integrin could be also detected ex vivo, e.g., on isolated cells and in tissues removed by biopsy.

The problem underlying the present invention is also solved by the technical teaching according to the attached independent claims. Preferred embodiments thereof may be taken from the dependent claims.

The invention is now further illustrated by reference to the following figures and examples from which further advantages, features and embodiments may be taken. It is understood that these examples are given for purpose of illustration only and not for purpose of limitation. All references cited herein are incorporated by reference.

EXAMPLE 1

Materials and Methods

Figure 1A:
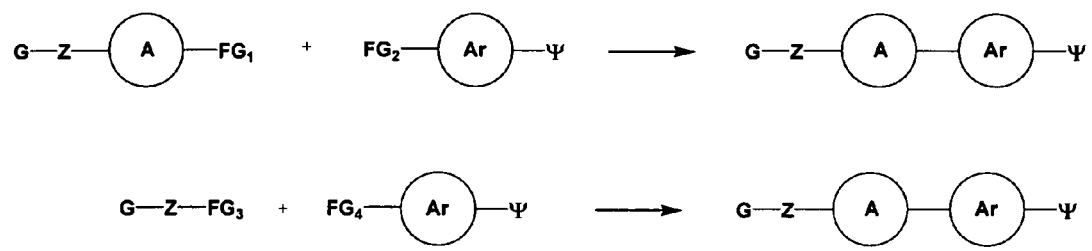
FIG. 1a and 1b show strategies for the synthesis of compounds having the general structure G-Z-A-Ar-Ψ.

Within the present application the following abbreviations are used:
Ac Acetyl
AIDS Acquired immunodeficiency syndrome
AMD Age related macular degeneration
bFGF Basic fibroblast growth factor
Boc tert-Buthoxycarbonyl
BSA Bovine serum albulmin
Cbz Benzyloxyformyl
CD31 Endothelial cell marker—platelet/endothelial cell adhesion molecule
COX Cyclooxygenase
Cpd. Compound
d Doublet
dba Dibenzylidenaceton
DCE Dichloroethane
DCM Dichloromethane
DIC Diisopropylcarbodiimide
DIPEA N,N-Diisopropylethylamine
DMF N,N-Dimethylformamide
DMSO Dimethylsulfoxide
DMSZ Deutsche Sammlung von Mikroorganismen und Zellkulturen
EC Endothelial cells
ECM Extracellular matrix
EDTA Ethylenediaminetetra-acetate
ELISA Enzyme-linked immunosorbent assay eq. Equivalent(s)
Et Ethyl
Fc Fragment of constant region of human immunoglobuline G1
FG Functional group
FITC Fluorescein isothiocyanate
Fmoc 9-Fluorenylmethyloxycarbonyl
GnRH Gonadotropin releasing hormone
h Hour
HATU O-(7-Azabenzotriazol-1-yl)-1,1,3,3-tetramethyluronium-hexafluorophosphate
HBTU O-(Benzotriazol-1-yl)-1,1,3,3-tetramethyluronium-Hexafluorophosphate
Hepes N-2-Hydroxyethylpiperazine-N'-2-ethanesulfonic acid
HIV Human immuno-deficiency virus
HPLC high-pressure liquid chromatography
HRP Horseradish peroxidase
iPr 2-Propyl
KHMDS Potassium-hexamethyldisilazane
LC/MS Liquid chromatography-mass spectrometry
m Multiples
Me Methyl
Me Methyl
MES 2-(N-Morpholino)-ethanesulfonic acid
min Minute(n)
ml Milliliter
MTBE Methyl-tert-butyl ether
NMR nuclear magnetic resonance
NO Nitric oxide
OD Optical density
OTf Trifluoromethanesulfonate
OTos Toluene-4-sulfonate
PBS Phosphate buffered saline
PDGF Platelet derived growth factor
PDR Proliferative diabetic retinopathy
PG Protecting group
PIDA Bisacetoxy iodobenzene
PMA Phorbol 12-myristate 13-acetate
PVP polyvinylpyrrolidone
PVR Proliferative vitreoretinopathy
RGD Argininyl-glycyl-aspartic acid
RNA Ribonucleic acid
RPE Retinal pigment epithelium
RPMI Medium developed at Roswell Park Memorial Institute
RT Room temperature
s Singulett
$^t$Bu tert-Butyl
TBAF Tetrabutyl ammonium fluoride
TFA Trifluoroacetic acid
TGFβ Transforming growth factor beta
THF Tetrahydrofuran
TIBS Tributhylsilane
TMB 3,3,5,5'-tetramethylethylenediamine
TMSCl Chlorotrimethylsilane
Tris Tris(hydroxymethyl)-aminomethane
TRITC Tetramethylrhodamine isothiocyanate
VEGF Vascular endothelial growth factor
Xantphos 4,5-bis(diphenylphosphino)-9,9-dimethylxanthene
Solvents:
Solvents were used in the assigned quality without further purification.
Acetonitrile (Gradient grade, J. T. Baker); dichlormethane (for synthesis, Merck Eurolab); diethylether (for synthesis, Merck Eurolab); N,N-dimethylformamide (LAB, Merck Eurolab); dioxane (for synthesis, Aldrich); methanol (for synthesis, Merck Eurolab).
Water:
Milli-Q Plus, Millipore, demineralized.
Reagents:
Reagents were synthesized according to or in analogy to literature procedures or purchased from Advanced ChemTech (Bamberg, Deutschland), Sigma-Aldrich-Fluka (Deisenhofen, Germany), Bachem (Heidelberg, Germany), J. T. Baker (Phillipsburg, USA), Lancaster (Mühlheim/Main, Germany), Merck Eurolab (Darmstadt, Germany), Neosystem (Strasbourg, France), Novabiochem (Bad Soden, Germany, from 2003 Merck Biosciences, Darmstadt, Germany) und Acros (Geel, Belgium, Vertriebsgesellschaft Fisher Scientific GmbH, Schwerte, Germany), Peptech (Cambridge, Mass., USA), Synthetech (Albany, Oreg., USA), Pharmacore (High Point, N.C., USA), Anaspec (San Jose, Calif., USA) or other companies and used in the assigned quality without further purification.

Plastic ware for biochemical assays were purchased from Greiner Bio-one (Germany), or Nunc (Nalge Europe Ltd).

General Remarks on the Synthesis of the Compounds According to the Present Invention The routes for the synthesis of compounds disclosed in this application by formula (I) mainly depend on the structures of the selected A- and Ar-moieties combined in a particular compound. The examples given below represent synthesis approaches that can be used to synthesize a wide range of compounds described in this application. Of course the following synthesis routes are non-limiting examples, and for any person skilled in the art, more particularly by any organic chemist many additional alternative routes for the synthesis of compounds described in this application are possible and feasible.

Synthesis of Z-A-Ar-Ψ Building Blocks for the Compounds According to the Present Invention In the compounds of formula (I) A is a five membered heterocylic ring which is connected to Ar. Preferably, A is selected from, but is not restricted to the group comprising furyl, thienyl, pyrrolyl, oxazolyl, isooxazolyl, thiazolyl, isothiazolyl, imidazolyl, pyrazolyl, triazolyl oxadiazolyl and thiadiazolyl which are bond to Ar. Such compounds can, in principle, be prepared according to methods described in the literature. Some citations as well as experimental examples are given below.

The synthesis of theses compounds can be achieved by, but is not restricted to, the two strategies outlined in FIG. 1a, whereby G can also be introduced later as outlined in FIG. 1b than for the first strategy in FIG. 1a.

According to the first strategy the two building blocks representing Z-A and Ar-Ψ in formula (I) or precursors are coupled. The key step in this synthesis is the coupling reaction of a Z-A-type building block, functionalized at A with a reactive group $FG_1$, to the aromate Ar of an Ar-Ψ-type building block, functionalized at Ar with a group $FG_2$. This approach is exemplified in examples 4 and 6 where the functional groups $FG_1$ are the boronic acid of the 4-formylfuran-2-boronic acid and the bromide of 5-bromo-thiophene-3-carbaldehyde. $FG_2$ is represented in these examples by the iodide of L-Boc-Phe(4-I)—OH and the boronic acid of 4-[2-methoxycarbonyl-2-(2,4,6-trimethyl-benzoylamino)-ethyl]-boronic acid, respectively.

Figure 1B:
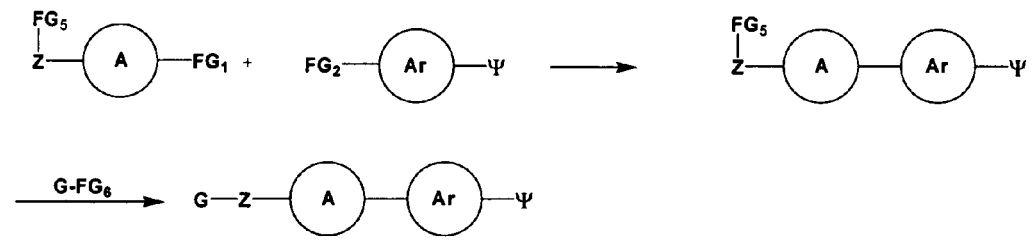

According to the second strategie in FIG. 1a two functionalized building blocks $Z-FG_3$ and $FG_4-Ar-Ψ$ are coupled. In contrast to the first strategy, the 5-membered heterocycle A is formed during this reaction from the reaction of $FG_3$ and $FG_4$.

The key step in this synthesis is the coupling reaction of a Z-type building block, functionalized at Z with a reactive group $FG_3$, to the aromate Ar of an Ar-Ψ-type building block, functionalized at Ar with a group $FG_4$. This approach is exemplified in examples 2, 3, 5 and 7. For example in step c) of example 2 the acetylene moiety of compound (3) and the chlorooximido acetate represent $FG_3$ and $FG_4$, respectively.

In both strategies the final G-Z-A-Ar-Ψ motive could be obtained by the reaction of a Z-A-Ar-Ψ-type building block with a functionalized G-type building block.

Synthesis of Building Blocks G-Z-A-Ar-Ψ

Generally speaking for a group of G-Z-A-type building blocks wherein Z is an alkyl chain, G is of type $R_9$—NH and A is an aromatic 5-membered heterocycle A. This class of building blocks can generally be obtained by methods described in the literature. Two examples for the synthesis are outlined in FIGS. 2a and 2b.

Figure 2A:
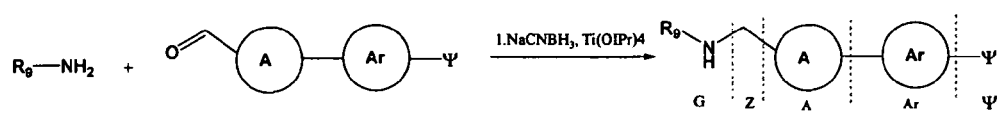
FIGS. 2a and 2b show two reactions for the introduction of G during the synthesis of compounds having the general structure G-Z-A-Ar-Ψ.

FIG. 2a shows the reaction of the amino group in the moiety G with a A-Ar-Ψ or Z-A-Ar-Ψ derivative by a reductive alkylation procedure. Examples for this procedure are the synthesis of compounds (6), (9), (11), (15), (19) and (22) given in examples 2 to 7.

As an alternative to the reductive amination reaction in FIG. 2a an alkylation reaction of a deprotonated Boc-protected amino-heterocycle G with a halogen or OTosyl modified Z-A-Ar-Ψ could be used. This is outlined in FIG. 2b.

Figure 2B:
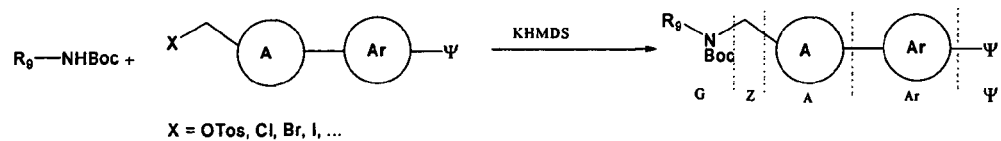

Using one of the procedures outlined in FIGS. 2a and 2b a variety of amino-heterocyclic radicals $R_9$—$NH_2$ representing moiety G can be connected to the systems described for moiety Z-A-Ar-Ψ in formula (I).

These two approaches can be similarly applied to many haloalkyl- or formylalkyl substituted aromatic 5-membered heterocycles A. Together with the wide range of available heterocyclic amines $R_9$—$NH_2$ numerous combinations can be selected to obtain a wide range of G-Z-A-Ar-Ψ compounds.

It should be understood, that with the procedures for the synthesis of G-Z-A-Ar-Ψ and Z-A-Ar-Ψ moieties given above not all related moieties described in this application can be synthesized, but some need more individual synthesis strategies. However, such strategies are known to the ones skilled in the art.

Synthesis of the Building Blocks Ar-Ψ

For the synthesis of building blocks of the Ar-Ψ-type preferably commercially available precursors are used that need only few transformation steps to become suitable building blocks to be used in the Z-A-Ar-Ψ coupling reaction. In a preferred class of compounds disclosed in this application Ar-Ψ-type building blocks can be described as substituted 2-amino-3-arylpropanoic acids. Examples for such 2-amino-3-arylpropanoic acid building blocks wherein aryl is phenyl, are given in examples 2 to 7 with building blocks (2), (7), (13), (17), and (20) that can easily be prepared from commercially available phenylalanine derivatives.

Synthesis approaches for substituted 2-amino-3-arylpropanoic acid derivatives include but are not limited to procedures described in the prior art like palladium catalyzed couplings of aryl or heteroaryl iodides with protected iodo(2-amino-2-carboxy-ethyl)zinc derivatives (R. F. W. Jackson et al., Tetrahedron Letters 1989, 30(43), 5941-5944) or glycine enolate based approaches, e.g., bislactimether alkylation (U. Schöllkopf, W. Hartwig, U. Groth, Angew. Chem. 1979, 91, 922-923) or alkylation of benzophenone imines prepared from glycine alkyl esters (M. J. O'Donnell et al., Tetrahedron Let. 1978, 19(30), 2641-2644).

These and other procedures as described in the prior art will enable any person skilled in the art, more particularly an organic chemist to synthesize any Ar-Ψ-type building block wherein Ar is an aromate as described before, especially wherein Ar is phenyl, pyridyl or thienyl.

Figure 3:
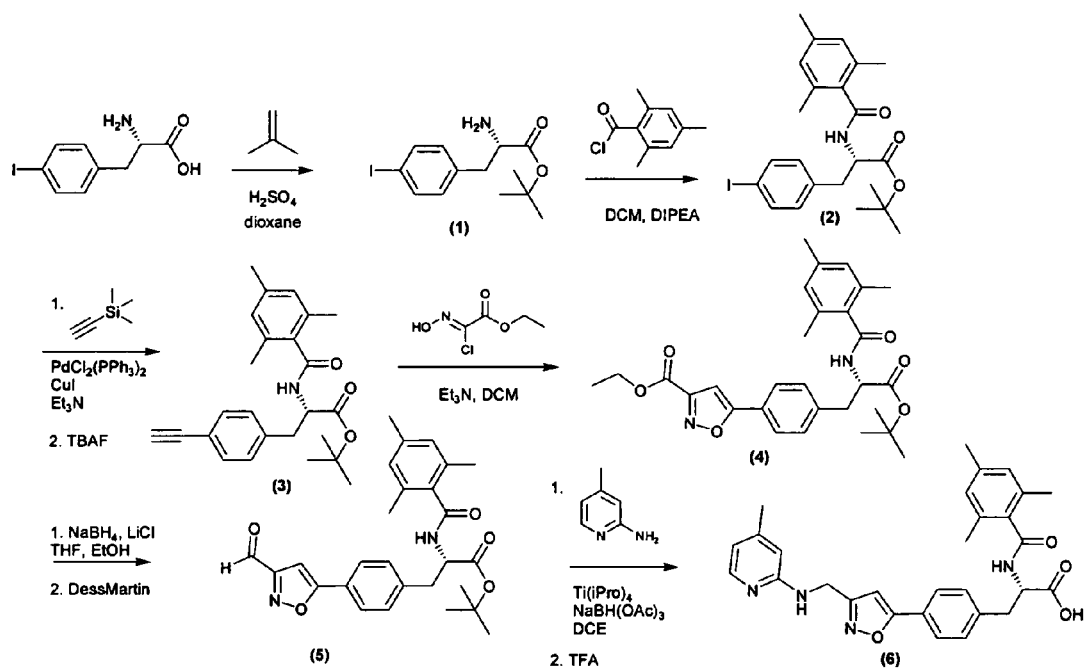
FIG. 3 shows the synthesis of 3-(4-{3-[(4-methyl-pyridin-2-ylamino)-methyl]-isoxazol-5-yl}-phenyl)-2-(2,4,6-trimethyl-benzoylamino)-propionic acid (6).
Figure 4:
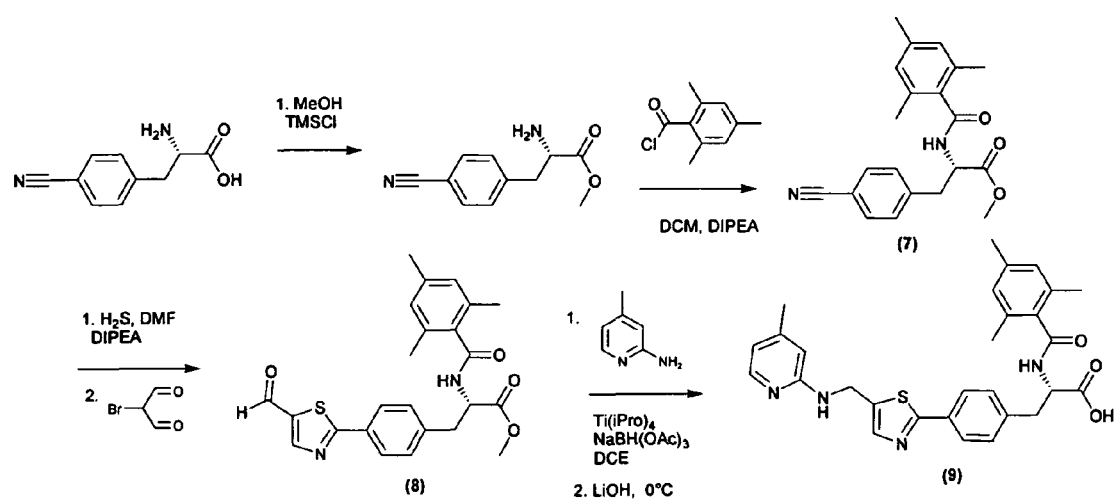
FIG. 4 shows the synthesis of 3-(4-{5-[(4-methyl-pyridin-2-ylamino)-methyl]-thiazol-2-yl}-phenyl)-2-(2,4,6-trimethyl-benzoylamino)-propionic acid (9).

Beside the possibility to synthesize Ar-Ψ-type building blocks, it is also possible to vary the structure of the Ψ-moiety which is defined by formula (II). For example in case of building block (2) in FIG. 3 this can be achieved by exchanging 2,4,6-trimethyl-benzoyl chloride in the reaction depicted in FIG. 3 by different carboxylic acid chlorides. This will affect changes in the structure of the Q-$R_2$-moiety which is a part of Ψ as shown by formula (II). In an analogous manner it would be possible to introduce these changes closer to the last step of a synthesis of compounds of formula (I). For example it is possible to exchange the 2,4,6-trimethyl-benzoic acid in FIG. 5 by a different carboxylic or activated acid derivatives thereof and couple them to compound (11) under appropriate conditions. By using this approach hundreds of derivatives of (12) differing in the structure of Q-$R_2$ can be prepared including those structures disclosed for $R_2$ in the present application.

Figure 5:
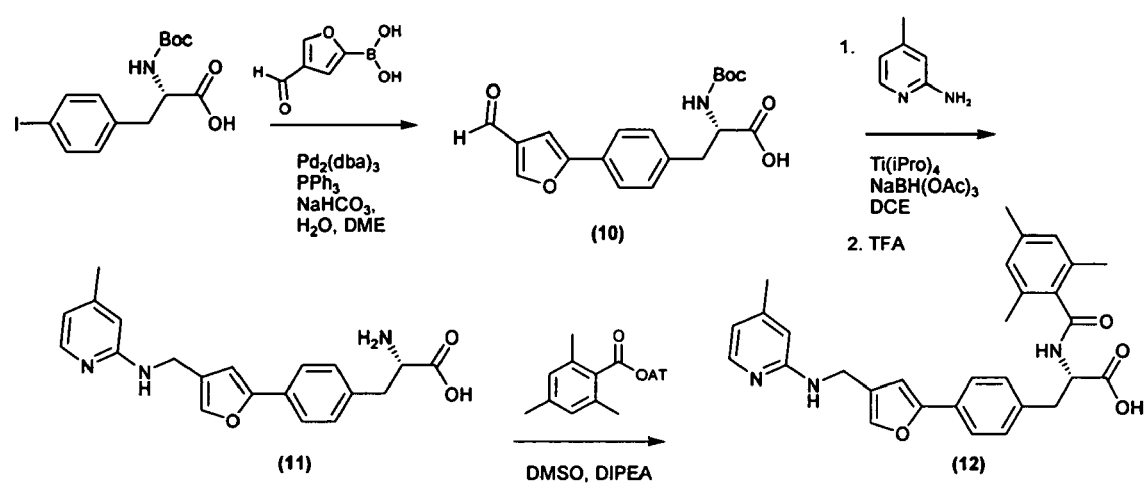
FIG. 5 shows the synthesis of 3-(4-{4-[(4-methyl-pyridin-2-ylamino)-methyl]-furan-2-yl}-phenyl)-2-(2,4,6-trimethyl-benzoylamino)-propionic acid (12).
Figure 6:
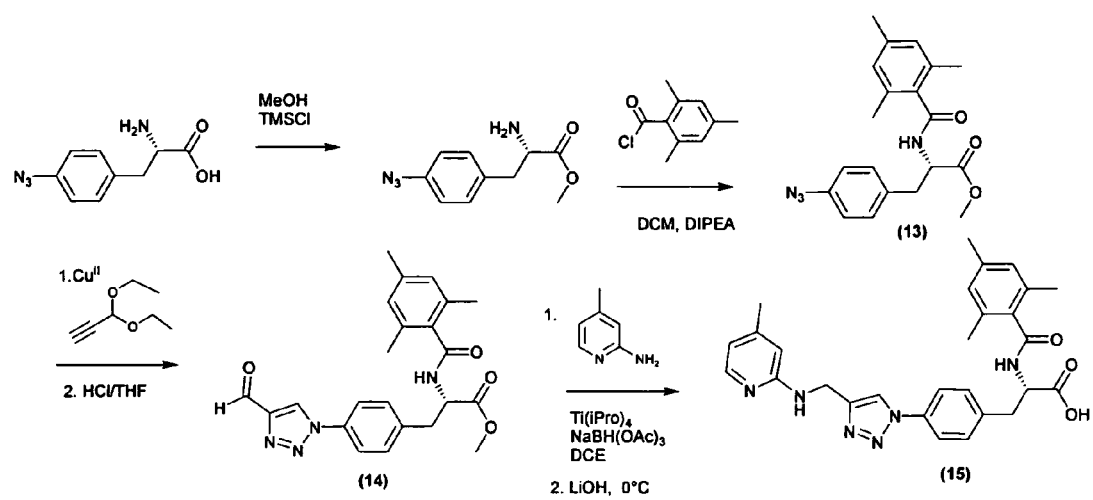
FIG. 6 shows the synthesis of 3-(4-{4-[(4-methyl-pyridin-2-ylamino)-methyl]-furan-2-yl}-phenyl)-2-(2,4,6-trimethyl-benzoylamino)-propionic acid (15).
Figure 7:
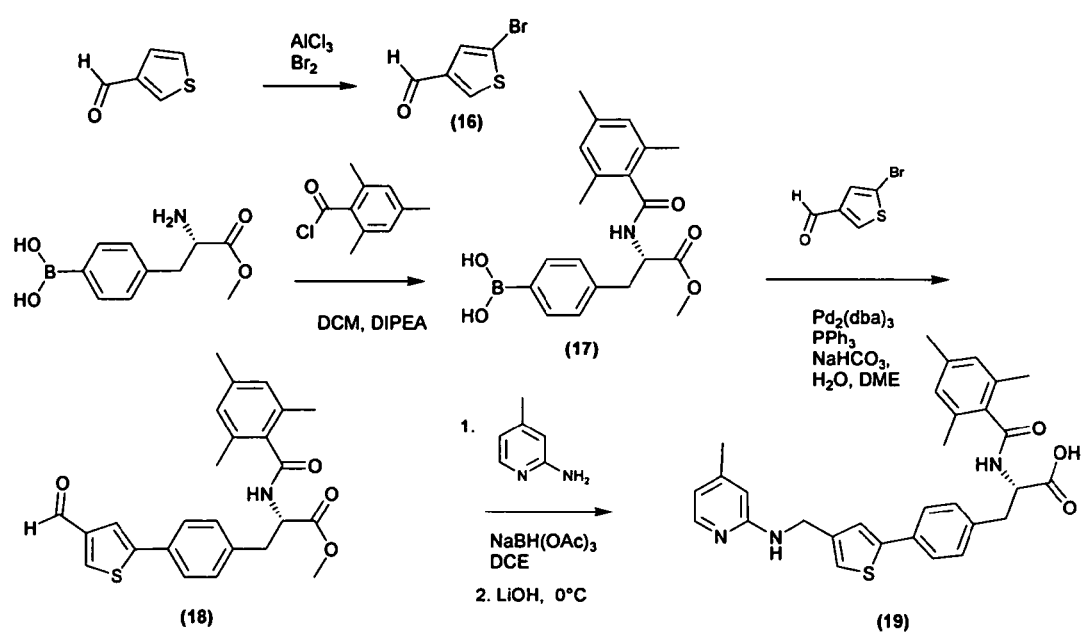
FIG. 7 shows the synthesis of 3-(4-{4-[(4-methyl-pyridin-2-ylamino)-methyl]-thiophen-2-yl}-phenyl)-2-(2,4,6-trimethyl-benzoylamino)-propionic acid (19).
Figure 8:
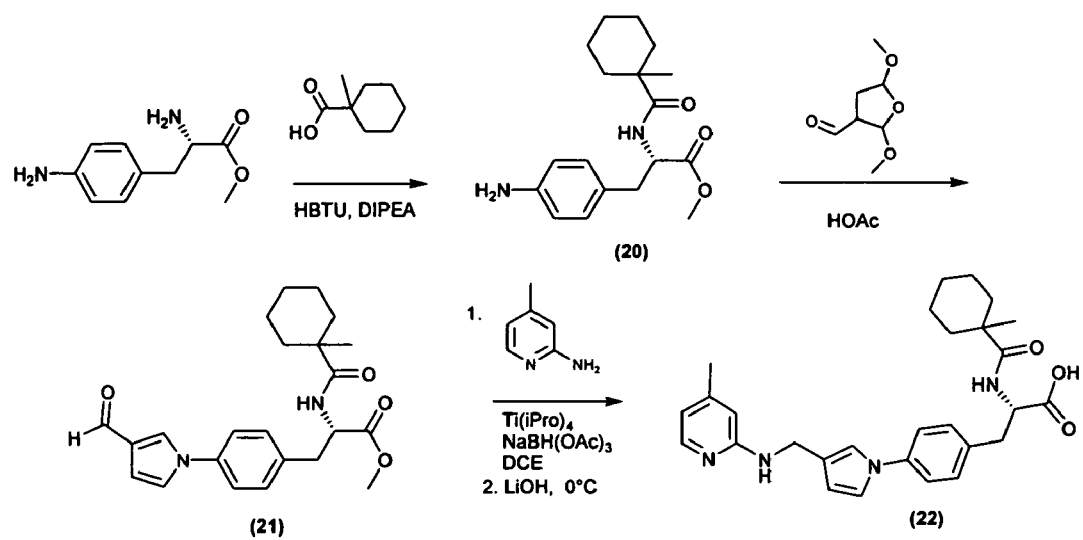
FIG. 8 shows the synthesis of 2-[(1-methyl-cyclohexanecarbonyl)-amino]-3-(4-{3-[(4-methyl-pyridin-2-ylamino)-methyl]-pyrrol-1-yl}-phenyl)-propionic acid (22).

In addition to the transformations of the primary amines like in compound (11) of FIG. 5 into amides as described above, it is also possible to transform the primary amines with appropriate reactants into the lactames disclosed for $R_2$ in the present application, where Q was a direct bond, according to methods described in the literature.

In the following examples 2 to 7 the synthesis of compounds of formula (I) are described where A is isoxazole, thiazole, furane triazole, thiophene and pyrrole respectively.

EXAMPLE 2

3-(4-{3-[(4-methyl-pyridin-2-ylamino)-methyl]-isoxazol-5-yl}-phenyl)-2-(2,4,6-trimethyl-benzoylamino)-propionic Acid (6)

a) Synthesis of 2-amino-3-(4-iodo-phenyl)-propionic Acid Tert-Butyl Ester (1)

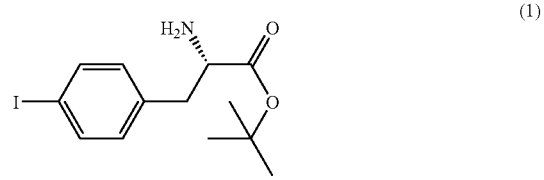

(1)

5 g of L-H-Phe(4-I)—OH were suspended in 500 ml of dioxane. 7 ml of concentrated $H_2SO_4$ were added and the suspension was saturated with isobutene. The reaction mixture was stirred for 4 days under an isobutene atmosphere (balloon). The solution was poured into saturated $NaHCO_3$ at 0° C. and the aqueous layer was extracted with 2.5 l of ethyl acetate. The combined organic layers were dried over $Na_2SO_4$ and solvent was removed at the evaporator to yield 3.68 g of (1).

ESI m/z obs.: 347.7 [M+H] (theor. 347.2)

b) Synthesis of 3-(4-iodo-phenyl)-2-(2,4,6-trimethyl-benzoylamino)-propionic Acid Tert-Butyl Ester (2)

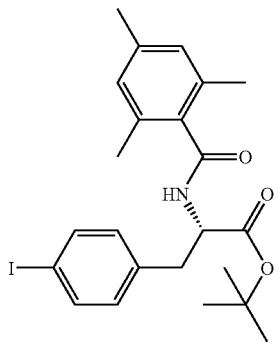

(2)

1.5 g (4.32 mmol) of (1) and 2.9 ml (17.3 mmol) of DIPEA were dissolved in 15 ml of DCM and cooled to 0° C. 1.73 g (9.51 mmol) of 2,4,6-trimethylbenzoyl chloride were added and the solution was stirred at room temperature for 3 h. The solution was poured into saturated $NaHCO_3$ and the aqueous layer was extracted with ethyl acetate. The organic layer was extracted with saturated $NaHCO_3$, brine and dried over $Na_2SO_4$. The solvent was removed at the evaporator. The product was purified by column chromatography on silica gel using ethyl acetate/hexane to give 1.83 g of (2).

ESI m/z obs.: 494.0 [M+H] (theor. 494.12)

c) Synthesis of 3-(4-ethynyl-phenyl)-2-(2,4,6-trimethyl-benzoylamino)-propionic Acid Tert-Butyl Ester (3)

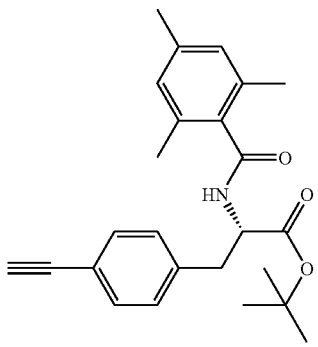

(3)

500 mg (1.01 mmol) of (2), 38 mg (0.203 mmol) of CuI and 71 mg (0.1 eq.) of $PdCl_2(PPh)_3$ were dissolved in 10 ml of $Et_3N$. to The solution was flushed with Argon and 1.68 ml (1.216 mmol) of ethynyl-trimethyl silane were added and stirred for 2 h at room temperature. The reaction mixture was poured into MTBE, washed with saturated $NaHCO_3$, brine and dried over $Na_2SO_4$. The solvent was removed at the evaporator. The crude product was dissolved in 20 ml of THF and cooled to −78° C. 2 ml (2 mmol) of 1 M TBAF solution in THF were added and the reaction mixture was stirred for 45 min at −78° C. 10 ml of water were added and the product was extracted with diethyl ether. The organic layer was extracted with saturated $NaHCO_3$, brine and dried over $Na_2SO_4$. The solvent was removed at the evaporator. The product was purified by column chromatography on silica gel using ethyl acetate/hexane to give 195 mg of (3).

ESI m/z obs.: 392.5 [M+H] (theor. 392.22)

d) Synthesis of 2 5-{4-[2-tert-butoxycarbonyl-2-(2,4,6-trimethyl-benzoylamino)-ethyl]-phenyl}-isoxazole-3-carboxylic Acid Ethyl Ester (4)

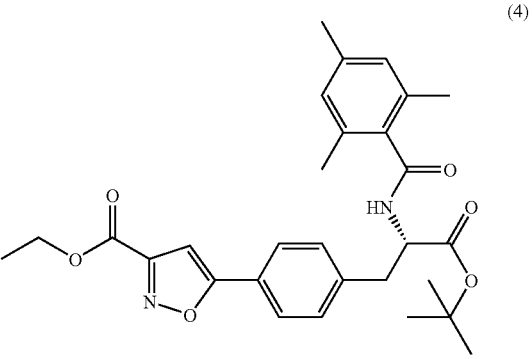

(4)

195 mg (0.498 mmol) of (3) and 377 mg (2.49 mmol) of ethyl chlorooximido acetate were dissolved in 4 ml of DCM and cooled to 0° C. 417 µl (2.99 mmol) of $Et_3N$ dissolved in 4 ml of DCM were added slowly (1 drop/7 seconds). After 3 h additional 3 eq. of ethyl chlorooximidoacetate and $Et_3N$ were added. The reaction mixture was poured into ethyl acetate, washed with saturated $NaHCO_3$, brine and dried over $Na_2SO_4$. The solvent was removed at the evaporator. The product was purified by column chromatography on silica gel using ethyl acetate/hexane to give 165 mg of (4).

ESI m/z obs.: 507.5 [M+H] (theor. 507.25)

e) Synthesis of 3-[4-(3-formyl-isoxazol-5-yl)-phenyl]-2-(2,4,6-trimethyl-benzoylamino)-propionic Acid Tert-Butyl Ester (5)

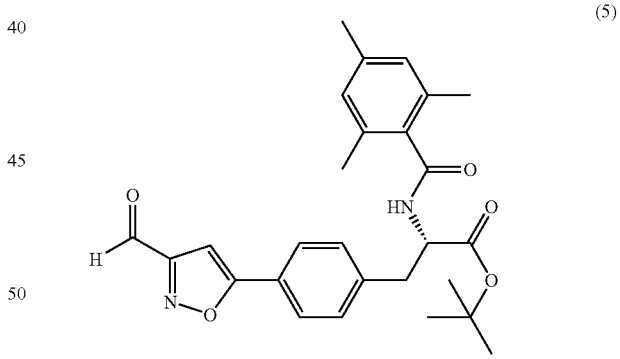

(5)

165 mg (0.326 mmol) of (4), 27 mg (0.65 mmol) of $NaBH_4$ and 30.1 mg (0.65 mmol) of LiCl were dissolved in 5 ml of dry THF/EtOH (3:1) at 0° C. and stirred for 16 h. The reaction mixture was poured into ethyl acetate, washed with saturated $NaHCO_3$, brine and dried over $Na_2SO_4$. The solvent was removed at the evaporator.

145 mg (0.312 mmol) of crude product were dissolved in 10 ml of DCM and 225 mg (0.531 mmol) of Dess Martin periodate were added. The solution was stirred for 30 min. The reaction mixture was poured into ethyl acetate, washed with saturated $NaHCO_3$, brine and dried over $Na_2SO_4$. The solvent was removed at the evaporator. The product was used in the next step without further purification.

ESI m/z obs.: 463.1 [M+H] (theor. 463.23)

f) Synthesis of 3-(4-{3-[(4-methyl-pyridin-2-ylamino)-methyl]-isoxazol-5-yl}-phenyl)-2-(2,4,6-trimethyl-benzoylamino)-propionic Acid (6)

(6)

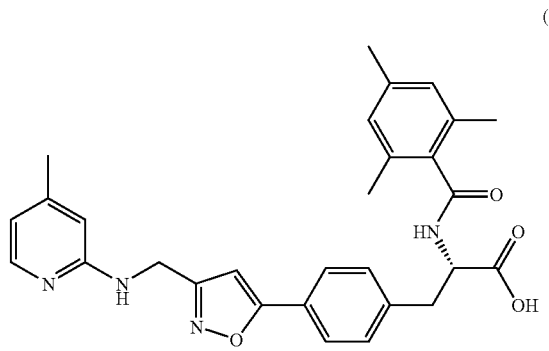

The crude product (5) was dissolved in 10 ml of dichloroethane (DCE) and 69 mg (0.63 mmol) of 4-methylpyridin-2-ylamine and 185 µl of Ti(iPrO)$_4$ were added. The solution was stirred for 2 h. 350 mg of NaHB(OAc)$_3$ were added to the reaction mixture. The suspension was stirred for 12 h. After pouring in ethyl acetate the organic layer was washed with saturated NaHCO$_3$, brine and dried over Na$_2$SO$_4$.

The crude product was dissolved in 1 ml of DCM. 200 l of triethyl silane and 5 ml of TFA were added. After 30 min the solvent was removed at the evaporator. The product was purified by HPLC to give 50 mg (6) as TFA salt.

ESI m/z obs.: 499.6 [M+H] (theor. 499.24)

EXAMPLE 3

3-(4-{5-[(4-methyl-pyridin-2-ylamino)-methyl]-thiazol-2-yl}-phenyl)-2-(2,4,6-trimethyl-benzoylamino)-propionic Acid (9)

a) Synthesis of 3-(4-cyano-phenyl)-2-(2,4,6-trimethyl-benzoylamino)-propionic Acid Methyl Ester (7)

(7)

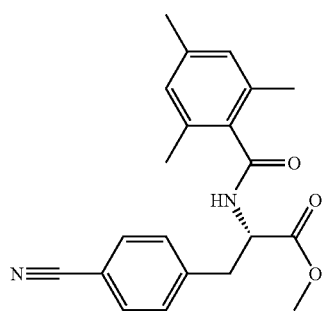

1 g (5.3 mmol) of L-H-Phe(4-CN)—OH and 1.3 ml (10.5 mmol) of trimethyl silyl chloride were dissolved in dry methanol and stirred for 12 h. The solvent was removed at the evaporator. The crude product was dissolved in 30 ml of DCM and 5.4 ml (31.8 mmol) of DIPEA were added. The solution was cooled to 0° C. and 1.9 ml (15.9 mmol) of 2,4,6-trimethylbenzoyl chloride were added and the solution was stirred for 4 h. After pouring in ethyl acetate the organic layer was washed with saturated NaHCO$_3$, brine and dried over Na$_2$SO$_4$. The solvent was removed at the evaporator. The product was purified by column chromatography on silica gel using ethyl acetate/hexane to give 1.55 g of (7).

ESI m/z obs.: 350.9 [M+H] (theor. 351.17)

b) Synthesis of 3-[4-(5-formyl-thiazol-2-yl)-phenyl]-2-(2,4,6-trimethyl-benzoylamino)-propionic Acid Methyl Ester (8)

(8)

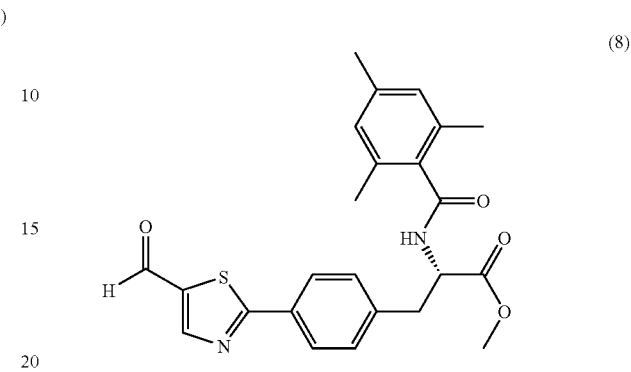

200 mg (0.6 mmol) of (7) and 306 µl (1.8 mmol) of DIPEA were dissolved in 10 ml of DMF. H$_2$S was bubbled through the solution and the reaction mixture was stirred under H$_2$S atmosphere over night at 50° C. After pouring in ethyl acetate the organic layer was washed with saturated NaHCO$_3$, brine and dried over Na$_2$SO$_4$. The solvent was removed at the evaporator. The thioamide was redissolved in 15 ml of 1,4-dioxane and 213 mg (1.4 mmol) of 2-bromo-malonaldehyde were added. The solution was stirred for 1 h at 60° C. After pouring in ethyl acetate the organic layer was washed with saturated NaHCO$_3$, water, brine and dried over Na$_2$SO$_4$. The solvent was removed at the evaporator. The product was purified by column chromatography on silica gel using ethyl acetate/hexane to give 180 g of (8).

ESI m/z obs.: 436.9 [M+H] (theor. 437.16)

c) Synthesis of 3-(4-{5-[(4-methyl-pyridin-2-ylamino)-methyl]-thiazol-2-yl}-phenyl)-2-(2,4,6-trimethyl-benzoylamino)-propionic Acid (9)

(9)

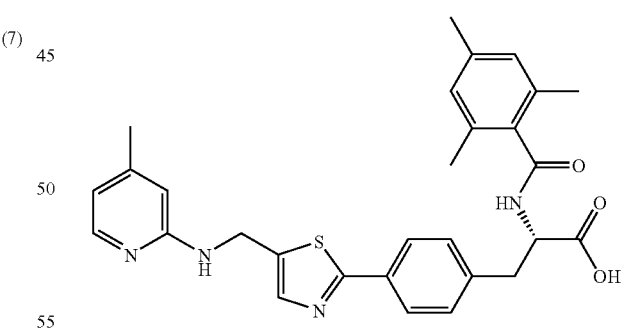

50 mg of (8) were dissolved in 10 ml of dichloroethane and 19 mg (1.5 eq.) of 4-methylpyridin-2-ylamine and 51 µl (1.5 eq.) of Ti(iPrO)$_4$ were added. The solution was stirred for 3 h. 117 mg (5 eq.) of NaHB(OAc)$_3$ were given to the reaction mixture. The suspension was stirred for 48 h at room temperature. After pouring in ethyl acetate the organic layer was washed with saturated NaHCO$_3$, brine and dried over Na$_2$SO$_4$.

The crude product was redissolved in 4 ml of 1,4-dioxane and 2 ml of water. The solution was cooled to 0° C. and 10 mg (1 eq.) of LiOH*H$_2$O were added. The solution was neutralized after 2 h with 1 M HCl and concentrated in vacuo. The product was purified by HPLC to give 30.4 mg of (9) as TFA salt.

ESI m/z obs.: 516.1 [M+H] (theor. 515.21)

EXAMPLE 4

3-(4-{4-[(4-methyl-pyridin-2-ylamino)-methyl]-furan-2-yl}-phenyl)-2-(2,4,6-trimethyl-benzoylamino)-propionic acid (12)

a) Synthesis of 2-tert-butoxycarbonylamino-3-[4-(4-formyl-furan-2-yl)-phenyl]-propionic Acid (10)

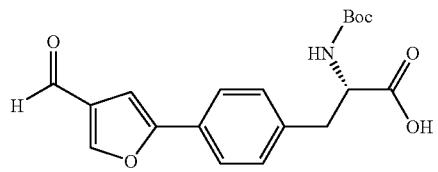

(10)

2.65 g (6.77 mmol) of L-Boc-Phe(4-I)—OH, 789 mg (14.0 mmol) of 4-formylfuran-2-boronic acid, 1.66 g (19.7 mmol) of $NaHCO_3$, 1.18 g (4.512 mmol) of $PPh_3$ and 584 mg (0.1 eq.) of $Pd_2(dba)_3$ were dissolved in 75 ml of DME and 75 ml of water. The reaction mixture was stirred at 80° C. for 5 h. DME was removed and the aqueous layer was acified with 1 M HCl. and the aqueous layer was extracted with ethyl acetate. The organic layer was washed with brine and dried over $Na_2SO_4$. The product was purified by column chromatography on silica gel using ethyl acetate/hexane to give 817 mg of (10).

b) Synthesis of 2-amino-3-(4-{4-[(4-methyl-pyridin-2-ylamino)-methyl]-furan-2-yl}-phenyl)-propionic Acid (11)

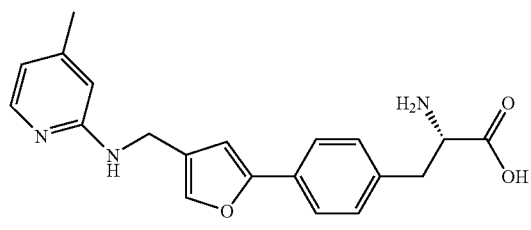

(11)

600 mg (1.67 mmol) of (10) were dissolved in 30 ml of dichloroethane (DCE) and 271 mg (2.5 mmol) of 4-methyl-pyridin-2-ylamine and 746 µl (2.5 mmol) of $Ti(iPrO)_4$ were added. The solution was stirred for 3 h at room temperature. 1.77 g (8.35 mmol) of $NaHB(OAc)_3$ were given to the reaction mixture. The suspension was stirred for 12 h. After pouring in ethyl acetate the organic layer was washed with brine. The aqueous layer was again extracted with DCM and the combined organic layers were dried over $Na_2SO_4$. The product was purified by column chromatography on silica gel using ethyl acetate/hexane and MeOH to give 400 mg of the crude ester.

The product was redissolved in 2 ml DCM and 5 ml of TFA were added. The solution was stirred for 30 min. and the solvents were removed to give 691 mg of (11) as TFA salt.

ESI m/z obs.: 352.1 [M+H] (theor. 352.17)

c) Synthesis of 3-(4-{4-[(4-methyl-pyridin-2-ylamino)-methyl]-furan-2-yl}-phenyl)-2-(2,4,6-trimethyl-benzoylamino)-propionic Acid (12)

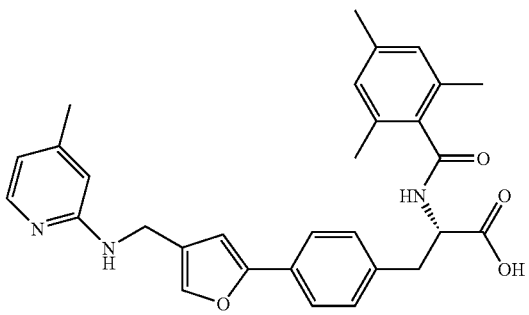

(12)

50 mg of (11) as 2HCl salt and 120 µl of DIPEA were dissolved in 1 ml of DMSO. 29 mg of the OAT ester of 2,4,6-trimethylbenzoic acid were added. The solution was stirred for 12 h and the product was purified by HPLC to give 10.8 mg of (12) as TFA salt.

ESI m/z obs.: 498.5 [M+H] (theor. 498.24)

EXAMPLE 5

3-(4-{4-[(4-methyl-pyridin-2-ylamino)-methyl]-furan-2-yl}-phenyl)-2-(2,4,6-trimethyl-benzoylamino)-propionic Acid (15)

a) Synthesis of 3-(4-azido-phenyl)-2-(2,4,6-trimethyl-benzoylamino)-propionic Acid Methyl Ester (13)

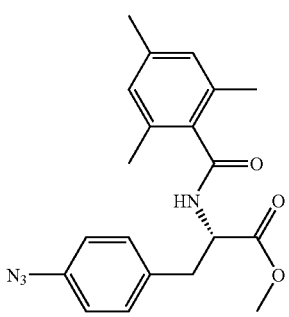

(13)

300 mg (1.45 mmol) of L-H-Phe(4-$N_3$)—OH and 1.4 ml (10 eq.) of trimethyl silyl chloride were dissolved in 4 ml of dry methanol and stirred for 12 h. The solvent was removed at the evaporator. The crude product was crystallized from ACN/diisopropyl ether to yield 351 mg of methyl ester.

The ester was dissolved in 10 ml of DCM and 746 µl (4.3 mmol) of DIPEA were added. The solution was cooled to 0° C. and 400 mg (2.18 mmol) of 2,4,6-trimethylbenzoyl chloride were added and the solution was stirred for 1 h. After pouring in ethyl acetate the organic layer was washed with saturated $NaHCO_3$, brine and dried over $Na_2SO_4$. The solvent was removed at the evaporator. The product was purified by column chromatography on silica gel using ethyl acetate/hexane to give 565 mg of (13).

ESI m/z obs.: 366.9 [M+H] (theor. 366.17)

b) Synthesis of 3-[4-(4-formyl-[1,2,3]triazol-1-yl)-phenyl]-2-(2,4,6-trimethyl-benzoylamino)-propionic Acid Methyl Ester (14)

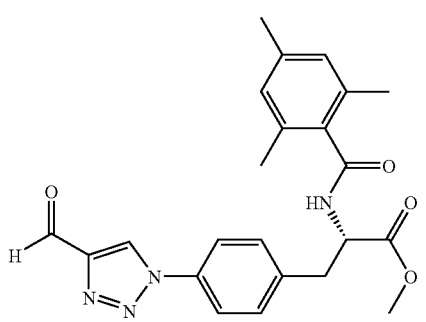

(14)

250 mg (0.68 mmol) of (13) and 684 µl (4.77 mmol) of 3,3-diethoxy-propyne were dissolved in 3 ml of dioxane. 500 µl of saturated Cu(AcO)$_2$ solution in H$_2$O were added and the solution was stirred for 10 min. After pouring in ethyl acetate the organic layer was washed with saturated NaHCO$_3$, water, brine and dried over Na$_2$SO$_4$. The crude product was dissolved in 500 µl THF with 10% of HCl and stirred for 1 h. The solution was poured in 20 ml of saturated NaHCO$_3$ solution and extracted with ethyl acetate. The organic layer was washed with saturated brine and dried over Na$_2$SO$_4$. The solvent was removed at the evaporator. The product was used in the next step without further purification.

c) Synthesis of 3-(4-{4-[(4-methyl-pyridin-2-ylamino)-methyl]-[1,2,3]triazol-1-yl}-phenyl)-2-(2,4,6-trimethyl-benzoylamino)-propionic Acid (15)

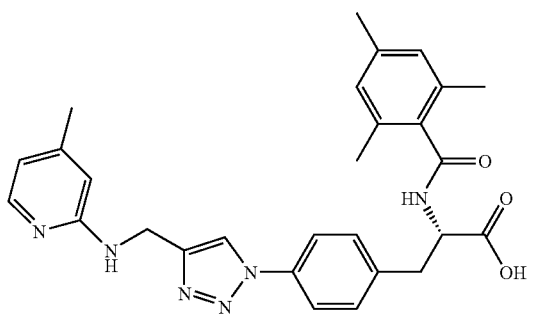

(15)

268 mg of (14) were dissolved in 20 ml of dichloroethane and 103 mg (1.5 eq.) of 4-methylpyridin-2-ylamine and 284 µl (1.5 eq.) of Ti(iPrO)$_4$ were added. The solution was stirred for 1 h at room temperature. 673 mg (5 eq.) of NaHB(OAc)$_3$ were given to the reaction mixture. The suspension was stirred for 2 h at room temperature. After pouring in ethyl acetate the organic layer was washed with saturated NaHCO$_3$, brine and dried over Na$_2$SO$_4$ to yield 471 mg of crude ester.

70 mg of the crude ester were redissolved in 4 ml of 1,4-dioxane and 2 ml of water. The solution was cooled to 0° C. and 3 eq. of LiOH*H$_2$O were added. The solution was neutralized after 2 h with NH$_4$Cl solution and concentrated in vacuo. The product was purified by HPLC to give 53.9 mg of (15) as TFA salt.

ESI m/z obs.: 499.4 [M+H] (theor.: 499.25)

EXAMPLE 6

3-(4-{4-[(4-methyl-pyridin-2-ylamino)-methyl]-thiophen-2-yl}-phenyl)-2-(2,4,6-trimethyl-benzoylamino)-propionic acid (19)

a) Synthesis of 5-bromo-thiophene-3-carbaldehyde (16)

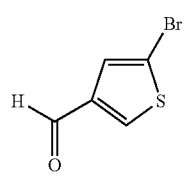

(16)

1 g (8.92 mmol) of thiophene-3-carbaldehyde and 2.97 g (2.5 eq.) of AlCl$_3$ were suspended in 20 ml of DCM. 426 µl (0.93 eq.) of bromine in 1 ml of DCM were added and the reaction mixture was heated for 3 h at 60° C. (oil bath). The solution was given into 100 ml of ice water and extracted with CHCl$_3$. The organic layer was washed with saturated Na$_2$S$_4$O$_3$, brine and dried over Na$_2$SO$_4$. The solvent was removed at the evaporator. The product was purified by column chromatography on silica gel using ethyl acetate/hexane to give 1.04 g of (16).

b) Synthesis of 4-[2-methoxycarbonyl-2-(2,4,6-trimethyl-benzoylamino)-ethyl]-boronic Acid (17)

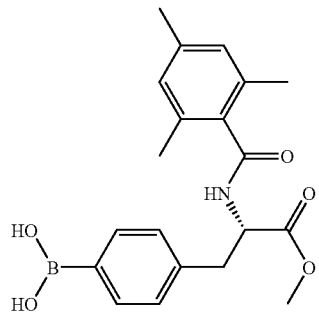

(17)

1.24 g (4.78 mmol) of L-H-Phe(4-B(OH)$_2$)—OMe were dissolved in 20 ml of DCM and 2.45 ml (14.3 mmol) of DIPEA were added. The solution was cooled to 0° C. and 960 mg (5.26 mmol) of 2,4,6-trimethylbenzoyl chloride were added and the reaction mixture was stirred for 1 h. The solution was acified with 1 M HCl (pH=4) and extracted with ethyl acetate. The organic layer was washed with saturated brine and dried over Na$_2$SO$_4$. The solvent was removed at the evaporator. The product was purified crystallization from ethyl acetate and hexane to give 683 mg of (17).

ESI m/z obs.: 370.5 [M+H] (theor. 370.18)

c) Synthesis of 3-[4-(4-formyl-thiophen-2-yl)-phenyl]-2-(2,4,6-trimethyl-benzoylamino)-propionic Acid Methyl Ester (18)

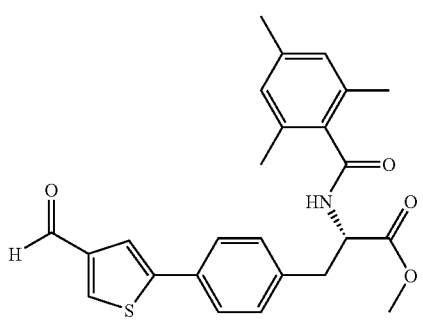

(18)

413 mg (1.12 mmol) of (17), 270 mg (1.41 mmol) of (16), 216 g (2.57 mmol) of NaHCO$_3$, 235 mg (0.894 mmol) of PPh$_3$ and 116 mg (0.1 eq.) of Pd$_2$(dba)$_3$ were dissolved in 20 ml of DME and 20 ml of water. The reaction mixture was stirred at 80° C. for 3 h. The DME was removed and the aqueous layer was acified with 1 M HCl. The aqueous layer was acified with 1M HCl and extracted with ethyl acetate. The organic layer was washed with brine and dried over Na$_2$SO$_4$. The product was purified by HPLC to give 99 mg of (18).

ESI m/z obs.: 436.1 [M+H] (theor. 436.16)

d) Synthesis of 3-(4-{4-[(4-methyl-pyridin-2-ylamino)-methyl]-thiophen-2-yl}-phenyl)-2-(2,4,6-trimethyl-benzoylamino)-propionic Acid (19)

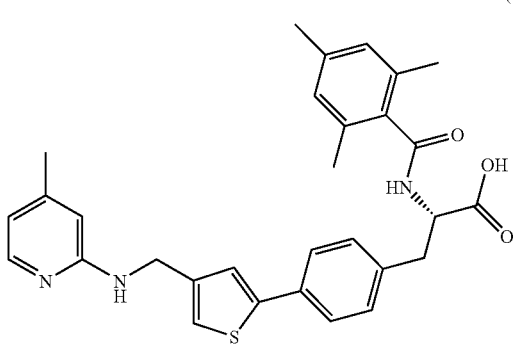

(19)

99 mg of (18) were dissolved in/ml of dichloroethane and 37 mg (1.5 eq.) of 4-methylpyridin-2-ylamine and 240 mg (5 eq.) of NaHB(OAc)$_3$ were added. The solution was stirred for 2.5 h. After pouring in ethyl acetate the organic layer was washed with saturated NaHCO$_3$, brine and dried over Na$_2$SO$_4$. The crude product was redissolved in 6 ml of 1,4-dioxane and 1 ml of water. The solution was cooled to 0° C. and 3 eq. of LiOH*H$_2$O were added. The solution was neutralized after 6 h with 1 M HCl and concentrated in vacuo. The product was purified by HPLC to give 39.1 mg of (19) as TFA salt.

ESI m/z obs.: 514.6 [M+H] (theor. 514.22)

EXAMPLE 7

2-[(1-methyl-cyclohexanecarbonyl)-amino]-3-(4-{3-[(4-methyl-pyridin-2-ylamino)-methyl]-pyrrol-1-yl}-phenyl)-propionic acid (22)

a) Synthesis of 3-(4-amino-phenyl)-2-[(1-methyl-cyclohexanecarbonyl)-amino]-propionic Acid Methyl Ester (20)

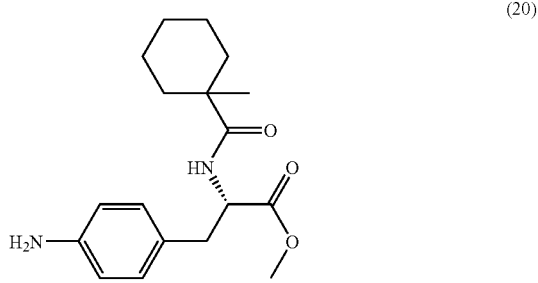

(20)

700 mg (4.92 mmol) of 1-methyl-cyclohexanecarboxylic acid, 1.74 ml (10.25 mmol) of DIPEA and 1.71 g (4.51 mmol) of HBTU were dissolved in 30 ml of DMF and stirred for 10 min. 790 mg (4.1 mmol) of L-H-Phe(4—NH$_2$)—OMe dissolved in 5 ml of DMF were added to the solution and stirred for additional 12 h. The solvent was evaporated and the crude product was dissolved in ethyl acetate. The organic layer was washed with saturated NaHCO$_3$, brine and dried over Na$_2$SO$_4$. The solvent was removed at the evaporator. The product was purified by column chromatography on silica gel using ethyl acetate/hexane to give 1.3 g of (20).

ESI m/z obs.: 319.1 [M+H] (theor. 319.20)

a) Synthesis of -[4-(3-formyl-pyrrol-1-yl)-phenyl]-2-[(1-methyl-cyclohexanecarbonyl)-amino]-propionic Acid Methyl Ester (21)

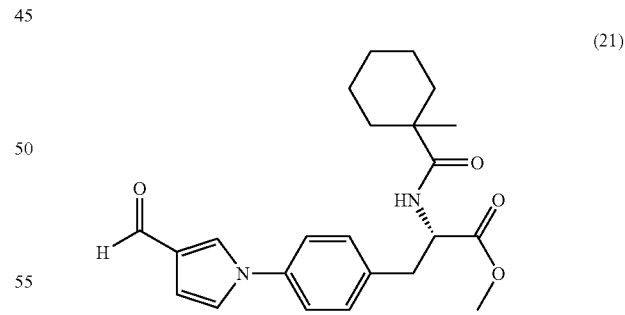

(21)

100 mg (0.314 mmol) of (20), 50 mg (0.314 mmol) of 2,5-dimethoxy-tetrahydro-furan-3-carbaldehyde were dissolved in 1 ml of HOAc. The reaction mixture was stirred at 110° C. (oil bath) for 1 h. The solvent was evaporated and the crude product was dissolved in ethyl acetate. The organic layer was washed with saturated NaHCO$_3$, brine and dried over Na$_2$SO$_4$. The solvent was removed at the evaporator and the product was used in the next step without further purification.

ESI m/z obs.: 397.0 [M+H] (theor. 397.21)

c) Synthesis of 2-[(1-methyl-cyclohexanecarbonyl)-amino]-3-(4-{3-[(4-methyl-pyridin-2-ylamino)-methyl]-pyrrol-1-yl}-phenyl)-propionic Acid (22)

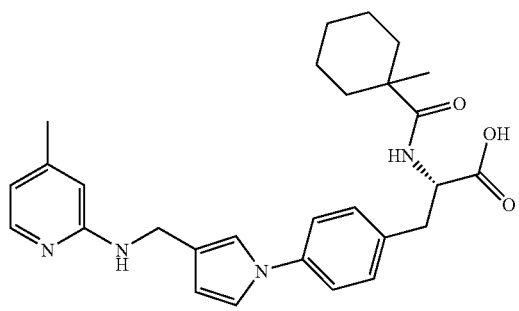

(22)

62 mg (0.157 mmol) of (21) were dissolved in 1 ml of dichloroethane and 39 mg (2 eq.) of 4-methylpyridin-2-ylamine and 56111 (1.2 eq.) of Ti(iPrO)$_4$ were added. The solution was stirred for 12 h. 166 mg (5 eq.) of NaHB(OAc)$_3$ were given to the reaction mixture. The suspension was stirred for 2 h at room temperature. After pouring in ethyl acetate the organic layer was washed with saturated NaHCO$_3$, brine and dried over Na$_2$SO$_4$ to yield 69 mg of crude product.

The crude product was redissolved in 1 ml of 1,4-dioxane and 0.5 ml of water. The solution was cooled to 0° C. and 4 eq. of LiOH*H$_2$O were added. The solution was concentrated in vacuo after 2 h. The product was purified by HPLC to give 16.9 mg of (22) as TFA salt.

ESI m/z obs.: 475.7 [M+H] (theor. 475.27)

It is to be acknowledged that according to the protocols described herein any of the compounds as specified in Table 1 and also many others comprised in this application, can be synthesized using derivatives of the staring materials. These minor changes in the staring can be preformed by any person skilled in the art, more particularly by any organic chemist. Some of the more preferred compounds according to the present invention are summarised in table 1 and include any pharmaceutically acceptable salt, solvate or prodrug thereof.

Table 1

| no | structure | name | formula | molecular weight | LCMS | synthesis in analogy to example |
|---|---|---|---|---|---|---|
| 6 | 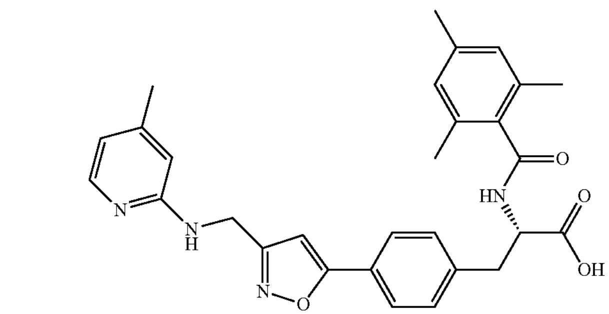 | 3-(4-{3-[(4-Methyl-pyridin-2-ylamino)-methyl]-isoxazol-5-yl}-phenyl)-2-(2,4,6-trimethyl-benzoylamino)-propionic acid | C29H30N4O4 | 498.57 | 499.6 | 2 |
| 9 | 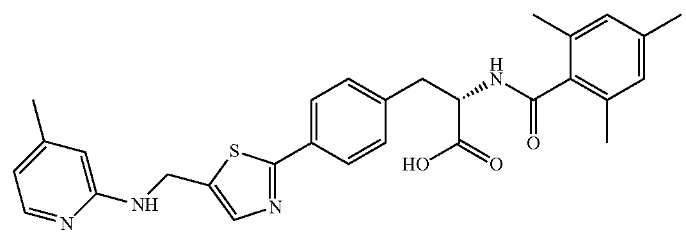 | 3-(4-{5-[(4-Methyl-pyridin-2-ylamino)-methyl]-thiazol-2-yl}-phenyl)-2-(2,4,6-trimethyl-benzoylamino)-propionic acid | C29H30N4O3S | 514.64 | 516.1 | 3 |
| 12 | 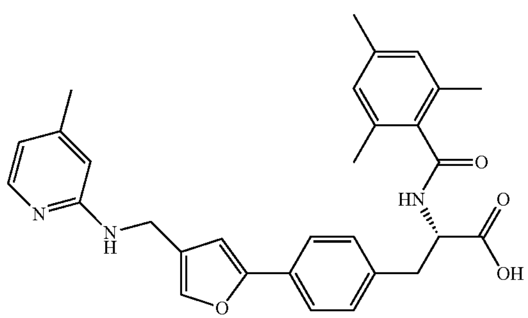 | 3-(4-{4-[(4-Methyl-pyridin-2-ylamino)-methyl]-furan-2-yl}-phenyl)-2-(2,4,6-trimethyl-benzoylamino)-propionic acid | C30H31N3O4 | 497.58 | 498.5 | 4 |

Table 1-continued

| no | structure | name | formula | molecular weight | LCMS | synthesis in analogy to example |
|---|---|---|---|---|---|---|
| 15 | 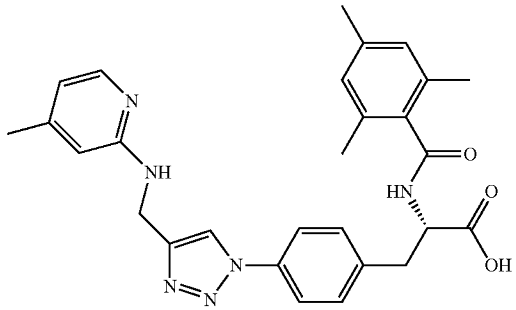 | 3-(4-{4-[(4-Methyl-pyridin-2-ylamino)-methyl]-[1,2,3]triazol-1-yl}-phenyl)-2-(2,4,6-trimethyl-benzoylamino)-propionic acid | C28H30N6O3 | 498.58 | 499.4 | 5 |
| 19 | 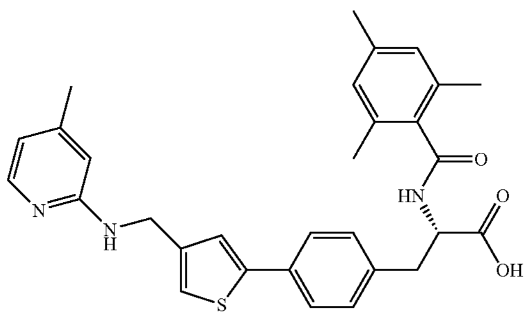 | 3-(4-{4-[(4-Methyl-pyridin-2-ylamino)-methyl]-thiophen-2-yl}-phenyl)-2-(2,4,6-trimethyl-benzoylamino)-propionic acid | C30H31N3O3S | 513.65 | 514.6 | 6 |
| 22 | 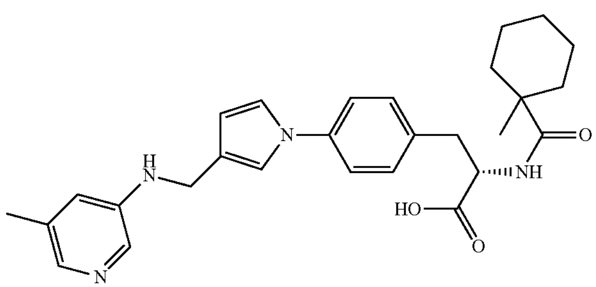 | 2-[(1-Methyl-cyclohexanecarbonyl)-amino]-3-(4-{3-[(4-methyl-pyridin-2-ylamino)-methyl]-pyrrol-1-yl}-phenyl)-propionic acid | C28H34N4O3 | 474.59 | 475.6 | 7 |

Table 1-continued

| no | structure | name | formula | molecular weight | LCMS | synthesis in analogy to example |
|---|---|---|---|---|---|---|
| 23 | 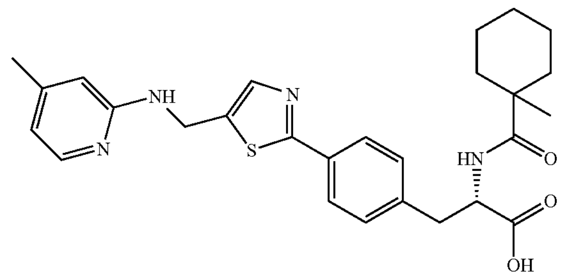 | 2-[(1-Methyl-cyclohexanecarbonyl)-amino]-3-(4-{5-[(4-methyl-pyridin-2-ylamino)-methyl]-thiazol-2-yl}-phenyl)-propionic acid | C27H32N4O3S | 492.63 | 493.2 | 3 |
| 24 | 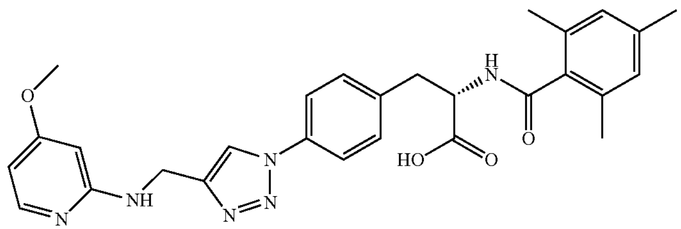 | 3-(4-{4-[(4-Methoxy-pyridin-2-ylamino)-methyl]-[1,2,3]triazol-1-yl]-phenyl)-2-(2,4,6-trimethyl-benzoylamino)-propionic acid | C28H30N6O4 | 514.58 | 515.6 | 5 |
| 25 | 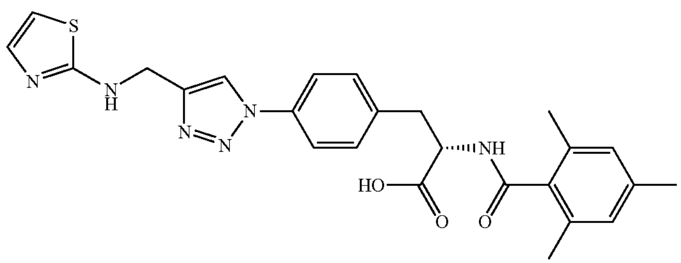 | 3-(4-{4-[(Thiazol-2-ylaminomethyl)-[1,2,3]triazol-1-yl]-phenyl)-2-(2,4,6-trimethyl-benzoylamino)-propionic acid | C25H26N6O3S | 490.58 | 491.3 | 5 |
| 26 | 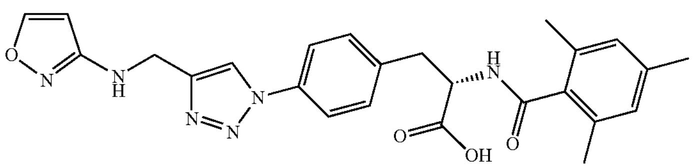 | 3-(4-{4-[(Isoxazol-3-ylaminomethyl)-[1,2,3]triazol-1-yl]-phenyl)-2-(2,4,6-trimethyl-benzoylamino)-propionic acid | C25H26N6O4 | 474.51 | 475.3 | 5 |

Table 1-continued

| no | structure | name | formula | molecular weight | LCMS | synthesis in analogy to example |
|---|---|---|---|---|---|---|
| 27 | 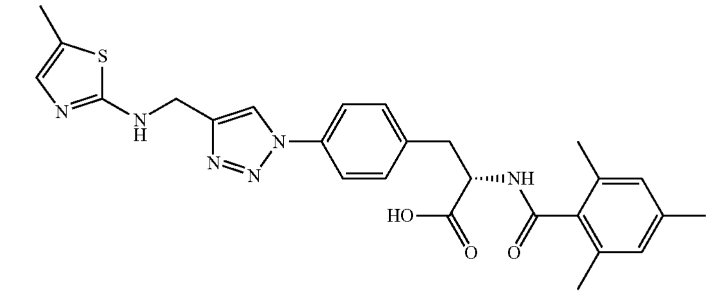 | 3-(4-{4-[(5-Methyl-thiazol-2-ylamino)-methyl]-[1,2,3]triazol-1-yl}-phenyl)-2-(2,4,6-trimethyl-benzoylamino)-propionic | C26H28N6O3S | 504.61 | 505.7 | 5 |
| 28 | 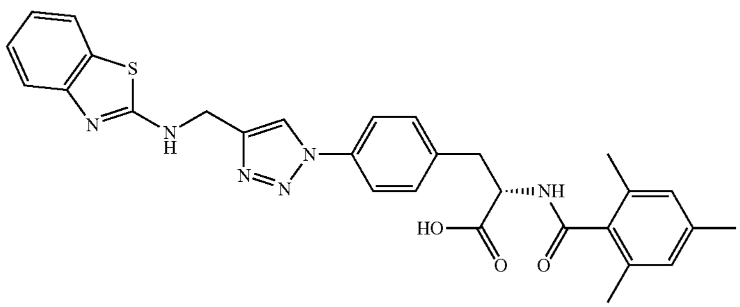 | 3-{4-[4-(Benzothiazol-2-ylamino-methyl)-[1,2,3]triazol-1-yl]-phenyl}-2-(2,4,6-trimethyl-benzoylamino)-propionic | C29H28N6O3S | 540.64 | 541.3 | 5 |
| 29 | 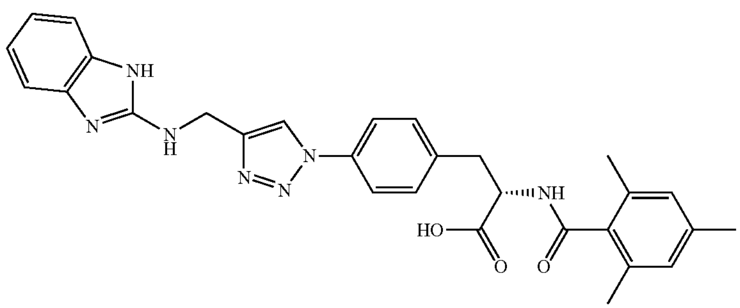 | 3-(4-{4-[(1H-Benzoimidazol-2-ylamino)-methyl]-[1,2,3]triazol-1-yl}-phenyl)-2-(2,4,6-trimethyl-benzoylamino)-propionic | C29H29N7O3 | 523.59 | 524.5 | 5 |

Table 1-continued

| no | structure | name | formula | molecular weight | LCMS | synthesis in analogy to example |
|---|---|---|---|---|---|---|
| 30 | 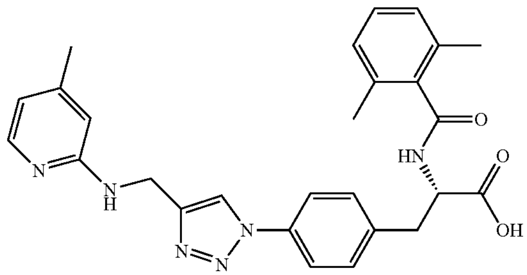 | 2-(2,6-Dimethyl-benzoylamino)-3-(4-{4-[(4-methyl-pyridin-2-ylamino)-methyl]-[1,2,3]triazol-1-yl}-phenyl)-propionic acid | C27H28N6O3 | 484.55 | 485.2 | 5 |
| 31 | 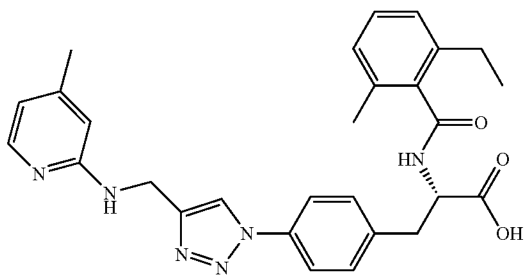 | 2-(2-Ethyl-6-methyl-benzoylamino)-3-(4-{4-[(4-methyl-pyridin-2-ylamino)-methyl]-[1,2,3]triazol-1-yl]-phenyl)-propionic acid | C28H30N6O3 | 498.58 | 499.5 | 5 |
| 32 | 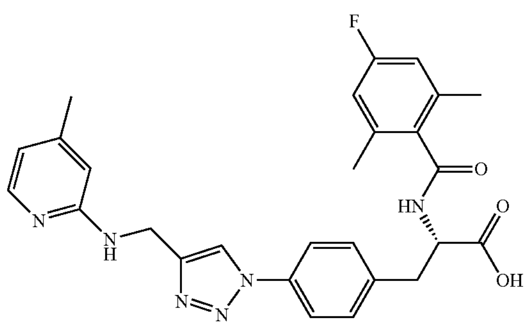 | 2-(4-Fluoro-2,6-dimethyl-benzoylamino)-3-(4-{4-[(4-methyl-pyridin-2-ylamino)-methyl]-[1,2,3]triazol-1-yl]-phenyl)-propionic acid | C27H27N6O3F | 502.54 | 503.2 | 5 |

Table 1-continued

| no | structure | name | formula | molecular weight | LCMS | synthesis in analogy to example |
|---|---|---|---|---|---|---|
| 33 | 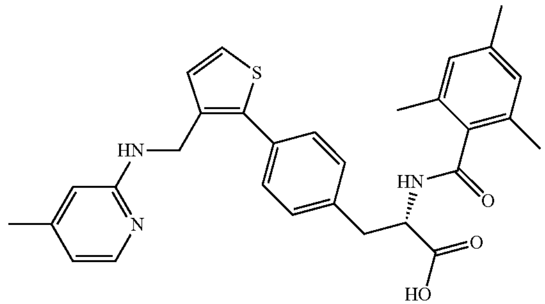 | 3-(4-{4-[(4-Methyl-pyridin-2-ylamino)-methyl]-thiophen-2-yl}-phenyl)-2-(2,4,6-trimethyl-benzoylamino)-propionic acid | C30H31N3O3S | 513.65 | 514.1 | 6 |
| 34 | 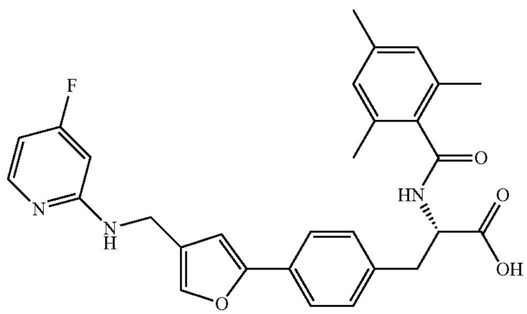 | 3-(4-{4-[(4-Fluoro-pyridin-2-ylamino)-methyl]-furan-2-yl}-phenyl)-2-(2,4,6-trimethyl-benzoylamino)-propionic acid | C29H28N3O4F | 501.55 | 502.9 | 7 |
| 35 | 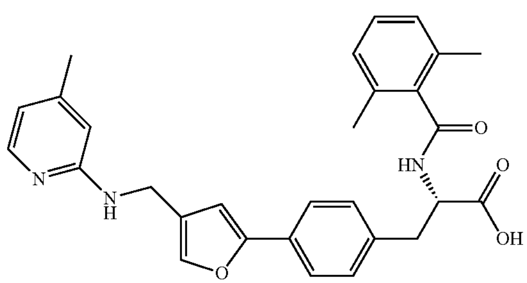 | 2-(2,6-Dimethyl-benzoylamino)-3-(4-{4-[(4-methyl-pyridin-2-ylamino)-methyl]-furan-2-yl}-phenyl)-propionic acid | C29H29N3O4 | 483.56 | 484.4 | 7 |

Table 1-continued

| no | structure | name | formula | molecular weight | LCMS | synthesis in analogy to example |
|---|---|---|---|---|---|---|
| 36 | 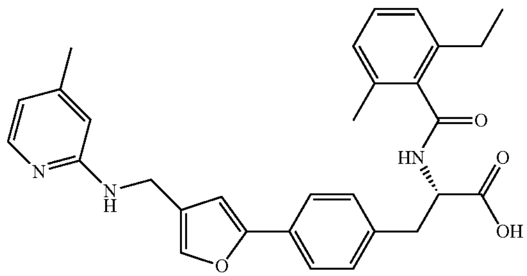 | 2-(2-Ethyl-6-methyl-benzoylamino)-3-(4-{4-[(4-methyl-pyridin-2-ylamino)-methyl]-furan-2-yl}-phenyl)-propionic acid | C30H31N3O4 | 497.58 | 498.6 | 7 |
| 37 | 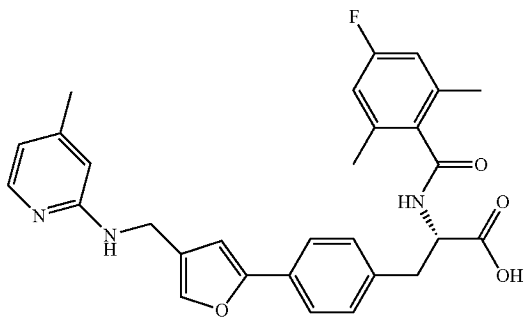 | 2-(4-Fluoro-2,6-dimethyl-benzoylamino)-3-(4-{4-[(4-methyl-pyridin-2-ylamino)-methyl]-furan-2-yl}-phenyl)-propionic acid | C29H28N3O4F | 501.55 | 502.6 | 7 |
| 38 | 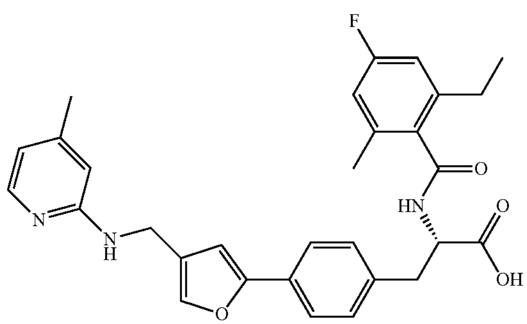 | 2-(2-Ethyl-4-fluoro-6-methyl-benzoylamino)-3-(4-{4-[(4-methyl-pyridin-2-ylamino)-methyl]-furan-2-yl}-phenyl)-propionic acid | C30H30N3O4F | 515.58 | 484.4 | 7 |

Table 1-continued

| no | structure | name | formula | molecular weight | LCMS | synthesis in analogy to example |
|---|---|---|---|---|---|---|
| 39 | 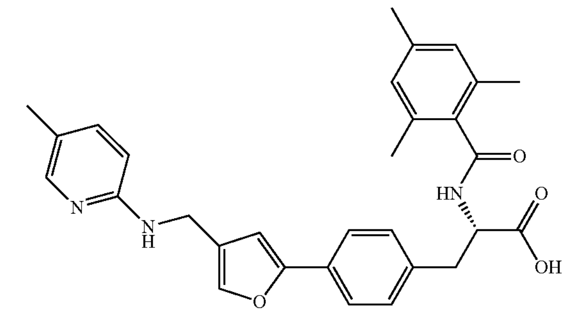 | 3-(4-{4-[(5-Methyl-pyridin-2-ylamino)-methyl]-furan-2-yl}-phenyl)-2-(2,4,6-trimethyl-benzoylamino)-propionic acid | C30H31N3O4 | 497.58 | 489.2 | 7 |
| 40 | 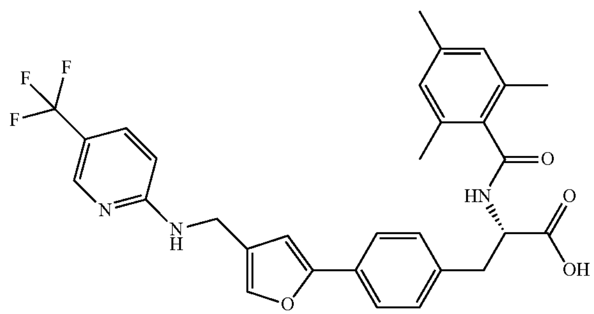 | 3-(4-{4-[(5-Trifluoromethyl-pyridin-2-ylamino)-methyl]-furan-2-yl}-phenyl)-2-(2,4,6-trimethyl-benzoylamino)-propionic acid | C30H28N3O4F3 | 551.56 | 552.0 | 7 |
| 41 | 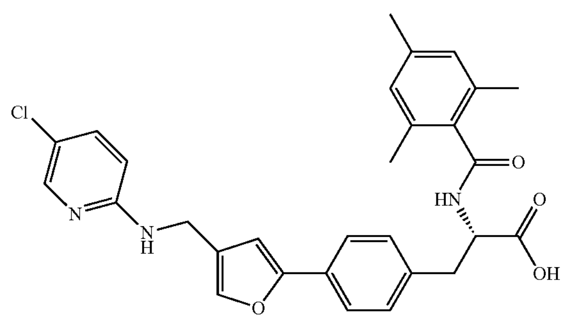 | 3-(4-{4-[(5-Chloro-pyridin-2-ylamino)-methyl]-furan-2-yl}-phenyl)-2-(2,4,6-trimethyl-benzoylamino)-propionic acid | C29H28N3O4Cl | 518.00 | 518.1 | 7 |

Table 1-continued

| no | structure | name | formula | molecular weight | LCMS | synthesis in analogy to example |
|---|---|---|---|---|---|---|
| 42 | 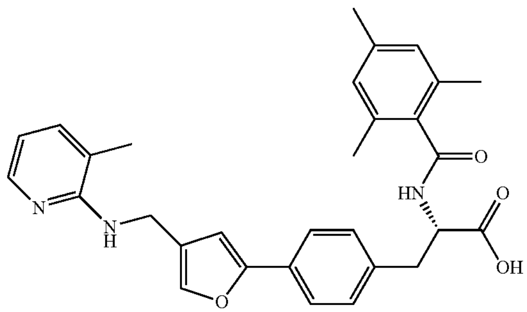 | 3-(4-{4-[(3-Methyl-pyridin-2-ylamino)-methyl]-furan-2-yl}-phenyl)-2-(2,4,6-trimethyl-benzoylamino)-propionic acid | C30H31N3O4 | 497.58 | 489.2 | 7 |
| 43 | 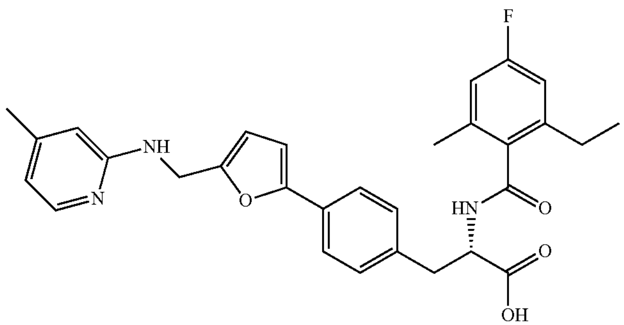 | 2-(2-Ethyl-4-fluoro-6-methyl-benzoylamino)-3-(4-{5-[(4-methyl-pyridin-2-ylamino)-methyl]-furan-2-yl}-phenyl)-propionic acid | C30H30N3O4F | 515.58 | 516.0 | 7 |
| 44 | 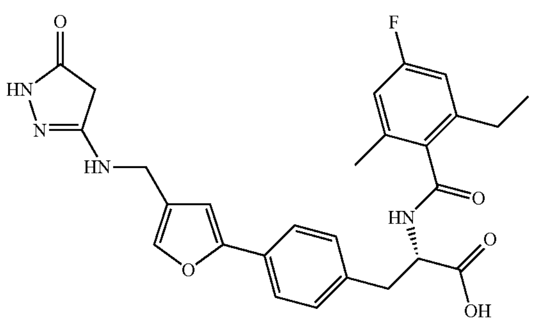 | 2-(2-Ethyl-4-fluoro-6-methyl-benzoylamino)-3-(4-{5-[(5-oxo-4,5-dihydro-1H-pyrazol-3-ylamino)-methyl]-furan-2-yl}-phenyl)-propionic acid | C27H27N4O5F | 506.53 | 507.1 | 7 |

Table 1-continued

| no | structure | name | formula | molecular weight | LCMS | synthesis in analogy to example |
|---|---|---|---|---|---|---|
| 45 | 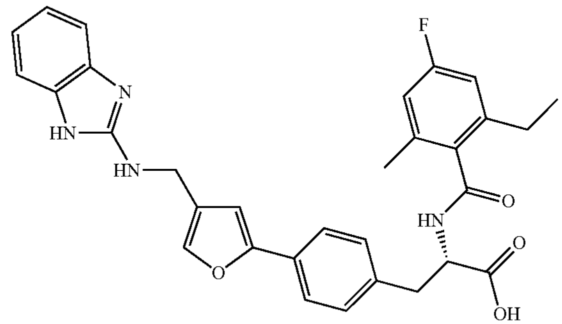 | 3-(4-{5-[(1H-Benzoimidazol-2-ylamino)-methyl]-furan-2-yl}-phenyl)-2-(2-ethyl-4-fluoro-6-methyl-benzoylamino)-propionic acid | C31H29N4O4F | 540.58 | 541.1 | 7 |
| 46 | 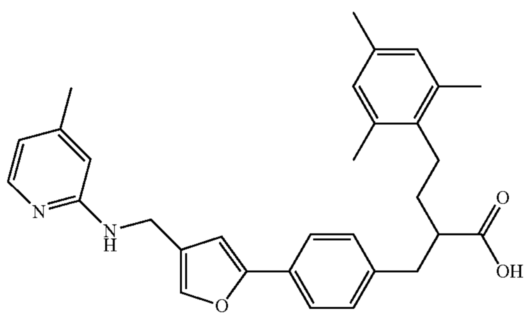 | [2-(4-{4-[(4-Methyl-pyridin-2-ylamino)-methyl]-furan-2-yl}-benzyl)-4-(2,4,6-trimethyl-phenyl)-butyric acid | C31H34N2O3 | 482.61 | 483.2 | 7 |

EXAMPLE 9

Biological Characterization of the Compounds of the Present Invention

1. Integrin Receptor Binding Assays

The $IC_{50}$ values of selected inhibitors were determined using competitive ELISA studies by inhibition of binding of integrin to the most active ligand of the integrin. The optimal concentrations of integrin and ligand were selected from ELISA binding studies with variable concentrations of both to obtain optimal signal noise ratio for further studies. $IC_{50}$ studies were performed with fixed concentration of ligand and integrin and a serial dilution of inhibitor. The plates were measured with SpectraMax Plus reader (Molecular Devices). The resulting inhibition curves were analyzed using Soft-MaxPro 4.0 software, the turning point describes the $IC_{50}$ value.

Fibronectin was purchased from Sigma and fibrinogen from Calbiochem. (EMD Biosciences, Darmstadt, Germany). The integrin alpha5beta1 extracellular domain Fc-fusion was expressed and purified as described (Coe, 2001, J. Biol. Chem., 276, 35854). Integrin alphaIIbbeta3 was purchased form Kordia (Kordia Life Science, Leiden, Netherlands)

1.1. alpha5beta1—Fibronectin Binding Assay

Fibronectin was diluted with coating buffer (15 mM $Na_2CO_3$, 35 mM $NaHCO_3$, pH 9.6) and coated with 100 µL/well to Nunc-Immuno maxisorp plates (Nalge Nunc Europe Ltd) over night at 4° C. After discarding the coating solution plates were washed 3 times with buffer 1 (25 mM Tris, pH 7.6, 150 mM NaCl, 1 mM $MnCl_2$, 1 mg/ml BSA) and blocked with 100 µL blocking buffer (3% BSA in PBS 0.1% Tween20) for 1 hour at room temperature. After washing the blocked plates (3 times) with buffer 1, integrin (50 µL) and either inhibitor (serial dilution in buffer 1) or buffer 1 (50 µL) were added to the wells and incubated for one hour at RT. Plates were then washed (3 times) with buffer 1 and incubated with 100 µL of anti-human-Fc-HRP antibody conjugate (Sigma-Aldrich, Taufkirchen, Germany) in buffer 1 for 1 hour at RT. After additional washing steps (3 times) with buffer 150 µL of HRP substrate solution TMB (Seramun, Germany) were added to the wells. Color development was stopped after 3-5 minutes with 50 µL 1 M $H_2SO_4$. The developed color was measured at 450 nm and analyzed as described above.

1.2. alphaIIbbeta3—Fibrinogen Binding Assay

Fibrinogen was diluted with coating buffer (15 mM $Na_2CO_3$, 35 mM $NaHCO_3$, pH 9.6) and coated with 100 µL/well to Nunc-Immuno maxisorp plates over night at 4° C. After discarding the coating solution plates were washed 3 times with buffer 1 (25 mM Tris, pH 7.6, 150 mM NaCl, 1 mM $MnCl_2$, 1 mg/ml BSA) and blocked with 100 µL blocking buffer (3% BSA in PBS 0.1% Tween20) for 1 hour at room temperature. After washing the blocked plates (3 times) with buffer 1, integrin alphaIIbbeta3 (50 µL) and either inhibitor (serial dilution in buffer 3, 25 mM Tris, pH 7.6, 150 mM NaCl, 1 mM $MnCl_2$, 1 mg/ml BSA 1 mM $MgCl_2$, 1 mM $CaCl_2$,) or buffer 3 (50 µL) were added to the wells and incubated for one hour at RT. Plates were then washed (3 times) with buffer 3 and incubated with 100 µL of anti-alphaIIbbeta3 antibody (anti CD41b, Pharmingen) in buffer 3 for 1 hour at RT. Plates were washed (3 times) with buffer 3 and incubated for 1 hour with 100 µL secondary antibody (anti-mouse-HRP conjugate, Sigma) in buffer 3. After additional washing steps (3 times) with buffer 3 50 µL of HRP substrate solution TMB (Seramun) were added to the wells. Color development was stopped after 3-5 minutes with 50 µL 1 M $H_2SO_4$. The developed color was measured at 450 nm and analyzed as described above.

The results of the various assays performed on some of the compounds according to the present invention are depicted as $IC_{50}$ values in table 2.

2. Cellular Inhibition Assays

Cell Adhesion Assay with HEK293

Cryopreservated cells were thawed and grown for 72 h in DMEM medium with 10% FCS, 2 mM glutamine, 100 U/ml penicillin and 100 µg/ml streptomycin before use.

Cells were detached with cell dissociation solution (Sigma) and suspended in growth medium, centrifuged and resuspended in buffer A (150 mM NaCl, 25 mM HEPES, 2 mM EDTA, pH 7.4). Cells were incubated for 30 min at 37° C. in a 5% $CO_2$. Subsequently, cells were washed with pre-warmed buffer B (150 mM NaCl, 25 mM HEPES pH 7.4) and resuspended in buffer B. 96-well Maxisorp-plate were coated with 0.01% poly-L-lysine, 10 µg/ml fibronectin (Chemicon; #F1904) in carbonate buffer or carbonate buffer alone (15 mM $Na_2CO_3$, 35 mM $NaHCO_3$, pH 9.6) for 1 h at RT. Plates were washed and blocked with 1% BSA for 30 min at RT. Cells were preincubated with test compound and adjusted DMSO concentrations for 10 min at RT. $7 \times 10^4$ cells per well were plated in triplicate and allowed to attach for 1 h at 37° C. in the presence of 2 mM $MgCl_2$. Cells were washed with PBS and adherent cells were fixed with 5% glutaraldehyde for 30 min.

Cells were subsequently washed and stained with 0.1% Crystal Violet for 1 hr at 37° C. Plates were washed and incorporated dye was solubilized with 10% acetic acid. Absorbance was measured at 570 nm using a Spectramax Plus 384 microtiter plate reader and analyzed with SoftMax-Pro (Molecular Devices). Minimal binding on BSA was substracted. $IC_{50}$ values were determined using XL-FIT.

TABLE 2

In vitro activities of selected compounds in different functional assays described in section 1.1-2.

| Compound Nr. | IC50 alpha5beta1 [nM] | IC50 alphaIIbbeta3 [nM] | IC50 alpha5beta1 in cell adhesion assay [nM] |
|---|---|---|---|
| 6 | <100 | >1 | <1 |
| 9 | <100 | >1 | <1 |
| 12 | <100 | >1 | <1 |
| 15 | <100 | >1 | <1 |
| 19 | <100 | >1 | <1 |
| 22 | <100 | >1 | <1 |
| 29 | <100 | >1 | <1 |
| 35 | <100 | >1 | <1 |
| 36 | <100 | >1 | <1 |
| 37 | <100 | >1 | <1 |
| 45 | <100 | >1 | <1 |

The features of the present invention disclosed in the specification, the sequence listing, the claims and/or the drawings may both separately and in any combination thereof be material for realizing the invention in various forms thereof.

The invention claimed is:

1. A compound of formula (I)

$$G\text{-}Z\text{-}A\text{-}Ar\text{-}\Psi \qquad (I)$$

wherein

A is a radical selected from the group consisting of aromatic heterocyclic 5-membered ring systems;

Ar is optionally substituted phenyl;

Z is a radical individually and independently selected from the group consisting of $(CH_2)_n$-E-$(CH_2)_m$-L-$(CH_2)_k$ and $(CH_2)_m$-L-$(CH_2)_k$,
wherein
E is a radical which is either absent or present, wherein if E is present, E is selected from the group consisting of O, S, NH, $NR^a$, CO, SO, $SO_2$, acetylene and substituted ethylene;
L is a radical which is either absent or present, wherein if L is present, L is individually and independently selected from the group consisting of O, S, NH, $NR^b$, CO, SO, $SO_2$, substituted ethylene and acetylene; and
k, m and n are individually and independently 0, 1, 2 or 3;
Ψ is a radical of formula (II)

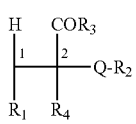

(II)

wherein
Q is a radical selected from the group consisting of a direct bond, C4 alkyl, C=O, C=S, O, S, $CR^aR^b$, $NR^a$—$NR^b$, N=N, $CR^a$=N, N=$CR^a$, (C=O)—O, O—(C=O), $SO_2$, $NR^a$, (C=O)—$NR^a$, $NR^a$—(C=O)—$NR^b$, $NR^c$—(C=O), O—(C=O)—$NR^c$, $NR^c$—(C=O)—O, $NR^c$—(C=S), (C=S)—$NR^c$, $NR^c$—(C=S)—$NR^d$, $NR^c$—$SO_2$ and $SO_2$—$NR^c$;
$R_1$, $R^a$, $R^b$, $R^c$ and $R^d$ are radicals which are individually and independently selected from the group consisting of H, alkyl, substituted alkyl, cycloalkyl, substituted cycloalkyl, heterocycloyl, substituted heterocycloyl, aryl, substituted aryl, heteroaryl, substituted heteroaryl, arylalkyl, substituted arylalkyl, heteroarylalkyl, substituted heteroarylalkyl, cycloalkylalkyl, substituted cycloalkylalkyl, heterocyclylalkyl, substituted heterocyclylalkyl, alkyloxy, substituted alkyloxy, alkyloxyalkyl, substituted alkyloxyalkyl, alkyloxycycloalkyl, substituted alkyloxycycloalkyl, alkyloxyheterocyclyl, substituted alkyloxyheterocyclyl, alkyloxyaryl, substituted alkyloxyaryl, alkyloxyheteroaryl, substituted alkyloxyheteroaryl, alkylthioalkyl, substituted alkylthioalkyl, alkylthiocycloalkyl, substituted alkylthiocycloalkyl, hydroxy, substituted hydroxy, oxo, thio, substituted thio, aminocarbonyl, substituted aminocarbonyl, formyl, substituted formyl, thioformyl, substituted thioformyl, amino, substituted amino, hydroxyl, substituted hydroxyl, mercapto, substituted mercapto, hydrazino, substituted hydrazino, diazene, substituted diazene, imine, substituted imine, amidino, substituted amidino, iminomethylamino, substituted iminomethylamino, ureido, substituted ureido, formylamino, substituted formylamino, aminocarbonyloxy, substituted aminocarbonyloxy, hydroxycarbonylamino, substituted hydroxycarbonylamino, hydroxycarbonyl, substituted hydroxycarbonyl, formyloxy, substituted formyloxy, thioformylamino, substituted thioformylamino, aminothiocarbonyl, substituted aminothiocarbonyl, thioureido, substituted thioureido, sulfonyl, substituted sulfonyl, sulfonamino, substituted sulfonamino, aminosulfonyl, substituted aminosulfonyl, cyano and halogen;

$R_2$ is a hydrophobic moiety;
$R_3$ is a radical selected from the group consisting of OH, C1-C8 alkyloxy, and aryl C0-C6 alkyloxy;
$R_4$ is a radical selected from the group consisting of hydrogen, halogen and C1-C4 alkyl; and
G is a radical containing pyridine.

2. The compound according to claim 1,
wherein
any of $R_1$, $R^a$, $R^b$, $R^c$ and $R^d$ is a radical individually and independently selected from the group consisting of hydrogen, alkyl, substituted alkyl, halogen, cyano, hydroxy, alkyloxy, substituted alkyloxy, oxo, aryl, substituted aryl, arylalkyl, substituted arylalkyl, amino, and substituted amino.

3. The compound according to claim 1,
wherein
any of $R_1$, $R^a$, $R^b$, $R^c$ and $R^d$ is a radical individually and independently selected from the group consisting of hydrogen, fluoro, chloro, bromo, methyl, ethyl, propyl, tert-butyl, phenyl, benzyl, hydroxyl, methoxy, oxo, amino, methylamino, acetylamino and cyano.

4. The compound according to claim 2,
wherein
one or several of the ring atoms of Ar is/are optionally individually and independently substituted with a substituent, wherein the substituent is $R_5$ and
wherein
$R_5$ is individually and independently selected from the group consisting of H, benzyl, substituted benzyl, phenyl, substituted phenyl, alkyl, substituted alkyl, cycloalkyl, substituted cycloalkyl, heterocyclyl, substituted heterocyclyl, aryl, substituted aryl, heteroaryl, substituted heteroaryl, arylalkyl, substituted arylalkyl, heteroarylalkyl, substituted heteroarylalkyl, cycloalkylalkyl, substituted cycloalkylalkyl, heterocyclylalkyl, substituted heterocyclylalkyl, alkyloxyalkyl, substituted alkyloxyalkyl, alkyloxycloalkyl, substituted alkyloxycycloalkyl, alkyloxyheterocyclyl, substituted alkyloxyheterocyclyl, alkyloxyaryl, substituted alkyloxyaryl, alkyloxyheteroaryl, substituted alkyloxyheteroaryl, alkylthioalkyl, substituted alkylthioalkyl, alkylthiocycloalkyl, substituted alkylthiocycloalkyl, (C=O)—$NHR^a$, (C=O)$R^a$, (C=S)$R^a$, $NHR^a$, $OR^a$, $SR^a$, $CH_2R^a$, $CR^aR^bR^c$, NH—$NHR^a$, N=$NR^a$, CH=$NR^a$, N=$CHR^a$, NH—(C=O)—$NHR^a$, NH—(C=O)$R^a$, O—(C=O)—$NHR^a$, NH—(C=O)—$OR^a$, (C=O)—$OR^a$, O—(C=O)$R^a$, NH—(C=S)$R^a$, (C=S)—$NHR^a$, NH—(C=S)—$NHR^a$, $SO_2R^a$, NH—$SO_2R^a$, $SO_2$—$NHR^a$, $NR^cR^a$, (C=O)—$NR^c$ $R^a$, $NR^cR^a$, $NR^c$—(C=O)—$NHR^a$, NH—(C=O)—$NR^cR^a$, $NR^c$—(C=O)—$NR^dR^a$, $NR^c$—(C=O)$R^a$, O—(C=O)—$NR^cR^a$, $NR^c$—(C=O)—$OR^a$, $NR^c$—(C=S)$R^a$, (C=S)—$NR^cR^a$, $NR^c$-(C=S)—$NHR^a$, NH—(C=S)—$NR^cR^a$, $NR^c$—(C=S)—$NR^dR^a$, $NR^c$—$SO_2R^a$, $SO_2$—$NR^cR^a$, $SCHF_2$, $OCHF_2$, CN, halogen, $CF_3$, $CCl_3$ and $OCF_3$,
wherein
any of $R^a$, $R^b$, $R^c$ and $R^d$ is as defined in claim 2.

5. The compound according to claim 4,
wherein
$R_5$ is selected from the consisting of hydrogen, alkyl, aryl, arylalkyl, halogen, hydroxy, amino, alkoxy, alkylamino, dialkylamino, alkylcarbonyl, alkylaminocarbonyl, dialkylaminocarbonyl, alkyloxycarbonyl, cylcoalkyl, alkylcarbonylamino, am inocarbonyl, cyano and alkylthio.

6. The compound according to claim 5,
wherein
$R_5$ is selected from the group consisting of hydrogen, fluoro, chloro, bromo, cyano, amino, methylamino, dimethylamino, methoxycarbonyl, aminocarbonyl, methylaminocarbonyl, dimethylaminocarbonyl, acetylamino, phenyl, benzyl, methyl, ethyl, propyl, tert-butyl, hydroxy, methoxy, trifluoromethyl, trifluoromethyloxy, difluoromethyloxy, acetyl, and methylthio.

7. The compound according to claim 6,
wherein
$R_5$ is hydrogen, fluoro, chloro, cyano, methylamino, dimethylamino, methylaminocarbonyl, acetylamino, phenyl, benzyl, methyl, ethyl, tert-butyl, hydroxy, methoxy, or trifluoromethyl.

8. The compound according to claim 7,
wherein
A and Ψ are connected to Ar in the positions para to each other; and
one or two of the ring atoms of Ar is/are optionally individually and independently substituted with methyl, ethyl, chloro, fluoro or methoxy.

9. The compound according to claim 8,
wherein
A is a radical selected from the group consisting of furyl, thienyl, pyrrolyl, oxazolyl, isooxazolyl, thiazolyl, isothiazolyl, imidazolyl, pyrazolyl, triazolyl, oxadiazolyl and thiadiazolyl,
wherein
one or several of the ring atoms of A are individually and independently substituted with 0, 1 or 2 $R_5$, wherein $R_5$ is hydrogen, fluoro, chloro, cyano, methylamino, dimethylamino, methylaminocarbonyl, acetylamino, phenyl, benzyl, methyl, ethyl, tert-butyl, hydroxy, methoxy, or trifluoromethyl.

10. The compound according to claim 9,
wherein
Z and Ar are bonded to A in positions meta to each other.

11. The compound according to claim 1,
wherein
one or several of the ring atoms of Ar is/are optionally individually and independently substituted with a substituent, wherein if substituted, the substituent is $R_5$, and
A is a radical selected from the group consisting of furyl, thienyl, pyrrolyl, oxazolyl, isooxazolyl, thiazolyl, isothiazolyl, imidazolyl, pyrazolyl, triazolyl, oxadiazolyl and thiadiazolyl,
wherein
one or several of the ring atoms of A are individually and independently substituted with 0, 1 or 2 $R_5$,
wherein
$R_5$ is hydrogen, fluoro, chloro, cyano, methylamino, dimethylamino, methylaminocarbonyl, acetylamino, phenyl, benzyl, methyl, ethyl, tert-butyl, hydroxy, methoxy, or trifluoromethyl,
wherein
G is $R_9$—NH,
wherein
$R_9$ is a radical selected from the group consisting of:
(a) pyridine,
wherein
any or several of the ring atoms of $R_9$ is/are optionally and individually and independently substituted with one or several substituents, wherein the substituent is $R^a$; and
if $R_9$ is substituted 2-pyridyl, $R_9$ is substituted with at least one $R^a$ that is other than hydrogen; and (b) 5,6- or 6,6-membered aromatic or combined aromatic/nonaromatic bicyclic ring systems comprising pyridine,
wherein any or several of the ring atoms of $R_9$ is/are optionally and individually and independently substituted with one or several substituents, wherein the substituent is $R^a$;
wherein
any of $R^a$, $R^b$ and $R^c$ is each and independently a radical individually and independently selected from the group consisting of hydrogen, fluoro, chloro, bromo, methyl, ethyl, propyl, tert-butyl, phenyl, benzyl, hydroxyl, methoxy, oxo, amino, methylamino, acetylamino and cyano.

12. The compound according to claim 11,
wherein
said pyridine is unsubstituted or substituted with one or more substituents $R_a$ individually and independently selected from the group consisting of hydrogen, fluoro, chloro, bromo, methyl, ethyl, propyl, tert-butyl, phenyl, benzyl, hydroxyl, methoxy, oxo, amino, methylamino, acetylamino and cyano;
if $R_9$ is substituted 2-pyridyl, $R_9$ is substituted in addition to the amino group of $R_9$—NH with at least one $R^a$ that is other than hydrogen; and
$R_9$ is connected to the NH group of G ortho to one of said ring N-atoms of $R_9$.

13. The compound according to claim 11,
wherein
G is a radical selected from the group consisting of 3,4-dihydro-quinolin-2-ylamino, 3H-pyrrolo[2,3-b]pyridin-2-ylamino, 3,4-dihydro-[1,8]naphthyridin-2-ylamino, pyridin-2-ylamino, 3,4,5,6-tetrahydro-pyridin-2-ylamino, and 1H-[1,8]naphthyridin-4-one-2-amino,
wherein
Z is attached to an amino group of G;
G is unsubstituted or substituted with one or more $R^a$ individually and independently selected from the group consisting of hydrogen, fluoro, chloro, bromo, methyl, ethyl, propyl, tert-butyl, phenyl, benzyl, hydroxyl, methoxy, oxo, amino, methylamino, acetylamino and cyano; and
if G is substituted pyridine-2-ylamino, the pyridine ring is substituted in addition to the amino group with at least one $R^a$ that is other than hydrogen.

14. The compound according to claim 1,
wherein
A and Ψ are connected to Ar in positions para to each other; and
one or two of the ring atoms of Ar is/are optionally individually and independently substituted with methyl, ethyl, chloro, fluoro or methoxy; and
A is a radical selected from the group consisting of furyl, thienyl, pyrrolyl, oxazolyl, isooxazolyl, thiazolyl, isothiazolyl, imidazolyl, pyrazolyl, triazolyh oxadiazolyl and thiadiazolyl,
wherein one or several of the ring atoms of A are individually and independently substituted with 0, 1 or 2 $R_5$,
wherein $R_5$ is hydrogen, fluoro, chloro, cyano, methylamino, dimethylamino, methylaminocarbonyl, acetylamino, phenyl, benzyl, methyl, ethyl, tert-butyl, hydroxy, methoxy, or trifluoromethyl wherein
G is a radical selected from the group consisting of:
(a) pyridine,
wherein
any or several of the ring atoms pyridine is/are optionally and individually and independently substituted with one or several substituents, wherein the substituent is $R^a$; and
if G is substituted pyridyl, the pyridyl ring is substituted with at least one $R^a$ that is not hydrogen; and
(b) 5,6- or 6,6-membered aromatic or combined aromatic/nonaromatic bicyclic ring systems comprising pyridine,
wherein
one or several of the ring atoms of G is/are optionally and individually and independently substituted with one or several substituents, wherein the substituent is $R^a$; and
wherein
any of $R^a$, $R^b$, $R^c$ and $R^d$ is a radical each individually and independently selected from the group consisting of hydrogen, fluoro, chloro, bromo, methyl, ethyl, propyl, tert-butyl, phenyl, benzyl, hydroxyl, methoxy, oxo, amino, methylamino, acetylamino and cyano.

15. The compound according to claim 14,
wherein
Z is connected to a ring atom of G that is adjacent to one of said ring N-atoms of G.

16. The compound according to claim 15,
wherein
G is a radical selected from the group consisting of 1,2,3,4-tetrahydro-[1,8]naphthyridin-2-yl, 1,2,3,4-tetrahydro-[1,8]naphthyridine-7-yl, 1H-pyrrolo[2,3-b]pyridin-2-yl, 1H-pyrrolo[2,3-b]pyridin-6-yl, 4,5,6,7-tetrahydro-3H-imidazo[4,5-b]pyridin-2-yl, 1H-pyrazolo[3,4-b]pyridin-6-yl, 2,3-dihydro-1H-pyrrolo[2,3-b]pyridine-6-yl, and 2-methylaminopyridin-6-yl
wherein
G is unsubstituted or substituted with one or more substituents $R^a$ each individually and independently selected from the group consisting of hydrogen, fluoro, chloro, bromo, methyl, ethyl, propyl, tert-butyl, phenyl, benzyl, hydroxyl, methoxy, oxo, amino, methylamino, acetylamino and cyano.

17. The compound according to claim 14,
wherein
G is a radical selected from the group consisting of 3,4,5,6-tetrahydro-pyridin-2-ylamino, 1,2,3,4-tetrahydro-[1,8]naphthyridine-7-yl, 2,3-dihydro-1H-pyrrolo[2,3-b]pyridine-6-yl, 2-methylaminopyridin-6-yl, 4-methylpyridin-2-ylamino, 5-methylpyridin-2-ylamino, 4-methoxypyridin-2-ylamino, and 4-fluoropyridin-2-ylamino.

18. The compound according to claim 1,
wherein
one or several of the ring atoms of Ar is/are optionally individually and independently substituted with a substituent, wherein if substituted, the substituent is $R_5$, and
A is a radical selected from the group consisting of furyl, thienyl, pyrrolyl, oxazolyl, isooxazolyl, thiazolyl, isothiazolyl, imidazolyl, pyrazolyl, triazolyl, oxadiazolyl and thiadiazolyl,
wherein
one or several of the ring atoms of A are individually and independently substituted with 0, 1 or 2 $R_5$,
wherein
$R_5$ is hydrogen, fluoro, chloro, cyano, methylamino, dimethylamino, methylaminocarbonyl, acetylamino, phenyl, benzyl, methyl, ethyl, tert-butyl, hydroxy, methoxy, or trifluoromethyl;
G is a radical selected from the group consisting of 3,4,5,6-tetrahydro-pyridin-2-ylamino, 1,2,3,4-tetrahydro-[1,8]naphthyridine-7-yl, 2,3-dihydro-1H-pyrrolo[2,3-b]pyridine-6-yl, 2-methylaminopyridin-6-yl, 4-methylpyridin-2-ylamino, 5-methylpyridin-2-ylamino, 4-methoxypyridin-2-ylamino, and 4-fluoropyridin-2-ylamino; and
wherein
Z is a direct bond, $CH_2$ or CO.

19. The compound according to claim 1,
wherein
one or several of the ring atoms of Ar is/are optionally individually and independently substituted with a substituent, wherein if substituted, the substituent is $R_5$, and
A is a radical selected from the group consisting of furyl, thienyl, pyrrolyl, oxazolyl, isooxazolyl, thiazolyl, isothiazolyl, imidazolyl, pyrazolyl, triazolyl oxadiazolyl and thiadiazolyl,
wherein
one or several of the ring atoms of A are individually and independently substituted with 0, 1 or 2 $R_5$,
wherein
$R_5$ is hydrogen, fluoro, chloro, cyano, methylamino, dimethylamino, methylaminocarbonyl, acetylamino, phenyl, benzyl, methyl, ethyl, tert-butyl, hydroxy, methoxy, or trifluoromethyl;
G is a radical selected from the group consisting of 3,4,5,6-tetrahydro-pyridin-2-ylamino, 1,2,3,4-tetrahydro-[1,8]naphthyridine-7-yl, 2,3-dihydro-1H-pyrrolo[2,3-b]pyridine-6-yl, 2-methylaminopyridin-6-yl, 4-methylpyridin-2-ylamino, 5-methylpyridin-2-ylamino, 4-methoxypyridin-2-ylamino and 4-fluoropyridin-2-ylamino; and
$R_2$ is a radical selected from the group consisting of phenyl, substituted phenyl, heterocyclyl, substituted heterocyclyl, aryl, substituted aryl, heteroaryl, substituted heteroaryl, cycloalkyl and substituted cycloalkyl,
wherein
Q is attached to $R_2$ at one of the ring atoms of $R_2$.

20. The compound according to claim 19,
wherein
$R_2$ is a radical of formula (III)

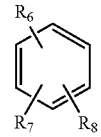

(III)

wherein
0 or 1 ring carbon atom in formula (III) is substituted by a nitrogen atom;
$R_6$, $R_7$ and $R_8$ are each radicals and individually and independently selected from the group consisting of hydrogen, halogen, cyano, alkyl, substituted alkyl, alkoxy, substituted alkoxy, aminocarbonyl, substituted aminocarbonyl, aryl, substituted aryl, heteroaryl, and substituted heteroaryl; and $R_2$ is attached to Q via a ring atom of the radical of formula (III).

21. The compound according to claim 19, wherein
$R_2$ is a radical of formula (IV)

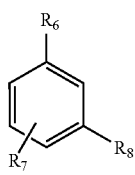

(IV)

wherein 0 or 1 ring carbon atom in formula (IV) is substituted by a nitrogen atom;

$R_6$, $R_7$ and $R_8$ are each radicals and individually and independently selected from the group consisting of hydrogen, fluoro, chloro, bromo, methyl, ethyl, propyl, tert-butyl, phenyl, benzyl, hydroxyl, methoxy, amino, acetylamino, cyano, nitro, benzyloxy, trifluoromethyl, 1-oxoethyl, dimethylaminocarbonyl, methylaminocarbonyl, aminocarbonyl, trifluoromethoxy, trichloromethyl, methoxycarbonyl, methylsulfonyl, trifluoromethylsulfonyl, methylthio, aminosulfonyl, methylaminosulfonyl, dimethylaminosulfonyl, 2-oxazolyl, 2-imidazolyl, 1-imidazolyl and 4,5-dihydro-oxazol-2-yl; and Q is attached to the ring of formula (IV) in the position ortho to $R_6$ and $R_8$.

22. The compound according to claim 21, wherein
$R_2$ is a radical selected from the group consisting of phenyl, 2,4,6-trimethylphenyl, 2,6-dimethylphenyl, 4-cyanophenyl, 2,4,6-tribromophenyl, 2-bromo-6-methylphenyl, 4-benzyloxyphenyl, 2-methylphenyl, 2-ethyl-6-methylphenyl, 2-methyl-6-trifluoromethylphenyl, 4-fluoro-2-ethyl-6-methylphenyl, 4-chloro-2-ethyl-6-methylphenyl, 4-cyano-2-ethyl-6-methylphenyl, 4-trifluoromethyl-2-ethyl-6-methylphenyl, 4-(1-oxoethyl)-2-ethyl-6-methylphenyl, 4-dimethylearbarnoyl-2-ethyl-6-methyl-phenyl, 4-methylcarbamoyl-2-ethyl-6-methyl-phenyl, 4-carbamoyl-2-ethyl-6-methyl-phenyl, 4-trifluoromethoxy-2-ethyl-6-methyl-phenyl, 4-(1H-imidazo-1-yl)-2-ethyl-6-methyl-phenyl, 4-fluoro-2,6-dimethylphenyl, 4-chloro-2,6-dimethylphenyl, 4-cyano-2,6-dimethylphenyl, 4-trifluoromethyl-2,6-dimethylphenyl, 4-(1-oxoethyl)-2,6-dimethylphenyl, 4-trifluoromethoxy-2,6-dimethylphenyl, 4-(1H-imidazo-1-yl)-2,6-dimethylphenyl, pyridine-3-yl, 2-methyl-pyridine-3-yl, 2-methyl-4-trifluoromethyl-pyridine-3-yl, 2,4-dimethyl-pyridine-3-yl, 4-chloro-2-methyl-6-methylthio-phenyl, 4-fluoro-2-methyl-6-methylthio-phenyl, 2-methyl-6-methylthio-phenyl, 4-fluoro-2-(2-propyl)-6-methylphenyl, 4-cyano-2-methyl-6-methylthio-phenyl, 4-trifluoromethyl-2-methyl-6-methylthio-phenyl, 2-isopropyl-6-methylphenyl, 4-fluoro-2-(2-propyl)-6-methylphenyl, 2-ethyl-4-methyl-pyridine-3-yl, 4-trichloromethyl-2-ethyl-6-methylphenyl, 4-nitro-2-ethyl-6-methylphenyl, 4-methyloxycarbonyl-2-ethyl-6-methylphenyl, 4-methylsulfonyl-2-ethyl-6-methylphenyl, 4-trifluoromethylsulfonyl-2-ethyl-6-methylphenyl, 4-aminosulfonyl-2-ethyl-6-methylphenyl, 4-methylaminosulfonyl-2-ethyl-6-methylphenyl, 4-dimethylaminosulfonyl-2-ethyl-6-methylphenyl, 4-methylaminocarbonyl-2-ethyl-6-methylphenyl, 4-dimethylaminocarbonyl-2-ethyl-6-methylphenyl, 4-am inocarbonyl-2-ethyl-6-methylphenyl, 2-ethyl-6-methyl-4-(2-oxazolyl)phenyl, 2-ethyl-6-methyl-4-(2-imidazolyl)phenyl, 4-trifluoromethylcarbonyl-2-ethyl-6-methylphenyl, 4-trichloromethyl-2,6-dimethylphenyl, 4-nitro-2,6-dimethylphenyl, 4-methyloxycarbonyl-2,6-dimethylphenyl, 4-methylsulfonyl-2,6-dimethylphenyl, 4-trifluoromethylsulfonyl-2,6-dimethylphenyl, 4-aminosulfonyl-2,6-dimethylphenyl, 4-methylaminosulfonyl-2,6dimethylphenyl, 4-dimethylaminosulfonyl-2,6-dimethylphenyl, 4-methylaminocarbonyl-2,6-dimethylphenyl, 4-dimethylaminocarbonyl-2,6-dimethylphenyl, 4-aminocarbonyl-2,6-dimethylphenyl, 2,6-dimethyl-4-(2-oxazolyl)phenyl, 2,6-dimethyl-4-(2-imidazolyl)phenyl and 4-trifluoromethylcarbonyl-2,6-dimethylphenyl.

23. The compound according claim 19, wherein
$R_2$ is a radical of formula (V)

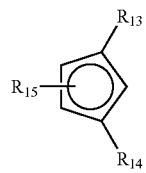

(V)

wherein 1, 2 or 3 ring atoms in formula (V) are hetero atoms selected from the group consisting of N, O and S;

$R_{13}$, $R_{14}$ and $R_{15}$ are each radicals and individually and independently selected from the group consisting of hydrogen, halogen, cyano, alkyl, substituted alkyl, alkoxy, substituted alkoxy, aryl, substituted aryl, heteroaryl, and substituted heteroaryl; and Q is attached to the ring in formula (V) in the position ortho to both $R_{13}$ and $R_{14}$.

24. The compound according to claim 23, wherein
$R_2$ is a radical selected from the group consisting of 3,5-dimethylisoxazol-4-yl, 5-methyl-3-trifluoromethyl-isoxazol-4-yl, 3-isopropyl-5-methylisoxazol-4-yl, 5-methyl-3-phenylisoxazol-4-yl, 3,5-diethylisoxazol-4-yl, 2-methyl-4,5,6,7-tetrahydrobenzofuran-3-yl, 2,4-dimethylfuran-3-yl, 1,3,5-trimethyl-1H-pyrazol-4-yl, 1-tert-butyl-3,5-dimethyl-1H-pyrazol-4-yl, 1-benzyl-3,5-dimethyl-1H-pyrazol-4-yl, 2,4-dimethylthiophen-3-yl and 3-ethyl-5-methylisoxazo1-4-yl.

25. The compound according to claim 19, wherein
$R_2$ is a cycloalkyl radical selected from the group consisting of cyclohexyl, cyclopentyl, 1-phenylcyclopentyl, 1-methyleyclohexyl, 1-phenylcyclohexyl, bicyclo[3.2.1]octane-6-yl, adamantan-1-yl, 2,2,6,6-tetramethylcyclohexyl, 2,4,6-trimethylcyclohexyl, and 2-methylcyclohexyl.

26. The compound according to claim 1, wherein
A and Ψ are connected to Ar in the positions para to each other; and one or two of the ring atoms of Ar is/are optionally individually and independently substituted with methyl, ethyl, chloro, fluoro or methoxy, and A is a radical selected from the group consisting of furyl, thienyl, pyrrolyl, oxazolyl, isooxazolyl, thiazolyl, isothiazolyl, imidazolyl, pyrazolyl, triazolyl, oxadiazolyl and thiadiazolyl, wherein one or several of the ring atoms of A are individually and independently substituted with 0, 1 or 2 $R_5$, wherein $R_5$ is hydrogen, fluoro, chloro, cyano, methylamino, dimethylamino, methylaminocarbonyl, acetylamino, phenyl, benzyl, methyl, ethyl, tert-butyl, hydroxy, methoxy, or trifluoromethyl;

G is a radical selected from the group consisting of 3,4,5,6-tetrahydro-pyridin-2-ylamino, 1,2,3,4-tetrahydro-[1,8]naphthyridine-7-yl, 2,3-dihydro-1H-pyrrolo[2,3-b]pyridine-6-yl, 2-methylaminopyridin-6-yl, 4-methylpyridin-2-ylamino, 5-methylpyridin-2-ylamino, 4-methoxypyridin-2-ylamino and 4-fluoropyridin-2-ylamino wherein $R_2$ is a radical selected from the group consisting of alkyl, branched alkyl, substituted branched alkyl, substituted alkyl, benzyl, substituted benzyl, arylalkyl, substituted arylalkyl, heteroarylalkyl, substituted heteroarylalkyl, cycloalkylalkyl, substituted cycloalkylalkyl, heterocyclylalkyl and substituted heterocyclylalkyl; and $R_2$ is attached via its alkyl moiety to Q.

27. The compound according to claim 26, wherein $R_2$ is a substituted alkyl radical selected from the group consisting of 1,1-dimethylethyl, 1,1-dimethylpropyl, 1-methyl-1-phenylethyl, 1-phenylpropyl, 2-methyl-1-phenylpropyl, 1-methylbutyl, 1-ethyl-1-methylpropyl, 1-ethylpropyl, and 1-isopropyl-2-methylpropyl.

28. The compound according to claim 1, wherein

A and Ψ are connected to Ar in the positions para to each other; and one or two of the ring atoms of Ar is/are optionally individually and independently substituted with methyl, ethyl, chloro, fluoro or methoxy and A is a radical selected from the group consisting of furyl, thienyl, pyrrolyl, oxazolyl, isooxazolyl, thiazolyl, isothiazolyl, imidazolyl, pyrazolyl, triazolyl, oxadiazolyl and thiadiazolyl, wherein one or several of the ring atoms of A are individually and independently substituted with 0, 1 or 2 $R_5$, wherein $R_5$ is each independently selected from the group consisting of hydrogen, fluoro, chloro, cyano, methylamino, dimethylamino, methylaminocarbonyl, acetylamino, phenyl, benzyl, methyl, ethyl, propyl, tert-butyl, hydroxy, methoxy, trifluoromethyl, furyl, thienyl, pyrrolyl, oxazolyl, isooxazolyl, thiazolyl, isothiazolyl, imidazolyl, pyrazolyl, triazolyl, oxadiazolyl and thiadiazolyl, G is a radical selected from the group consisting of 3,4,5,6-tetrahydro-pyridin-2-ylamino, 2,3-dihydro-1H-pyrrolo[2,3-b]pyridine-6-yl, 2-methylaminopyridin-6-yl, 4-methylpyridin-2-ylamino, 5-methylpyridin-2-ylamino, 4-methoxypyridin-2-ylamino and 4-fluoropyridin-2-ylamino;

$R_2$ is a radical selected from the group consisting of phenyl, 2,4,6-trimethylphenyl, 2,6-dimethylphenyl, 4-cyanophenyl, 2,4,6-tribromophenyl, 2-bromo-6-methylphenyl, 4-benzyloxyphenyl, 2-methylphenyl, 2-ethyl-6-methylphenyl, 2-methyl-6-trifluoromethylphenyl, 4-fluoro-2-ethyl-6-methylphenyl, 4-chloro-2-ethyl-6-methylphenyl, 4-cyano-2-ethyl-6-methylphenyl, 4-trifluoromethyl-2-ethyl-6-methylphenyl, 4-(1-oxoethyl)-2-ethyl-6-methylphenyl, 4-dimethylcarbamoyl-2-ethyl-6-methyl-phenyl, 4-methylcarbamoyl-2-ethyl-6-methyl-phenyl, 4-carbamoyl-2-ethyl-6-methyl-phenyl, 4-trifluoromethoxy-2-ethyl-6-methyl-phenyl, 4-(1H-imidazo-1-yl)-2-ethyl-6-methyl-phenyl, 4-fluoro-2,6-dimethylphenyl, 4-chloro-2,6-dimethylphenyl, 4-cyano-2,6-dimethylphenyl, 4-trifluoromethyl-2,6-dimethylphenyl, 4-(1-oxoethyl)-2,6-dimethylphenyl, 4-trifluoromethoxy-2,6-dimethylphenyl, 4-(1H-imidazo-1-yl)-2,6-dimethylphenyl, pyridine-3-yl, 2-methyl-pyridine-3-yl, 2-methyl-4-trifluoromethyl-pyridine-3-yl, 2,4-dimethyl-pyridine-3-yl, 4-chloro-2-methyl-6-methylthio-phenyl, 4-fluoro-2-methyl-6-methylthio-phenyl, 2-methyl-6-methylthio-phenyl, 4-fluoro-2-(2-propyl)-6-methylphenyl, 4-cyano-2-methyl-6-methylthio-phenyl, 4-trifluoromethyl-2-methyl-6-methylthio-phenyl, 2-isopropyl-6-methylphenyl, 4-fluoro-2-(2-propyl)-6-methylphenyl, 2-ethyl-4-methyl-pyridine-3-yl, 4-trichloromethyl-2-ethyl-6-methylphenyl, 4-nitro-2-ethyl-6-methylphenyl, 4-methyloxycarbonyl-2-ethyl-6-methylphenyl, 4-methylsulfonyl-2-ethyl-6-methylphenyl, 4-trifluoromethylsulfonyl-2-ethyl-6-methylphenyl, 4-aminosulfonyl-2-ethyl-6-methylphenyl, 4-methylaminosulfonyl-2-ethyl-6-methylphenyl, 4-dimethylaminosulfonyl-2-ethyl-6-methylphenyl, 4-methylaminocarbonyl-2-ethyl-6-methylphenyl, 4-dimethylaminocarbonyl-2-ethyl-6-methylphenyl, 4-aminocarbonyl-2-ethyl-6-methylphenyl, 2-ethyl-6-methyl-4-(2-oxazolyl)phenyl, 2-ethyl-6-methyl-4-(2-imidazolyp phenyl, 4-trifluoromethylcarbonyl-2-ethyl-6-methylphenyl, 4-trichloromethyl-2,6-dimethylphenyl, 4-nitro-2,6-dimethylphenyl, 4-methyloxycarbonyl-2,6-dimethylphenyl, 4-methylsulfonyl-2,6-dimethylphenyl, 4-trifluoromethylsulfonyl-2,6-dimethylphenyl, 4-aminosulfonyl-2,6-dimethylphenyl, 4-methylaminosulfonyl-2,6-dimethylphenyl, 4-dimethylaminosulfonyl-2,6-dimethylphenyl, 4-methylaminocarbonyl-2,6-dimethylphenyl, 4-dimethylaminocarbonyl-2,6-dimethylphenyl, 4-aminocarbonyl-2,6-dimethylphenyl, 2,6-dimethyl-4-(2-oxazolyl)phenyl, 2,6-dimethyl-4-(2-imidazolyl)phenyl and 4-trifluoromethylcarbonyl-2,6-dimethylphenyl wherein Q is selected from the group consisting of C1-C3 alkyl, NHCO, CONH and $NHSO_2$.

29. The compound according to claim 1, wherein one or several of the ring atoms of Ar is/are optionally individually and independently substituted with a substituent, wherein if substituted, the substituent is $R_5$ and A is a radical selected from the group consisting of furyl, thienyl, pyrrolyl, oxazolyl, isooxazolyl, thiazolyl, isothiazolyl, imidazolyl, pyrazolyl, triazolyl oxadiazolyl and thiadiazolyl, wherein one or several of the ring atoms of A are individually and independently substituted with 0, 1 or 2 $R_5$, wherein R₅ is hydrogen, fluoro, chloro, cyano, methylamino, dimethylamino, methylaminocarbonyl, acetylamino, phenyl, benzyl, methyl, ethyl, tert-butyl, hydroxy, methoxy, or trifluoromethyl;

G is a radical selected from the group consisting of 3,4,5,6-tetrahydro-pyridin-2-ylamino, 1,2,3,4-tetrahydro-[1,8]naphthyridine-7-yl, 2,3-dihydro-1H-pyrrolo[2,3-b]pyridine-6-yl, 2-methylaminopyridin-6-yl, 4-methylpyridin-2-ylamino, 5-methylpyridin-2-ylamino, 4-methoxypyridin-2-ylamino and 4-fluoropyridin-2-ylamino wherein Q is a direct bond;

R₂ is a lactame radical selected from the group consisting of azetidine-2-ones, pyrrolidine-2-ones, and piperidine-2-ones, wherein any of the lactame radicals is either geminal substituted with Rᵃ and Rᵇ wherein Rᵃ and Rᵇ are individually and independently selected; or ortho-fused with an aromatic or nonaromatic 5- or 6-membered ring; or spiro-fused with a nonaromatic 5- or 6-membered ring, wherein ring atoms of the rings that are ortho- or spiro-fused to the said lactame rings are individually and independently substituted with 0, 1, 2, 3 or 4 Rᶜ;

Rᵃ Rᵇ and Rᶜ are individually and independently selected from the group consisting of hydrogen, fluoro, chloro, bromo, methyl, ethyl, propyl, tert-butyl, phenyl, benzyl, hydroxyl, methoxy, oxo, amino, methylamino, acetylamino and cyano; and said lactames are directly bound at their ring N-atom to C-atom number 2 in formula (II).

30. The compound according to claim 29, wherein

R₂ is a radical selected from the group consisting of formulas (VI) to (XI)

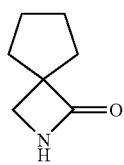

(VI)

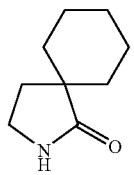

(VII)

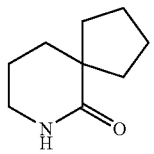

(VIII)

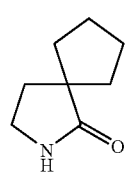

(IX)

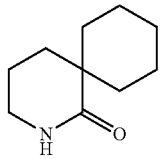

(X)

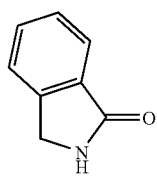

(XI)

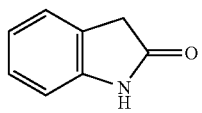

wherein any of the formulas (VI) to (XI) is directly bound to C-atom number 2 in formula (II) at the ring N-atoms of the respective formulas (VI) to (XI);

the cycloalkyl rings spiro-fused to the heterocycles in any of the formulas (VI) to (XI) are optionally ortho-fused with an aromatic 5- or 6-membered ring; and any of the formulas (VI) to (XI) is individually and independently substituted with 0, 1 or 2 Rᵃ, wherein Rᵃ is individually and independently selected from the group consisting of hydrogen, fluoro, chloro, bromo, methyl, ethyl, propyl, pert-butyl, phenyl, benzyl, hydroxyl, methoxy, oxo, amino, methylamino, acetylamino and cyano.

31. The compound according to claim 29, wherein

R₂ is a radical selected from the group consisting of formulas (XII) to (XVI)

(XII)

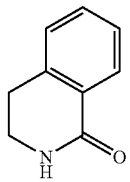

(XIII)

(XIV)

(XV)

(XVI)

wherein
any of the formulas (XII) to (XVI) is directly bound to C-atom number 2 in formula (II) at the ring N-atom of the respective formulas (XII) to (XVI); and
any of the formulas (XII) to (XVI) is independently and individually substituted with 0, 1 or 2 $R^a$,
   wherein
   $R^a$ is individually and independently selected from the group consisting of hydrogen, fluoro, chloro, bromo, methyl, ethyl, propyl, tert-butyl, phenyl, benzyl, hydroxyl, methoxy, oxo, amino, methylamino, acetylamino and cyano.

32. The compound according claim 29,
wherein
$R_2$ is a radical selected from the group consisting of formulas (XVII) to (XXI)

(XVII)

(XVIII)

(XIX)

(XX)

(XXI)

wherein
any of the formulas (XVII) to (XXI) is directly bound to C-atom number 2 in formula (II) at the ring N-atom;

$R_{15}$, $R_{16}$, $R_{17}$, $R_{18}$, $R_{19}$, $R_{20}$, $R_{21}$, $R_{22}$, $R_{23}$ and $R_{24}$ are each radicals and are individually and independently selected from the group consisting of hydrogen, halogen, C1-C6 alkyl, C3-C6 cycloalkyl, substituted C3-C6 cycloalkyl, phenyl, substituted phenyl, benzyl, and substituted benzyl; and
any of the formulas (XVII) to (XXI) is independently and individually substituted with 0, 1 or 2 $R^a$,
   wherein
   $R^a$ is individually and independently selected from the group consisting of hydrogen, fluoro, chloro, bromo, methyl, ethyl, propyl, tert-butyl, phenyl, benzyl, hydroxyl, methoxy, oxo, amino, methylamino, acetylamino and cyano.

33. A compound having formula (XXII)

(XXII)

$$G-Z-A-Ar$$

wherein
Ar is a phenyl radical;
A is a radical from the group consisting of furyl, thienyl, pyrrolyl, oxazolyl, isooxazolyl, thiazolyl, isothiazolyl, imidazolyl, pyrazolyl, triazolyl, oxadiazolyl and thiadiazolyl,
wherein
ring atoms are individually and independently substituted with 0, 1 or 2 substituents $R^a$,
wherein
$R^a$ is individually and independently selected from the group consisting of hydrogen, fluoro, chloro, bromo, methyl, ethyl, propyl, tert-butyl, phenyl, benzyl, hydroxyl, methoxy, oxo, amino, methylamino, acetylamino and cyano; and
Z and the Ar ring in structure (XXII) are connected to A in positions meta to each other;
Q is selected from the group consisting of a direct bond, C1-C4 alkyl, CO—NH, NH—CO, CO—NH, NH—SO$_2$ and SO$_2$—NH;
$R_2$ is a radical selected from the group consisting of phenyl, 2,4,6-trimethylphenyl, 2,6-dimethylphenyl, 4-cyanophenyl, 2,4,6-tribromophenyl, 2-bromo-6-methylphenyl, 4-benzyloxyphenyl, 2-methylphenyl, 2-ethyl-6-methylphenyl, 2-methyl-6-trifluoromethylphenyl, 4-fluoro-2-ethyl-6-methylphenyl, 4-chloro-2-ethyl-6-methylphenyl, 4-cyano-2-ethyl-6-methylphenyl, 4-trifluoromethyl-2-ethyl-6-methylphenyl, 4-(1-oxoethyl)-2-ethyl-6-methylphenyl, 4-dimethylcarbamoyl-2-ethyl-6-methyl-phenyl, 4-methylcarbamoyl-2-ethyl-6-methyl-phenyl, 4-carbamoyl-2-ethyl-6-methyl-phenyl, 4-trifluoromethoxy-2-ethyl-6-methyl-phenyl, 4-(1H-imidazo-1-yl)-2-ethyl-6-methyl-phenyl, 4-fluoro-2,6-dimethylphenyl, 4-chloro-2,6-dimethylphenyl, 4-cyano-2,6-dimethylphenyl, 4-trifluoromethyl-2,6-dimethylphenyl, 4-(1-oxoethyl)-2,6-dimethylphenyl, 4-trifluoromethoxy-2,6-dimethylphenyl, 4-(1H-imidazo-1-yl)-2,6-dimethylphenyl, pyridine-3-yl, 2-methyl-pyridine-3-yl, 2-methyl-4-trifluoromethyl-pyridine-3-yl, 2,4-dimethyl-pyridine-3-yl, 4-chloro-2-methyl-6-methylthio-phenyl, 4-fluoro-2-methyl-6-methylthio-phenyl, 2-methyl-6-methylthio-phenyl, 4-fluoro-2-(2-propyl)-6-methylphenyl, 4-cyano-2-methyl-6-methylthio-phenyl, 4-trifluoromethyl-2-methyl-6-methylthio-phenyl, 2-isopropyl-6-methylphenyl, 4-fluoro-2-(2-propyl)-6-methylphenyl, 2-ethyl-4-methyl-pyridine-3-yl, 4-trichloromethyl-2-ethyl-6-methylphenyl, 4-nitro-2-ethyl-6-methylphenyl, 4-methyloxycarbonyl-2-ethyl-6-methylphenyl, 4-methylsulfonyl-2-ethyl-6-methylphenyl, 4-trifluoromethylsulfonyl-2-ethyl-6-methylphenyl, 4-aminosulfonyl-2-ethyl-6-methylphenyl, 4-methylaminosulfonyl-2-ethyl-6-methylphenyl, 4-dimethylaminosulfonyl-2-ethyl-6-methylphenyl, 4-methylaminocarbonyl-2-ethyl-6-methylphenyl, 4-dimethylaminocarbonyl-2-ethyl-6-methylphenyl, 4-aminocarbonyl-2-ethyl-6-methylphenyl, 2-ethyl-6-methyl-4-(2-oxazolyl)phenyl, 2-ethyl-6-methyl-4-(2-imidazolyl)phenyl, 4-trifluoromethylcarbonyl-2-ethyl-6-methylphenyl, 4-trichloromethyl-2,6-dimethylphenyl, 4-nitro-2,6-dimethylphenyl, 4-methyloxycarbonyl-2,6-dimethylphenyl, 4-methylsulfonyl-2,6-dimethylphenyl, 4-trifluoromethylsulfonyl-2,6-dimethylphenyl, 4-aminosulfonyl-2,6-dimethylphenyl, 4-methylaminosulfonyl-2,6-dimethylphenyl, 4-dimethylaminosulfonyl-2,6-dimethylphenyl, 4-methylaminocarbonyl-2,6-dimethylphenyl, 4-dimethylaminocarbonyl-2,6-dimethylphenyl, 4-aminocarbonyl-2,6-dimethylphenyl, 2,6-dimethyl-4-(2-oxazolyl)phenyl, 2,6-dimethyl-4-(2-imidazolyl)phenyl and 4-trifluoromethylearbonyl-2,6-dimethylphenyl;

$R_3$ is a radical selected from the group consisting of OH, OMe and OEt;

Z is selected from the group consisting of a direct bond, $CH_2$, $CH_2$—$CH_2$ and CO; and G is $R_9$—NH, wherein $R_9$ is a radical selected from the group consisting of:
(a) pyridine,
wherein
any or several of the ring atoms of $R_9$ is/are optionally and individually and independently substituted with one or several substituents, wherein the substituent is $R^a$; and
if $R_9$ is substituted 2-pyridyl, $R_9$ is substituted with at least one $R^a$ that is other than hydrogen; and
(b) 5,6- or 6,6-membered aromatic or combined aromatic/nonaromatic bicyclic ring systems comprising pyridine,
wherein any or several of the ring atoms of $R_9$ is/are optionally and individually and independently substituted with one or several substituents, wherein the substituent is $R^a$.

34. The compound according to claim 33, having formula (XXIII)

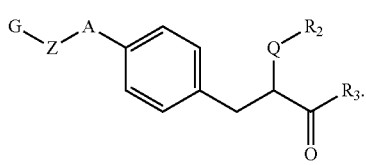

(XXIII)

35. The compound according to claim 34,
wherein
Q is selected from the group consisting of a direct bond, NH—CO and $NHSO_2$; and Z is selected from the group consisting of a direct bond, $CH_2$ and CO.

36. The compound according to claim 35,
wherein
A is furyl and the compound is represented by one of formulas (XXIV) to (XXVI),

(XXIV)

(XXV)

(XXVI)

wherein the furyl and the phenyl ring atoms in formulas (XXIV) to (XXVI) are each and independently substituted with 0, 1 or 2 $R_5$, wherein $R_5$ is hydrogen, fluoro, chloro, cyano, methylamino, dimethylamino, methylaminocarbonyl, acetylamino, phenyl, benzyl, methyl, ethyl, tert-butyl, hydroxy, methoxy, or trifluoromethyl.

37. The compound according to claim 36, having one of formulas (XXVII) to (XXIX),

(XXVII)

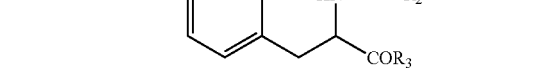
(XXVIII)

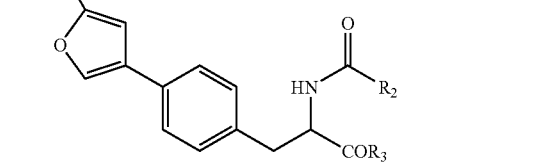

-continued (XXIX)

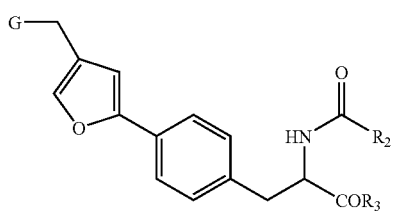

wherein

R₂ is a radical selected from the group consisting of phenyl, 2,4,6-trimethylphenyl, 2,6-dimethylphenyl, 4-cyanophenyl, 2,4,6-tribromophenyl, 2-bromo-6-methylphenyl, 4-benzyloxyphenyl, 2-methylphenyl, 2-ethyl-6-methylphenyl, 2-methyl-6-trifluoromethylphenyl, 4-fluoro-2-ethyl-6-methylphenyl, 4-chloro-2-ethyl-6-methylphenyl, 4-cyano-2-ethyl-6-methylphenyl, 4-trifluoromethyl-2-ethyl-6-methylphenyl, 4-(1-oxoethyl)-2-ethyl-6-methylphenyl, 4-dimethylcarbarnoyl-2-ethyl-6-methyl-phenyl, 4-methylcarbamoyl-2-ethyl-6-methyl-phenyl, 4-carbamoyl-2-ethyl-6-methyl-phenyl, 4-trifluoromethoxy-2-ethyl-6-methyl-phenyl, 4-(1H-imidazo-1-yl)-2-ethyl-6-methyl-phenyl, 4-fluoro-2,6-dimethylphenyl, 4-chloro-2,6-dimethylphenyl, 4-cyano-2,6-dimethylphenyl, 4-trifluoromethyl-2,6-dimethylphenyl, 4-(1-oxoethyl)-2,6-dimethylphenyl, 4-trifluoromethoxy-2,6-dimethylphenyl, 4-(1H-imidazo-1-yl)-2,6-dimethylphenyl, pyridine-3-yl, 2-methyl-pyridine-3-yl, 2-methyl-4-trifluoromethyl-pyridine-3-yl, 2,4-dimethyl-pyridine-3-yl, 4-chloro-2-methyl-6-methylthio-phenyl, 4-fluoro-2-methyl-6-methylthio-phenyl, 2-methyl-6-methylthio-phenyl, 4-fluoro-2-(2-propyl)-6-methylphenyl, 4-cyano-2-methyl-6-methylthio-phenyl, 4-trifluoromethyl-2-methyl-6-methylthio-phenyl, 2-isopropyl-6-methylphenyl, 4-fluoro-2-(2-propyl)-6-methylphenyl, 2-ethyl-4-methyl-pyridine-3-yl, 4-trichloromethyl-2-ethyl-6-methylphenyl, 4-nitro-2-ethyl-6-methylphenyl, 4-methyloxycarbonyl-2-ethyl-6-methylphenyl, 4-methylsulfonyl-2-ethyl-6-methylphenyl, 4-trifluoromethylsulfonyl-2-ethyl-6-methylphenyl, 4-aminosulfonyl-2-ethyl-6-methylphenyl, 4-methylaminosulfonyl-2-ethyl-6-methylphenyl, 4-dimethylaminosulfonyl-2-ethyl-6-methylphenyl, 4-methylaminocarbonyl-2-ethyl-6-methylphenyl, 4-dimethylaminocarbonyl-2-ethyl-6-methylphenyl, 4-aminocarbonyl-2-ethyl-6-methylphenyl, 2-ethyl-6-methyl-4-(2-oxazolyl)phenyl, 2-ethyl-6-methyl-4-(2-imidazolyl)phenyl, 4-trifluoromethylcarbonyl-2-ethyl-6-methylphenyl, 4-trichloromethyl-2,6-dimethylphenyl, 4-nitro-2,6-dimethylphenyl, 4-methyloxycarbonyl-2,6-dimethylphenyl, 4-methylsulfonyl-2,6-dimethylphenyl, 4-trifluoromethylsulfonyl-2,6-dimethylphenyl, 4-aminosulfonyl-2,6-dimethylphenyl, 4-methylaminosulfonyl-2,6-dimethylphenyl, 4-dimethylaminosulfonyl-2,6-dimethylphenyl, 4-methylaminocarbonyl-2,6-dimethylphenyl, 4-dimethylaminocarbonyl-2,6-dimethylphenyl, 4-aminocarbonyl-2,6-dimethylphenyl, 2,6-dimethyl-4-(2-oxazolyl)phenyl, 2,6-dimethyl-4-(2-imidazolyl)phenyl and 4-trifluoromethylcarbonyl-2,6-dimethylphenyl; and G is a radical selected from the group consisting of 3,4,5,6-tetrahydro-pyridin-2-ylamino, 4-methylpyridin-2-ylamino, 5-methylpyridin-2-ylamino, 4-methoxypyridin-2-ylamino, and 4-fluoropyridin-2-ylamino.

38. The compound according to claim 35,
wherein
A is pyrrolyl and the compound is represented by one of formulas (XXX) to (XXXIII)

(XXX)

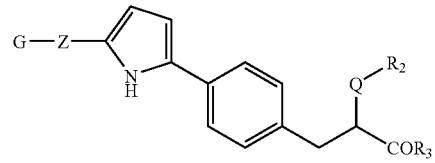

(XXXI)

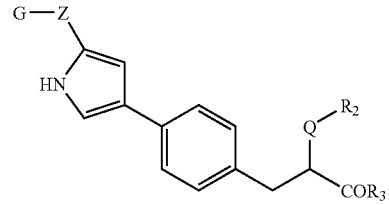

(XXXII)

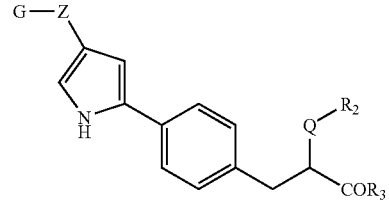

(XXXIII)

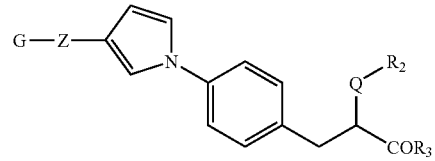

wherein
the pyrrolyl and the phenyl ring atoms in formulas (XXX) to (XXXIII) are each and independently substituted with 0, 1 or 2 R₅,
wherein
R₅ is hydrogen, fluoro, chloro, cyano, methylamino, dimethylamino, methylaminocarbonyl, acetylamino, phenyl, benzyl, methyl, ethyl, tert-butyl, hydroxy, methoxy, or trifluoromethyl.

39. The compound according to claim 38, having one of formulas (XXXIV) to (XXXVII)

(XXXIV)

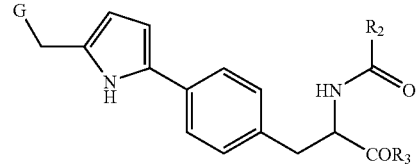

-continued (XXXV)

(XXXVI)

(XXXVII)

wherein
any NH-moiety of the pyrrolyl rings in formulas (XXXIV), (XXXV) and (XXXVI) is optionally substituted with methyl;

$R_2$ is a radical selected from the group consisting of phenyl, 2,4,6-trimethylphenyl, 2,6-dimethylphenyl, 4-cyanophenyl, 2,4,6-tribromophenyl, 2-bromo-6-methylphenyl, 4-benzyloxyphenyl, 2-methylphenyl, 2-ethyl-6-methylphenyl, 2-methyl-6-trifluoromethylphenyl, 4-fluoro-2-ethyl-6-methylphenyl, 4-chloro-2-ethyl-6-methylphenyl, 4-cyano-2-ethyl-6-methylphenyl, 4-trifluoromethyl-2-ethyl-6-methylphenyl, 4-(1-oxoethyl)-2-ethyl-6-methylphenyl, 4-dimethylcarbamoyl-2-ethyl-6-methyl-phenyl, 4-methylcarbamoyl-2-ethyl-6-methyl-phenyl, 4-carbamoyl-2-ethyl-6-methyl-phenyl, 4-trifluoromethoxy-2-ethyl-6-methyl-phenyl, 4-(1H-imidazo-1-yl)-2-ethyl-6-methyl-phenyl, 4-fluoro-2,6-dimethylphenyl, 4-chloro-2,6-dimethylphenyl, 4-cyano-2,6-dimethylphenyl, 4-trifluoromethyl-2,6-dimethylphenyl, 4-(1-oxoethyl)-2,6-dimethylphenyl, 4-trifluoromethoxy-2,6-dimethylphenyl, 4-(1H-imidazo-1-yl)-2,6-dimethylphenyl, pyridine-3-yl, 2-methyl-pyridine-3-yl, 2-methyl-4-trifluoromethyl-pyridine-3-yl, 2,4-dimethyl-pyridine-3-yl, 4-chloro-2-methyl-6-methylthio-phenyl, 4-fluoro-2-methyl-6-methylthio-phenyl, 2-methyl-6-methylthio-phenyl, 4-fluoro-2-(2-propyl)-6-methylphenyl, 4-cyano-2-methyl-6-methylthio-phenyl, 4-trifluoromethyl-2-methyl-6-methylthio-phenyl, 2-isopropyl-6-methylphenyl, 4-fluoro-2-(2-propyl)-6-methylphenyl, 2-ethyl-4-methyl-pyridine-3-yl, 4-trichloromethyl-2-ethyl-6-methylphenyl, 4-nitro-2-ethyl-6-methylphenyl, 4-methyloxycarbonyl-2-ethyl-6-methylphenyl, 4-methylsulfonyl-2-ethyl-6-methylphenyl, 4-trifluoromethylsulfonyl-2-ethyl-6-methylphenyl, 4-aminosulfonyl-2-ethyl-6-methylphenyl, 4-methylaminosulfonyl-2-ethyl-6-methylphenyl, 4-dimethylaminosulfonyl-2-ethyl-6-methylphenyl, 4-methylaminocarbonyl-2-ethyl-6-methylphenyl, 4-dimethylaminocarbonyl-2-ethyl-6-methylphenyl, 4-aminocarbonyl-2-ethyl-6-methylphenyl, 2-ethyl-6-methyl-4-(2-oxazolyl)phenyl, 2-ethyl-6-methyl-4-(2-imidazolyl)phenyl, 4-trifluoromethylearbonyl-2-ethyl-6-methylphenyl, 4-trichloromethyl-2,6-dimethylphenyl, 4-nitro-2,6-dimethylphenyl, 4-methyloxycarbonyl-2,6-dimethylphenyl, 4-methylsulfonyl-2,6-dimethylphenyl, 4-trifluoromethylsulfonyl-2,6-dimethylphenyl, 4-aminosulfonyl-2,6-dimethylphenyl, 4-methylaminosulfonyl-2,6-dimethylphenyl, 4-dimethylaminosulfonyl-2,6-dimethylphenyl, 4-methylaminocarbonyl-2,6-dimethylphenyl, 4-dimethylaminocarbonyl-2,6-dimethylphenyl, 4-aminocarbonyl-2,6-dimethylphenyl, 2,6-dimethyl-4-(2-oxazolyl)phenyl, 2,6-dimethyl-4-(2-imidazolyl)phenyl and 4-trifluoromethylcarbonyl-2,6-dimethylphenyl; and G is a radical selected from the group consisting of 3,4,5,6-tetrahtdro-pyridin-2-ylamino, 4-methylpyridin-2-ylamino, 5-methylpyridin-2-ylamino, 4-methoxypyridin-2-ylamino, and 4-fluoropyridin-2-ylamino.

40. The compound according to claim 35,
wherein
A is pyrazolyl and the compound is represented by one of formulas (XXXVIII) to (XXXIX)

(XXXVIII)

(XXXIX)

wherein
the pyrazolyl and the phenyl ring atoms in formulas (XXXVIII) to (XXXIX) are each and independently substituted with 0, 1 or 2 $R_5$,
wherein
$R_5$ is hydrogen, fluoro, chloro, cyano, methylamino, dimethylamino, methylaminocarbonyl, acetylamino, phenyl, benzyl, methyl, ethyl, tert-butyl, hydroxy, methoxy, or trifluoromethyl.

41. The compound according to claim 40, having one of formulas (XL) to (XLI)

(XL)

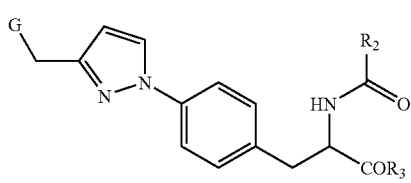

(XLI)

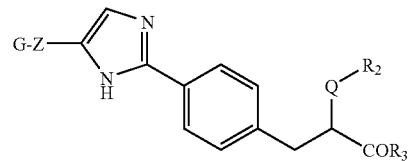

(XLII)

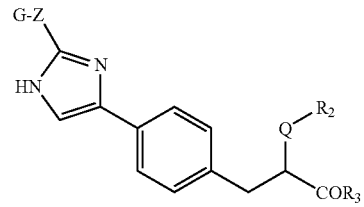

(XLIII)

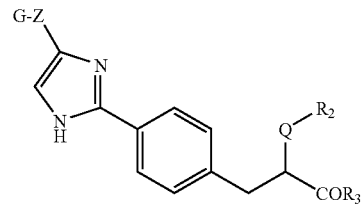

(XLIV)

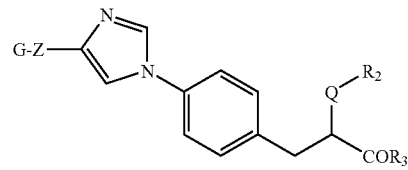

(XLV)

wherein $R_2$ is a radical selected from the group consisting of phenyl, 2,4,6-trimethylphenyl, 2,6-dimethylphenyl, 4-cyanophenyl, 2,4,6-tribromophenyl, 2-bromo-6-methylphenyl, 4-benzyloxyphenyl, 2-methylphenyl, 2-ethyl-6-methylphenyl, 2-methyl-6-trifluoromethylphenyl, 4-fluoro-2-ethyl-6-methylphenyl, 4-chloro-2-ethyl-6-methylphenyl, 4-cyano-2-ethyl-6-methylphenyl, 4-trifluoromethyl-2-ethyl-6-methylphenyl, 4-(1-oxoethyl)-2-ethyl-6-methylphenyl, 4-dimethylcarbamoyl-2-ethyl-6-methyl-phenyl, 4-methylcarbamoyl-2-ethyl-6-methyl-phenyl, 4-carbamoyl-2-ethyl-6-methyl-phenyl, 4-trifluoromethoxy-2-ethyl-6-methyl-phenyl, 4-(1H-imidazo-1-yl)-2-ethyl-6-methyl-phenyl, 4-fluoro-2,6-dimethylphenyl, 4-chloro-2,6-dimethylphenyl, 4-cyano-2,6-dimethylphenyl, 4-trifluoromethyl-2,6-dimethylphenyl, 4-(1-oxoethyl)-2,6-dimethylphenyl, 4-trifluoromethoxy-2,6-dimethylphenyl, 4-(1H-imidazo-1-yl)-2,6-dimethylphenyl, pyridine-3-yl, 2-methyl-pyridine-3-yl, 2-methyl-4-trifluoromethyl-pyridine-3-yl, 2,4-dimethyl-pyridine-3-yl, 4-chloro-2-methyl-6-methylthio-phenyl, 4-fluoro-2-methyl-6-methylthio-phenyl, 2-methyl-6-methylthio-phenyl, 4-fluoro-2-(2-propyl)-6-methylphenyl, 4-cyano-2-methyl-6-methylthio-phenyl, 4-trifluoromethyl-2-methyl-6-methylthio-phenyl, 2-isopropyl-6-methylphenyl, 4-fluoro-2-(2-propyl)-6-methylphenyl, 2-ethyl-4-methyl-pyridine-3-yl, 4-trichloromethyl-2-ethyl-6-methylphenyl, 4-nitro-2-ethyl-6-methylphenyl, 4-methyloxycarbonyl-2-ethyl-6-methylphenyl, 4-methylsulfonyl-2-ethyl-6-methylphenyl, 4-trifluoromethylsulfonyl-2-ethyl-6-methylphenyl, 4-aminosulfonyl-2-ethyl-6-methylphenyl, 4-methylaminosulfonyl-2-ethyl-6-methylphenyl, 4-dimethylaminosulfonyl-2-ethyl-6-methylphenyl, 4-methylaminocarbonyl-2-ethyl-6-methylphenyl, 4-dimethylaminocarbonyl-2-ethyl-6-methylphenyl, 4-aminocarbonyl-2-ethyl-6-methylphenyl, 2-ethyl-6-methyl-4-(2-oxazolyl)phenyl, 2-ethyl-6-methyl-4-(2-imidazoly)phenyl, 4-trifluoromethylcarbonyl-2-ethyl-6-methylphenyl, 4-trichloromethyl-2,6-dimethylphenyl, 4-nitro-2,6-dimethylphenyl, 4-methyloxycarbonyl-2,6-dimethylphenyl, 4-methylsulfonyl-2,6-dimethylphenyl, 4-trifluoromethylsulfonyl-2,6-dimethylphenyl, 4-aminosulfonyl-2,6-dimethylphenyl, 4-methylaminosulfonyl-2,6-dimethylphenyl, and 4-dimethylaminosulfonyl-2,6-dimethylphenyl; and G is a radical selected from the group consisting of 3,4,5,6-tetrahydro-pyridin-2-ylamino, 4-methylpyridin-2-ylamino, 5-methylpyridin-2-ylamino, 4-methoxypyridin-2-ylamino, and 4-fluoropyridin-2-ylamino.

42. The compound according to claim 35, wherein

A is imidazolyl and the compound is represented by one of formulas (XLII) to (XLV)

wherein the imidazolyl and the phenyl ring atoms in formulas (XLII) to (XLV) are each and independently substituted with 0, 1 or 2 $R_5$, wherein $R_5$ is hydrogen, fluoro, chloro, cyano, methylamino, dimethylamino, methylaminocarbonyl, acetylamino, phenyl, benzyl, methyl, ethyl, tert-butyl, hydroxy, methoxy, or trifluoromethyl.

43. The compound according to claim 42, having one of formulas (XLVI) to (XLIX)

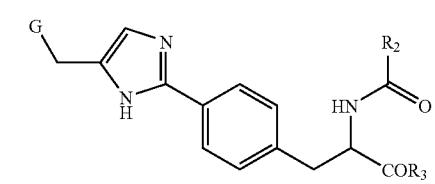

(XLVI)

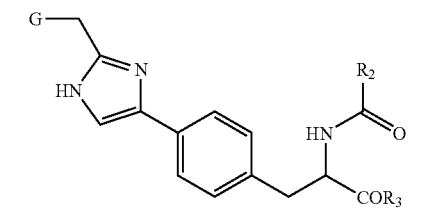

(XLVII)

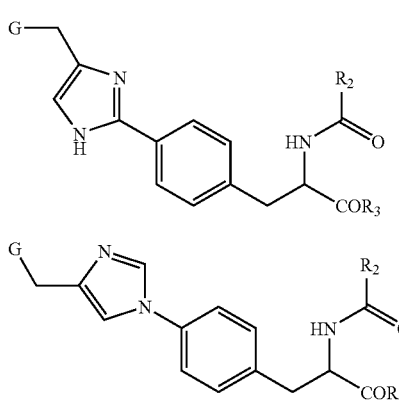

(XLVIII)

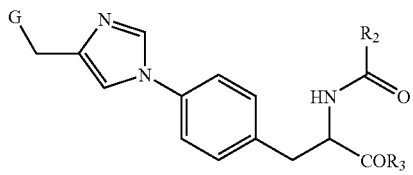

(XLIX)

wherein any NH-moiety of the imidazolyl rings in formulas (XLVI) to (XLVIII) is optionally substituted with methyl R₂ is a radical selected from the group consisting of phenyl, 2,4,6-trimethylphenyl, 2,6-dimethylphenyl, 4-cyanophenyl, 2,4,6-tribromophenyl, 2-bromo-6-methylphenyl, 4-benzyloxyphenyl, 2-methylphenyl, 2-ethyl-6-methylphenyl, 2-methyl-6-trifluoromethylphenyl, 4-fluoro-2-ethyl-6-methylphenyl, 4-chloro-2-ethyl-6-methylphenyl, 4-cyano-2-ethyl-6-methylphenyl, 4-trifluoromethyl-2-ethyl-6-methylphenyl, 4-(1-oxoethyl)-2-ethyl-6-methylphenyl, 4-dimethylcarbamoyl-2-ethyl-6-methyl-phenyl, 4-methylcarbamoyl-2-ethyl-6-methyl-phenyl, 4-carbamoyl-2-ethyl-6-methyl-phenyl, 4-trifluoromethoxy-2-ethyl-6-methyl-phenyl, 4-(1H-imidazo-1-yl)-2-ethyl-6-methyl-phenyl, 4-fluoro-2,6-dimethylphenyl, 4-chloro-2,6-dimethylphenyl, 4-cyano-2,6-dimethylphenyl, 4-trifluoromethyl-2,6-dimethylphenyl, 4-(1-oxoethyl)-2,6-dimethylphenyl, 4-trifluoromethoxy-2,6-dimethylphenyl, 4-(1H-imidazo-1-yl)-2,6-dimethylphenyl, pyridine-3-yl, 2-methyl-pyridine-3-yl, 2-methyl-4-trifluoromethyl-pyridine-3-yl, 2,4-dimethyl-pyridine-3-yl, 4-chloro-2-methyl-6-methylthio-phenyl, 4-fluoro-2-methyl-6-methylthio-phenyl, 2-methyl-6-methylthio-phenyl, 4-fluoro-2-(2-propyl)-6-methylphenyl, 4-cyano-2-methyl-6-methylthio-phenyl, 4-trifluoromethyl-2-methyl-6-methylthio-phenyl, 2-isopropyl-6-methylphenyl, 4-fluoro-2-(2-propyl)-6-methylphenyl, 2-ethyl-4-methyl-pyridine-3-yl, 4-trichloromethyl-2-ethyl-6-methylphenyl, 4-nitro-2-ethyl-6-methylphenyl, 4-methyloxycarbonyl-2-ethyl-6-methylphenyl, 4-methylsulfonyl-2-ethyl-6-methylphenyl, 4-trifluoromethylsulfonyl-2-ethyl-6-methylphenyl, 4-aminosulfonyl-2-ethyl-6-methylphenyl, 4-methylaminosulfonyl-2-ethyl-6-methylphenyl, 4-dimethylaminosulfonyl-2-ethyl-6-methylphenyl, 4-methylaminocarbonyl-2-ethyl-6-methylphenyl, 4-dimethylaminocarbonyl-2-ethyl-6-methylphenyl, 4-aminocarbonyl-2-ethyl-6-methylphenyl, 2-ethyl-6-methyl-4-(2-oxazolyl)phenyl, 2-ethyl-6-methyl-4-(2-imidazolyl)phenyl, 4-trifluoromethylcarbonyl-2-ethyl-6-methylphenyl, 4-trichloromethyl-2,6-dimethylphenyl, 4-nitro-2,6-dimethylphenyl, 4-methyloxycarbonyl-2,6-dimethylphenyl, 4-methylsulfonyl-2,6-dimethylphenyl, 4-trifluoromethylsulfonyl-2,6-dimethylphenyl, 4-aminosulfonyl-2,6-dimethylphenyl, 4-methylaminosulfonyl-2,6-dimethylphenyl, 4-dimethylaminosulfonyl-2,6-dimethylphenyl, 4-methylaminocarbonyl-2,6-dimethylphenyl, 4-dimethylaminocarbonyl-2,6-dimethylphenyl, 4-aminocarbonyl-2,6-dimethylphenyl, 2,6-dimethyl-4-(2-oxazolyl)phenyl, 2,6-dimethyl-4-(2-imidazolyl)phenyl and 4-trifluoromethylcarbonyl-2,6-dimethylphenyl; and G is a radical selected from the group consisting of 3,4,5,6-tetrahydro-pyridin-2-ylamino, 4-methylpyridin-2-ylamino, 5-methylpyridin-2-ylamino, 4-methoxypyridin-2-ylamino, and 4-fluoropyridin-2-ylamino.

44. The compound according to claim 35, wherein

A is thienyl and the compound is represented by one of formulas (L) to (LII)

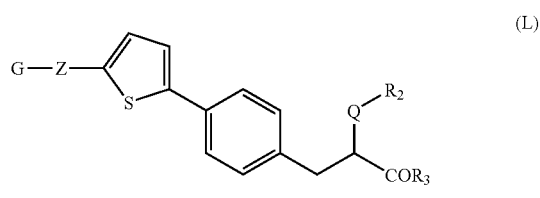

(L)

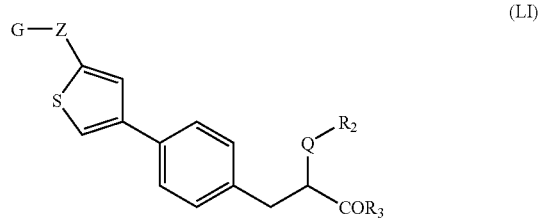

(LI)

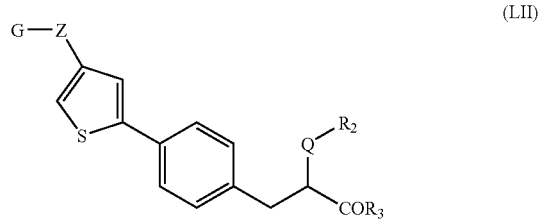

(LII)

wherein the thienyl and the phenyl ring atoms in formulas (L) to (LII) are each and independently substituted with 0, 1 or 2 $R_5$, wherein $R_5$ is hydrogen, fluoro, chloro, cyano, methylamino, dimethylamino, methylaminocarbonyl, acetylamino, phenyl, benzyl, methyl, ethyl, tert-butyl, hydroxy, methoxy, or trifluoromethyl.

45. The compound according to claim 44, having one of formulas (LIII) to (LV)

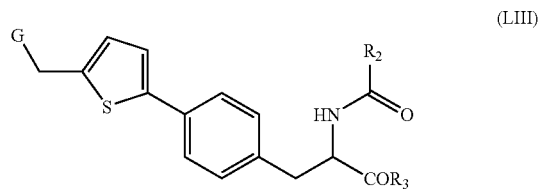

(LIII)

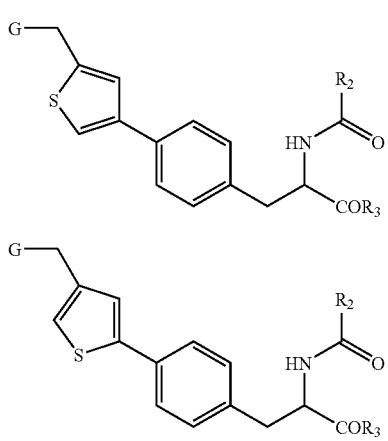

(LIV)

(LV)

wherein
R₂ is a radical selected from the group consisting of phenyl, 2,4,6-trimethylphenyl, 2,6-dimethylphenyl, 4-cyanophenyl, 2,4,6-tribromophenyl, 2-bromo-6-methylphenyl, 4-benzyloxyphenyl, 2-methylphenyl, 2-ethyl-6-methylphenyl, 2-methyl-6-trifluoromethylphenyl, 4-fluoro-2-ethyl-6-methylphenyl, 4-chloro-2-ethyl-6-methylphenyl, 4-cyano-2-ethyl-6-methylphenyl, 4-trifluoromethyl-2-ethyl-6-methylphenyl, 4-(1-oxoethyl)-2-ethyl-6-methylphenyl, 4-dimethylcarbamoyl-2-ethyl-6-methyl-phenyl, 4-methylcarbamoyl-2-ethyl-6-methyl-phenyl, 4-carbamoyl-2-ethyl-6-methyl-phenyl, 4-trifluoromethoxy-2-ethyl-6-methyl-phenyl, 4-(1H-imidazo-1-yl)-2-ethyl-6-methyl-phenyl, 4-fluoro-2,6-dimethylphenyl, 4-chloro-2,6-dimethylphenyl, 4-cyano-2,6-dimethylphenyl, 4-trifluoromethyl-2,6-dimethylphenyl, 4-(1-oxoethyl)-2,6-dimethylphenyl, 4-trifluoromethoxy-2,6-dimethylphenyl, 4-(1H-imidazo-1-yl)-2,6-dimethylphenyl, pyridine-3-yl, 2-methyl-pyridine-3-yl, 2-methyl-4-trifluoromethyl-pyridine-3-yl, 2,4-dimethyl-pyridine-3-yl, 4-chloro-2-methyl-6-methylthio-phenyl, 4-fluoro-2-methyl-6-methylthio-phenyl, 2-methyl-6-methylthio-phenyl, 4-fluoro-2-(2-propyl)-6-methylphenyl, 4-cyano-2-methyl-6-methylthio-phenyl, 4-trifluoromethyl-2-methyl-6-methylthio-phenyl, 2-isopropyl-6-methylphenyl, 4-fluoro-2-(2-propyl)-6-methylphenyl, 2-ethyl-4-methyl-pyridine-3-yl, 4-trichloromethyl-2-ethyl-6-methylphenyl, 4-nitro-2-ethyl-6-methylphenyl, 4-methyloxycarbonyl-2-ethyl-6-methylphenyl, 4-methylsulfonyl-2-ethyl-6-methylphenyl, 4-trifluoromethylsulfonyl-2-ethyl-6-methylphenyl, 4-aminosulfonyl-2-ethyl-6-methylphenyl, 4-methylaminosulfonyl-2-ethyl-6-methylphenyl, 4-dimethylaminosulfonyl-2-ethyl-6-methylphenyl, 4-methylaminocarbonyl-2-ethyl-6-methylphenyl, 4-dimethylaminocarbonyl-2-ethyl-6-methylphenyl, 4-aminocarbonyl-2-ethyl-6-methylphenyl, 2-ethyl-6-methyl-4-(2-oxazolyl)phenyl, 2-ethyl-6-methyl-4-(2-imidazolyl)phenyl, 4-trifluoromethylcarbonyl-2-ethyl-6-methylphenyl, 4-trichloromethyl-2,6-dimethylphenyl, 4-nitro-2,6-dimethylphenyl, 4-methyloxycarbonyl-2,6-dimethylphenyl, 4-methylsulfonyl-2,6-dimethylphenyl, 4-trifluoromethylsulfonyl-2,6-dimethylphenyl, 4-aminosulfonyl-2,6-dimethylphenyl, 4-methylaminosulfonyl-2,6-dimethylphenyl, 4-dimethylaminosulfonyl-2,6-dimethylphenyl, 4-methylaminocarbonyl-2,6-dimethylphenyl, 4-dimethylaminocarbonyl-2,6-dimethylphenyl, 4-aminocarbonyl-2,6-dimethylphenyl, 2,6-dimethyl-4-(2-oxazolyl)phenyl, 2,6-dimethyl-4-(2-imidazolyl)phenyl and 4-trifluoromethylcarbonyl-2,6-dimethylphenyl; and G is a radical selected from the group consisting of 3,4,5,6-tetrahydro-pyridin-2-ylamino, 4-methylpyridin-2-ylamino, 5-methylpyridin-2-ylamino, 4-methoxypyridin-2-ylamino, and 4-fluoropyridin-2-ylamino.

46. The compound according to claim 35,
wherein
A is isoxazolyl and the compound is represented by one of formulas (LVI) to (LVII)

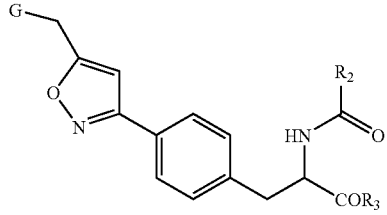

(LVI)

(LVII)

wherein
the isoxazolyl and the phenyl rings in formulas (LVI) to (LVII) are each and independently substituted with 0, 1 or 2 R₅,
wherein
R₅ is hydrogen, fluoro, chloro, cyano, methylamino, dimethylamino, methylaminocarbonyl, acetylamino, phenyl, benzyl, methyl, ethyl, tert-butyl, hydroxy, methoxy, or trifluoromethyl.

47. The compound according to claim 46, having one of formulas (LVIII) to (LIX)

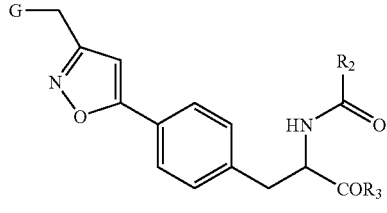

(LVIII)

(LIX)

wherein
R₂ is a radical selected from the group consisting of phenyl, 2,4,6-trimethylphenyl, 2,6-dimethylphenyl, 4-cyanophenyl, 2,4,6-tribromophenyl, 2-bromo-6-methylphenyl, 4-benzyloxyphenyl, 2-methylphenyl, 2-ethyl-6-methylphenyl, 2-methyl-6-trifluoromethylphenyl, 4-fluoro-2-ethyl-6-methylphenyl, 4-chloro-2-ethyl-6-methylphenyl, 4-cyano-2-ethyl-6-methylphenyl, 4-trifluoromethyl-2-ethyl-6-methylphenyl, 4-(1-oxoethyl)-2-ethyl-6-methylphenyl, 4-dimethylcarbamoyl-2-ethyl-6-methyl-phenyl, 4-methylcarbamoyl-2-ethyl-6-methyl-phenyl, 4-carbamoyl-2-ethyl-6-methyl-phenyl, 4-trifluoromethoxy-2-ethyl-6-methyl-phenyl, 4-(1H-imidazo-1-yl)-2-ethyl-6-methyl-phenyl, 4-fluoro-2,6-dimethylphenyl, 4-chloro-2,6-dimethylphenyl, 4-cyano-2,6-dimethylphenyl, 4-trifluoromethyl-2,6-dimethylphenyl, 4-(1-oxoethyl)-2,6-dimethylphenyl, 4-trifluoromethoxy-2,6-dimethylphenyl, 4-(1H-imidazo-1-yl)-2,6-dimethylphenyl, pyridine-3-yl, 2-methyl-pyridine-3-yl, 2-methyl-4-trifluoromethyl-pyridine-3-yl, 2,4-dimethyl-pyridine-3-yl, 4-chloro-2-methyl-6-methylthio-phenyl, 4-fluoro-2-methyl-6-methylthio-phenyl, 2-methyl-6-methylthio-phenyl, 4-fluoro-2-(2-propyl)-6-methylphenyl, 4-cyano-2-methyl-6-methylthio-phenyl, 4-trifluoromethyl-2-methyl-6-methylthio-phenyl, 2-isopropyl-6-methylphenyl, 4-fluoro-2-(2-propyl)-6-methylphenyl, 2-ethyl-4-methyl-pyridine-3-yl, 4-trichloromethyl-2-ethyl-6-methylphenyl, 4-nitro-2-ethyl-6-methylphenyl, 4-methyloxycarbonyl-2-ethyl-6-methylphenyl, 4-methylsulfonyl-2-ethyl-6-methylphenyl, 4-trifluoromethylsulfonyl-2-ethyl-6-methylphenyl, 4-aminosulfonyl-2-ethyl-6-methylphenyl, 4-methylaminosulfonyl-2-ethyl-6-methylphenyl, 4-dimethylaminosulfonyl-2-ethyl-6-methylphenyl, 4-methylaminocarbonyl-2-ethyl-6-methylphenyl, 4-dimethylaminocarbonyl-2-ethyl-6-methylphenyl, 4-aminocarbonyl-2-ethyl-6-methylphenyl, 2-ethyl-6-methyl-4-(2-oxazolyl)phenyl, 2-ethyl-6-methyl-4-(2-imidazolyl)phenyl, 4-trifluoromethylcarbonyl-2-ethyl-6-methylphenyl, 4-trichloromethyl-2,6-dimethylphenyl, 4-nitro-2,6-dimethylphenyl, 4-methyloxycarbonyl-2,6-dimethylphenyl, 4-methylsulfonyl-2,6-dimethylphenyl, 4-trifluoromethylsulfonyl-2,6-dimethylphenyl, 4-aminosulfonyl-2,6-dimethylphenyl, 4-methylaminosulfonyl-2,6-dimethylphenyl, 4-dimethylaminosulfonyl-2,6-dimethylphenyl, 4-methylaminocarbonyl-2,6-dimethylphenyl, 4-dimethylaminocarbonyl-2,6-dimethylphenyl, 4-aminocarbonyl-2,6-dimethylphenyl, 2,6-dimethyl-4-(2-oxazolyl)phenyl, 2,6-dimethyl-4-(2-imidazolyl)phenyl and 4-trifluoromethylcarbonyl-2,6-dimethylphenyl; and G is a radical selected from the group consisting of 3,4,5,6-tetrahydro-pyridin-2-ylamino, 4-methylpyridin-2-ylamino, 5-methylpyridin-2-ylamino, 4-methoxypyridin-2-ylamino, and 4-fluoropyridin-2-ylamino.

48. The compound according to claim 35,
wherein
A is oxazolyl and the compound is represented by one of formulas (LX) to (LXIII)

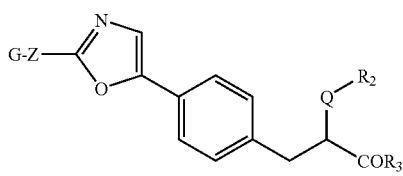
(LX)

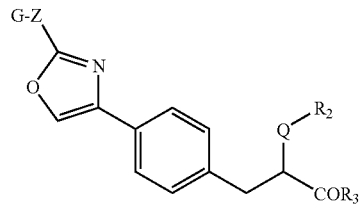
(LXI)

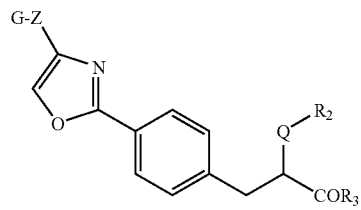
(LXII)

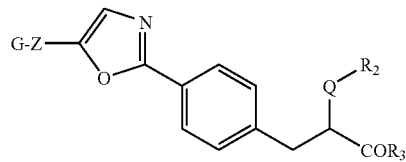
(LXIII)

wherein
the oxazolyl and the phenyl ring atoms in formulas (LX) to (LXIII) are each and independently substituted with 0, 1 or 2 $R_5$,
wherein
$R_5$ is hydrogen, fluoro, chloro, cyano, methylamino, dimethylamino, methylaminocarbonyl, acetylamino, phenyl, benzyl, methyl, ethyl, tert-butyl, hydroxy, methoxy, or trifluoromethyl.

49. The compound according to claim 48, having one of formulas (LXIV) to (LXVII)

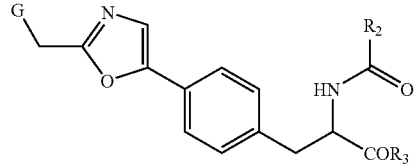
(LXIV)

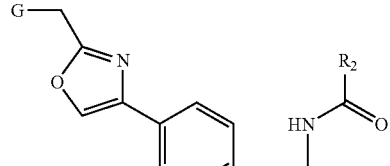
(LXV)

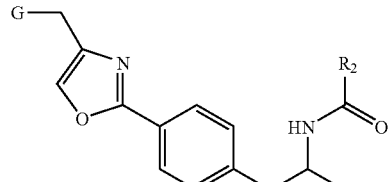
(LXVI)

-continued (LXVII)

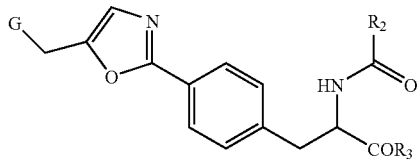

wherein
R₂ is a radical selected from the group consisting of phenyl, 2,4,6-trimethylphenyl, 2,6-dimethylphenyl, 4-cyanophenyl, 2,4,6-tribromophenyl, 2-bromo-6-methylphenyl, 4-benzyloxyphenyl, 2-methylphenyl, 2-ethyl-6-methylphenyl, 2-methyl-6-trifluoromethylphenyl, 4-fluoro-2-ethyl-6-methylphenyl, 4-chloro-2-ethyl-6-methylphenyl, 4-cyano-2-ethyl-6-methylphenyl, 4-trifluoromethyl-2-ethyl-6-methylphenyl, 4-(1-oxoethyl)-2-ethyl-6-methylphenyl, 4-dimethylcarbamoyl-2-ethyl-6-methyl-phenyl, 4-methylcarbamoyl-2-ethyl-6-methyl-phenyl, 4-carbamoyl-2-ethyl-6-methyl-phenyl, 4-trifluoromethoxy-2-ethyl-6-methyl-phenyl, 4-(1H-imidazo-1-yl)-2-ethyl-6-methyl-phenyl, 4-fluoro-2,6-dimethylphenyl, 4-chloro-2,6-dimethylphenyl, 4-cyano-2,6-dimethylphenyl, 4-trifluoromethyl-2,6-dimethylphenyl, 4-(1-oxoethyl)-2,6-dimethylphenyl, 4-trifluoromethoxy-2,6-dimethylphenyl, 4-(1H-imidazo-1-yl)-2,6-dimethylphenyl, pyridine-3-yl, 2-methyl-pyridine-3-yl, 2-methyl-4-trifluoromethyl-pyridine-3-yl, 2,4-dimethyl-pyridine-3-yl, 4-chloro-2-methyl-6-methylthio-phenyl, 4-fluoro-2-methyl-6-methylthio-phenyl, 2-methyl-6-methylthio-phenyl, 4-fluoro-2-(2-propyl)-6-methylphenyl, 4-cyano-2-methyl-6-methylthio-phenyl, 4-trifluoromethyl-2-methyl-6-methylthio-phenyl, 2-isopropyl-6-methylphenyl, 4-fluoro-2-(2-propyl)-6-methylphenyl, 2-ethyl-4-methyl-pyridine-3-yl, 4-trichloromethyl-2-ethyl-6-methylphenyl, 4-nitro-2-ethyl-6-methylphenyl, 4-methyloxycarbonyl-2-ethyl-6-methylphenyl, 4-methylsulfonyl-2-ethyl-6-methylphenyl, 4-trifluoromethylsulfonyl-2-ethyl-6-methylphenyl, 4-aminosulfonyl-2-ethyl-6-methylphenyl, 4-methylaminosulfonyl-2-ethyl-6-methylphenyl, 4-dimethylaminosulfonyl-2-ethyl-6-methylphenyl, 4-methylaminocarbonyl-2-ethyl-6-methylphenyl, 4-dimethylaminocarbonyl-2-ethyl-6-methylphenyl, 4-aminocarbonyl-2-ethyl-6-methylphenyl, 2-ethyl-6-methyl-4-(2-oxazolyl)phenyl, 2-ethyl-6-methyl-4-(2-imidazolyl)phenyl, 4-trifluoromethylcarbonyl-2-ethyl-6-methylphenyl, 4-trichloromethyl-2,6-dimethylphenyl, 4-nitro-2,6-dimethylphenyl, 4-methyloxycarbonyl-2,6-dimethylphenyl, 4-methylsulfonyl-2,6-dimethylphenyl, 4-trifluoromethylsulfonyl-2,6-dimethylphenyl, 4-aminosulfonyl-2,6-dimethylphenyl, 4-methylaminosulfonyl-2,6-dimethylphenyl, 4-dimethylaminosulfonyl-2,6-dimethylphenyl, 4-methylaminocarbonyl-2,6-dimethylphenyl, 4-dimethylaminocarbonyl-2,6-dimethylphenyl, 4-aminocarbonyl-2,6-dimethylphenyl, 2,6-dimethyl-4-(2-oxazolyl)phenyl, 2,6-dimethyl-4-(2-imidazolyl)phenyl and 4-trifluoromethylcarbonyl-2,6-dimethylphenyl; and
G is a radical selected from the group consisting of 3,4,5,6-tetrahydro-pyridin-2-ylamino, 4-methylpyridin-2-ylamino, 5-methylpyridin-2ylamino, 4-methoxypyridin-2-ylamino, and 4-fluoropyridin-2-ylamino.

50. The compound according to claim 35,
wherein
A is thiazolyl and the compound is represented by one of formulas (LXVIII) to (LXXI)

(LXVIII)

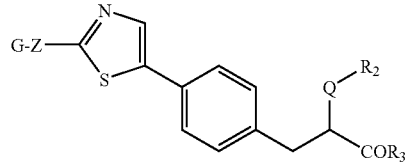

(LXIX)

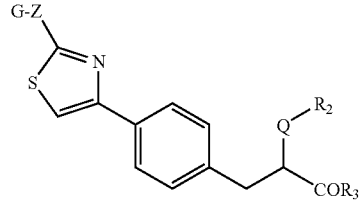

(LXX)

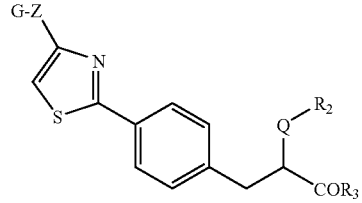

(LXXI)

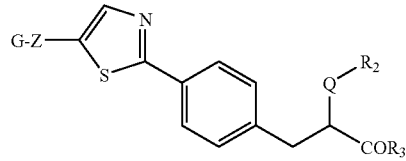

wherein
the thiazolyl and the phenyl ring atoms in formulas (LXVIII) to (LXXI) are each and independently substituted with 0, 1 or 2 R₅,
wherein
R₅ is hydrogen, fluoro, chloro, cyano, methylamino, dimethylamino, methylaminocarbonyl, acetylamino, phenyl, benzyl, methyl, ethyl, tert-butyl, hydroxy, methoxy, or trifluoromethyl.

51. The compound according to claim 50, having one of formulas (LXXII) to (LXXV)

(LXXII)

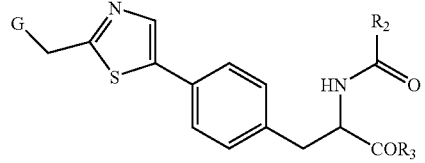

(LXXIII)

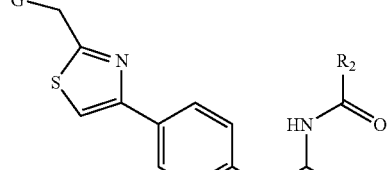

-continued

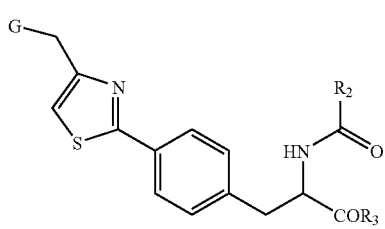
(LXXIV)

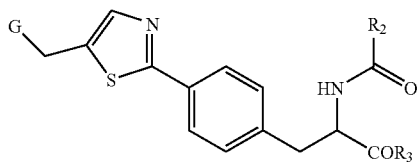
(LXXV)

wherein

R₂ is a radical selected from the group consisting of phenyl, 2,4,6-trimethylphenyl, 2,6-dimethylphenyl, 4-cyanophenyl, 2,4,6-tribromophenyl, 2-bromo-6-methylphenyl, 4-benzyloxyphenyl, 2-methylphenyl, 2-ethyl-6-methylphenyl, 2-methyl-6-trifluoromethylphenyl, 4-fluoro-2-ethyl-6-methylphenyl, 4-chloro-2-ethyl-6-methylphenyl, 4-cyano-2-ethyl-6-methylphenyl, 4-trifluoromethyl-2-ethyl-6-methylphenyl, 4-(1-oxoethyl)-2-ethyl-6-methylphenyl, 4-dimethylcarbamoyl-2-ethyl-6-methyl-phenyl, 4-methylcarbamoyl-2-ethyl-6-methyl-phenyl, 4-carbamoyl-2-ethyl-6-methyl-phenyl, 4-trifluoromethoxy-2-ethyl-6-methyl-phenyl, 4-(1H-imidazo-1-yl)-2-ethyl-6-methyl-phenyl, 4-fluoro-2,6-dimethylphenyl, 4-chloro-2,6-dimethylphenyl, 4-cyano-2,6-dimethylphenyl, 4-trifluoromethyl-2,6-dimethylphenyl, 4-(1-oxoethyl)-2,6-dimethylphenyl, 4-trifluoromethoxy-2,6-dimethylphenyl, 4-(1H-imidazo-1-yl)-2,6-dimethylphenyl, pyridine-3-yl, 2-methyl-pyridine-3-yl, 2-methyl-4-trifluoromethyl-pyridine-3-yl, 2,4-dimethyl-pyridine-3-yl, 4-chloro-2-methyl-6-methylthio-phenyl, 4-fluoro-2-methyl-6-methylthio-phenyl, 2-methyl-6-methylthio-phenyl, 4-fluoro-2-(2-propyl)-6-methylphenyl, 4-cyano-2-methyl-6-methylthio-phenyl, 4-trifluoromethyl-2-methyl-6-methylthio-phenyl, 2-isopropyl-6-methylphenyl, 4-fluoro-2-(2-propyl)-6-methylphenyl, 2-ethyl-4-methyl-pyridine-3-yl, 4-trichloromethyl-2-ethyl-6-methylphenyl, 4-nitro-2-ethyl-6-methylphenyl, 4-methyloxycarbonyl-2-ethyl-6-methylphenyl, 4-methylsulfonyl-2-ethyl-6-methylphenyl, 4-trifluoromethylsulfonyl-2-ethyl-6-methylphenyl, 4-aminosulfonyl-2-ethyl-6-methylphenyl, 4-methylaminosulfonyl-2-ethyl-6-methylphenyl, 4-dimethylaminosulfonyl-2-ethyl-6-methylphenyl, 4-methylaminocarbonyl-2-ethyl-6-methylphenyl, 4-dimethylaminocarbonyl-2-ethyl-6-methylphenyl, 4-aminocarbonyl-2-ethyl-6-methylphenyl, 2-ethyl-6-methyl-4-(2-oxazolyl)phenyl, 2-ethyl-6-methyl-4-(2-imidazolyl)phenyl, 4-trifluoromethylcarbonyl-2-ethyl-6-methylphenyl, 4-trichloromethyl-2,6-dimethylphenyl, 4-nitro-2,6-dimethylphenyl, 4-methyloxycarbonyl-2,6-dimethylphenyl, 4-methylsulfonyl-2,6-dimethylphenyl, 4-trifluoromethylsulfonyl-2,6-dimethylphenyl, 4-aminosulfonyl-2,6-dimethylphenyl, 4-methylaminosulfonyl-2,6-dimethylphenyl, 4-dimethylaminosulfonyl-2,6-dimethylphenyl, 4-methylaminocarbonyl-2,6-dimethylphenyl, 4-dimethylaminocarbonyl-2,6-dimethylphenyl, 4-aminocarbonyl-2,6-dimethylphenyl, 2,6-dimethyl-4-(2-oxazolyephenyl, 2,6-dimethyl-4-(2-imidazolyl)phenyl and 4-trifluoromethylcarbonyl-2,6-dimethylphenyl; and G is a radical selected from the group consisting of 3,4,5,6-tetrahydro-pyridin-2-ylamino, 4-methylpyridin-2-ylamino, 5-methylpyridin-2-ylamino, 4-methoxypyridin-2-ylamino, and 4-fluoropyridin-2-ylamino.

52. The compound according to claim 35, wherein

A is thiadiazoyl and the compound is represented by one of formulas (LXXVI) to (LXXVIII),

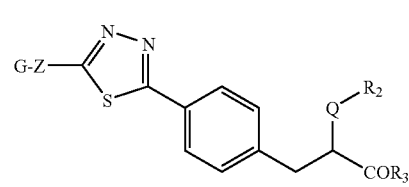
(LXXVI)

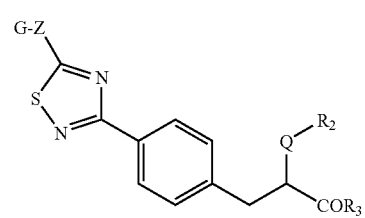
(LXXVII)

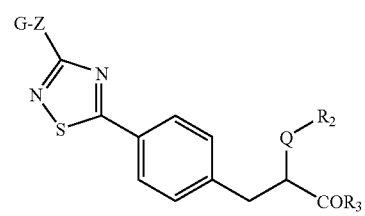
(LXXVIII)

wherein the thiadiazolyl and the phenyl ring atoms in formulas (LXXVI) to (LXXVIII) are each and independently substituted with 0, 1 or 2 $R_5$, wherein $R_5$ is hydrogen, fluoro, chloro, cyano, methylamino, dimethylamino, methylaminocarbonyl, acetylamino, phenyl, benzyl, methyl, ethyl, tert-butyl, hydroxy, methoxy, or trifluoromethyl.

53. The compound according to claim 52, having one of formulas (LXXIX) to (LXXXI)

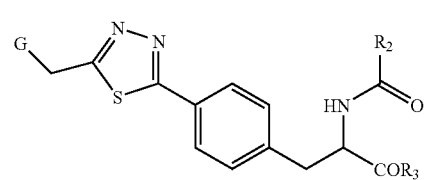
(LXXIX)

(LXXX)

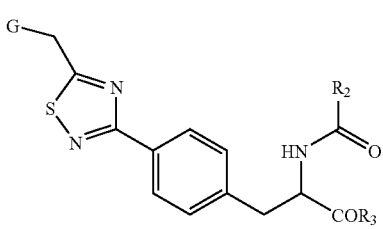

(LXXXI)

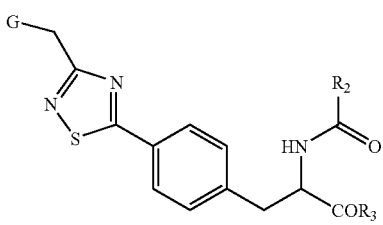

wherein

R$_2$ is a radical selected from the group consisting of phenyl, 2,4,6-trimethylphenyl, 2,6-dimethylphenyl, 4-cyanophenyl, 2,4,6-tribromophenyl, 2-bromo-6-methylphenyl, 4-benzyloxyphenyl, 2-methylphenyl, 2-ethyl-6-methylphenyl, 2-methyl-6-trifluoromethylphenyl, 4-fluoro-2-ethyl-6-methylphenyl, 4-chloro-2-ethyl-6-methylphenyl, 4-cyano-2-ethyl-6-methylphenyl, 4-trifluoromethyl-2-ethyl-6-methylphenyl, 4-(1-oxoethyl)-2-ethyl-6-methylphenyl, 4-dimethylcarbamoyl-2-ethyl-6-methyl-phenyl, 4-methylcarbamoyl-2-ethyl-6-methyl-phenyl, 4-carbamoyl-2-ethyl-6-methyl-phenyl, 4-trifluoromethoxy-2-ethyl-6-methyl-phenyl, 4-(1H-imidazo-1-yl)-2-ethyl-6-methyl-phenyl, 4-fluoro-2,6-dimethylphenyl, 4-chloro-2, 6-dimethylphenyl, 4-cyano-2, 6-dimethylphenyl, 4-trifluoromethyl-2,6-dimethylphenyl, 4-(1-oxoethyl)-2,6-dimethylphenyl, 4-trifluoromethoxy-2,6-dimethylphenyl, 4-(1H-imidazo-1-yl)-2,6-dimethylphenyl, pyridine-3-yl, 2-methyl-pyridine-3-yl, 2-methyl-4-trifluoromethyl-pyridine-3-yl, 2,4-dimethyl-pyridine-3-yl, 4-chloro-2-methyl-6-methylthio-phenyl, 4-fluoro-2-methyl-6-methylthio-phenyl, 2-methyl-6-methylthio-phenyl, 4-fluoro-2-(2-propyl)-6-methylphenyl, 4-cyano-2-methyl-6-methylthio-phenyl, 4-trifluoromethyl-2-methyl-6-methylthio-phenyl, 2-isopropyl-6-methylphenyl, 4-fluoro-2-(2-propyl)-6-methylphenyl, 2-ethyl-4-methyl-pyridine-3-yl, 4-trichloromethyl-2-ethyl-6-methylphenyl, 4-nitro-2-ethyl-6-methylphenyl, 4-methyloxycarbonyl-2-ethyl-6-methylphenyl, 4-methylsulfonyl-2-ethyl-6-methylphenyl, 4-trifluoromethylsulfonyl-2-ethyl-6-methylphenyl, 4-aminosulfonyl-2-ethyl-6-methylphenyl, 4-methylaminosulfonyl-2-ethyl-6-methylphenyl, 4-dimethylaminosulfonyl-2-ethyl-6-methylphenyl, 4-methylaminocarbonyl-2-ethyl-6-methylphenyl, 4-dimethylaminocarbonyl-2-ethyl-6-methylphenyl, 4-aminocarbonyl-2-ethyl-6-methylphenyl, 2-ethyl-6-methyl-4-(2-oxazolyl)phenyl, 2-ethyl-6-methyl-4-(2-imidazolyl)phenyl, 4-trifluoromethylcarbonyl-2-ethyl-6-methylphenyl, 4-trichloromethyl-2,6-dimethylphenyl, 4-nitro-2,6-dimethylphenyl, 4-methyloxycarbonyl-2,6-dimethylphenyl, 4-methylsulfonyl-2,6-dimethylphenyl, 4-trifluoromethylsulfonyl-2,6-dimethylphenyl, 4-aminosulfonyl-2,6-dimethylphenyl, 4-methylaminosulfonyl-2,6-dimethylphenyl, 4-dimethylaminosulfonyl-2,6-dimethylphenyl, 4-methylaminocarbonyl-2,6-dimethylphenyl, 4-dimethylaminocarbonyl-2,6-dimethylphenyl, 4-aminocarbonyl-2,6-dimethylphenyl, 2,6-dimethyl-4-(2-oxazolyl)phenyl, 2,6-dimethyl-4-(2-imidazolyl)phenyl and 4-trifluoromethylcarbonyl-2,6-dimethylphenyl; and G is a radical selected from the group consisting of 3,4,5,6-tetrahydro-pyridin-2-ylamino, 4-methylpyridin-2-ylamino, 5-methylpyridin-2-ylamino, 4-methoxypyridin-2-ylamino, and 4-fluoropyridin-2-ylamino.

54. The compound according to claim 35, wherein

A is oxadiazolyl and the compound is represented by formula (LXXXII)

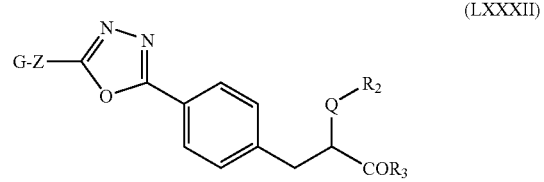

(LXXXII)

wherein the oxadiazolyl and the phenyl ring atoms in formula (LXXXII) are each and independently substituted with 0, 1 or 2 R$_5$, wherein R$_5$ is hydrogen, fluoro, chloro, cyano, methylamino, dimethylamino, methylaminocarbonyl, acetylamino, phenyl, benzyl, methyl, ethyl, tert-butyl, hydroxy, methoxy, or trifluoromethyl.

55. The compound according to claim 54, having formula (LXXXIII)

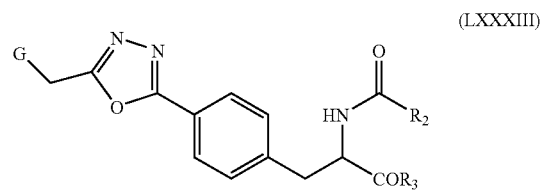

(LXXXIII)

wherein

R$_2$ is a radical selected from the group consisting of phenyl, 2,4,6-trimethylphenyl, 2,6-dimethylphenyl, 4-cyanophenyl, 2,4,6-tribromophenyl, 2-bromo-6-methylphenyl, 4-benzyloxyphenyl, 2-methylphenyl, 2-ethyl-6-methylphenyl, 2-methyl-6-tri fluoromethylphenyl, 4-fluoro-2-ethyl-6-methylphenyl, 4-chloro-2-ethyl-6-methylphenyl, 4-cyano-2-ethyl-6-methylphenyl, 4-trifluoromethyl-2-ethyl-6-methylphenyl, 4-(1-oxoethyl)-2-ethyl-6-methylphenyl, 4-dimethylcarbamoyl-2-ethyl-6-methyl-phenyl, 4-methylcarbamoyl-2-ethyl-6-methyl-phenyl, 4-carbamoyl-2-ethyl-6-methyl-phenyl, 4-trifluoromethoxy-2-ethyl-6-methyl-phenyl, 4-(1H-imidazo-1-yl)-2-ethyl-6-methyl-phenyl, 4-fluoro-2,6-dimethylphenyl, 4-chloro-2,6-dimethylphenyl, 4-cyano-2,6-dimethylphenyl, 4-trifluoromethyl-2,6-dimethylphenyl, 4-(1-oxoethyl)-2,6-dimethylphenyl, 4-trifluoromethoxy-2,6-dimethylphenyl, 4-(1H-imidazo-1-yl)-2,6-dimethylphenyl, pyridine-3-yl, 2-methyl-pyridine-3-yl, 2-methyl-4-trifluoromethyl-pyridine-3-yl, 2,4-dimethyl-pyridine-3-yl, 4-chloro-2-methyl-6-methylthio-phenyl, 4-fluoro-2-methyl-6- methylthio-phenyl, 2-methyl-6-methylthio-phenyl, 4-fluoro-2-(2-propyl)-6-methylphenyl, 4-cyano-2-methyl-6-methylthio-phenyl, 4-trifluoromethyl-2-methyl-6-methylthio-phenyl, 2-isopropyl-6-methylphenyl, 4-fluoro-2-(2-propyl)-6-methylphenyl, 2-ethyl-4-methyl-pyridine-3-yl, 4-trichloromethyl-2-ethyl-6-methylphenyl, 4-nitro-2-ethyl-6-methylphenyl, 4-methyloxycarbonyl-2-ethyl-6-methylphenyl, 4-methylsulfonyl-2-ethyl-6-methylphenyl, 4-trifluoromethylsulfonyl-2-ethyl-6-methylphenyl, 4-aminosulfonyl-2-ethyl-6-methylphenyl, 4-methylaminosulfonyl-2-ethyl-6-methylphenyl, 4-dimethylaminosulfonyl-2-ethyl-6-methylphenyl, 4-methylaminocarbonyl-2-ethyl-6-methylphenyl, 4-dimethylaminocarbonyl-2-ethyl-6-methylphenyl, 4-aminocarbonyl-2-ethyl-6-methylphenyl, 2-ethyl-6-methyl-4-(2-oxazolyl)phenyl, 2-ethyl-6-methyl-4-(2-imidazolyl)phenyl, 4-trifluoromethylcarbonyl-2-ethyl-6-methylphenyl, 4-trichloromethyl-2,6-dimethylphenyl, 4-nitro-2,6-dimethylphenyl, 4-methyloxycarbonyl-2,6-dimethylphenyl, 4-methylsulfonyl-2,6-dimethylphenyl, 4-trifluoromethylsulfonyl-2,6-dimethylphenyl, 4-aminosulfonyl-2,6-dimethylphenyl, 4-methylaminosulfonyl-2,6-dimethylphenyl, 4-dimethylaminosulfonyl-2,6-dimethylphenyl, 4-methylaminocarbonyl-2,6-dimethylphenyl, 4-dimethylaminocarbonyl-2,6-dimethylphenyl, 4-aminocarbonyl-2,6-dimethylphenyl, 2,6-dimethyl-4-(2-oxazolyl)phenyl, 2,6-dimethyl-4-(2-imidazolyl)phenyl and 4-trifluoromethylcarbonyl-2,6-dimethylphenyl; and G is a radical selected from the group consisting of 3,4,5,6-tetrahydro-pyridin-2-ylamino, 4-methylpyridin-2-ylamino, 5-methylpyridin-2-ylamino, 4-methoxypyridin-2-ylamino, and 4-fluoropyridin-2-ylamino.

56. The compound according to claim 35,
wherein
A is isothiazolyl and the compound is represented by one of formulas (LXXXIV) to (LXXXV)

(LXXXIV)

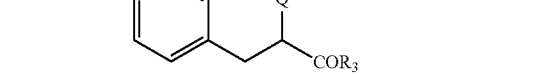

(LXXXV)

wherein
the isothiazolyl and the phenyl ring atoms in formulas (LXXXIV) to (LXXXV) are each and independently substituted with 0, 1 or 2 $R_5$,
wherein
$R_5$ is hydrogen, fluoro, chloro, cyano, methylamino, dimethylamino, methylaminocarbonyl, acetylamino, phenyl, benzyl, methyl, ethyl, tert-butyl, hydroxy, methoxy, or trifluoromethyl.

57. The compound according to claim 56, having one of formulas (LXXXVI) to (LXXXVII)

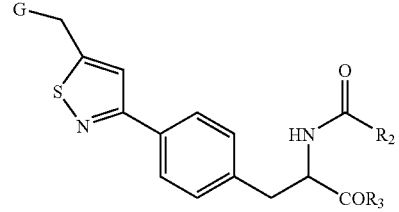

(LXXXVI)

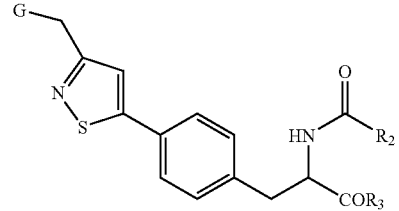

(LXXXVII)

wherein
$R_2$ is a radical selected from the group consisting of phenyl, 2,4,6-trimethylphenyl, 2,6-dimethylphenyl, 4-cyanophenyl, 2,4,6-tribromophenyl, 2-bromo-6-methylphenyl, 4-benzyloxyphenyl, 2-methylphenyl, 2-ethyl-6-methylphenyl, 2-methyl-6-trifluoromethylphenyl, 4-fluoro-2-ethyl-6-methylphenyl, 4-chloro-2-ethyl-6-methylphenyl, 4-cyano-2-ethyl-6-methylphenyl, 4-trifluoromethyl-2-ethyl-6-methylphenyl, 4-(1-oxoethyl)-2-ethyl-6-methylphenyl, 4-dimethylcarbamoyl-2-ethyl-6-methyl-phenyl, 4-methylcarbamoyl-2-ethyl-6-methyl-phenyl, 4-carbamoyl-2-ethyl-6-methyl-phenyl, 4-trifluoromethoxy-2-ethyl-6-methyl-phenyl, 4-(1H-imidazo-1-yl)-2-ethyl-6-methyl-phenyl, 4-fluoro-2,6-dimethylphenyl, 4-chloro-2,6-dimethylphenyl, 4-cyano-2,6-dimethylphenyl, 4-trifluoromethyl-2,6-dimethylphenyl, 4-(1-oxoethyl)-2,6-dimethylphenyl, 4-trifluoromethoxy-2,6-dimethylphenyl, 4-(1H-imidazo-1-yl)-2,6-dimethylphenyl, pyridine-3-yl, 2-methyl-pyridine-3-yl, 2-methyl-4-trifluoromethyl-pyridine-3-yl, 2,4-dimethyl-pyridine-3-yl, 4-chloro-2-methyl-6-methylthio-phenyl, 4-fluoro-2-methyl-6-methylthio-phenyl, 2-methyl-6-methylthio-phenyl, 4-fluoro-2-(2-propyl)-6-methylphenyl, 4-cyano-2-methyl-6-methylthio-phenyl, 4-trifluoromethyl-2-methyl-6-methylthio-phenyl, 2-isopropyl-6-methylphenyl, 4-fluoro-2-(2-propyl)-6-methylphenyl, 2-ethyl-4-methyl-pyridine-3-yl, 4-trichloromethyl-2-ethyl-6-methylphenyl, 4-nitro-2-ethyl-6-methylphenyl, 4-methyloxycarbonyl-2-ethyl-6-methylphenyl, 4-methylsulfonyl-2-ethyl-6-methylphenyl, 4-trifluoromethylsulfonyl-2-ethyl-6-methylphenyl, 4-aminosulfonyl-2-ethyl-6-methylphenyl, 4-methylaminosulfonyl-2-ethyl-6-methylphenyl, 4-dimethylaminosulfonyl-2-ethyl-6-methylphenyl, 4-methylaminocarbonyl-2-ethyl-6-methylphenyl, 4-dimethylaminocarbonyl-2-ethyl-6-methylphenyl, 4-aminocarbonyl-2-ethyl-6-methylphenyl, 2-ethyl-6-methyl-4-(2-oxazolyl)phenyl, 2-ethyl-6-methyl-4-(2-imidazolyl)phenyl, 4-trifluoromethylcarbonyl-2-ethyl-6-methylphenyl, 4-trichloromethyl-2,6-dimethylphenyl, 4-nitro-2,6-dimethylphenyl, 4-methyloxycarbonyl-2,6-dimethylphenyl, 4-methylsulfonyl-2,6-dimethylphenyl, 4-trifluoromethylsulfonyl-2,6-dimethylphenyl, 4-aminosulfonyl-2,6-dimethylphenyl, 4-methylaminosulfonyl-2,6-dimethylphenyl, 4-dimethylaminosulfonyl-2,6-dimethylphenyl, 4-methylaminocarbonyl-2,6-dimethylphenyl, 4-dimethylaminocarbonyl-2,6-dimethylphenyl, 4-aminocarbonyl-2,6-dimethylphenyl, 2,6-dimethyl-4-(2-oxazolyl)phenyl, 2,6-dimethyl-4-(2-imidazolyl)phenyl and 4-trifluoromethylcarbonyl-2,6-dimethylphenyl; and G is a radical selected from the group consisting of 3,4,5,6-tetrahydro-pyridin-2-ylamino, 4-methylpyridin-2-ylamino, 5-methylpyridin-2-ylamino, 4-methoxypyridin-2-ylamino, and 4-fluoropyridin-2-ylamino.

58. The compound according to claim 35, wherein

A is trialzolyl and the compound is represented by one of formulas (LXXVII) to (XC)

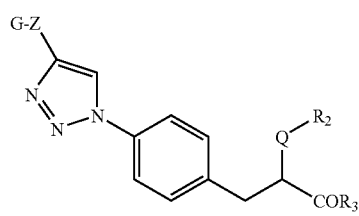
(LXXXVIII)

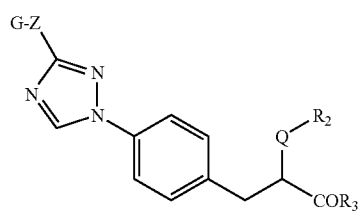
(LXXXIX)

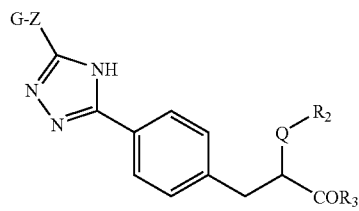
(XC)

wherein the triazolyl and the phenyl ring atoms in formulas (LXXXVIII) to (XC) are each and independently substituted with 0, 1 or 2 $R_5$, wherein $R_5$ is hydrogen, fluoro, chloro, cyano, methylamino, dimethylamino, methylaminocarbonyl, acetylamino, phenyl, benzyl, methyl, ethyl, tert-butyl, hydroxy, methoxy, or trifluoromethyl.

59. The compound according to claim 58, having one of formulas (XCI) to (XCIII)

(XCI)

(XCII)

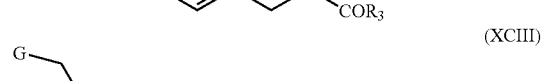
(XCIII)

wherein $R_2$ is a radical selected from the group consisting of phenyl, 2,4,6-trimethylphenyl, 2,6-dimethylphenyl, 4-cyanophenyl, 2,4,6-tribromophenyl, 2-bromo-6-methylphenyl, 4-benzyloxyphenyl, 2-methylphenyl, 2-ethyl-6-methylphenyl, 2-methyl-6-trifluoromethylphenyl, 4-fluoro-2-ethyl-6-methylphenyl, 4-chloro-2-ethyl-6-methylphenyl, 4-cyano-2-ethyl-6-methylphenyl, 4-trifluoromethyl-2-ethyl-6-methylphenyl, 4-(1-oxoethyl)-2-ethyl-6-methylphenyl, 4-dimethylcarbamoyl-2-ethyl-6-methyl-phenyl, 4-methylcarbamoyl-2-ethyl-6-methyl-phenyl, 4-carbamoyl-2-ethyl-6-methyl-phenyl, 4-trifluoromethoxy-2-ethyl-6-methyl-phenyl, 4-(1H-imidazo-1-yl)-2-ethyl-6-methyl-phenyl, 4-fluoro-2,6-dimethylphenyl, 4-chloro-2,6-dimethylphenyl, 4-cyano-2,6-dimethylphenyl, 4-trifluoromethyl-2,6-dimethylphenyl, 4-(1-oxoethyl)-2,6-dimethylphenyl, 4-trifluoromethoxy-2,6-dimethylphenyl, 4-(1H-imidazo-1-yl)-2,6-dimethylphenyl, pyridine-3-yl, 2-methyl-pyridine-3-yl, 2-methyl-4-trifluoromethyl-pyridine-3-yl, 2,4-dimethyl-pyridine-3-yl, 4-chloro-2-methyl-6-methylthio-phenyl, 4-fluoro-2-methyl-6-methylthio-phenyl, 2-methyl-6-methylthio-phenyl, 4-fluoro-2-(2-propyl)-6-methylphenyl, 4-cyano-2-methyl-6-methylthio-phenyl, 4-trifluoromethyl-2-methyl-6-methylthio-phenyl, 2-isopropyl-6-methylphenyl, 4-fluoro-2-(2-propyl)-6-methylphenyl, 2-ethyl-4-methyl-pyridine-3-yl, 4-trichloromethyl-2-ethyl-6-methylphenyl, 4-nitro-2-ethyl-6-methylphenyl, 4-methyloxycarbonyl-2-ethyl-6-methylphenyl, 4-methylsulfonyl-2-ethyl-6-methylphenyl, 4-trifluoromethylsulfonyl-2-ethyl-6-methylphenyl, 4-aminosulfonyl-2-ethyl-6-methylphenyl, 4-methylaminosulfonyl-2-ethyl-6-methylphenyl, 4-dimethylaminosulfonyl-2-ethyl-6-methylphenyl, 4-methylaminocarbonyl-2- ethyl-6-methylphenyl, 4-dimethylaminocarbonyl-2-ethyl-6-methylphenyl, 4-aminocarbonyl-2-ethyl-6-methylphenyl, 2-ethyl-6-methyl-4-(2-oxazolyl)phenyl, 2-ethyl-6-methyl-4-(2-imidazolyl)phenyl, 4-trifluoromethylcarbonyl-2-ethyl-6-methylphenyl, 4-trichloromethyl-2,6-dimethylphenyl, 4-nitro-2,6-dimethylphenyl, 4-methyloxycarbonyl-2,6-dimethylphenyl, 4-methylsulfonyl-2,6-dimethylphenyl, 4-trifluoromethylsulfonyl-2,6-dimethylphenyl, 4-aminosulfonyl-2,6-dimethylphenyl, 4-methylaminosulfonyl-2,6-dimethylphenyl, 4-dimethylaminosulfonyl-2,6-dimethylphenyl, 4-methylaminocarbonyl-2,6-dimethylphonyl, 4-dimethylaminocarbonyl-2,6-dimethylphenyl, 4-aminocarbonyl-2,6-dimethylphenyl, 2,6-dimethyl-4-(2-oxazolyl)phenyl, 2,6-dimethyl-4-(2-imidazolyl)phenyl and 4-trifluoromethylcarbonyl-2,6-dimethylphenyl; and G is a radical selected from the group consisting of 3,4,5,6-tetrahydro-pyridin-2-ylamino, 4-methylpyridin-2-ylamino, 5-methylpyridin-2-ylamino, 4-methoxypyridin-2-ylamino, and 4-fluoropyridin-2-ylamino.

60. The compound according to claim 35, wherein $R_2$ is a radical selected from the group consisting of formulas (VI) to (XI)

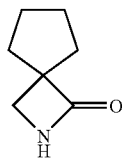

(VI)

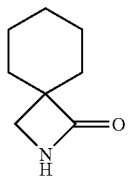

(VII)

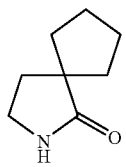

(VIII)

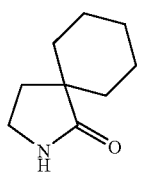

(IX)

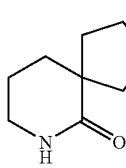

(X)

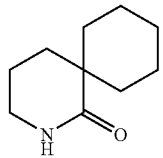

(XI)

wherein any of the formulas (VI) to (XI) is directly bound to C-atom number 2 in formula (II) at the ring N-atoms of the respective formulas (VI) to (XI);

the cycloalkyl rings spiro-fused to the heterocycles in any of the formulas (VI) to (XI) are optionally ortho-fused with an aromatic 5- or 6-membered ring; and any of the formulas (VI) to (XI) is individually and independently substituted with 0, 1 or 2 $R^a$, wherein $R^a$ is each individually and independently selected from the group consisting of hydrogen, fluoro, chloro, bromo, methyl, ethyl, propyl, tert-butyl, phenyl, benzyl, hydroxyl, methoxy, oxo, amino, methylamino, acetylamino and cyano;

Q is a direct bond;

G is a radical selected from the group consisting of 3,4,5,6-tetrahydro-pyridin-2-ylamino, 4-methylpyridin-2-ylamino, 5-methylpyridin-2-ylamino, 4-methoxypyridin-2-ylamino, and 4-fluoropyridin-2-ylamino;

$R_5$ is H; and

Z is a radical selected from the group consisting of $CH_2$ and CO.

61. The compound according to claim 1, wherein the compound is selected from the group consisting of:

compound (6) 3-(4-{3-[(4-Methyl-pyridin-2-ylamino)-methyl]-isoxazol-5-yl}-phenyl)-2-(2,4,6-trimethyl-benzoylamino)-propionic acid, compound (9) 3-(4-{5-[(4-Methyl-pyridin-2-ylamino)-methyl]-thiazol-2-yl}-phenyl)-2-(2,4,6-trimethyl-benzoylamino)-propionic acid, compound (12) 3-(4-{4-[(4-Methyl-pyridin-2-ylamino)-methyl]-furan-2-yl}-phenyl)-2-(2,4,6-trimethyl-benzoylamino)-propionic acid, compound (15) 3-(4-{4-[(4-Methyl-pyridin-2-ylamino)-methyl]-[1,2,3]triazol-1-yl}-phenyl)-2-(2,4,6-trimethyl-benzoylamino)-propionic acid, compound (19) 3-(4-{4-[(4-Methyl-pyridin-2-ylamino)-methyl]-thiophen-2-yl}-phenyl)-2-(2,4,6-trimethyl-benzoylamino)-propionic acid, compound (22) 2-[(1-Methyl-cyclohexanecarbonyl)-amino]-3-(4-{3-[(4-methyl-pyridin-2-ylamino)-methyl]-pyrrol-1-yl}-phenyl)-propionic acid, compound (23) 2-[(1-Methyl-cyclohexanecarbonyl)-amino]-3-(4-{5-[(4-methyl-pyridin-2-ylamino)-methyl]-thiazol-2-yl}-phenyl)-propionic acid, compound (24) 3-(4-{4-[(4-Methoxy-pyridin-2-ylamino)-methyl]-[1,2,3]triazol-1-yl}-phenyl)-2-(2,4,6-trimethyl-benzoylamino)-propionic acid, compound (30) 2-(2,6-Dimethyl-benzoylamino)-3-(4-{4-[(4-methyl-pyridin-2-ylamino)-methyl]-[1,2,3]triazol-1-yl}-phenyl)-propionic acid, compound (31) 2-(2-Ethyl-6-methyl-benzoylamino)-3-(4-{4-[(4-methyl-pyridin-2-ylamino)-methyl]-[1,2,3]triazol-1-yl}-phenyl)-propionic acid, compound (32) 2-(4-Fluoro-2,6-dimethyl-benzoylamino)-3-(4-{4-[(4-methyl-pyridin-2-ylamino)-methyl]-[1,2,3]triazol-1-yl}-phenyl)-propionic acid, compound (33) 3-(4-{4-[(4-Methyl-pyridin-2-ylamino)-methyl]-thiophen-2-yl}-phenyl)-2-(2,4,6-trimethyl-benzoylamino)-propionic acid, compound (34) 3-(4-{4-[(4-Fluoro-pyridin-2-ylamino)-methyl]-furan-2-yl}-phenyl)-2-(2,4,6-trimethyl-benzoylamino)-propionic acid, compound (35) 2-(2,6-Dimethyl-benzoylamino)-3-(4-{4-[(4-methyl-pyridin-2-ylamino)-methyl]-furan-2-yl}-phenyl)-propionic acid, compound (36) 2-(2-Ethyl-6-methyl-benzoylamino)-3-(4-{4-[(4-methyl-pyridin-2-ylamino)-methyl]-furan-2-yl}-phenyl)-propionic acid, compound (37) 2-(4-Fluoro-2,6-dimethyl-benzoylamino)-3-(4-{4-[(4-methyl-pyridin-2-ylamino)-methyl]-furan-2-yl}-phenyl)-propionic acid, compound (38) 2-(2-Ethyl-4-fluoro-6-methyl-benzoylamino)-3-(4-{4-[(4-methyl-pyridin-2-ylamino)-methyl]-furan-2-yl}-phenyl)-propionic acid, compound (39) 3-(4-{4-[(5-Methyl-pyridin-2-ylamino)-methyl]-furan-2-yl}-phenyl)-2-(2,4,6-trimethyl-benzoylamino)-propionic acid, compound (40) 3-(4-{4-[(5-Trifluoromethyl-pyridin-2-ylamino)-methyl]-furan-2-yl}-phenyl)-2-(2,4,6-trimethyl-benzoylamino)-propionic acid, compound (41) 3-(4-{4-[(5-Chloro-pyridin-2-ylamino)-methyl]-furan-2-yl}-phenyl)-2-(2,4,6-trimethyl-benzoylamino)-propionic acid, compound (42) 3-(4-{4-[(3-Methyl-pyridin-2-ylamino)-methyl]-furan-2-yl}-phenyl)-2-(2,4,6-trimethyl-benzoylamino)-propionic acid, compound (43) 2-(2-Ethyl-4-fluoro-6-methyl-benzoylamino)-3-(4-{5-[(4-methyl-pyridin-2-ylamino)-methyl]-furan-2-yl}-phenyl)-propionic acid, compound (46) [2-(4-{4-[(4-Methyl-pyridin-2-ylamino)-methyl]-furan-2-yl}-benzyl)-4-(2,4,6-trimethyl-phenyl)-butyric acid, compound (49) 3-(4-(5-((4-methylpyridin-2-ylamino)methyl)furan-2-yl)phenyl)-2-(2,4,6-trimethylbenzamido)propanoic acid, compound (50) 3-(4-(5-((4-methoxypyridin-2-ylamino)methyl)furan-2-yl)phenyl)-2-(2,4,6-trimethylbenzamido)propanoic acid, compound (53) 2-(2-ethyl-4-fluoro-6-methylbenzamido)-3-(4-(5-((4-methoxypyridin-2-ylamino)methyl)furan-2-yl)phenyl)propanoic acid, compound (56) 3-(4-(5-((4-methylpyridin-2-ylamino)methyl)furan-3-yl)phenyl)-2-(2,4,6-trimethylbenzamido)propanoic acid, compound (57) 3-(4-(5-((4-methoxypyridin-2-ylamino)methyl)furan-3-yl)phenyl)-2-(2,4,6-trimethylbenzamido)propanoic acid, compound (60) 2-(2-ethyl-4-fluoro-6-methylbenzamido)-3-(4-(5-((4-methylpyridin-2-ylamino)methyl)furan-3-yl)phenyl)propanoic acid, compound (61) 2-(2-ethyl-4-fluoro-6-methylbenzamido)-3-(4-(5-((4-methoxypyridin-2-ylamino)methyl)furan-3-yl)phenyl)propanoic acid, compound (64) 3-(4-(4-((4-methoxypyridin-2-ylamino)methyl)furan-2-yl)phenyl)-2-(2,4,6-trimethylbenzamido)propanoic acid, compound (66) 2-(2-ethyl-4-fluoro-6-methylbenzamido)-3-(4-(4-((4-methoxypyridin-2-ylamino)methyl)furan-2-yl)phenyl)propanoic acid, compound (69) 3-(4-(5-((4-methylpyridin-2-ylamino)methyl)-1H-pyrrol-2-yl)phenyl)-2-(2,4,6-trimethylbenzamido)propanoic acid, compound (70) 3-(4-(5-((4-methoxypyridin-2-ylamino)methyl)-1H-pyrrol-2-yl)phenyl)-2-(2,4,6-trimethylbenzamido)propanoic acid, compound (73) 2-(2-ethyl-4-fluoro-6-methylbenzamido)-3-(4-(5-((4-methylpyridin-2-ylamino)methyl)-1H-pyrrol-2-yl)phenyl)propanoic acid, compound (74) 2-(2-ethyl-4-fluoro-6-methylbenzamido)-3-(4-(5-((4-methoxypyridin-2-ylamino)methyl)-1H-pyrrol-2-yl)phenyl)propanoic acid, compound (77) 3-(4-(5-((4-methylpyridin-2-ylamino)methyl)-1H-pyrrol-3-yl)phenyl)-2-(2,4,6-trimethylbenzamido)propanoic acid, compound (78) 3-(4-(5-((4-methoxypyridin-2-ylamino)methyl)-1H-pyrrol-3-yl)phenyl)-2-(2,4,6-trimethylbenzamido)propanoic acid, compound (81) 2-(2-ethyl-4-fluoro-6-methylbenzamido)-3-(4-(5-((4-methylpyridin-2-ylamino)methyl)-1H-pyrrol-3-yl)phenyl)propanoic acid, compound (82) 2-(2-ethyl-4-fluoro-6-methylbenzamido)-3-(4-(5-((4-methoxypyridin-2-ylamino)methyl)-1H-pyrrol-3-yl)phenyl)propanoic acid, compound (85) 3-(4-(4-((4-methylpyridin-2-ylamino)methyl)-1H-pyrrol-2-yl)phenyl)-2-(2,4,6-trimethylbenzamido)propanoic acid, compound (86) 3-(4-(4-((4-methoxypyridin-2-ylamino)methyl)-1H-pyrrol-2-yl)phenyl)-2-(2,4,6-trimethylbenzamido)propanoic acid, compound (89) 2-(2-ethyl-4-fluoro-6-methylbenzamido)-3-(4-(4-((4-methylpyridin-2-ylamino)methyl)-1H-pyrrol-2-yl)phenyl)propanoic acid, compound (90) 2-(2-ethyl-4-fluoro-6-methylbenzamido)-3-(4-(4-((4-methoxypyridin-2-ylamino)methyl)-1H-pyrrol-2-yl)phenyl)propanoic acid, compound (93) 3-(4-(3-((4-methylpyridin-2-ylamino)methyl)-1H-pyrrol-1-yl)phenyl)-2-(2,4,6-trimethylbenzamido)propanoic acid, compound (94) 3-(4-(3-((4-methoxypyridin-2-ylamino)methyl)-1H-pyrrol-1-yl)phenyl)-2-(2,4,6-trimethylbenzamido)propanoic acid, compound (97) 2-(2-ethyl-4-fluoro-6-methylbenzamido)-3-(4-(3-((4-methylpyridin-2-ylamino)methyl)-1H-pyrrol-1-yl)phenyl)propanoic acid, compound (98) 2-(2-ethyl-4-fluoro-6-methylbenzamido)-3-(4-(3-((4-methoxypyridin-2-ylamino)methyl)-1H-pyrrol-1-yl)phenyl)propanoic acid, compound (101) 3-(4-(4-((4-methylpyridin-2-ylamino)methyl)-1H-pyrazol-1-yl)phenyl)-2-(2,4,6-trimethylbenzamido)propanoic acid, compound (102) 3-(4-(4-((4-methoxypyridin-2-ylamino)methyl)-1H-pyrazol-1-yl)phenyl)-2-(2,4,6-trimethylbenzamido)propanoic acid, compound (105) 2-(2-ethyl-4-fluoro-6-methylbenzamido)-3-(4-(4-((4-methylpyridin-2-ylamino)methyl)-1H-pyrazol-1-yl)phenyl)propanoic acid, compound (106) 2-(2-ethyl-4-fluoro-6-methylbenzamido)-3-(4-(4-((4-methoxypyridin-2-ylamino)methyl)-1H-pyrazol-1-yl)phenyl)propanoic acid, compound (109) 3-(4-(3-((4-methylpyridin-2-ylamino)methyl)-1H-pyrazol-1-yl)phenyl)-2-(2,4,6-trimethylbenzamido)propanoic acid, compound (110) 3-(4-(3-((4-methoxypyridin-2-ylamino)methyl)-1H-pyrazol-1-yl)phenyl)-2-(2,4,6-trimethylbenzamido)propanoic acid, compound (113) 2-(2-ethyl-4-fluoro-6-methylbenzamido)-3-(4-(3-((4-methylpyridin-2-ylamino)methyl)-1H-pyrazol-1-yl)phenyl)propanoic acid, compound (114) 2-(2-ethyl-4-fluoro-6-methylbenzamido)-3-(4-(3-((4-methoxypyridin-2-ylamino)methyl)-1H-pyrazol-1-yl)phenyl)propanoic acid, compound (117) 3-(4-(5-((4-methylpyridin-2-ylamino)methyl)-1H-imidazol-2-yl)phenyl)-2-(2,4,6-trimethylbenzamido)propanoic acid, compound (118) 3-(4-(5-((4-methoxypyridin-2-ylamino)methyl)-1H-imidazol-2-yl)phenyl)-2-(2,4,6-trimethylbenzamido)propanoic acid, compound (121) 2-(2-ethyl-4-fluoro-6-methylbenzamido)-3-(4-(5-((4-methylpyridin-2-ylamino)methyl)-1H-imidazol-2-yl)phenyl)propanoic acid, compound (122) 2-(2-ethyl-4-fluoro-6-methylbenzamido)-3-(4-(5-((4-methoxypyridin-2-ylamino)methyl)-1H-imidazol-2-yl)phenyl)propanoic acid, compound (125) 3-(4-(2-((4-methylpyridin-2-ylamino)methyl)-1H-imidazol-4-yl)phenyl)-2-(2,4,6-trimethylbenzamido)propanoic acid, compound (126) 3-(4-(2-((4-methoxypyridin-2-ylamino)methyl)-1H-imidazol-4-yl)phenyl)-2-(2,4,6-trimethylbenzamido)propanoic acid, compound (129) 2-(2-ethyl-4-fluoro-6-methylbenzamido)-3-(4-(2-((4-methylpyridin-2-ylamino)methyl)-1H-imidazol-4-yl)phenyl)propanoic acid, compound (130) 2-(2-ethyl-4-fluoro-6-methylbenzamido)-3-(4-(2-((4-methoxypyridin-2-ylamino)methyl)-1H-imidazol-4-yl)phenyl)propanoic acid, compound (133) 3-(4-(4-((4-methylpyridin-2-ylamino)methyl)-1H-imidazol-1-yl)phenyl)-2-(2,4,6-trimethylbenzamido)propanoic acid, compound (134) 3-(4-(4-((4-methoxypyridin-2-ylamino)methyl)-1H-imidazol-1-yl)phenyl)-2-(2,4,6-trimethylbenzamido)propanoic acid, compound (137) 2-(2-ethyl-4-fluoro-6-methylbenzamido)-3-(4-(4-((4-methylpyridin-2-ylamino)methyl)-1H-imidazol-1-yl)phenyl)propanoic acid, compound (138) 2-(2-ethyl-4-fluoro-6-methylbenzamido)-3-(4-(4-((4-methoxypyridin-2-ylamino)methyl)-1H-imidazol-1-yl)phenyl)propanoic acid, compound (141) 3-(4-(5-((4-methylpyridin-2-ylamino)methyl)thiophen-2-yl)phenyl)-2-(2,4,6-trimethylbenzamido)propanoic acid, compound (142) 3-(4-(5-((4-methoxypyridin-2-ylamino)methyl)thiophen-2-yl)phenyl)-2-(2,4,6-trimethylbenzamido)propanoic acid, compound (145) 2-(2-ethyl-4-fluoro-6-methylbenzamido)-3-(4-(5-((4-methylpyridin-2-ylamino)methyl)thiophen-2-yl)phenyl)propanoic acid, compound (146) 2-(2-ethyl-4-fluoro-6-methylbenzamido)-3-(4-(5-((4-methoxypyridin-2-ylamino)methyl)thiophen-2-yl)phenyl)propanoic acid, compound (149) 3-(4-(5-((4-methylpyridin-2-ylamino)methyl)thiophen-3-yl)phenyl)-2-(2,4,6-trimethylbenzamido)propanoic acid, compound (150) 3-(4-(5-((4-methoxypyridin-2-ylamino)methyl)thiophen-3-yl)phenyl)-2-(2,4,6-trimethylbenzamido)propanoic acid, compound (153) 2-(2-ethyl-4-fluoro-6-methylbenzamido)-3-(4-(5-((4-methylpyridin-2-ylamino)methyl)thiophen-3-yl)phenyl)propanoic acid, compound (154) 2-(2-ethyl-4-fluoro-6-methylbenzamido)-3-(4-(5-((4-methoxypyridin-2-ylamino)methyl)thiophen-3-yl)phenyl)propanoic acid, compound (157) 3-(4-(4-((4-methoxypyridin-2-ylamino)methyl)thiophen-2-yl)phenyl)-2-(2,4,6-trimethylbenzamido)propanoic acid, compound (160) 2-(2-ethyl-4-fluoro-6-methylbenzamido)-3-(4-(4-((4-methylpyridin-2-ylamino)methyl)thiophen-2-yl)phenyl)propanoic acid, compound (161) 2-(2-ethyl-4-fluoro-6-methylbenzamido)-3-(4-(4-((4-methoxypyridin-2-ylamino)methyl)thiophen-2-yl)phenyl)propanoic acid, compound (164) 3-(4-(5-((4-methylpyridin-2-ylamino)methyl)isoxazol-3-yl)phenyl)-2-(2,4,6-trimethylbenzamido)propanoic acid, compound (165) 3-(4-(5-((4-methoxypyridin-2-ylamino)methyl)isoxazol-3-yl)phenyl)-2-(2,4,6-trimethylbenzamido)propanoic acid, compound (168) 2-(2-ethyl-4-fluoro-6-methylbenzamido)-3-(4-(5-((4-methylpyridin-2-ylamino)methyl)isoxazol-3-yl)phenyl)propanoic acid, compound (169) 2-(2-ethyl-4-fluoro-6-methylbenzamido)-3-(4-(5-((4-methoxypyridin-2-ylamino)methyl)isoxazol-3-yl)phenyl)propanoic acid, compound (172) 3-(4-(3-((4-methoxypyridin-2-ylamino)methyl)isoxazol-5-yl)phenyl)-2-(2,4,6-trimethylbenzamido)propanoic acid, compound (175) 2-(2-ethyl-4-fluoro-6-methylbenzamido)-3-(4-(3-((4-methylpyridin-2-ylamino)methyl)isoxazol-5-yl)phenyl)propanoic acid, compound (176) 2-(2-ethyl-4-fluoro-6-methylbenzamido)-3-(4-(3-((4-methoxypyridin-2-ylamino)methyl)isoxazol-5-yl)phenyl)propanoic acid, compound (179) 3-(4-(2-((4-methylpyridin-2-ylamino)methyl)oxazol-5-yl)phenyl)-2-(2,4,6-trimethylbenzamido)propanoic acid, compound (180) 3-(4-(2-((4-methoxypyridin-2-ylamino)methyl)oxazol-5-yl)phenyl)-2-(2,4,6-trimethylbenzamido)propanoic acid, compound (183) 2-(2-ethyl-4-fluoro-6-methylbenzamido)-3-(4-(2-((4-methylpyridin-2-ylamino)methyl)oxazol-5-yl)phenyl)propanoic acid, compound (184) 2-(2-ethyl-4-fluoro-6-methylbenzamido)-3-(4-(2-((4-methoxypyridin-2-ylamino)methyl)oxazol-5-yl)phenyl)propanoic acid, compound (187) 3-(4-(2-((4-methylpyridin-2-ylamino)methyl)oxazol-4-yl)phenyl)-2-(2,4,6-trimethylbenzamido)propanoic acid, compound (188) 3-(4-(2-((4-methoxypyridin-2-ylamino)methyl)oxazol-4-yl)phenyl)-2-(2,4,6-trimethylbenzamido)propanoic acid, compound (191) 2-(2-ethyl-4-fluoro-6-methylbenzamido)-3-(4-(2-((4-methylpyridin-2-ylamino)methyl)oxazol-4-yl)phenyl)propanoic acid, compound (192) 2-(2-ethyl-4-fluoro-6-methylbenzamido)-3-(4-(2-((4-methoxypyridin-2-ylamino)methyl)oxazol-4-yl)phenyl)propanoic acid, compound (195) 3-(4-(4-((4-methylpyridin-2-ylamino)methyl)oxazol-2-yl)phenyl)-2-(2,4,6-trimethylbenzamido)propanoic acid, compound (196) 3-(4-(4-((4-methoxypyridin-2-ylamino)methyl)oxazol-2-yl)phenyl)-2-(2,4,6-trimethylbenzamido)propanoic acid, compound (199) 2-(2-ethyl-4-fluoro-6-methylbenzamido)-3-(4-(4-((4-methylpyridin-2-ylamino)methyl)oxazol-2-yl)phenyl)propanoic acid, compound (200) 2-(2-ethyl-4-fluoro-6-methylbenzamido)-3-(4-(4-((4-methoxypyridin-2-ylamino)methyl)oxazol-2-yl)phenyl)propanoic acid, compound (203) 3-(4-(5-((4-methylpyridin-2-ylamino)methyl)oxazol-2-yl)phenyl)-2-(2,4,6-trimethylbenzamido)propanoic acid, compound (204) 3-(4-(5-((4-methoxypyridin-2-ylamino)methyl)oxazol-2-yl)phenyl)-2-(2,4,6-trimethylbenzamido)propanoic acid,
compound (207) 2-(2-ethyl-4-fluoro-6-methylbenzamido)-3-(4-(5-((4-methylpyridin-2-ylamino)methyl)oxazol-2-yl)phenyl)propanoic acid,
compound (208) 2-(2-ethyl-4-fluoro-6-methylbenzamido)-3-(4-(5-((4-methoxypyridin-2-ylamino)methyl)oxazol-2-yl)phenyl)propanoic acid,
compound (211) 3-(4-(2-((4-methylpyridin-2-ylamino)methyl)thiazol-5-yl)phenyl)-2-(2,4,6-trimethylbenzamido)propanoic acid,
compound (212) 3-(4-(2-((4-methoxypyridin-2-ylamino)methyl)thiazol-5-yl)phenyl)-2-(2,4,6-trimethylbenzamido)propanoic acid,
compound (215) 2-(2-ethyl-4-fluoro-6-methylbenzamido)-3-(4-(2-((4-methylpyridin-2-ylamino)methyl)thiazol-5-yl)phenyl)propanoic acid,
compound (216) 2-(2-ethyl-4-fluoro-6-methylbenzamido)-3-(4-(2-((4-methoxypyridin-2-ylamino)methyl)thiazol-5-yl)phenyl)propanoic acid,
compound (218) 2-(4-chloro-2-ethyl-6-methylbenzamido)-3-(4-(5-((4-methylpyridin-2-ylamino)methyl)furan-2-yl)phenyl)propanoic acid,
compound (219) 2-(4-chloro-2-ethyl-6-methylbenzamido)-3-(4-(5-((4-methylpyridin-2-ylamino)methyl)furan-3-yl)phenyl)propanoic acid,
compound (221) 3-(4-(2-((4-methylpyridin-2-ylamino)methyl)thiazol-4-yl)phenyl)-2-(2,4,6-trimethylbenzamido)propanoic acid,
compound (222) 3-(4-(2-((4-methoxypyridin-2-ylamino)methyl)thiazol-4-yl)phenyl)-2-(2,4,6-trimethylbenzamido)propanoic acid,
compound (225) 2-(2-ethyl-4-fluoro-6-methylbenzamido)-3-(4-(2-((4-methylpyridin-2-ylamino)methyl)thiazol-4-yl)phenyl)propanoic acid,
compound (226) 2-(2-ethyl-4-fluoro-6-methylbenzamido)-3-(4-(2-((4-methoxypyridin-2-ylamino)methyl)thiazol-4-yl)phenyl)propanoic acid,
compound (229) 3-(4-(4-((4-methylpyridin-2-ylamino)methyl)thiazol-2-yl)phenyl)-2-(2,4,6-trimethylbenzamido)propanoic acid,
compound (230) 3-(4-(4-((4-methoxypyridin-2-ylamino)methyl)thiazol-2-yl)phenyl)-2-(2,4,6-trimethylbenzamido)propanoic acid,
compound (233) 2-(2-ethyl-4-fluoro-6-methylbenzamido)-3-(4-(4-((4-methylpyridin-2-ylamino)methyl)thiazol-2-yl)phenyl)propanoic acid,
compound (234) 2-(2-ethyl-4-fluoro-6-methylbenzamido)-3-(4-(4-((4-methoxypyridin-2-ylamino)methyl)thiazol-2-yl)phenyl)propanoic acid,
compound (237) 3-(4-(5-((4-methoxypyridin-2-ylamino)methyl)thiazol-2-yl)phenyl)-2-(2,4,6-trimethylbenzamido)propanoic acid,
compound (240) 2-(2-ethyl-4-fluoro-6-methylbenzamido)-3-(4-(5-((4-methylpyridin-2-ylamino)methyl)thiazol-2-yl)phenyl)propanoic acid,
compound (241) 2-(2-ethyl-4-fluoro-6-methylbenzamido)-3-(4-(5-((4-methoxypyridin-2-ylamino)methyl)thiazol-2-yl)phenyl)propanoic acid,
compound (244) 3-(4-(5-((4-methylpyridin-2-ylamino)methyl)-1,3,4-thiadiazol-2-yl)phenyl)-2-(2,4,6-trimethylbenzamido)propanoic acid,
compound (245) 3-(4-(5-((4-methoxypyridin-2-ylamino)methyl)-1,3,4-thiadiazol-2-yl)phenyl)-2-(2,4,6-trimethylbenzamido)propanoic acid,
compound (248) 2-(2-ethyl-4-fluoro-6-methylbenzamido)-3-(4-(5-((4-methylpyridin-2-ylamino)methyl)-1,3,4-thiadiazol-2-yl)phenyl)propanoic acid,
compound (249) 2-(2-ethyl-4-fluoro-6-methylbenzamido)-3-(4-(5-((4-methoxypyridin-2-ylamino)methyl)-1,3,4-thiadiazol-2-yl)phenyl)propanoic acid,
compound (252) 3-(4-(5-((4-methylpyridin-2-ylamino)methyl)-1,2,4-thiadiazol-3-yl)phenyl)-2-(2,4,6-trimethylbenzamido)propanoic acid,
compound (253) 3-(4-(5-((4-methoxypyridin-2-ylamino)methyl)-1,2,4-thiadiazol-3-yl)phenyl)-2-(2,4,6-trimethylbenzamido)propanoic acid,
compound (256) 2-(2-ethyl-4-fluoro-6-methylbenzamido)-3-(4-(5-((4-methylpyridin-2-ylamino)methyl)-1,2,4-thiadiazol-3-yl)phenyl)propanoic acid,
compound (257) 2-(2-ethyl-4-fluoro-6-methylbenzamido)-3-(4-(5-((4-methoxypyridin-2-ylamino)methyl)-1,2,4-thiadiazol-3-yl)phenyl)propanoic acid,
compound (260) 3-(4-(3-((4-methylpyridin-2-ylamino)methyl)-1,2,4-thiadiazol-5-yl)phenyl)-2-(2,4,6-trimethylbenzamido)propanoic acid,
compound (261) 3-(4-(3-((4-methoxypyridin-2-ylamino)methyl)-1,2,4-thiadiazol-5-yl)phenyl)-2-(2,4,6-trimethylbenzamido)propanoic acid,
compound (264) 2-(2-ethyl-4-fluoro-6-methylbenzamido)-3-(4-(3-((4-methylpyridin-2-ylamino)methyl)-1,2,4-thiadiazol-5-yl)phenyl)propanoic acid,
compound (265) 2-(2-ethyl-4-fluoro-6-methylbenzamido)-3-(4-(3-((4-methoxypyridin-2-ylamino)methyl)-1,2,4-thiadiazol-5-yl)phenyl)propanoic acid,
compound (268) 3-(4-(5-((4-methylpyridin-2-ylamino)methyl)-1,3,4-oxadiazol-2-yl)phenyl)-2-(2,4,6-trimethylbenzamido)propanoic acid,
compound (269) 3-(4-(5-((4-methoxypyridin-2-ylamino)methyl)-1,3,4-oxadiazol-2-yl)phenyl)-2-(2,4,6-trimethylbenzamido)propanoic acid,
compound (272) 2-(2-ethyl-4-fluoro-6-methylbenzamido)-3-(4-(5-((4-methylpyridin-2-ylamino)methyl)-1,3,4-thiadiazol-2-yl)phenyl)propanoic acid,
compound (273) 2-(2-ethyl-4-fluoro-6-methylbenzamido)-3-(4-(5-((4-methoxypyridin-2-ylamino)methyl)-1,3,4-thiadiazol-2-yl)phenyl)propanoic acid,
compound (276) 3-(4-(5-((4-methylpyridin-2-ylamino)methyl)-1,2,4-thiadiazol-3-yl)phenyl)-2-(2,4,6-trimethylbenzamido)propanoic acid,
compound (277) 3-(4-(5-((4-methoxypyridin-2-ylamino)methyl)-1,2,4-thiadiazol-3-yl)phenyl)-2-(2,4,6-trimethylbenzamido)propanoic acid,
compound (280) 2-(2-ethyl-4-fluoro-6-methylbenzamido)-3-(4-(5-((4-methylpyridin-2-ylamino)methyl)-1,2,4-thiadiazol-3-yl)phenyl)propanoic acid,
compound (281) 2-(2-ethyl-4-fluoro-6-methylbenzamido)-3-(4-(5-((4-methoxypyridin-2-ylamino)methyl)-1,2,4-thiadiazol-3-yl)phenyl)propanoic acid,
compound (284) 3-(4-(3-((4-methylpyridin-2-ylamino)methyl)-1,2,4-thiadiazol-5-yl)phenyl)-2-(2,4,6-trimethylbenzamido)propanoic acid,
compound (285) 3-(4-(3-((4-methoxypyridin-2-ylamino)methyl)-1,2,4-thiadiazol-5-yl)phenyl)-2-(2,4,6-trimethylbenzamido)propanoic acid,
compound (288) 2-(2-ethyl-4-fluoro-6-methylbenzamido)-3-(4-(3-((4-methylpyridin-2-ylamino)methyl)-1,2,4-thiadiazol-5-yl)phenyl)propanoic acid,
compound (289) 2-(2-ethyl-4-fluoro-6-methylbenzamido)-3-(4-(3-((4-methoxypyridin-2-ylamino)methyl)-1,2,4-thiadiazol-5-yl)phenyl)propanoic acid, compound (292) 3-(4-(5-((4-methylpyridin-2-ylamino)methyl)-1,3,4-oxadiazol-2-yl)phenyl)-2-(2,4,6-trimethylbenzamido)propanoic acid, compound (293) 3-(4-(5-((4-methoxypyridin-2-ylamino)methyl)-1,3,4-oxadiazol-2-yl)phenyl)-2-(2,4,6-trimethylbenzamido)propanoic acid, compound (296) 2-(2-ethyl-4-fluoro-6-methylbenzamido)-3-(4-(5-((4-methylpyridin-2-ylamino)methyl)-1,3,4-oxadiazol-2-yl)phenyl)propanoic acid, compound (297) 2-(2-ethyl-4-fluoro-6-methylbenzamido)-3-(4-(5-((4-methoxypyridin-2-ylamino)methyl)-1,3,4-oxadiazol-2-yl)phenyl)propanoic acid, compound (300) 3-(4-(5-((4-methylpyridin-2-ylamino)methyl)isothiazol-3-yl)phenyl)-2-(2,4,6-trimethylbenzamido)propanoic acid, compound (301) 3-(4-(5-((4-methoxypyridin-2-ylamino)methyl)isothiazol-3-yl)phenyl)-2-(2,4,6-trimethylbenzamido)propanoic acid, compound (304) 2-(2-ethyl-4-fluoro-6-methylbenzamido)-3-(4-(5-((4-methylpyridin-2-ylamino)methyl)isothiazol-3-yl)phenyl)propanoic acid, compound (305) 2-(2-ethyl-4-fluoro-6-methylbenzamido)-3-(4-(5-((4-methoxypyridin-2-ylamino)methyl)isothiazol-3-yl)phenyl)propanoic acid, compound (308) 3-(4-(3-((4-methylpyridin-2-ylamino)methyl)isothiazol-5-yl)phenyl)-2-(2,4,6-trimethylbenzamido)propanoic acid, compound (309) 3-(4-(3-((4-methoxypyridin-2-ylamino)methyl)isothiazol-5-yl)phenyl)-2-(2,4,6-triethylbenzamido)propanoic acid, compound (312) 2-(2-ethyl-4-fluoro-6-methylbenzamido)-3-(4-(3-((4-methylpyridin-2-ylamino)methyl)isothiazol-5-yl)phenyl)propanoic acid, compound (313) 2-(2-ethyl-4-fluoro-6-methylbenzamido)-3-(4-(3-((4-methoxypyridin-2-ylamino)methyl)isothiazol-5-yl)phenyl)propanoic acid, compound (317) 2-(2-ethyl-4-fluoro-6-methylbenzamido)-3-(4-(4-((4-methylpyridin-2-ylamino)methyl)-1H-1,2,3-triazol-1-yl)phenyl)propanoic acid, compound (318) 2-(2-ethyl-4-fluoro-6-methylbenzamido)-3-(4-(4-((4-methoxypyridin-2-ylamino)methyl)-1H-1,2,3-triazol-1-yl)phenyl)propanoic acid, compound (321) 3-(4-(3-((4-methylpyridin-2-ylamino)methyl)-1H-1,2,4-triazol-1-yl)phenyl)-2-(2,4,6-trimethylbenzamido)propanoic acid, compound (322) 3-(4-(3-((4-methoxypyridin-2-ylamino)methyl)-1H-1,2,4-triazol-1-yl)phenyl)-2-(2,4,6-trimethylbenzamido)propanoic acid, compound (325) 2-(2-ethyl-4-fluoro-6-methylbenzamido)-3-(4-(3-((4-methylpyridin-2-ylamino)methyl)-1H-1,2,4-triazol-1-yl)phenyl)propanoic acid, compound (326) 2-(2-ethyl-4-fluoro-6-methylbenzamido)-3-(4-(3-((4-methoxypyridin-2-ylamino)methyl)-1H-1,2,4-triazol-1-yl)phenyl)propanoic acid, compound (329) 3-(4-(5-((4-methylpyridin-2-ylamino)methyl)-4H-1,2,4-triazol-3-yl)phenyl)-2-(2,4,6-trimethylbenzamido)propanoic acid, compound (330) 3-(4-(5-((4-methoxypyridin-2-ylamino)methyl)-4H-1,2,4-triazol-3-yl)phenyl)-2-(2,4,6-trimethylbenzamido)propanoic acid, compound (333) 2-(2-ethyl-4-fluoro-6-methylbenzamido)-3-(4-(5-((4-methylpyridin-2-ylamino)methyl)-4H-1,2,4-triazol-3-yl)phenyl)propanoic acid, compound (334) 2-(2-ethyl-4-fluoro-6-methylbenzamido)-3-(4-(5-((4-methoxypyridin-2-ylamino)methyl)-4H-1,2,4-triazol-3-yl)phenyl)propanoic acid, compound (335) 2-(4-chloro-2-ethyl-6-methylbenzamido)-3-(4-(4-((4-methylpyridin-2-ylamino)methyl)furan-2-yl)phenyl)propanoic acid, compound (336) 2-(4-chloro-2-ethyl-6-methylbenzamido)-3-(4-(5-((4-methylpyridin-2-ylamino)methyl)-1H-pyrrol-2-yl)phenyl)propanoic acid, compound (337) 2-(4-chloro-2-ethyl-6-methylbenzamido)-3-(4-(5-((4-methylpyridin-2-ylamino)methyl)-1H-pyrrol-3-yl)phenyl)propanoic acid, compound (338) 2-(4-chloro-2-ethyl-6-methylbenzamido)-3-(4-(4-((4-methylpyridin-2-ylamino)methyl)-1H-pyrrol-2-yl)phenyl)propanoic acid, compound (339) 2-(4-chloro-2-ethyl-6-methylbenzamido)-3-(4-(3-((4-methylpyridin-2-ylamino)methyl)-1H-pyrrol-1-yl)phenyl)propanoic acid, compound (340) 2-(4-chloro-2-ethyl-6-methylbenzamido)-3-(4-(4-((4-methylpyridin-2-ylamino)methyl)-1H-pyrazol-1-yl)phenyl)propanoic acid, compound (341) 2-(4-chloro-2-ethyl-6-methylbenzamido)-3-(4-(3-((4-methylpyridin-2-ylamino)methyl)-1H-pyrazol-1-yl)phenyl)propanoic acid, compound (342) 2-(4-chloro-2-ethyl-6-methylbenzamido)-3-(4-(5-((4-methylpyridin-2-ylamino)methyl)-1H-imidazol-2-yl)phenyl)propanoic acid, compound (343) 2-(4-chloro-2-ethyl-6-methylbenzamido)-3-(4-(2-((4-methylpyridin-2-ylamino)methyl)-1H-imidazol-4-yl)phenyl)propanoic acid, compound (344) 2-(4-chloro-2-ethyl-6-methylbenzamido)-3-(4-(4-((4-methylpyridin-2-ylamino)methyl)-1H-imidazol-1-yl)phenyl)propanoic acid, compound (345) 2-(4-chloro-2-ethyl-6-methylbenzamido)-3-(4-(5-((4-methylpyridin-2-ylamino)methyl)thiophen-2-yl)phenyl)propanoic acid, compound (346) 2-(4-chloro-2-ethyl-6-methylbenzamido)-3-(4-(5-((4-methylpyridin-2-ylamino)methyl)thiophen-3-yl)phenyl)propanoic acid, compound (347) 2-(4-chloro-2-ethyl-6-methylbenzamido)-3-(4-(4-((4-methylpyridin-2-ylamino)methyl)thiophen-2-yl)phenyl)propanoic acid, compound (348) 2-(4-chloro-2-ethyl-6-methylbenzamido)-3-(4-(5-((4-methylpyridin-2-ylamino)methyl)isoxazol-3-yl)phenyl)propanoic acid, compound (349) 2-(4-chloro-2-ethyl-6-methylbenzamido)-3-(4-(3-((4-methylpyridin-2-ylamino)methyl)isoxazol-5-yl)phenyl)propanoic acid, compound (350) 2-(4-chloro-2-ethyl-6-methylbenzamido)-3-(4-(2-((4-methylpyridin-2-ylamino)methyl)oxazol-5-yl)phenyl)propanoic acid, compound (351) 2-(4-chloro-2-ethyl-6-methylbenzamido)-3-(4-(2-((4-methylpyridin-2-ylamino)methyl)oxazol-4-yl)phenyl)propanoic acid, compound (352) 2-(4-chloro-2-ethyl-6-methylbenzamido)-3-(4-(4-((4-methylpyridin-2-ylamino)methyl)oxazol-2-yl)phenyl)propanoic acid, compound (353) 2-(4-chloro-2-ethyl-6-methylbenzamido)-3-(4-(5-((4-methylpyridin-2-ylamino)methyl)oxazol-2-yl)phenyl)propanoic acid, compound (354) 2-(4-chloro-2-ethyl-6-methylbenzamido)-3-(4-(2-((4-methylpyridin-2-ylamino)methyl)thiazol-5-yl)phenyl)propanoic acid, compound (355) 2-(4-chloro-2-ethyl-6-methylbenzamido)-3-(4-(2-((4-methylpyridin-2-ylamino)methyl)thiazol-4-yl)phenyl)propanoic acid, compound (356) 2-(4-chloro-2-ethyl-6-methylbenzamido)-3-(4-(4-((4-methylpyridin-2-ylamino)methyl)thiazol-2-yl)phenyl)propanoic acid, compound (357) 2-(4-chloro-2-ethyl-6-methylbenzamido)-3-(4-(5-((4-methylpyridin-2-ylamino)methyl)thiazol-2-yl)phenyl)propanoic acid, compound (358) 2-(4-chloro-2-ethyl-6-methylbenzamido)-3-(4-(5-((4-methylpyridin-2-ylamino)methyl)-1,3,4-thiadiazol-2-yl)phenyl)propanoic acid, compound (359) 2-(4-chloro-2-ethyl-6-methylbenzamido)-3-(4-(5-((4-methylpyridin-2-ylamino)methyl)-1,2,4-thiadiazol-3-yl)phenyl)propanoic acid, compound (360) 2-(4-chloro-2-ethyl-6-methylbenzamido)-3-(4-(3-((4-methylpyridin-2-ylamino)methyl)-1,2,4-thiadiazol-5-yl)phenyl)propanoic acid, compound (361) 2-(4-chloro-2-ethyl-6-methylbenzamido)-3-(4-(5-((4-methylpyridin-2-ylamino)methyl)-1,3,4-oxadiazol-2-yl)phenyl)propanoic acid, compound (362) 2-(4-chloro-2-ethyl-6-methylbenzamido)-3-(4-(5-((4-methylpyridin-2-ylamino)methyl)isothiazol-3-yl)phenyl)propanoic acid, compound (363) 2-(4-chloro-2-ethyl-6-methylbenzamido)-3-(4-(3-((4-methylpyridin-2-ylamino)methyl)isothiazol-5-yl)phenyl)propanoic acid, compound (364) 2-(4-chloro-2-ethyl-6-methylbenzamido)-3-(4-(4-((4-methylpyridin-2-ylamino)methyl)-1H-1,2,3-triazol-1-yl)phenyl)propanoic acid, compound (365) 2-(4-chloro-2-ethyl-6-methylbenzamido)-3-(4-(3-((4-methylpyridin-2-ylamino)methyl)-1H-1,2,4-triazol-1-yl)phenyl)propanoic acid, compound (366) 2-(4-chloro-2-ethyl-6-methylbenzamido)-3-(4-(5-((4-methylpyridin-2-ylamino)methyl)-4H-1,2,4-triazol-3-yl)phenyl)propanoic acid, compound (367) 2-(4-cyano-2-ethyl-6-methylbenzamido)-3-(4-(5-((4-methylpyridin-2-ylamino)methyl)furan-2-yl)phenyl)propanoic acid, compound (368) 2-(4-cyano-2-ethyl-6-methylbenzamido)-3-(4-(5-((4-methylpyridin-2-ylamino)methyl)furan-3-yl)phenyl)propanoic acid, compound (369) 2-(4-cyano-2-ethyl-6-methylbenzamido)-3-(4-(4-((4-methylpyridin-2-ylamino)methyl)furan-2-yl)phenyl)propanoic acid, compound (370) 2-(4-cyano-2-ethyl-6-methylbenzamido)-3-(4-(5-((4-methylpyridin-2-ylamino)methyl)-1H-pyrrol-2-yl)phenyl)propanoic acid, compound (371) 2-(4-cyano-2-ethyl-6-methylbenzamido)-3-(4-(5-((4-methylpyridin-2-ylamino)methyl)-1H-pyrrol-3-yl)phenyl)propanoic acid, compound (372) 2-(4-cyano-2-ethyl-6-methylbenzamido)-3-(4-(4-((4-methylpyridin-2-ylamino)methyl)-1H-pyrrol-2-yl)phenyl)propanoic acid, compound (373) 2-(4-cyano-2-ethyl-6-methylbenzamido)-3-(4-(3-((4-methylpyridin-2-ylamino)methyl)-1H-pyrrol-1-yl)phenyl)propanoic acid, compound (374) 2-(4-cyano-2-ethyl-6-methylbenzamido)-3-(4-(4-((4-methylpyridin-2-ylamino)methyl)-1H-pyrazol-1-yl)phenyl)propanoic acid, compound (375) 2-(4-cyano-2-ethyl-6-methylbenzamido)-3-(4-(3-((4-methylpyridin-2-ylamino)methyl)-1H-pyrazol-1-yl)phenyl)propanoic acid, compound (376) 2-(4-cyano-2-ethyl-6-methylbenzamido)-3-(4-(5-((4-methylpyridin-2-ylamino)methyl)-1H-imidazol-2-yl)phenyl)propanoic acid, compound (377) 2-(4-cyano-2-ethyl-6-methylbenzamido)-3-(4-(2-((4-methylpyridin-2-ylamino)methyl)-1H-imidazol-4-yl)phenyl)propanoic acid, compound (378) 2-(4-cyano-2-ethyl-6-methylbenzamido)-3-(4-(4-((4-methylpyridin-2-ylamino)methyl)-1H-imidazol-1-yl)phenyl)propanoic acid, compound (379) 2-(4-cyano-2-ethyl-6-methylbenzamido)-3-(4-(5-((4-methylpyridin-2-ylamino)methyl)thiophen-2-yl)phenyl)propanoic acid, compound (380) 2-(4-cyano-2-ethyl-6-methylbenzamido)-3-(4-(5-((4-methylpyridin-2-ylamino)methyl)thiophen-3-yl)phenyl)propanoic acid, compound (381) 2-(4-cyano-2-ethyl-6-methylbenzamido)-3-(4-(4-((4-methylpyridin-2-ylamino)methyl)thiophen-2-yl)phenyl)propanoic acid, compound (382) 2-(4-cyano-2-ethyl-6-methylbenzamido)-3-(4-(5-((4-methylpyridin-2-ylamino)methyl)isoxazol-3-yl)phenyl)propanoic acid, compound (383) 2-(4-cyano-2-ethyl-6-methylbenzamido)-3-(4-(3-((4-methylpyridin-2-ylamino)methyl)isoxazol-5-yl)phenyl)propanoic acid, compound (384) 2-(4-cyano-2-ethyl-6-methylbenzamido)-3-(4-(2-((4-methylpyridin-2-ylamino)methyl)oxazol-5-yl)phenyl)propanoic acid, compound (385) 2-(4-cyano-2-ethyl-6-methylbenzamido)-3-(4-(2-((4-methylpyridin-2-ylamino)methyl)oxazol-4-yl)phenyl)propanoic acid, compound (386) 2-(4-cyano-2-ethyl-6-methylbenzamido)-3-(4-(4-((4-methylpyridin-2-ylamino)methyl)oxazol-2-yl)phenyl)propanoic acid, compound (387) 2-(4-cyano-2-ethyl-6-methylbenzamido)-3-(4-(5-((4-methylpyridin-2-ylamino)methyl)oxazol-2-yl)phenyl)propanoic acid, compound (388) 2-(4-cyano-2-ethyl-6-methylbenzamido)-3-(4-(2-((4-methylpyridin-2-ylamino)methyl)thiazol-5-yl)phenyl)propanoic acid, compound (389) 2-(4-cyano-2-ethyl-6-methylbenzamido)-3-(4-(2-((4-methylpyridin-2-ylamino)methyl)thiazol-4-yl)phenyl)propanoic acid, compound (390) 2-(4-cyano-2-ethyl-6-methylbenzamido)-3-(4-(4-((4-methylpyridin-2-ylamino)methyl)thiazol-2-yl)phenyl)propanoic acid, compound (391) 2-(4-cyano-2-ethyl-6-methylbenzamido)-3-(4-(5-((4-methylpyridin-2-ylamino)methyl)thiazol-2-yl)phenyl)propanoic acid, compound (392) 2-(4-cyano-2-ethyl-6-methylbenzamido)-3-(4-(5-((4-methylpyridin-2-ylamino)methyl)-1,3,4-thiadiazol-2-yl)phenyl)propanoic acid, compound (393) 2-(4-cyano-2-ethyl-6-methylbenzamido)-3-(4-(5-((4-methylpyridin-2-ylamino)methyl)-1,2,4-thiadiazol-3-yl)phenyl)propanoic acid, compound (394) 2-(4-cyano-2-ethyl-6-methylbenzamido)-3-(4-(3-((4-methylpyridin-2-ylamino)methyl)-1,2,4-thiadiazol-5-yl)phenyl)propanoic acid, compound (395) 2-(4-cyano-2-ethyl-6-methylbenzamido)-3-(4-(5-((4-methylpyridin-2-ylamino)methyl)-1,3,4-oxadiazol-2-yl)phenyl)propanoic acid, compound (396) 2-(4-cyano-2-ethyl-6-methylbenzamido)-3-(4-(5-((4-methylpyridin-2-ylamino)methyl)isothiazol-3-yl)phenyl)propanoic acid, compound (397) 2-(4-cyano-2-ethyl-6-methylbenzamido)-3-(4-(3-((4-methylpyridin-2-ylamino)methyl)isothiazol-5-yl)phenyl)propanoic acid, compound (398) 2-(4-cyano-2-ethyl-6-methylbenzamido)-3-(4-(4-((4-methylpyridin-2-ylamino)methyl)-1H-1,2,3-triazol-1-yl)phenyl)propanoic acid, compound (399) 2-(4-cyano-2-ethyl-6-methylbenzamido)-3-(4-(3-((4-methylpyridin-2-ylamino)methyl)-1H-1,2,4-triazol-1-yl)phenyl)propanoic acid, compound (400) 2-(4-cyano-2-ethyl-6-methylbenzamido)-3-(4-(5-((4-methylpyridin-2-ylamino)methyl)-4H-1,2,4-triazol-3-yl)phenyl)propanoic acid.

62. The compound according to claim 1, wherein the compound comprises a further moiety selected from the group consisting of a targeted moiety, a delivery moiety, and a detection moiety.

63. The compound according to claim 62, wherein the further moiety is attached or incorporated, to said compound.

64. The compound according to claim 62, wherein the detection moiety is a label, wherein the label is selected from the group consisting of radionuclide labels, paramagnetic material, X-ray attenuating material, immune labels, colored labels, infrared labels, chemiluminescent labels, luminescent labels, fluorescent labels, enzyme substrates, enzymes, and labels complexing detectable ions.

65. The compound according to claim 62, wherein the targeted moiety is a pharmaceutically active moiety selected from the group consisting of cytotoxins, chemotherapeutics, antibodies, radionuclides and cytotoxic proteins.

66. The compound according to claim 62, wherein the targeted moiety is selected from the group consisting of antibodies, linker molecules and liposomes.

67. A pharmaceutical composition comprising a compound according to claim 1 and a pharmaceutically acceptable carrier, diluent or excipient.

68. The pharmaceutical composition according to claim 67 comprising an additional pharmaceutically active compound.

69. The pharmaceutical composition according to claim 67, wherein the compound is present as a pharmaceutically acceptable salt or a pharmaceutically active solvate.

70. The pharmaceutical composition according to claim 67, wherein the compound is either alone or in combination with any of the ingredients of the composition present in a multitude of individualised dosages and/or administration forms.

71. The pharmaceutical composition according to claim 67 for the treatment of a disease mediated by or involving alpha5beta1 integrin.

72. The pharmaceutical composition according to claim 67 for the treatment of a disease, wherein the disease is based on pathological angiogenesis and/or on interaction of an integrin with a ligand, wherein the ligand is present on the extracellular matrix and/or in body fluids and/or on any cell surface.

73. The pharmaceutical composition according to claim 67, for use together with a method of treatment for a disease based on pathological angiogenesis and/or on interaction of an integrin with a ligand, wherein the ligand is present on the extracellular matrix and/or in body fluids and/or on any cell surface.

74. The pharmaceutical composition according to claim 73, wherein the method of treatment is a sequential or combination therapy with the treatment selected from the group consisting of chemotherapy, anti-proliferative, anti-hormone therapy, radiation therapy, photodynamic therapy, surgery, anti-fibrotic therapy, anti-inflammatory therapy, immunosuppressive therapy and anti-angiogenic therapy.

* * * * *

UNITED STATES PATENT AND TRADEMARK OFFICE
CERTIFICATE OF CORRECTION

PATENT NO. : 8,309,735 B2
APPLICATION NO. : 12/300530
DATED : November 13, 2012
INVENTOR(S) : Zischinsky et al.

Page 1 of 2

It is certified that error appears in the above-identified patent and that said Letters Patent is hereby corrected as shown below:

In the Claims:

Column 126, claim 5, line 62, the word "group" was deleted and should read "R5 is selected from the group consisting of";

Column 128, claim 14, line 59, the word "triazolyh" should read "triazolyl,";

Column 131, claim 22, line 44, the word "4- dimethylearbarnoyl" should read "dimethylcarbamoyl";

Column 132, claim 22, line 4, the word "4-am inocarbonyl-2" should read "4-aminocarbonyl-2";

Column 132, claim 22, line 12, the word "2,6dimethylphenyl" should read "2,6-dimethylphenyl";

Column 132, claim 24, line 55, the word "methylisoxazo" should read "methylisoxazol";

Column 132, claim 25, line 60, the word "methyleyclohexyl" should read "methylcyclohexyl";

Column 136, claim 30, line 38, the word "pert-butyl" should read "tert-butyl";

Column 138, claim 33, line 28, the word "selected" was deleted and should read "A is a radical selected from the group";

Column 139, claim 33, line 28, the word "4-trifluoromethylearbonyl" should read "4-trifluoromethylcarbonyl";

Signed and Sealed this
Twenty-fifth Day of February, 2014

Michelle K. Lee
*Deputy Director of the United States Patent and Trademark Office*

CERTIFICATE OF CORRECTION (continued)
U.S. Pat. No. 8,309,735 B2

Column 141, claim 37, line 21, the word "4-dimethylcarbarnoyl" should read "4-dimethylcarbamoyl";

Column 144, claim 39, lines 2-3, the word "trifluoromethylearbonyl" should read "trifluoromethylcarbonyl";

Column 144, claim 39, line 18, the word "tetrahtdro" should read "tetrahydro";

Column 145, claim 41, line 51, the word "(2-imidazoly)" should read "(2-imidazolyl)";

Column 151, claim 47, line 8, the word "methylearbamoyl" should read "methylcarbamoyl";

Column 153, claim 49, line 66, the word "2ylamino" should read "2-ylamino";

Column 156, claim 51, line 1, the word "(2-oxazolyephenyl" should read "(2-oxazolyl)phenyl";

Column 163, claim 59, line 13, the word "dimethylphonyl" should read "dimethylphenyl"; and Column 171, claim 61, lines 30-31, the word "triethylbenzamido" should read "trimethylbenzamido".